(12) United States Patent
Bürli et al.

(10) Patent No.: US 9,765,054 B2
(45) Date of Patent: Sep. 19, 2017

(54) HISTONE DEACETYLASE INHIBITORS AND COMPOSITIONS AND METHODS OF USE THEREOF

(75) Inventors: Roland W. Bürli, Hertfordshire (GB); Andrew J. Stott, Cambridge (GB); Perla Breccia, Cambridge (GB); Celia Dominguez, Los Angeles, CA (US); Ignacio Muñoz-Sanjuàn, West Hollywood, CA (US); Christopher A. Luckhurst, Cambridge (GB); Samantha J. Hughes, Essex (GB); Alan F. Haughan, Cambridge (GB)

(73) Assignee: CHDI Foundation, Inc., New York, NY (US)

( * ) Notice: Subject to any disclaimer, the term of this patent is extended or adjusted under 35 U.S.C. 154(b) by 408 days.

(21) Appl. No.: 13/981,107

(22) PCT Filed: Jan. 23, 2012

(86) PCT No.: PCT/US2012/022216
§ 371 (c)(1),
(2), (4) Date: Feb. 24, 2014

(87) PCT Pub. No.: WO2012/103008
PCT Pub. Date: Aug. 2, 2012

(65) Prior Publication Data
US 2014/0163009 A1 Jun. 12, 2014

Related U.S. Application Data

(60) Provisional application No. 61/435,678, filed on Jan. 24, 2011.

(51) Int. Cl.
| | | |
|---|---|---|
| *A61K 31/415* | (2006.01) | |
| *A61K 31/505* | (2006.01) | |
| *A61K 31/519* | (2006.01) | |
| *C07D 231/12* | (2006.01) | |
| *C07D 239/26* | (2006.01) | |
| *C07D 319/08* | (2006.01) | |
| *C07D 487/04* | (2006.01) | |
| *C07D 401/06* | (2006.01) | |
| *C07C 259/08* | (2006.01) | |
| *C07D 205/04* | (2006.01) | |
| *C07D 207/10* | (2006.01) | |
| *C07D 209/44* | (2006.01) | |
| *C07D 209/46* | (2006.01) | |
| *C07D 209/82* | (2006.01) | |
| *C07D 211/58* | (2006.01) | |
(Continued)

(52) U.S. Cl.
CPC .......... *C07D 401/06* (2013.01); *C07C 259/08* (2013.01); *C07C 311/14* (2013.01); *C07D 205/04* (2013.01); *C07D 207/10* (2013.01); *C07D 209/44* (2013.01); *C07D 209/46* (2013.01); *C07D 209/82* (2013.01); *C07D 211/58* (2013.01); *C07D 211/70* (2013.01); *C07D 213/56* (2013.01); *C07D 213/74* (2013.01); *C07D 215/18* (2013.01); *C07D 231/12* (2013.01); *C07D 233/61* (2013.01); *C07D 233/64* (2013.01); *C07D 237/08* (2013.01); *C07D 239/26* (2013.01); *C07D 263/32* (2013.01); *C07D 265/36* (2013.01); *C07D 267/14* (2013.01); *C07D 277/30* (2013.01); *C07D 295/155* (2013.01); *C07D 317/46* (2013.01); *C07D 319/18* (2013.01); *C07D 401/04* (2013.01); *C07D 409/08* (2013.01); *C07D 413/04* (2013.01); *C07D 417/08* (2013.01); *C07D 471/04* (2013.01); *C07D 487/04* (2013.01); *C07D 491/10* (2013.01); *C07C 2101/02* (2013.01); *C07C 2101/14* (2013.01)

(58) Field of Classification Search
CPC .. C07D 231/12; C07D 239/26; C07D 319/08; C07D 487/04
See application file for complete search history.

(56) References Cited

U.S. PATENT DOCUMENTS 7,125,871 B2 * 10/2006 Collado Cano ....... C07C 237/24
514/237.5
7,576,108 B2  8/2009 Weichert et al.
(Continued)

FOREIGN PATENT DOCUMENTS

EP       2060565       5/2009
WO   WO 02/22577       3/2002
(Continued)

OTHER PUBLICATIONS

Pd(II)-Catalyzed Enantioselective C-H Activation of Cyclopropanes. Wasa et al. JACS, 2011, 133, 19598.*
(Continued)

*Primary Examiner* — Brian McDowell
(74) *Attorney, Agent, or Firm* — Sheppard Mullin Richter & Hampton LLP

(57) ABSTRACT

Provided are certain histone deacetylase (HDAC) inhibitors of Formula I, compositions thereof, and methods of their use.

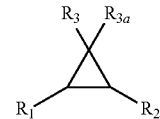

Formula I

27 Claims, No Drawings

(51) Int. Cl.

| | |
|---|---|
| C07D 211/70 | (2006.01) |
| C07D 213/56 | (2006.01) |
| C07D 213/74 | (2006.01) |
| C07D 215/18 | (2006.01) |
| C07D 233/61 | (2006.01) |
| C07D 237/08 | (2006.01) |
| C07D 263/32 | (2006.01) |
| C07D 265/36 | (2006.01) |
| C07D 267/14 | (2006.01) |
| C07D 277/30 | (2006.01) |
| C07D 295/155 | (2006.01) |
| C07D 317/46 | (2006.01) |
| C07D 319/18 | (2006.01) |
| C07D 401/04 | (2006.01) |
| C07D 409/08 | (2006.01) |
| C07D 413/04 | (2006.01) |
| C07D 417/08 | (2006.01) |
| C07D 471/04 | (2006.01) |
| C07D 491/10 | (2006.01) |
| C07C 311/14 | (2006.01) |
| C07D 233/64 | (2006.01) |

(56) References Cited

U.S. PATENT DOCUMENTS

| | | | |
|---|---|---|---|
| 9,505,736 | B2 | 11/2016 | Dominguez et al. |
| 2009/0181943 | A1 | 7/2009 | Tessier et al. |
| 2010/0152254 | A1 | 6/2010 | Bialer et al. |
| 2010/0168463 | A1 | 7/2010 | Hirara et al. |
| 2017/0042892 | A1 | 2/2017 | Dominguez et al. |

FOREIGN PATENT DOCUMENTS

| | | |
|---|---|---|
| WO | WO 2005/011661 | 2/2005 |
| WO | WO 2005/028447 | 3/2005 |

OTHER PUBLICATIONS

Braña et al., "Synthesis and Biological Evaluation of Novel 2-(1H-imidazol-4-yl)cyclopropane carboxylic Acids: Key Intermediates for $H_3$ Histamine Receptor Ligands", Bioorganic & Medicinal Chemistry Letters (2002), vol. 12, No. 24, pp. 3561-3563.

Eyal et al., "Histone deacetylases inhibition and tumor cells cytotoxicity by CNDS-active VPA constitutional isomers and derivatives", Biochemical Pharmacology (2005), vol. 69, No. 10, pp. 1501-1508.

Pellicciari et al., "Syntheis and Pharacological Characterization of All Sixteen Stereoisomers of 2-(2'-Carboxy-3'-phenylcyclopropyl)glycine. Focus on (2S,1'S,2'S,3'R)-2-(2'-Carboxy-3'-phenylcyclopropyl)glycine, a Novel and Selective Group II Metabotropic Glutamate Receptors Antagonist", Journal of Medicinal Chemistry (1996), vol. 39, No. 11, pp. 2259-2269.

International Search Report dated May 10, 2012 and International Preliminary Report on Patentability and Written Opinion for PCT/US2012/022216 dated Jul. 30, 2013 (8 pages).

Search Report for Singapore Application No. 201305550-4 dated Jul. 4, 2015 (7 pages).

English Translation of the TIPO's Search Report for ROC Patent Application No. 101102386 dated Apr. 22, 2015 (1 page).

Supplementary European Search Report for EP 12 73 8982 dated Jun. 13, 2014 (9 pages).

Walbrick et al., "A General Method for Synthesizing Optically Active 1,3-Disubstituted Allene Hydrocarbons", Journal of the American Chemical Society (1968), vol. 90, No. 11, pp. 2895-2901.

Warner et al., "Electron Demand in the Transition State of the Cyclopropylidene to Allen Ring Opening", J. Org. Chem. (1992), vol. 57, No. 23, pp. 6294-6300.

International Search Report dated Dec. 19, 2013 and International Preliminary Report on Patentability and Written Opinion for PCT/US2013/050664 dated Jan. 20, 2015 (10 pages).

C. Colussi et al., "Histone Deacetylase Inhibitors: Keeping Momentum for Neuromuscular and Cardiovascular Diseases Treatment," Pharmacological Research 62 (2010), pp. 3-10.

* cited by examiner

HISTONE DEACETYLASE INHIBITORS AND COMPOSITIONS AND METHODS OF USE THEREOF

This application claims the benefit of priority of U.S. Application No. 61/435,678, filed Jan. 24, 2011, which is incorporated herein by reference for all purposes.

Provided herein are certain histone deacetylase (HDAC) inhibitors, compositions thereof, and methods of their use.

Histone deacetylases (HDACs) are zinc-containing enzymes which catalyse the removal of acetyl groups from the ε-amino termini of lysine residues clustered near the amino terminus of nucleosomal histones. There are 11 known metal-dependent human histone deacetylases, grouped into four classes based on the structure of their accessory domains. Class I includes HDAC1, HDAC2, HDAC3, and HDAC8 and have homology to yeast RPD3. HDAC4, HDAC5, HDAC7, and HDAC9 belong to Class IIa and have homology to yeast HDAC1. HDAC6 and HDAC10 contain two catalytic sites and are classified as Class IIb, whereas HDAC11 has conserved residues in its catalytic center that are shared by both Class I and Class II deacetylases and is sometimes placed in Class IV.

Provided is a compound of Formula I

Formula I or a pharmaceutically acceptable salt thereof wherein
$R_1$ and $R_2$ are independently chosen from optionally substituted alkyl, optionally substituted cycloalkyl, optionally substituted heterocycloalkyl, optionally substituted aryl, and optionally substituted heteroaryl;
$R_3$ is chosen from —COOH, —C(O)NH(OH) and —N(OH)C(O)$R_4$;
$R_{3a}$ is chosen from hydrogen and lower alkyl optionally substituted with halo; and
$R_4$ is chosen from hydrogen and lower alkyl;
wherein if $R_1$ and $R_2$ are both phenyl and $R_{3a}$ is hydrogen, then $R_3$ is —N(OH)C(O)H or —C(O)NH(OH).

Also provided is a pharmaceutical composition comprising a compound, or a pharmaceutically acceptable salt thereof, described herein and at least one pharmaceutically acceptable excipient.

Also provided is a method of treating a condition or disorder mediated by at least one histone deacetylase in a subject in need of such a treatment which method comprises administering to the subject a therapeutically effective amount of a compound, or a pharmaceutically acceptable salt thereof, described herein.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having 1 to 4 carbons.

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, cyclopentenyl and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge. "Lower alkoxy" refers to alkoxy groups having 1 to 4 carbons.

"Aryl" indicates an aromatic carbon ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl", as defined herein, regardless of the point of attachment (e.g., both quinolin-5-yl and quinolin-2-yl are heteroaryl groups). In some instances, aryl is phenyl or naphthyl. In certain instances, aryl is phenyl.

Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

The term "halo" includes fluoro, chloro, bromo, and iodo, and the term "halogen" includes fluorine, chlorine, bromine, and iodine.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$—$O^-$). Additionally, when sulfur is present in a heteroaryl ring, it may, where the nature of the adjacent atoms and groups permits, exist in an oxidized state (i.e., $S^+$—$O^-$ or $SO_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-b]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic).

Examples of monocyclic heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl.

When nitrogen is present in a heterocycloalkyl ring, it may, where the nature of the adjacent atoms and groups permits, exist in an oxidized state (i.e., $N^+$—$O^-$). Examples include piperidinyl N-oxide and morpholinyl-N-oxide. Additionally, when sulfur is present in a heterocycloalkyl ring, it may, where the nature of the adjacent atoms and groups permits, exist in an oxidized state (i.e., $S^+$—$O^-$ or —$SO_2$—). Examples include thiomorpholine S-oxide and thiomorpholine S,S-dioxide.

In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). When nitrogen is present in a heterocycloalkenyl ring, it may, where the nature of the adjacent atoms and groups permits, exist in an oxidized state (i.e., $N^+$—$O^-$). Additionally, when sulfur is present in a heterocycloalkenyl ring, it may, where the nature of the adjacent atoms and groups permits, exist in an oxidized state (i.e., $S^+$—$O^-$ or —$SO_2$—). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation lower alkyl), cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from —$R^a$, —$OR^b$, —O($C_1$-$C_2$ alkyl)O— (e.g., methylenedioxy-), —$SR^b$, guanidine, guanidine wherein one or more of the guanidine hydrogens are replaced with a lower-alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from optionally substituted $C_1$-$C_6$ alkyl, optionally substituted cycloalkyl, optionally substituted aryl, optionally substituted heterocycloalkyl, and optionally substituted heteroaryl;

$R^b$ is chosen from H, optionally substituted $C_1$-$C_6$ alkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O) (phenyl), —C(O)$C_1$-$C_4$ alkyl, —C(O)$C_1$-$C_4$ phenyl, —C(O) $C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

The term "substituted alkoxy" refers to alkoxy wherein the alkyl constituent is substituted (i.e., —O-(substituted alkyl)) wherein "substituted alkyl" is as described herein.

The term "substituted amino" refers to the group —$NHR^d$ or —$NR^dR^d$ where each $R^d$ is independently chosen from hydroxy, optionally substituted alkyl, optionally substituted cycloalkyl, optionally substituted acyl, aminocarbonyl, optionally substituted aryl, optionally substituted heteroaryl, optionally substituted heterocycloalkyl, optionally substituted alkoxycarbonyl, sulfinyl and sulfonyl, each as described herein, and provided that only one $R^d$ may be hydroxyl. The term "substituted amino" also refers to N-oxides of the groups —$NHR^d$, and $NR^dR^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Aminocarbonyl" encompasses a group of the formula —(C=O)(optionally substituted amino) wherein substituted amino is as described herein.

"Acyl" refers to the groups (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3$(C=O)—.

By "alkoxycarbonyl" is meant an ester group of the formula (alkoxy)(C=O)— attached through the carbonyl carbon wherein the alkoxy group has the indicated number of carbon atoms. Thus a $C_1$-$C_6$alkoxycarbonyl group is an alkoxy group having from 1 to 6 carbon atoms attached through its oxygen to a carbonyl linker.

By "amino" is meant the group —$NH_2$.

The term "sulfinyl" includes the groups —S(O)—H, —S(O)-(optionally substituted ($C_1$-$C_6$)alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups —S(O$_2$)—H, —S(O$_2$)-(optionally substituted (C$_1$-C$_6$)alkyl), —S(O$_2$)-optionally substituted aryl), —S(O$_2$)-optionally substituted heteroaryl), —S(O$_2$)-(optionally substituted heterocycloalkyl), —S(O$_2$)-(optionally substituted alkoxy), —S(O$_2$)-optionally substituted aryloxy), —S(O$_2$)-optionally substituted heteroaryloxy), —S(O$_2$)-(optionally substituted heterocyclyloxy); and —S(O$_2$)-(optionally substituted amino).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl are as described herein.

The term "substituted alkoxy" refers to alkoxy wherein the alkyl constituent is substituted (i.e., —O-(substituted alkyl)) wherein "substituted alkyl" is as described herein.

The term "substituted alkoxycarbonyl" refers to the group (substituted alkyl)-O—C(O)— wherein the group is attached to the parent structure through the carbonyl functionality and wherein substituted alkyl is as described herein.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all tautomeric forms and crystal forms of the compound.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—(CH$_2$)$_n$—COOH where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

"Prodrugs" described herein include any compound that becomes a compound of Formula I when administered to a patient, e.g., upon metabolic processing of the prodrug. Examples of prodrugs include derivatives of functional groups, such as a carboxylic acid group, in the compounds of Formula I. Exemplary prodrugs of a carboxylic acid group include, but are not limited to, carboxylic acid esters such as alkyl esters, hydroxyalkyl esters, arylalkyl esters, and aryloxyalkyl esters. Other exemplary prodrugs include lower alkyl esters such as ethyl ester, acyloxyalkyl esters such as pivaloyloxymethyl (POM), glycosides, and ascorbic acid derivatives. The term "compound" is intended to include prodrugs.

Other exemplary prodrugs include amides of carboxylic acids. Exemplary amide prodrugs include metabolically labile amides that are formed, for example, with an amine and a carboxylic acid. Exemplary amines include NH$_2$, primary, and secondary amines such as NHR$^x$, and NR$^y$R$^x$, wherein R$^x$ is hydrogen, (C$_1$-C$_{18}$)-alkyl, (C$_3$-C$_7$)-cycloalkyl, (C$_3$-C$_7$)-cycloalkyl-(C$_1$-C$_4$)-alkyl-, (C$_6$-C$_{14}$)-aryl which is unsubstituted or substituted by a residue (C$_1$-C$_2$)-alkyl, (C$_1$-C$_2$)-alkoxy, fluoro, or chloro; heteroaryl-, (C$_6$-C$_{14}$)-aryl-(C$_1$-C$_4$)-alkyl- where aryl is unsubstituted or substituted by a residue (C$_1$-C$_2$)-alkyl, (C$_1$-C$_2$)-alkoxy, fluoro, or chloro; or heteroaryl-(C$_1$-C$_4$)-alkyl- and in which R$^y$ has the meanings indicated for R$^x$ with the exception of hydrogen or wherein R$^x$ and R$^y$, together with the nitrogen to which they are bound, form an optionally substituted 4- to 7-membered heterocycloalkyl ring which optionally includes one or two additional heteroatoms chosen from nitrogen, oxygen, and sulfur. A discussion of prodrugs is provided in T. Higuchi and V. Stella, Pro-drugs as Novel Delivery Systems, Vol. 14 of the A.C.S. Symposium Series, in Edward B. Roche, ed., Bioreversible Carriers in Drug Design, American Pharmaceutical Association and Pergamon Press, 1987, and in Design of Prodrugs, ed. H. Bundgaard, Elsevier, 1985.

A "solvate" is formed by the interaction of a solvent and a compound. The term "compound" is intended to include solvates of compounds. Similarly, "salts" includes solvates of salts. Suitable solvates are pharmaceutically acceptable solvates, such as hydrates, including monohydrates and hemi-hydrates.

A "chelate" is formed by the coordination of a compound to a metal ion at two (or more) points. The term "compound" is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound".

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry.

"Hydrogen bond acceptor" refers to a group comprising an oxygen or nitrogen, such as an oxygen or nitrogen that is sp$^2$-hybridized, an ether oxygen, or the oxygen of a sulfoxide or N-oxide.

The term "hydrogen bond donor" refers to an oxygen, nitrogen, or heteroaromatic carbon that bears a hydrogen. group containing a ring nitrogen or a heteroaryl group containing a ring nitrogen.

As used herein the terms "group", "radical" or "fragment" are synonymous and are intended to indicate functional groups or fragments of molecules attachable to a bond or other fragments of molecules.

The term "active agent" is used to indicate a compound or a pharmaceutically acceptable salt thereof which has biological activity. In some embodiments, an "active agent" is a compound or pharmaceutically acceptable salt thereof having pharmaceutical utility. For example an active agent may be an anti-neurodegenerative therapeutic.

The term "therapeutically effective amount" means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease responsive to inhibition of HDAC activity.

As used herein, the terms "histone deacetylase" and "HDAC" are intended to refer to anyone of a family of enzymes that remove $N^\epsilon$-acetyl groups from the $\epsilon$-amino groups of lysine residues of a protein (for example, a histone, or tubulin). Unless otherwise indicated by context, the term "histone" is meant to refer to any histone protein, including H1, H2A, H2B, H3, H4, and H5, from any species. In some embodiments, the histone deacetylase is a human HDAC, including, but not limited to, HDAC-4, HDAC-5, HDAC-6, HDAC-7, HDAC-9, and HDAC-10. In some embodiments, the at least one histone deacetylase is selected from HDAC-4, HDAC-5, HDAC-7, and HDAC-9. In some embodiments, the histone deacetylase is a class IIa HDAC. In some embodiments, the histone deacetylase is HDAC-4. In some embodiments, the histone deacetylase is HDAC-5. In some embodiments, the histone deacetylase is derived from a protozoal or fungal source.

The terms "histone deacetylase inhibitor" and "inhibitor of histone deacetylase" are intended to mean a compound, or a pharmaceutically acceptable salt thereof, described herein which is capable of interacting with a histone deacetylase and inhibiting its enzymatic activity.

The term "a condition or disorder mediated by HDAC" or "a condition or disorder mediated by histone deacetylase" as used herein refers to a condition or disorder in which HDAC and/or the action of HDAC is important or necessary, e.g., for the onset, progress, expression, etc. of that condition, or a condition which is known to be treated by HDAC inhibitors (such as, e.g., trichostatin A).

The term "effect" describes a change or an absence of a change in cell phenotype or cell proliferation. "Effect" can also describe a change or an absence of a change in the catalytic activity of HDAC. "Effect" can also describe a change or an absence of a change in an interaction between HDAC and a natural binding partner.

The term "inhibiting histone deacetylase enzymatic activity" is intended to mean reducing the ability of a histone deacetylase to remove an acetyl group from a protein, such as but not limited to a histone or tubulin. The concentration of inhibitor which reduces the activity of a histone deacetylase to 50% of that of the uninhibited enzyme is determined as the $IC_{50}$ value. In some embodiments, such reduction of histone deacetylase activity is at least 50%, such as at least about 75%, for example, at least about 90%. In some embodiments, histone deacetylase activity is reduced by at least 95%, such as by at least 99%. In some embodiments, the compounds and pharmaceutical acceptable salts thereof described herein have an $IC_{50}$ value less than 100 nanomolar. In some embodiments, the compounds and pharmaceutical acceptable salts thereof described herein have an $IC_{50}$ value from 100 nanomolar to 1 micromolar. In some embodiments, the compounds and pharmaceutical acceptable salts thereof described herein have an $IC_{50}$ value from 1 to 25 micromolar.

In some embodiments, such inhibition is specific, i.e., the histone deacetylase inhibitor reduces the ability of a histone deacetylase to remove an acetyl group from a protein at a concentration that is lower than the concentration of the inhibitor that is required to produce another, unrelated biological effect. In some embodiments, the concentration of the inhibitor required for histone deacetylase inhibitory activity is at least 2-fold lower, such as at least 5-fold lower, for example, at least 10-fold lower, such as at least 20-fold lower than the concentration required to produce an unrelated biological effect.

"Treatment" or "treating" means any treatment of a disease state in a patient, including
a) preventing the disease, that is, causing the clinical symptoms of the disease not to develop;
b) inhibiting the disease;
c) slowing or arresting the development of clinical symptoms; and/or
d) relieving the disease, that is, causing the regression of clinical symptoms.

"Subject" or "patient" refers to an animal, such as a mammal, that has been or will be the object of treatment, observation or experiment. The methods described herein may be useful in both human therapy and veterinary applications. In some embodiments, the subject is a mammal; and in some embodiments the subject is human.

Provided is a compound of Formula I

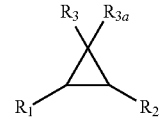

Formula I or a pharmaceutically acceptable salt thereof wherein
$R_1$ and $R_2$ are independently chosen from optionally substituted alkyl, optionally substituted cycloalkyl, optionally substituted heterocycloalkyl, optionally substituted aryl, and optionally substituted heteroaryl;
$R_3$ is chosen from —COOH, —C(O)NH(OH) and —N(OH)C(O)R$_4$;
$R_{3a}$ is chosen from hydrogen and lower alkyl optionally substituted with halo; and
$R_4$ is chosen from hydrogen and lower alkyl;
wherein if $R_1$ and $R_2$ are both phenyl and $R_{3a}$ is hydrogen, then $R_3$ is —N(OH)C(O)H or —C(O)NH(OH).

In some embodiments, $R_1$ is chosen from alkyl, cycloalkyl, aryl, heterocycloalkyl, and heteroaryl, each of which is optionally substituted with one, two, or three groups independently chosen from —R$_{11}$, —OR$_{12}$, halo, —NR$_{12}$R$_{13}$, —C(O)R$_{12}$, —C(O)OR$_{12}$, —C(O)NR$_{12}$R$_{13}$, —OC(O)R$_{12}$, —OC(O)OR$_{11}$, —OC(O)NR$_{12}$R$_{13}$, —NR$_{13}$C(O)R$_{12}$, —NR$_{13}$C(O)OR$_{11}$, —NR$_{13}$C(O)NR$_{12}$R$_{13}$, —S(O)R$_{11}$, —SO$_2$R$_{11}$, —SO$_2$NR$_{12}$R$_{13}$, and —NR$_{13}$SO$_2$R$_{11}$, wherein
$R_{11}$ is chosen from optionally substituted $C_1$-$C_6$ alkyl, optionally substituted cycloalkyl, optionally substituted cycloalkenyl, optionally substituted aryl, optionally substituted heterocycloalkyl, optionally substituted heterocycloalkenyl, and optionally substituted heteroaryl;

$R_{12}$ is chosen from H, optionally substituted $C_1$-$C_6$ alkyl, optionally substituted cycloalkyl, optionally substituted aryl, optionally substituted arylalkyl, optionally substituted heterocycloalkyl, optionally substituted heteroaryl, and optionally substituted heteroarylalkyl; and $R_{13}$ is chosen from hydrogen and optionally substituted $C_1$-$C_4$ alkyl.

In some embodiments, $R_1$ is phenyl optionally substituted with one, two, or three groups independently chosen from —$R_{11}$, —$OR_{12}$, halo, —$C(O)R_{12}$, —$NR_{12}R_{13}$, and —$NR_{13}SO_2R_{11}$.

In some embodiments, $R_1$ is phenyl optionally substituted with one, two or three groups independently selected from
halo,
lower alkyl,
aryl optionally substituted with one or two groups independently chosen from lower alkyl, trifluoromethyl, cycloalkyl, phenyl, and benzyloxy,
heteroaryl optionally substituted with one or two groups independently chosen from lower alkyl, trifluoromethyl, cycloalkyl, and phenyl,
(cycloalkyl)sulfonamido, and
heterocycloalkyl optionally substituted with one or two groups independently chosen from halo, lower alkyl, trifluoromethyl, cycloalkyl, heterocycloalkyl, and phenyl.

In some embodiments, $R_1$ is phenyl optionally substituted with one, two or three groups independently selected from halo, lower alkyl, oxazol-2-yl, oxazol-5-yl, pyrimidin-2-yl, pyrimidin-5-yl, pyridazin-3-yl, pyridazin-4-yl, 1H-pyrazol-1-yl, (cycloalkyl)sulfonamido, 1H-imidazol-1-yl, imidazol-2-yl, 1,2,3,6-tetrahydropyridin-4-yl, azetidin-1-yl, pyrrolidin-1-yl, 2-oxa-6-azaspiro[3.3]heptan-6-yl, phenyl, hexahydropyrrolo[1,2-a]pyrazin-2(1H)-yl, piperidin-1-yl, piperazin-1-yl, and 6,7-dihydropyrazolo[1,5-a]pyrimidin-4(5H)-yl, each of which is optionally substituted with one or two groups independently chosen from halo, lower alkyl, trifluoromethyl, phenyl, cycloalkyl, benzyl, benzyloxy, and pyrrolidin-1-yl.

In some embodiments, $R_1$ is chosen from phenyl, 2-methylphenyl, 3-methylphenyl, 4-methylphenyl, 2-fluorophenyl, 3-fluorophenyl, 4-fluorophenyl, 2-bromophenyl, 3-bromophenyl, 4-bromophenyl, 4-(1-benzyl-1,2,3,6-tetrahydropyridin-4-yl)phenyl, 4-(pyrimidin-2-yl)phenyl, 4-(pyrimidin-5-yl)phenyl, 4-(5-methylpyrimidin-2-yl)phenyl, 3-(5-fluoropyrimidin-2-yl)phenyl, 4-(5-chloropyrimidin-2-yl)phenyl, 4-(5-fluoropyrimidin-2-yl)phenyl, 4-(4-(trifluoromethyl)pyrimidin-2-yl)phenyl, 4-(5-trifluoromethylpyrimidin-2-yl)phenyl, 4-(5-cyclopropylpyrimidin-2-yl)phenyl, 4-(pyridazin-3-yl)phenyl, 4-(pyridazin-4-yl)phenyl, 4-(1H-imidazol-1-yl)phenyl, 4-(1-methyl-1H-imidazol-2-yl)phenyl, 4-(5-methyl-1H-imidazol-2-yl)phenyl, 4-(1H-pyrazol-1-yl)phenyl, 4-(3-methyl-1H-pyrazol-1-yl)phenyl, 4-(3-(trifluoromethyl)-1H-pyrazol-1-yl)phenyl, 3-(oxazol-5-yl)phenyl, 4-(oxazol-2-yl)phenyl, 4-(oxazol-5-yl)phenyl, 4-(2-methyloxazol-5-yl)phenyl, 4-(2-cyclopropyloxazol-5-yl)phenyl, 4-(2-phenyloxazol-5-yl)phenyl, 4-(cyclopropanesulfonamido)phenyl, 4-(3,3-dimethylazetidin-1-yl)phenyl, 4-(3,3-difluoropyrrolidin-1-yl)phenyl, 4-(2-oxa-6-azaspiro[3.3]heptan-6-yl)phenyl, 3'-(benzyloxy)biphenyl-4-yl, 3-(hexahydropyrrolo[1,2-a]pyrazin-2(1H)-yl)phenyl, 3-(4-(pyrrolidin-1-yl)piperidin-1-yl)phenyl, 4-(4-methylpiperazin-1-yl)phenyl, 4-(4-isopropylpiperazin-1-yl)phenyl, and 3-(6,7-dihydropyrazolo[1,5-a]pyrimidin-4(5H)-yl)phenyl.

In some embodiments, $R_1$ is chosen from 4-(1-benzyl-1,2,3,6-tetrahydropyridin-4-yl)phenyl, 4-(pyrimidin-2-yl)phenyl, 4-(5-methylpyrimidin-2-yl)phenyl, 4-(5-chloropyrimidin-2-yl)phenyl, 4-(5-fluoropyrimidin-2-yl)phenyl, 4-(4-(trifluoromethyl)pyrimidin-2-yl)phenyl, 4-(5-cyclopropylpyrimidin-2-yl)phenyl, 4-(pyridazin-3-yl)phenyl, 4-(pyridazin-4-yl)phenyl, 4-(5-methyl-1H-imidazol-2-yl)phenyl), 4-(5-(trifluoromethyl)-1H-imidazol-2-yl)phenyl, 3-chloro-4-(5-methyl-1H-imidazol-2-yl)phenyl, 3-fluoro-4-(5-methyl-1H-imidazol-2-yl)phenyl, 4-(1H-pyrazol-1-yl)phenyl, 3-(oxazol-5-yl)phenyl, 4-(oxazol-2-yl)phenyl, 4-(oxazol-5-yl)phenyl, 4-(2-cyclopropyloxazol-5-yl)phenyl, 4-(4-isopropylpiperazin-1-yl)phenyl, and 3-(6,7-dihydropyrazolo[1,5-a]pyrimidin-4(5H)-yl)phenyl.

In some embodiments, $R_1$ is chosen from 1,2,3,4-tetrahydroquinolin-6-yl, 2,3,4,5-tetrahydrobenzo[f][1,4]oxazepin-7-yl, 1,2,3,4-tetrahydropyrrolo[1,2-a]pyrazin-7-yl, imidazo[1,2-a]pyridin-7-yl, imidazo[1,2-a]pyridin-3-yl, pyrrolo[1,2-a]pyrimidin-4-yl, 1,5-naphthyridin-4-yl, 2,3-dihydrobenzo[b][1,4]dioxin-6-yl, benzo[d][1,3]dioxol-5-yl, and 1-oxo-isoindolin-5-yl, each of which is optionally substituted with one or two groups independently chosen from halo and lower alkyl optionally substituted with one, two, or three halo groups.

In some embodiments, $R_1$ is heteroaryl optionally substituted with one, two, or three groups independently chosen from —$R_{11}$, —$OR_{12}$, halo, and —$NR_{13}SO_2R_{11}$.

In some embodiments, $R_1$ is chosen from pyridin-3-yl, pyridin-4-yl, 1H-pyrazol-4-yl, pyrimidin-5-yl, pyridazin-4-yl, benzo[d]isoxazol-3-yl, benzo[d]oxazol-6-yl, and thiazol-5-yl, each of which is optionally substituted with one, two, or three groups independently chosen from —$R_{11}$, —$OR_{12}$, halo, and —$NR_{13}SO_2R_{11}$.

In some embodiments, $R_1$ is chosen from pyridin-3-yl, pyridin-4-yl, 1H-pyrazol-4-yl, pyrimidin-5-yl, pyridazin-4-yl, benzo[d]isoxazol-3-yl, benzo[d]oxazol-6-yl, and thiazol-5-yl, each of which is optionally substituted with one or two groups independently chosen from halo, lower alkyl, 2,2,2-trifluoroethylamino, trifluoromethyl, 2,2,2-trifluoroethyl, cycloalkyl, cyclopropylmethyl, 1H-pyrazol-1-yl optionally substituted with lower alkyl, pyrimidin-2-yl optionally substituted with lower alkyl or halo, oxazol-5-yl optionally substituted with lower alkyl, piperazin-1-yl optionally substituted with lower alkyl, piperidin-4-yl optionally substituted with 2,2,2-trifluoroethyl, and pyridin-2-yl optionally substituted with lower alkyl or trifluoromethyl.

In some embodiments, $R_1$ is chosen from 2-cyclopropylpyridin-4-yl, 6-(trifluoromethyl)pyridin-3-yl, 2-(trifluoromethyl)pyridin-4-yl, 5-(trifluoromethyl)pyridin-3-yl, 2-(2,2,2-trifluoroethylamino)pyridin-4-yl, 6-(2,2,2-trifluoroethylamino)pyridin-3-yl, 6-(3-methyl-1H-pyrazol-1-yl)pyridin-3-yl, 6-(5-methylpyrimidin-2-yl)pyridin-3-yl, 6-(2-methyloxazol-5-yl)pyridin-3-yl, 6-(5-chloropyrimidin-2-yl)pyridin-3-yl, 6-(4-isopropylpiperazin-1-yl)pyridin-3-yl, 2,6-dicyclopropylpyridin-4-yl, 6-(5-fluoropyrimidin-2-yl)pyridin-3-yl, 2-(5-chloropyrimidin-2-yl)-6-cyclopropylpyridin-4-yl, 1-methyl-1H-pyrazol-4-yl, 1-(2,2,2-trifluoroethyl)-1H-pyrazol-4-yl, 1-(cyclopropylmethyl)-1H-pyrazol-4-yl, 1-cyclopropyl-1H-pyrazol-4-yl, 1,3-dimethyl-1H-pyrazol-4-yl, 1-(1-(2,2,2-trifluoroethyl)piperidin-4-yl)-1H-pyrazol-4-yl, 1-(5-(trifluoromethyl)pyridin-2-yl)-1H-pyrazol-4-yl, 1-(5-(trifluoromethyl)pyridin-2-yl)-1H-pyrazol-4-yl, pyrimidin-5-yl, 2-cyclopropylpyrimid-5-yl, 3-cyclopropylpyrimid-5-yl, pyridazin-4-yl, 6-cyclopropylpyridazin-4-yl, benzo[d]isoxazol-3-yl, 2-isopropylbenzo[d]oxazol-6-yl, and 2-methylthiazol-5-yl.

In some embodiments, $R_2$ is chosen from cycloalkyl, heterocycloalkyl, alkyl, aryl and heteroaryl, each of which is optionally substituted with one, two, or three groups independently chosen from —$R_{21}$, —$OR_{22}$, halo, and —$NR_{23}SO_2R_{21}$, wherein
  $R_{21}$ is chosen from optionally substituted $C_1$-$C_6$ alkyl, optionally substituted cycloalkyl, optionally substituted aryl, optionally substituted heterocycloalkyl, and optionally substituted heteroaryl;
  $R_{22}$ is chosen from H, optionally substituted $C_1$-$C_6$ alkyl, optionally substituted cycloalkyl, optionally substituted aryl, optionally substituted arylalkyl, optionally substituted heterocycloalkyl, optionally substituted heteroaryl, and optionally substituted heteroarylalkyl; and
  $R_{23}$ is chosen from hydrogen and optionally substituted $C_1$-$C_4$ alkyl.

In some embodiments, $R_2$ is chosen from cyclohexyl, thiophen-2-yl, thiazol-5-yl, and phenyl, each of which is optionally substituted with one, two, or three groups independently chosen from —$R_{21}$, —$OR_{22}$, and halo.

In some embodiments, $R_2$ is thiophen-2-yl or phenyl, each of which is optionally substituted with one, two, or three groups independently chosen from lower alkyl, lower alkoxy, trifluoromethyl, and halo.

In some embodiments, $R_2$ is chosen from phenyl, 2-chlorophenyl, 2-fluorophenyl, 2-methylphenyl, 2-trifluoromethylphenyl, 3-fluorophenyl, 3-methylphenyl, 3-trifluoromethylphenyl, 4-fluorophenyl, 5-methylthiophen-2-yl, 3-fluoro-5-methylthiophen-2-yl, 5-methyl-3-(trifluoromethyl)thiophen-2-yl, and 5-(trifluoromethyl)thiophen-2-yl.

In some embodiments, $R_2$ is chosen from phenyl, 2-fluorophenyl, 3-fluorophenyl, and 4-fluorophenyl.

In some embodiments, $R_2$ is phenyl.

In some embodiments, $R_3$ is chosen from —C(O)NH(OH) and —N(OH)C(O)$R_4$.

In some embodiments, $R_3$ is —C(O)NH(OH).

In some embodiments, $R_3$ is —N(OH)C(O)$R_4$ wherein $R_4$ is hydrogen.

In some embodiments, $R_3$ is —N(OH)C(O)$R_4$ wherein $R_4$ is methyl.

In some embodiments, $R_{3a}$ is —$CF_3$. In some embodiments, $R_{3a}$ is hydrogen or methyl.

Also provided is a compound of Formula II or a pharmaceutically acceptable salt thereof,

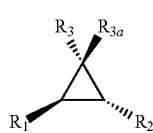

Formula II wherein $R_1$, $R_2$, $R_3$, and $R_{3a}$ are as described for compounds of Formula I.

Also provided is a compound of Formula III or a pharmaceutically acceptable salt thereof,

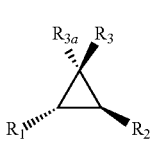

Formula III wherein $R_1$, $R_2$, $R_3$, and $R_{3a}$ are as described for compounds of Formula I.

Also provided is a compound of Formula IV or a pharmaceutically acceptable salt thereof,

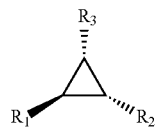

Formula IV wherein $R_1$, $R_2$, and $R_3$ are as described for compounds of Formula I.

Also provided is a compound of Formula V or a pharmaceutically acceptable salt thereof,

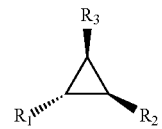

Formula V wherein $R_1$, $R_2$, and $R_3$ are as described for compounds of Formula I.F Also provided is a compound chosen from
trans-N-Hydroxy-2,3-diphenylcyclopropanecarboxamide;
(1R*,2R*,3R*)-2-Cyclohexyl-N-hydroxy-3-phenylcyclopropanecarboxamide;
(1R*,2R*,3R*)—N-Hydroxy-2-(2-isopropoxyphenyl)-3-phenylcyclopropanecarboxamide;
(1R*,2R*,3R)-2-(2-Fluorophenyl)-N-hydroxy-3-phenylcyclopropanecarboxamide;
(1S*,2R*,3R*)-2-(2-Fluorophenyl)-N-hydroxy-3-phenylcyclopropanecarboxamide;
(1R*,2R*,3R*)-2-(2-Bromophenyl)-N-hydroxy-3-phenylcyclopropanecarboxamide;
(1R*,2R*,3R*)-2-(3-Bromophenyl)-N-hydroxy-3-phenylcyclopropanecarboxamide;
(1R*,2R*,3R)-2-(4-Bromophenyl)-N-hydroxy-3-phenylcyclopropanecarboxamide;
(1R*,2R*,3R*)—N-Hydroxy-2-phenyl-3-o-tolylcyclopropanecarboxamide;
(1R*,2R*,3R*)—N-Hydroxy-2-phenyl-3-m-tolylcyclopropanecarboxamide;
(1R*,2R*,3R*)—N-Hydroxy-2-phenyl-3-p-tolylcyclopropanecarboxamide;
(1R*,2R*,3R*)-2-(4-(cyclopropanesulfonamido)phenyl)-N-hydroxy-3-phenylcyclopropanecarboxamide;
(1S*,2R*,3R*)-2-Cyclopentyl-N-hydroxy-3-phenylcyclopropanecarboxamide;
(1R,2R,3R)—N-Hydroxy-2-(1-methyl-1H-pyrazol-4-yl)-3-phenylcyclopropanecarboxamide;
(1R*,2R*,3R*)—N-Hydroxy-2-phenyl-3-(pyrimidin-5-yl)cyclopropanecarboxamide;
(1R,2R,3R)-2-(2,3-Dihydrobenzo[b][1,4]dioxin-6-yl)-N-hydroxy-3-phenylcyclopropanecarboxamide;
(1R,2R,3R)-2-(8-Chloro-2,3-dihydrobenzo[b][1,4]dioxin-6-yl)-N-hydroxy-3-phenylcyclopropanecarboxamide;
(1S,2R,3R)-2-(8-Chloro-2,3-dihydrobenzo[b][1,4]dioxin-6-yl)-3-(2-fluorophenyl)-N-hydroxycyclopropanecarboxamide;
(1R*,2R*,3R*)—N-Hydroxy-2-phenyl-3-(pyridazin-4-yl)cyclopropanecarboxamide;

(1R,2R,3R)-2-(2-Cyclopropylpyridin-4-yl)-N-hydroxy-3-phenylcyclopropanecarboxamide;
(1S,2R,3R)-2-(2-Cyclopropylpyridin-4-yl)-3-(2-fluorophenyl)-N-hydroxycyclopropanecarboxamide;
(1R,2R,3R)-2-(2-Cyclopropylpyridin-4-yl)-3-(4-fluorophenyl)-N-hydroxycyclopropanecarboxamide;
(1R,2R,3R)-2-(2,2-Difluorobenzo[d][1,3]dioxol-5-yl)-N-hydroxy-3-phenylcyclopropanecarboxamide;
(1R,2R,3R)—N-Hydroxy-2-phenyl-3-(6-(trifluoromethyl)pyridin-3-yl)cyclopropanecarboxamide;
(1R,2R,3R)—N-Hydroxy-2-phenyl-3-(2-(trifluoromethyl)pyridin-4-yl)cyclopropanecarboxamide;
(1R,2R,3R)—N-Hydroxy-2-(1-oxo-2-(2,2,2-trifluoroethyl)isoindolin-5-yl)-3-phenylcyclopropanecarboxamide;
(1R,2R,3R)—N-hydroxy-2-(2-isopropylbenzo[d]oxazol-6-yl)-3-phenylcyclopropanecarboxamide;
(1R,2R,3R)—N-Hydroxy-2-(3-(oxazol-5-yl)phenyl)-3-phenylcyclopropanecarboxamide;
(1R,2R,3R)—N-Hydroxy-2-(4-(oxazol-5-yl)phenyl)-3-phenylcyclopropanecarboxamide;
(1R*,2R*,3R*)-2-(4-(1H-imidazol-1-yl)phenyl)-N-hydroxy-3-phenylcyclopropanecarboxamide;
(1R,2R,3R)-2-(4-(2-Cyclopropyloxazol-5-yl)phenyl)-N-hydroxy-3-phenylcyclopropanecarboxamide;
(1R*,2R*,3R*)—N-Hydroxy-2-phenyl-3-(4-(2-phenyloxazol-5-yl)phenyl)cyclopropanecarboxamide;
(1R*,2R*,3R*)-2-(4-(5-Fluoropyrimidin-2-yl)phenyl)-N-hydroxy-3-phenylcyclopropanecarboxamide;
(1R*,2R*,3R*)-2-(3-(5-Fluoropyrimidin-2-yl)phenyl)-N-hydroxy-3-phenylcyclopropanecarboxamide;
(1R*,2R*,3R*)-2-(4-(5-Cyclopropylpyrimidin-2-yl)phenyl)-N-hydroxy-3-phenylcyclopropanecarboxamide;
(1R*,2R*,3R*)-2-(4-(4-Trifluoromethylpyrimidin-2-yl)phenyl)-N-hydroxy-3-phenylcyclopropanecarboxamide;
(1R,2R,3R)-2-(4-(5-Trifluoromethylpyrimidin-2-yl)phenyl)-N-hydroxy-3-phenylcyclopropanecarboxamide;
(1R*,2R*,3R*)—N-Hydroxy-2-phenyl-3-(4-(pyridazin-3-yl)phenyl)cyclopropanecarboxamide;
(1R*,2R*,3R*)—N-Hydroxy-2-phenyl-3-(4-(pyridazin-4-yl)phenyl)cyclopropanecarboxamide;
(1R*,2R*,3R*)—N-Hydroxy-2-phenyl-3-(4-(pyrimidin-2-yl)phenyl)cyclopropanecarboxamide;
(1R*,2R*,3R*)—N-Hydroxy-2-phenyl-3-(4-(pyrimidin-5-yl)phenyl)cyclopropanecarboxamide;
(1R,2R,3R)-2-(4-(5-Chloropyrimidin-2-yl)phenyl)-N-hydroxy-3-phenylcyclopropanecarboxamide;
(1R*,2R*,3R*)—N-Hydroxy-2-(4-(5-methylpyrimidin-2-yl)phenyl)-3-phenylcyclopropanecarboxamide;
(1R*,2R*,3R*)—N-Hydroxy-2-(4-(5-methyl-1H-imidazol-2-yl)phenyl)-3-phenylcyclopropanecarboxamide;
(1R*,2R*,3R*)-2-(4-(2-cyclopropylisoindolin-5-yl)phenyl)-N-hydroxy-3-phenylcyclopropanecarboxamide;
(1R,2R,3R)-2-(3'-(Benzyloxy)-[1,1'-biphenyl]-4-yl)-N-hydroxy-3-phenylcyclopropanecarboxamide;
(1R*,2R*,3R*)-2-(4'-(9H-carbazol-9-yl)-[,1'-biphenyl]-4-yl)-N-hydroxy-3-phenylcyclopropanecarboxamide;
(1R,2R,3R)—N-hydroxy-2-(4-(4-methyl-3,4-dihydro-2H-benzo[b][1,4]oxazin-7-yl)phenyl)-3-phenylcyclopropanecarboxamide;
(1R*,2R*,3R*)—N-Hydroxy-2-(4-(4-isopropylpiperazin-1-yl)phenyl)-3-phenylcyclopropanecarboxamide;
(1R*,2R*,3R*)—N-Hydroxy-2-(3-(4-isopropylpiperazin-1-yl)phenyl)-3-phenylcyclopropanecarboxamide;
(1R*,2R*,3R*)—N-Hydroxy-2-(4-(3,3-difluoropyrrolidin-1-yl)phenyl)-3-phenylcyclopropanecarboxamide;
(1R*,2R*,3R*)-2-(4-(3,3-Dimethylazetidin-1-yl)phenyl)-N-hydroxy-3-phenylcyclopropanecarboxamide;
(1R*,2R*,3R*)-2-(4-(2-Oxa-6-azaspiro[3.3]heptan-6-yl)phenyl)-N-hydroxy-3-phenylcyclopropanecarboxamide;
(1R*,2R*,3R*)-2-(3-(Hexahydropyrrolo[1,2-a]pyrazin-2(1H)-yl)phenyl)-N-hydroxy-3-phenylcyclopropanecarboxamide;
(1R*,2R*,3R*)—N-Hydroxy-2-phenyl-3-(3-(4-(pyrrolidin-1-yl)piperidin-1-yl)phenyl)cyclopropanecarboxamide;
(1R,2R,3R)-2-(3-(6,7-Dihydropyrazolo[1,5-a]pyrimidin-4(5H)-yl)phenyl)-N-hydroxy-3-phenylcyclopropanecarboxamide;
(1R*,2R*,3R*)—N-Hydroxy-2-(4-(4-methylpiperazin-1-yl)phenyl)-3-phenylcyclopropanecarboxamide;
(1R*,2R*,3R*)—N-Hydroxy-2-(4-(oxazol-2-yl)phenyl)-3-phenylcyclopropanecarboxamide;
(1R*,2R*,3R*)—N-Hydroxy-2-(4-(1-methyl-1H-imidazol-2-yl)phenyl)-3-phenylcyclopropanecarboxamide;
(1R*,2S*,3S*)-2-(4-(5-Fluoropyrimidin-2-yl)phenyl)-N-hydroxy-1-methyl-3-phenylcyclopropanecarboxamide;
(1R*,2R*,3R*)-2-(4-(1H-pyrazol-1-yl)phenyl)-N-hydroxy-3-phenylcyclopropanecarboxamide;
(1R,2R,3R)—N-Hydroxy-2-phenyl-3-(5-(trifluoromethyl)pyridin-3-yl)cyclopropanecarboxamide;
(1R,2R,3R)-2-(4-(1-Benzyl-1,2,3,6-tetrahydropyridin-4-yl)phenyl)-N-hydroxy-3-phenylcyclopropanecarboxamide;
(1S,2R,3R)-2-(2-fluorophenyl)-N-hydroxy-3-(4-(2-methyloxazol-5-yl)phenyl)cyclopropanecarboxamide;
(1S,2R,3S)-2-(2-fluorophenyl)-N-hydroxy-1-methyl-3-(4-(2-methyloxazol-5-yl)phenyl)cyclopropanecarboxamide;
(1S,2R,3R)-2-(2-fluorophenyl)-N-hydroxy-3-(4-(3-methyl-1H-pyrazol-1-yl)phenyl)cyclopropanecarboxamide;
(1S,2R,3R)-2-(2-fluorophenyl)-N-hydroxy-3-(4-(3-(trifluoromethyl)-1H-pyrazol-1-yl)phenyl)cyclopropanecarboxamide;
(1S,2R,3R)-2-(2-fluorophenyl)-N-hydroxy-3-(4-(isopropyl(2-morpholinoethyl)amino)phenyl)cyclopropanecarboxamide;
(1R,2R,3R)-2-(2-cyclopropylpyrimidin-5-yl)-N-hydroxy-3-phenylcyclopropanecarboxamide;
(1R,2R,3R)-2-(benzo[d]isoxazol-3-yl)-N-hydroxy-3-phenylcyclopropanecarboxamide;
(1R,2R,3R)-2-(6-cyclopropylpyridazin-4-yl)-N-hydroxy-3-phenylcyclopropanecarboxamide;
(1S,2R,3R)-2-(2-fluorophenyl)-N-hydroxy-3-(6-(3-methyl-1H-pyrazol-1-yl)pyridin-3-yl)cyclopropanecarboxamide;
(1S,2R,3R)-2-(6-(5-chloropyrimidin-2-yl)pyridin-3-yl)-3-(2-fluorophenyl)-N-hydroxycyclopropanecarboxamide;
(1R,2R,3R)-2-(5-chloro-6-(4-isopropylpiperazin-1-yl)pyridin-3-yl)-N-hydroxy-3-phenylcyclopropanecarboxamide;
(1S,2R,3R)-2-(2-fluorophenyl)-3-(6-(5-fluoropyrimidin-2-yl)pyridin-3-yl)-N-hydroxycyclopropanecarboxamide;
(1S,2R,3R)-2-(2-fluorophenyl)-N-hydroxy-3-(6-(5-methylpyrimidin-2-yl)pyridin-3-yl)cyclopropanecarboxamide;
(1R,2R,3R)—N-hydroxy-2-(6-(2-methyloxazol-5-yl)pyridin-3-yl)-3-phenylcyclopropanecarboxamide;
(1R,2R,3R)-2-(5-chloro-6-(2-methyloxazol-5-yl)pyridin-3-yl)-N-hydroxy-3-phenylcyclopropanecarboxamide;
(1S,2R,3R)-2-(2-fluorophenyl)-N-hydroxy-3-(2-(2,2,2-trifluoroethylamino)pyridin-4-yl)cyclopropanecarboxamide;
(1R,2R,3R)—N-hydroxy-2-phenyl-3-(1-(2,2,2-trifluoroethyl)-1H-pyrazol-4-yl)cyclopropanecarboxamide;
(1R,2R,3R)-2-(1-cyclopropyl-1H-pyrazol-4-yl)-N-hydroxy-3-phenylcyclopropanecarboxamide;
(1R,2R,3R)—N-hydroxy-2-phenyl-3-(1-(1-(2,2,2-trifluoroethyl)piperidin-4-yl)-1H-pyrazol-4-yl)cyclopropanecarboxamide;
(1R,2R,3R)-2-(1,3-dimethyl-1H-pyrazol-4-yl)-N-hydroxy-3-phenylcyclopropanecarboxamide;

(1R,2R,3S)—N-hydroxy-2-(2-methylthiazol-5-yl)-3-phenylcyclopropanecarboxamide;
(1R,2R,3R)-2-(8-chloro-1,2,3,4-tetrahydroquinolin-6-yl)-N-hydroxy-3-phenylcyclopropanecarboxamide;
(1R,2R,3R)—N-hydroxy-2-phenyl-3-(4-(2,2,2-trifluoroethyl)-2,3,4,5-tetrahydrobenzo[f][1,4]oxazepin-7-yl)cyclopropanecarboxamide;
(1R,2R,3R)—N-hydroxy-2-(1-methyl-2-(2,2,2-trifluoroethyl)-1,2,3,4-tetrahydropyrrolo[1,2-a]pyrazin-7-yl)-3-phenylcyclopropanecarboxamide;
(1R,2R,3R)-2-(1-fluoro-2-(2,2,2-trifluoroethyl)-1,2,3,4-tetrahydropyrrolo[1,2-a]pyrazin-7-yl)-N-hydroxy-3-phenylcyclopropanecarboxamide;
(1R,2R,3R)—N-hydroxy-2-phenyl-3-(2-(2,2,2-trifluoroethyl)-1,2,3,4-tetrahydropyrrolo[1,2-a]pyrazin-7-yl)cyclopropanecarboxamide;
(1R,2R,3R)—N-hydroxy-2-phenyl-3-(7-(2,2,2-trifluoroethyl)-5,6,7,8-tetrahydroimidazo[1,2-a]pyrazin-2-yl)cyclopropanecarboxamide;
(1R,2R,3R)—N-hydroxy-2-phenyl-3-(2-(trifluoromethyl)imidazo[1,2-a]pyridin-7-yl)cyclopropanecarboxamide;
(1R,2R,3R)—N-hydroxy-2-(imidazo[1,2-a]pyridin-3-yl)-3-phenylcyclopropanecarboxamide;
(1R,2R,3R)—N-hydroxy-2-phenyl-3-(pyrrolo[1,2-a]pyrimidin-4-yl)cyclopropanecarboxamide;
(1R,2R,3R)—N-hydroxy-2-(1,5-naphthyridin-4-yl)-3-phenylcyclopropanecarboxamide;
(1S,2S,3R)-2-(2-cyclopropylpyridin-4-yl)-N-hydroxy-3-(2-methylthiazol-5-yl)cyclopropanecarboxamide;
(1S,2S,3R)-2-(2-cyclopropylpyridin-4-yl)-N-hydroxy-3-(5-(trifluoromethyl)thiophen-2-yl)cyclopropanecarboxamide;
(1R,2R,3R)-2-(1-((5-fluoropyridin-2-yl)methyl)-1H-pyrazol-4-yl)-N-hydroxy-3-phenylcyclopropanecarboxamide;
(1S,2R,3S)-2-(3-fluoro-5-methylthiophen-2-yl)-N-hydroxy-3-(1-methyl-1H-pyrazol-4-yl)cyclopropanecarboxamide;
(1S,2S,3R)—N-hydroxy-2-(1-methyl-1H-pyrazol-4-yl)-3-(5-methyl-3-(trifluoromethyl)thiophen-2-yl)cyclopropanecarboxamide;
(1S,2S,3R)—N-hydroxy-2-(1-methyl-1H-pyrazol-4-yl)-3-(5-methylthiophen-2-yl)cyclopropanecarboxamide;
(1R,2R,3R)—N-hydroxy-2-(1-methyl-1H-pyrazol-4-yl)-3-o-tolylcyclopropanecarboxamide;
(1R,2R,3R)—N-hydroxy-2-(1-methyl-1H-pyrazol-4-yl)-3-(2-(trifluoromethyl)phenyl)cyclopropanecarboxamide;
(1S,2R,3R)-2-(2-chlorophenyl)-N-hydroxy-3-(1-methyl-1H-pyrazol-4-yl)cyclopropanecarboxamide;
(1R,2R,3R)-2-(3-fluorophenyl)-N-hydroxy-3-(1-methyl-1H-pyrazol-4-yl)cyclopropanecarboxamide;
(1R,2R,3R)—N-hydroxy-2-(1-methyl-1H-pyrazol-4-yl)-3-m-tolylcyclopropanecarboxamide;
(1R,2R,3R)—N-hydroxy-2-(1-methyl-1H-pyrazol-4-yl)-3-(3-(trifluoromethyl)phenyl)cyclopropanecarboxamide;
(1R,2R,3R)-2-(3-chlorophenyl)-N-hydroxy-3-(1-methyl-1H-pyrazol-4-yl)cyclopropanecarboxamide;
(1S,2S,3R)-2-(2-cyclopropylpyridin-4-yl)-3-(3-fluoro-5-methylthiophen-2-yl)-N-hydroxycyclopropanecarboxamide;
(1S,2S,3R)-2-(2-cyclopropylpyridin-4-yl)-N-hydroxy-3-(5-methyl-3-(trifluoromethyl)thiophen-2-yl)cyclopropanecarboxamide;
(1S,2S,3R)-2-(2-cyclopropylpyridin-4-yl)-N-hydroxy-3-(5-methylthiophen-2-yl)cyclopropanecarboxamide;
(1R,2R,3R)—N-hydroxy-2-phenyl-3-(4-(5-(trifluoromethyl)-1H-imidazol-2-yl)phenyl)cyclopropanecarboxamide;
(1R,2R,3R)-2-(3-chloro-4-(5-methyl-1H-imidazol-2-yl)phenyl)-N-hydroxy-3-phenylcyclopropanecarboxamide; and
(1R,2R,3R)-2-(3-fluoro-4-(5-methyl-1H-imidazol-2-yl)phenyl)-N-hydroxy-3-phenylcyclopropanecarboxamide,
or a pharmaceutically acceptable salt thereof.

Methods for obtaining the compounds, or pharmaceutically acceptable salts thereof, described herein will be apparent to those of ordinary skill in the art, suitable procedures being described, for example, in examples below, and in the references cited herein.

Also provided is a method for inhibiting at least one histone deacetylase. In some embodiments, the at least one histone deacetylase is a class IIa HDAC. In some embodiments, the at least one histone deacetylase is selected from HDAC-4, HDAC-5, HDAC-7, and HDAC-9. In some embodiments, the inhibition is in a cell. In some embodiments, the compound, or pharmaceutically acceptable salt thereof, described herein is selective for inhibiting at least one class II histone deacetylase. In some embodiments, the compound, or pharmaceutically acceptable salt thereof, described herein is a selective inhibitor of HDAC-4 and/or HDAC-5.

Also provided is a method of treating a condition or disorder mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a neurodegenerative pathology. Accordingly, also provided is a method of treating a neurodegenerative pathology mediated by HDAC in a subject in need of such a treatment, comprising administering to the subject a therapeutically effective amount of at least one compound, or pharmaceutically acceptable salt thereof, described herein.

In some embodiments, the neurodegenerative pathology is chosen from Alzheimer's disease, Parkinson's disease, neuronal intranuclear inclusion disease (NIID), Dentatorubral pallidolusyian atrophy (DRPLA), Friedreich's ataxia, Rubenstein-Taubi Sydrome, and polyglutamine diseases such as Huntington's disease; spinocerebellar ataxia 1 (SCA 1), spinocerebellar ataxia 7 (SCA 7), seizures, striatonigral degeneration, progressive supranuclear palsy, torsion dystonia, spasmodic torticollis, dyskinesis, familial tremor, Gilles de la Tourette syndrome, diffuse Lewy body disease, progressive supranuclear palsy, Pick's disease, primary lateral sclerosis, progressive neural muscular atrophy, spinal muscular atrophy, hypertrophic interstitial polyneuropathy, retinitis pigmentosa, hereditary optic atrophy, hereditary spastic paraplegia, Shy-Drager syndrome, Kennedy's disease, protein-aggregation-related neurodegeneration, Machado-Joseph's disease, spongiform encephalopathy, prion-related disease, multiple sclerosis (MS), progressive supranuclear palsy (Steel-Richardson-Olszewski disease), Ilallervorden-Spdtz disease, progressive familial myoclonic epilepsy, cerebellar degeneration, Shy-Drager syndrome, motor neuron disease, Werdnig-Hoffman disease, Wohlfart-Kugelberg-Welander disease, Charcot-Mane-Tooth disease, Dejenne-Sottas disease, retimtis pigmentosa, Lebei's disease, progressive systemic sclerosis, dermatomyositis, and mixed connective tissue disease.

In some embodiments, the neurodegenerative pathology is an acute or chronic degenerative disease of the eye. Acute or chronic degenerative diseases of the eye include glaucoma, dry age-related macular degeneration, retinitis pigmentosa and other forms of heredodegenerative retinal disease, retinal detachment, macular pucker, ischemia affecting the outer retina, cellular damage associated with diabetic retinopathy and retinal ischemia, damage associated with laser therapy, ocular neovascular, diabetic retinopathy, rubeosis iritis, uveitis, Fuch's heterochromatic iridocyclitis, neovascular glaucoma, corneal neovascularization, retinal ischemia, choroidal vascular insufficiency, choroidal thrombosis, carotid artery ischemia, contusive ocular injury, retinopathy of permaturity, retinal vein occlusion, proliferative vitreoretinopathy, corneal angiogenesis, retinal microvasculopathy, and retinal eduema.

In some embodiments, the condition or disorder mediated by HDAC comprises a fibrotic disease such as liver fibrosis, cystic fibrosis, cirrhosis, and fibrotic skin diseases, e.g., hypertrophic scars, keloid, and Dupuytren's contracture. Accordingly, also provided is a method of treating a fibrotic disease mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a psychological disorder, such as depression, bipolar disease and dementia. In some embodiments, the condition or disorder mediated by HDAC comprises depression. Accordingly, also provided is a method of treating a psychological disorder, such as depression, mediated by HDAC in a subject in need of such a treatment, comprising administering to the subject a therapeutically effective amount of at least one compound, or pharmaceutically acceptable salt thereof, described herein. In some embodiments, the depression is chosen from major depressive disorder, and bipolar disorder.

In some embodiments, the condition or disorder mediated by HDAC comprises anxiety. Accordingly, also provided is a method of treating an anxiety mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises schizophrenia. Accordingly, also provided is a method of treating a schizophrenia mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a motor neuron disease, muscle atrophy/muscle wasting disorders, or amyotrophic lateral sclerosis (ALS). Accordingly, also provided is a method of treating a motor neuron disease, muscle atrophy/muscle wasting disorders, or amyotrophic lateral sclerosis (ALS) mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a cardiovascular condition. Accordingly, also provided is a method of treating a cardiovascular condition mediated by HDAC in a subject in need of such a treatment, comprising administering to the subject a therapeutically effective amount of at least one compound, or pharmaceutically acceptable salt thereof, described herein. In some embodiments, the cardiovascular condition is chosen from cardiomyopathy, cardiac hypertrophy, myocardial ischemia, heart failure, cardiac restenosis, and arteriosclerosis.

In some embodiments, the condition or disorder mediated by HDAC comprises cancer. Accordingly, also provided is a method of treating cancer mediated by HDAC in a subject in need of such a treatment, comprising administering to the subject a therapeutically effective amount of at least one compound, or pharmaceutically acceptable salt thereof, described herein. In some embodiments, the cancer is chosen from lymphoma, pancreatic cancer, colorectal cancer, hepatocellular carcinoma, Waldenstrom macroglobulinemia, hormone refractory cancer of the prostate, and leukaemia, breast cancer, lung cancer, ovarian cancer, prostate cancer, head and neck cancer, renal cancer, gastric cancer, brain cancer, B-cell lymphoma, peripheral T-cell lymphoma, and cutaneous T-cell lymphoma. In some further embodiments, the cancer is chosen from the following cancer types. Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma, cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma; and the sensitization of tumors to radiotherapy by administering the compound according to the invention before, during or after irradiation of the tumor for treating cancer.

In some embodiments, the condition or disorder mediated by HDAC comprises a condition or disorder treatable by immune modulation. Accordingly, also provided is a method of treating a condition or disorder treatable by immune modulation mediated by HDAC in a subject in need of such a treatment, comprising administering to the subject a therapeutically effective amount of at least one compound, or pharmaceutically acceptable salt thereof, described herein. In some embodiments, the condition or disorder treatable by immune modulation is chosen from asthma, irritable bowel syndrome, Crohn's disease, ulcerative colitis, bowel motility disorders, hypertension, rheumatoid arthritis, osteoarthritis, juvenile chronic arthritis, graft versus host disease, psoriasis, spondyloarthropathy, inflammatory bowel disease, alcoholic hepatitis, Sjogren's syndrome, ankylosing spondylitis, membranous glomerulopathy, discogenic pain, systemic lupus erythematosus, allergic bowel disease, coeliac disease, bronchitis, cystic fibrosis, rheumatoid spondylitis, osteoarthritis, uveitis, intis, and conjunctivitis, ischemic bowel disease, psoriasis, eczema, dermatitis, septic arthritis, gout, pseudogout, juvenile arthritis, Still's disease, Henoch-Schonlein purpura, psoriatic arthritis, myalgia, reactive arthritis (Reiter's syndrome), hemochromatosis, Wegener's granulomatosis, familial Mediterranean fever (FMF), HBDS (hyperimmunoglobulinemia D and periodic fever syndrome), TRAPS (TNF-alpha receptor associated periodic fever syndrome), chronic obstructive pulmonary disease, neonatal-onset multisystem inflammatory disease (NOMID), cryopyrin-associated periodic syndrome (CAPS), and familial cold autoinflammatory syndrome (FCAS).

In some embodiments, the condition or disorder mediated by HDAC comprises an allergic disease. Accordingly, also provided is a method of treating an allergic disease, mediated by HDAC in a subject in need of such a treatment, comprising administering to the subject a therapeutically effective amount of at least one compound, or pharmaceutically acceptable salt thereof, described herein. Allergic diseases include, but are not limited to, respiratory allergic diseases such as allergic rhinitis, hypersensitivity lung diseases, hypersensitivity pneumonitis, eosinophilic pneumonias, Loeffler's syndrome, chronic eosinophilic pneumonia, delayed-type hypersensitivity, interstitial lung diseases (ILD), idiopathic pulmonary fibrosis, polymyositis, dermatomyositis, systemic anaphylaxis, drug allergies (e.g., to penicillin or cephalosporins), and insect sting allergies.

In some embodiments, the condition or disorder mediated by HDAC comprises an infectious disease such as a fungal infection, bacterial infection, viral infection, and protozoal infection, e.g., malaria, giardiasis, leishmaniasis, Chaga's disease, dysentery, toxoplasmosis, and coccidiosis. In some embodiments, the condition or disorder mediated by HDAC comprises malaria. Accordingly, also provided is a method of treating an infectious disease, such as malaria, mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises autism or Rett syndrome. Accordingly, also provided is a method of treating autism or Rett syndrome mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a hematological disorder such as thalassemia, anemia, and sickle cell anemia. Accordingly, also provided is a method of treating a hematological disorder mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a metabolic disease such as prediabetes or diabetes (type I or II). Accordingly, also provided is a method of treating a metabolic disease, such as prediabetes or diabetes (type I or II), mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a disorder that may also be treated by progenitor/stem cell based therapies such as: disorders related to diabetes (organ failure, cerrosis, and hepatitis); central nervous system (CNS) disorders associated with dysregulation of progenitor cells in the brain (e.g., post-traumatic stress disorder (PTSD); tumors (e.g., retinoblastomas); disorders affecting oligodendrycoyte progenitor cells (e.g., astrocytomas and ependimal cell tumors); multiple sclerosis; demyelinating disorders such as the leukodystrophies; neuropathies associated with white matter loss; and cerebellar disorders such as ataxia; and olfactory progenitor disorders (e.g., anosmic conditions). Accordingly, also provided is a method of treating a disorder that is mediated by HDAC in a subject in need of such a treatment, comprising administering to the subject a therapeutically effective amount of at least one compound, or pharmaceutically acceptable salt thereof, described herein, either before, during, or after a treatment with progenitor/stem cell based therapies.

In some embodiments, the condition or disorder mediated by HDAC comprises a disorder related to the proliferation of epithelial and mesenchymal cells (e.g., tumors, wound healing, and surgeries). Accordingly, also provided is a method of treating a disorder related to the proliferation of epithelial and mesenchymal cells that is mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a disorder related to the proliferation of bone progenitors (e.g., osteoblasts and osteoclasts), disorders related to hair and epidermal progenitors (e.g., hair loss, cutaneous tumors, skin regeneration, burns, and cosmetic surgery); and disorders related to bone loss during menopause. Accordingly, also provided is a method of treating disorders related to the proliferation of bone progenitors, disorders related to hair and epidermal progenitors, or disorders related to bone loss that are mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC is a viral disorder for which blood cells become sensitized to other treatments after HDAC inhibition, following administering to the subject a therapeutically effective amount of at least one compound, or pharmaceutically acceptable salt thereof, as described herein.

In some embodiments, the condition or disorder mediated by HDAC is an immune disorder that may be co-treated with TNFa or other immune modulators, upon administering to the subject a therapeutically effective amount of at least one compound, or pharmaceutically acceptable salt thereof, as described herein.

In some embodiments, the condition or disorder mediated by HDAC comprises a graft rejection or transplant rejection. Accordingly, also provided is a method of treating a disorder related to a graft rejection or a transplant rejection that is mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a blood pressure disorder related to nitric oxide (NO) regulation (e.g., hypertension, erectile dysfunction, asthma; and ocular disorders as glaucoma). Accordingly, also provided is a method of treating a blood pressure disorder related to nitric oxide (NO) regulation that is mediated by HDAC in a subject in need of such a treatment, comprising administering to the subject a therapeutically effective amount of at least one compound, or pharmaceutically acceptable salt thereof, described herein. In some embodiments, the condition or disorder is a cardiac hypertrophic disorder. Accordingly, also provided is a method of treating a cardiac hypertrophic disorder that is mediated by HDAC in a subject in need of such a treatment, comprising administering to the subject a therapeutically effective amount of at least one compound, or pharmaceutically acceptable salt thereof, described herein.

Also provided are methods of treatment in which at least one compound, or pharmaceutically acceptable salt thereof, described herein is the only active agent given to the subject and also includes methods of treatment in which at least one compound, or pharmaceutically acceptable salt thereof, described herein is given to the subject in combination with one or more additional active agents.

In general, the compounds, or pharmaceutically acceptable salts thereof, described herein will be administered in a therapeutically effective amount by any of the accepted modes of administration for agents that serve similar utilities. The actual amount of the compound, i.e., the active ingredient, will depend upon numerous factors such as the severity of the disease to be treated, the age and relative health of the subject, the potency of the compound used, the route and form of administration, and other factors well know to the skilled artisan. The drug can be administered at least once a day, such as once or twice a day.

In some embodiments, the compounds, or pharmaceutically acceptable salts thereof, described herein are administered as a pharmaceutical composition. Accordingly, provided are pharmaceutical compositions comprising at least one compound, or pharmaceutically acceptable salt thereof, described herein, together with at least one pharmaceutically acceptable vehicle chosen from carriers, adjuvants, and excipients.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the compound, or pharmaceutically acceptable salt thereof, is sufficient to provide a practical quantity of material for administration per unit dose of the compound, or pharmaceutically acceptable salt thereof.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound, or pharmaceutically acceptable salt thereof, described herein.

Effective concentrations of at least one compound, or pharmaceutically acceptable salt thereof, described herein are mixed with a suitable pharmaceutically acceptable vehicle. In instances in which the compound, or pharmaceutically acceptable salt thereof, exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate.

Upon mixing or addition of a compound, or pharmaceutically acceptable salt thereof, described herein, the resulting mixture may be a solution, suspension, emulsion or the like. The form of the resulting mixture depends upon a number of factors, including the intended mode of administration and the solubility of the compound, or pharmaceutically acceptable salt thereof, in the chosen vehicle. The effective concentration sufficient for ameliorating the symptoms of the disease treated may be empirically determined.

The compounds, or pharmaceutically acceptable salts thereof, described herein may be administered orally, topically, parenterally, intravenously, by intramuscular injection, by inhalation or spray, sublingually, transdermally, via buccal administration, rectally, as an ophthalmic solution, or by other means, in dosage unit formulations.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of at least one compound, or pharmaceutically acceptable salt thereof, described herein. In some embodiments, oral pharmaceutical compositions contain at least 5% (weight %) of at least one compound, or pharmaceutically acceptable salt thereof, described herein. Some embodiments contain from 25% to 50% or from 5% to 75% of at least one compound, or pharmaceutically acceptable salt thereof, described herein.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

The compound, or pharmaceutically acceptable salt thereof, described herein can be incorporated into oral liquid preparations such as aqueous or oily suspensions, solutions, emulsions, syrups, or elixirs, for example. Moreover, pharmaceutical compositions containing these at least one compound, or pharmaceutically acceptable salt thereof, can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such pharmaceutical compositions may also be coated by conventional methods, typically with pH or time-dependent coatings, such that the compound, or pharmaceutically acceptable salt thereof, is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

The compound, or pharmaceutically acceptable salt thereof, described herein may be administered parenterally in a sterile medium. Parenteral administration includes subcutaneous injections, intravenous, intramuscular, intrathecal injection or infusion techniques. The compound, or pharmaceutically acceptable salt thereof, described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

The compound, or pharmaceutically acceptable salt thereof, described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

The compound, or pharmaceutically acceptable salt thereof, described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. The compound, or pharmaceutically acceptable salt thereof, described herein may also be formulated for transdermal administration as a transdermal patch.

Topical pharmaceutical compositions comprising at least one compound, or pharmaceutically acceptable salt thereof, described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows.

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The compound, or pharmaceutically acceptable salt thereof, described herein may also be topically administered in the form of liposome delivery systems, such as small unilamellar vesicles, large unilamellar vesicles, and multi-lamellar vesicles. Liposomes can be formed from a variety of phospholipids, such as cholesterol, stearylamine or phosphatidylcholines.

Other pharmaceutical compositions useful for attaining systemic delivery of the compound, or pharmaceutically acceptable salt thereof, include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the compound, or pharmaceutically acceptable salt thereof, described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of at least one compound, or pharmaceutically acceptable salt thereof, described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

Also provided are packaged pharmaceutical compositions. Such packaged compositions include a pharmaceutical composition comprising at least one compound, or pharmaceutically acceptable salt thereof, described herein, and instructions for using the composition to treat a subject (typically a human patient). In some embodiments, the instructions are for using the pharmaceutical composition to treat a subject suffering a condition or disorder mediated by HDAC. The packaged pharmaceutical composition can include providing prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the compound, or pharmaceutically acceptable salt thereof, can be administered alone, as mixtures, or in combination with other active agents.

The methods described herein include methods for treating Huntington's disease, including treating memory and/or cognitive impairment associated with Huntington's disease, comprising administering to a subject, simultaneously or sequentially, at least one compound, or pharmaceutically acceptable salt thereof, described herein and one or more additional agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. In methods using simultaneous administration, the agents can be present in a combined composition or can be administered separately. As a result, also provided are pharmaceutical compositions comprising at least one compound, or pharmaceutically acceptable salt thereof, described herein and one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. Similarly, also provided are packaged pharmaceutical compositions containing a pharmaceutical composition comprising at least one compound, or pharmaceutically acceptable salt thereof, described herein, and another composition comprising one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone.

Also provided are methods for Alzheimer's disease, including treating memory and/or cognitive impairment associated with Alzheimer's disease, comprising administering to a subject, simultaneously or sequentially, at least one compound, or pharmaceutically acceptable salt thereof, described herein and one or more additional agents used in the treatment of Alzheimer's disease such as, but not limited to, Reminyl, Cognex, Aricept, Exelon, Akatinol, Neotropin, Eldepryl, Estrogen and Clioquinol. In methods using simultaneous administration, the agents can be present in a combined composition or can be administered separately. Also provided are pharmaceutical compositions comprising at least one compound, or pharmaceutically acceptable salt thereof, described herein, and one or more additional pharmaceutical agents used in the treatment of Alzheimer's disease such as, but not limited to, Reminyl, Cognex, Aricept, Exelon, Akatinol, Neotropin, Eldepryl, Estrogen and Clioquinol. Similarly, also provided are packaged pharmaceutical compositions containing a pharmaceutical composition comprising at least one compound, or pharmaceutically acceptable salt thereof, described herein, and another composition comprising one or more additional pharmaceutical agents used in the treatment of Alzheimer's disease such as, but not limited to Reminyl, Cognex, Aricept, Exelon, Akatinol, Neotropin, Eldepryl, Estrogen and Clioquinol.

Also provided are methods for treating cancer comprising administering to a subject, simultaneously or sequentially, at least one compound, or pharmaceutically acceptable salt thereof, described herein and one or more additional agents used in the treatment of cancer such as, but not limited to, the following categories of anti-tumor agents (i) other cell cycle inhibitory agents that work by the same or different mechanisms from those defined hereinbefore, for example cyclin dependent kinase (CDK) inhibitors, in particular CDK2 inhibitors;

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5.alpha.-dihydroreductase (for example finasteride), anti-invasion agents (for example metalloproteinase inhibitors like marimastat and inhibitors of urokinase plasminogen activator receptor function) and inhibitors of growth factor function, (such growth factors include for example vascular endothelial growth factor, epithelial growth factor, platelet derived growth factor and hepatocyte growth factor such inhibitors include growth factor antibodies, growth factor receptor antibodies, tyrosine kinase inhibitors and serine/threonine kinase inhibitors);

(iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan);

(iv) antiangiogenic agents that work by different mechanisms from those defined hereinbefore (for example receptor tyrosine kinases like Tie-2, inhibitors of integrin .alpha.v-.beta.3 function, angiostatin, razoxin, thalidomide), and including vascular targeting agents; and (v) differentiation agents (for example retinoic acid and vitamin D).

In methods using simultaneous administration, the agents can be present in a combined composition or can be administered separately. Also provided are pharmaceutical compositions comprising at least one compound, or pharmaceutically acceptable salt thereof, described herein, and one or more anti-tumor agent as described herein. Similarly, also provided are packaged pharmaceutical compositions containing a pharmaceutical composition comprising at least one compound, or pharmaceutically acceptable salt thereof, described herein, and another composition comprising one or more one or more anti-tumor agent as described herein. When used in combination with one or more additional pharmaceutical agent or agents, the described herein may be administered prior to, concurrently with, or following administration of the additional pharmaceutical agent or agents.

In some embodiments, the compounds, or pharmaceutically acceptable salts thereof, described herein, are administered in conjunction with surgery or radiotherapy, optionally in combination with one or more additional agents used in the treatment of cancer.

The dosages of the compounds described herein depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compound, or pharmaceutically acceptable salt thereof, described herein is typically administered at dosage levels and in a manner customary for HDAC inhibitors. For example, the compound, or pharmaceutically acceptable salt thereof, can be administered, in single or multiple doses, by oral administration at a dosage level of generally 0.001-100 mg/kg/day, for example, 0.01-100 mg/kg/day, such as 0.1-70 mg/kg/day, for example, 0.5-10 mg/kg/day. Unit dosage forms can contain generally 0.01-1000 mg of at least one compound, or pharmaceutically acceptable salt thereof, described herein, for example, 0.1-50 mg of at least one compound, or pharmaceutically acceptable salt thereof, described herein. For intravenous administration, the compounds can be administered, in single or multiple dosages, at a dosage level of, for example, 0.001-50 mg/kg/day, such as 0.001-10 mg/kg/day, for example, 0.01-1 mg/kg/day. Unit dosage forms can contain, for example, 0.1-10 mg of at least one compound, or pharmaceutically acceptable salt thereof, described herein.

A labeled form of a compound, or pharmaceutically acceptable salt thereof, described herein can be used as a diagnostic for identifying and/or obtaining compounds that have the function of modulating an activity of HDAC as described herein. The compound, or pharmaceutically acceptable salt thereof, described herein may additionally be used for validating, optimizing, and standardizing bioassays.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

EXAMPLES

The compounds, or pharmaceutically acceptable salts thereof, compositions, and methods described herein are further illustrated by the following non-limiting examples.

As used herein, the following abbreviations have the following meanings. If an abbreviation is not defined, it has its generally accepted meaning.

Abbreviations

[bmim][PF$_6$]: 1-Butyl-3-methylimidazolium hexafluorophosphate
BOP: Benzotriazole-1-yl-oxy-tris-(dimethylamino)-phosphonium hexafluorophosphate
DCM: Dichloromethane
DCE: Dichloroethane
DIPEA: Diisopropylethylamine
DMA: Dimethylacetamide
DME: Dimethoxyethane
DMF: Dimethylformamide
DMSO: Dimethylsulfoxide
ES+: Electrospray Positive Ionisation
ES−: Electrospray Negative Ionisation
Et$_2$O: Diethyl ether
EtOAc: Ethyl acetate
h: Hour
HPLC: High Performance Liquid Chromatography
i-hex: iso-Hexane
LCMS: Liquid Chromatography Mass Spectrometry
LiHMDS: Lithium bis(trimethylsilyl)amide
M: Mass
MeCN: Acetonitrile
MeOH: Methanol
NMP: N-Methyl pyrrolidinone
Pd/C: Palladium on carbon
Pd$_2$(dba)$_3$: Tris(dibenzylideneacetone)dipalladium(0)
Pd(dppf)C$_2$: [1,1'-Bis(diphenylphosphino)ferrocene]dichloropalladium(II)
Pd(PPh$_3$)$_4$: Tetrakis(triphenylphosphine)palladium(0)
o-tol: ortho-Tolyl
Rh$_2$(OAc)$_4$: Rhodium(II) acetate
RT: Retention time
r.t.: Room temperature
RuPhos: 2-Dicyclohexylphosphino-2',6'-di-iso-propoxy-1,1'-biphenyl
THF: Tetrahydrofuran
Xantphos: 4,5-Bis(diphenylphosphino)-9,9-dimethylxanthene Analytical Conditions Compounds were named with the aid of the Cambridgesoft Chemistry Cartridge (v. 9.0.0.182) software.

All reactions involving air- or moisture-sensitive reagents were performed under a nitrogen atmosphere using dried solvents and glassware.

Racemic mixtures of the cyclopropyl core are denoted using asterisks e.g. (1R*,2R*,3R*). Chirally pure compounds are denoted without asterisks e.g. (1R,2R,3R).

| Analytical Condition | Method | Description |
|---|---|---|
| 10 cm_ESI_Formic_MeCN, 10 cm_ESCl_Formic_MeCN | 1 | Solvents: Acetonitrile (far UV grade) with 0.1% (v/v) formic acid. Water (high purity via PureLab Option unit) with 0.1% formic acid |

| Analytical Condition | Method | Description | |
|---|---|---|---|
| | | Column: | Phenomenex Luna 5 μm C18 (2), 100 × 4.6 mm (Plus guard cartridge) |
| | | Flow Rate: | 2 mL/min |
| | | gradient: | A: Water/formic acid |
| | | | B: MeCN/formic acid |
| | | Time | A %    B % |
| | | 0.00 | 95    5 |
| | | 3.50 | 5    95 |
| | | 5.50 | 5    95 |
| | | 5.60 | 95    5 |
| | | 6.50 | 95    5 |
| | | Typical Injections 2-7 μL (concentration ~0.2-1.0 mg/mL) | |
| 15 cm_Bicarb_GeminiNX_HPLC_MeCN | 2 | Solvents: | 100% Acetonitrile (Far UV grade) Water (High purity via PureLab Ultra unit) with 10 mM Ammonium Bicarbonate |
| | | Column: | Phenomenex, Gemini NX, 3 μm C18, 150 × 4.6 mm. |
| | | Flow Rate: | 1 mL/min |
| | | gradient: | A: 10 mM Ammonium Bicarbonate in water |
| | | | B: 100% MeCN |
| | | Time | A %    B % |
| | | 0.00 | 95.5    4.5 |
| | | 3.00 | 95.5    4.4 |
| | | 9.00 | 0    100 |
| | | 13.6 | 0    100 |
| | | 13.7 | 95.5    4.5 |
| | | 15 | 95.5    4.5 |
| | | Typical Injections | 2-7 μL (concentration ~0.2-1 mg/mL) |
| 15 cm_Formic_Ascentis_HPLC_MeCN | 3 | Solvents: | Acetonitrile (Far UV grade) with 0.1% (V/V) formic acid Water (High purity via PureLab Ultra unit) with 0.1% formic acid |
| | | Column: | Supelco, Ascentis ® Express C18 or Hichrom Halo C18, 2.7 μm C18, 150 × 4.6 mm. |
| | | Flow Rate: | 1 mL/min |
| | | gradient: | A: Water/formic |
| | | | B: MeCN/formic |
| | | Time | A %    B % |
| | | 0.00 | 96    4 |
| | | 3.00 | 96    4 |
| | | 9.00 | 0    100 |
| | | 13.6 | 0    100 |
| | | 13.7 | 96    4 |
| | | 15 | 96    4 |
| | | Typical Injections 2-7 μL (concentration ~0.2-1 mg/mL) | |
| 10 cm_ESCl_bicarb_MeCN | 4 | Solvents: | Acetonitrile (Far UV grade) Water (High purity via PureLab Option unit) with 10 mM ammonium bicarbonate (ammonium hydrogen carbonate) |
| | | Column: | Waters Xterra MS 5 m C18, 100 × 4.6 mm. (Plus guard cartridge) |
| | | Flow Rate: | 2 mL/min |
| | | gradient: | A: Water/Bicarb |
| | | | B: MeCN |
| | | Time | A %    B % |
| | | 0.00 | 95    5 |
| | | 0.50 | 95    5 |
| | | 4.00 | 5    95 |
| | | 5.50 | 5    95 |
| | | 5.60 | 95    5 |
| | | 6.50 | 95    5 |
| | | Typical Injections 2-7 μL (concentration ~0.2-1 mg/mL) | |
| 10 cm_Formic_ACE-AR_HPLC_CH3CN | 5 | Solvents: | Acetonitrile (Far UV grade) with 0.1% (VN) formic acid Water (High purity via PureLab Ultra |

| Analytical Condition | Method | Description | | |
|---|---|---|---|---|
| | | | unit) with 0.1% formic acid | |
| | | Column: | Hichrom ACE 3 C18-AR mixed mode column 100 × 4.6 mm | |
| | | Flow Rate: | 1 mL/min | |
| | | gradient: | A: Water/formic B: MeCN/formic | |
| | | Time | A % | B % |
| | | 0.00 | 98 | 2 |
| | | 3.00 | 98 | 2 |
| | | 12.00 | 0 | 100 |
| | | 15.4 | 0 | 100 |
| | | 15.5 | 98 | 2 |
| | | 17 | 98 | 2 |
| | | Typical Injections 0.2-10 μL | | |

| Analytical Condition | Method | Description | | |
|---|---|---|---|---|
| 10 cm_Formic_ACE-AR_HPLC_CH3OH_Slow | 6 | Solvents: | Methanol (AR grade) with 0.1% (V/V) formic acid Water (High purity via PureLab Ultra unit) with 0.1% formic acid | |
| | | Column: | Hichrom ACE 3 C18-AR mixed mode column 100 × 4.6 mm | |
| | | Flow Rate: | 1 mL/min | |
| | | gradient: | A: Water/formic B: MeOH/formic | |
| | | Time | A % | B % |
| | | 0.00 | 98 | 2 |
| | | 3.00 | 98 | 2 |
| | | 12.00 | 0 | 100 |
| | | 15.4 | 0 | 100 |
| | | 15.5 | 98 | 2 |
| | | 17 | 98 | 2 |
| | | Typical Injections 0.2-10 μL | | |

Synthetic Section

Method A (Hydroxamic Acid Formation)

To a stirred solution of ester (0.30 mmol) in THF/MeOH (1:1, 3 mL) was added hydroxylamine (0.2 mL, 50% aqueous solution, 3.00 mmol) and potassium hydroxide (33 mg, 0.60 mmol). The mixture was stirred at r.t. for 2 h, neutralized with 1 M HCl$_{(aq)}$ and extracted with DCM. The combined organic layers were washed with brine (10 mL), passed through a phase separator and concentrated.

Method B (Hydroxamic Acid Formation)

To a stirred solution of acid (0.26 mmol), BOP (0.29 mmol) and triethylamine (0.78 mmol) in pyridine (1 mL) was added hydroxylamine hydrochloride (0.29 mmol). The reaction mixture was stirred at r.t. for 2 h, diluted with water (10 mL) and extracted into EtOAc (3×20 mL). The combined organic layers were washed with water (2×20 mL), dried (MgSO$_4$) and concentrated.

Method C (Wittig Reaction)

To a stirred solution of triethyl phosphonoacetate (24.4 mmol) in THF (30 mL) at 0° C. was added sodium hydride (24.4 mmol) portionwise. The mixture was stirred for 1 h before addition of aldehyde (12.2 mmol). The reaction mixture was allowed to warm to r.t. and stirred for 17 h, before quenching with water (50 mL) and extracting into EtOAc (2×50 mL). The organic layers were combined and washed with water (2×50 mL), dried (MgSO$_4$), filtered and concentrated.

Method D (Heck Reaction-1)

To a stirred solution of aryl bromide (4.42 mmol) in anhydrous DMF (16 mL) was added ethyl acrylate (5.75 mmol), Pd(OAc)$_2$ (0.44 mmol), DABCO (8.84 mmol) and potassium carbonate (8.84 mmol). The solution was degassed under nitrogen for 15 min before heating to 125° C. for 17 h. The mixture was cooled, diluted with H$_2$O (30 mL) and extracted into DCM (2×30 mL). The organic layers were washed with H$_2$O (3×50 mL) and brine (2×50 mL), passed through a phase separator and concentrated.

Method E (Heck Reaction-2)

A stirred mixture of aryl bromide (10.0 mmol), ethyl acrylate (15.0 mmol), palladium acetate (1.00 mmol), P(o-tol)$_3$ (2.00 mmol) and triethylamine (20.0 mmol) in MeCN (50 mL) was degassed with nitrogen for 15 min and heated to 80° C. for 3-18 h. The reaction mixture was cooled and the MeCN removed in vacuo. The residue was partitioned between DCM and H$_2$O and the organic layers were passed through a phase separator and concentrated.

Method F (Cyclopropanation Reaction)

A mixture of sulfonium salt (8.92 mmol), acrylate (5.96 mmol) and 12-crown-4 (8.92 mmol) in DCM (20 mL) was cooled to −20° C. LiHMDS (8.92 mL) was then added dropwise. After complete addition, the mixture was warmed to r.t, stirred for 2 h and quenched with H$_2$O (30 mL). The layers were separated and the organic phase was washed with brine (2×30 mL), separated, dried (MgSO$_4$), filtered and concentrated.

Method G (Suzuki Coupling from Boronate on Scaffold)

To a stirred solution of cyclopropyl bromo scaffold (3.02 mmol) in dioxane (5 mL) was added bis-pinacolato diboron (3.32 mmol), Pd(dppf)Cl$_2$ (0.30 mmol) and potassium acetate (15.1 mmol). The mixture was degassed with nitrogen and heated to 100° C. for 2 h. The reaction mixture was diluted with H$_2$O (20 mL) and extracted into DCM (2×20 mL). The organic layers were passed through a phase separator and concentrated. The crude residue was dissolved in dioxane and an aliquot (0.66 mmol) was added to a reaction tube. To this was added heterocyclic halide (0.69 mmol), Pd(PPh$_3$)$_4$ (0.066 mmol), and aqueous Na$_2$CO$_3$ (5 mL, 1 M solution). The reaction was heated at 100° C. for 2 h. The mixture was diluted with H$_2$O (10 mL) and extracted into DCM (20 mL). The organic layers were passed through a phase separator and concentrated.

Method H (Suzuki Coupling)

A mixture of cyclopropyl bromo scaffold (2.00 mmol), boronic ester (or acid) (2.40 mmol), 1 N Na$_2$CO$_3$ (6.00 mmol) and Pd(PPh$_3$)$_4$ (0.10 mmol) in dioxane (6 mL) was stirred at 100° C. for 3 h. The reaction mixture was diluted with water and extracted into DCM. The organic layer was dried and concentrated and the crude mixture was purified by flash silica column chromatography.

Method I (Buchwald Reaction)

To a stirred solution of aryl bromide (0.76 mmol) and amine (0.86 mmol) in dioxane (4 mL), was added XantPhos (0.048 mmol), cesium carbonate (1.66 mmol) and Pd$_2$(dba)$_3$ (0.024 mmol). The mixture was stirred for 16 h at 90° C., diluted with water and extracted into DCM (20 mL). The organic layers were passed through a phase separator and concentrated and the crude mixture was purified by flash silica column chromatography.

Example 1

Reaction Scheme 1

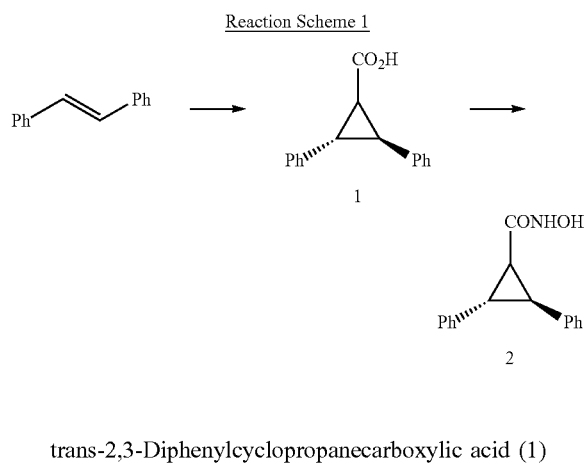

trans-2,3-Diphenylcyclopropanecarboxylic acid (1)

To a stirred solution of trans-stilbene (1.0 g, 5.6 mmol) and copper sulphate (44 mg, 0.28 mmol) in toluene (50 mL) at 75° C. was added ethyl diazoacetate (1.16 mL, 11.1 mmol) dropwise. Evolution of nitrogen was observed. The mixture was stirred for 15 min, allowed to cool to r.t. and concentrated in vacuo. The residue was taken-up in EtOH (25 mL) and filtered. The filtrate was concentrated and purified by flash silica column chromatography (gradient elution petroleum ether to 2.5% EtOAc in petroleum ether). The ethyl ester intermediate was then dissolved in MeOH (5 mL) and aqueous 2 M LiOH (10 mL) and stirred at 50° C. for 16 h. The mixture was washed with Et$_2$O (30 mL) and the basic aqueous solution acidified using aqueous 1 M HCl. The resulting precipitate was collected by filtration to give the title compound (62 mg, 5%) as a white solid.

trans-N-Hydroxy-2,3-diphenylcyclopropanecarboxamide (2)

Following method B, from compound I (62 mg, 0.26 mmol). The crude material was purified by preparative HPLC and PEAX cartridge (DCM:MeOH, 1:1). The solvent was removed in vacuo to afford the title compound (25 mg, 38%) as a white solid. LCMS (ES+) 254 (M+H)+, (ES−) 252 (M−H)−, RT 2.97 min (Analytical method 1). $^1$H NMR δ (ppm) (DMSO-d$_6$): 10.55 (1H, s), 8.69 (1H, s), 7.36-7.16 (10H, m), 3.09 (1H, dd, J=6.8, 5.4 Hz), 2.83 (1H, dd, J=9.6, 6.8 Hz), 2.20 (1H, dd, J=9.6, 5.4 Hz).

Example 2

Reaction Scheme 2

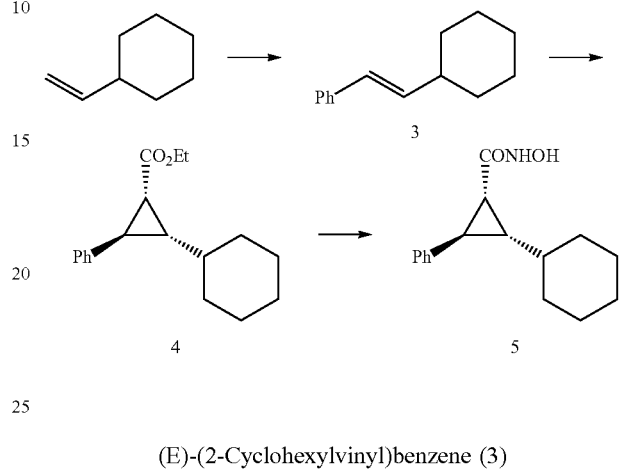

(E)-(2-Cyclohexylvinyl)benzene (3)

To a stirred solution of K$_3$PO$_4$ (11.4 g, 53.8 mmol) in DMA (15 mL) was added bromobenzene (3.0 g, 19 mmol), vinylcyclohexane (5.04 g, 45.8 mmol) and palladium acetate (213 mg, 0.95 mmol). The mixture was stirred at 140° C. for 16 h, allowed to cool to r.t., diluted with water (50 mL) and extracted into EtOAc (2×50 mL). The combined organic layers were washed with water (2×50 mL) and brine (2×50 mL), separated, dried (MgSO$_4$), filtered and concentrated. Purification by flash silica column chromatography (i-hex) gave the title compound as a colourless oil (2.30 g, 65%).

(1R*,2R*,3R*)-Ethyl-2-cyclohexyl-3-phenylcyclopropanecarboxylate (4)

To a stirred solution of 3 (1.50 g, 8.06 mmol) and Rh$_2$(OAc)$_4$ (106 mg, 0.806 mmol) in anhydrous DCM (10 mL) was added ethyl diazoacetate (0.85 mL, 8.06 mmol) in DCM (10 mL) at a rate of 0.2 mL/h. After complete addition the mixture was stirred for 1 h at r.t. Purification by flash silica column chromatography (gradient elution of i-hex to 2% EtOAc in i-hex) gave the title compound as a colourless oil (400 mg, 18%).

(1R*,2R*,3R*)-2-Cyclohexyl-N-hydroxy-3-phenylcyclopropanecarboxamide (5)

Following method A from compound 4 (750 mg, 2.76 mmol). Purification by preparative HPLC gave the title compound as a white solid (10 mg, 3%). LCMS (ES+) 260 (M+H)+, 258 (M−H)−, RT 9.41 min (Analytical method 3). $^1$H NMR δ (ppm) (DMSO-d$_6$): 10.51 (1H, s), 8.76 (1H, s), 7.30-7.22 (2H, m), 7.18-7.12 (1H, m), 7.08 (2H, d, J=7.6 Hz), 2.33-2.27 (1H, m), 1.82-1.58 (7H, m), 1.31-1.00 (6H, m).

Example 3

Reaction Scheme 3

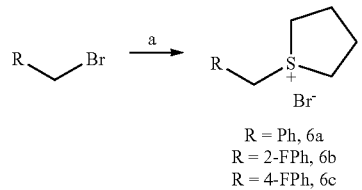

R = Ph, 6a
R = 2-FPh, 6b
R = 4-FPh, 6c

1-Benzyltetrahydrothiophenium bromide (6a)

To a stirred solution of benzyl bromide (27 mL, 227 mmol) in acetone at r.t. was added tetrahydrothiophene (10.0 mL, 114 mmol). The solution was stirred for 16 h and the resulting precipitate filtered and washed with acetone (3×50 mL) and dried under air, to give the title compound as a white solid (51.9 g, 88%).

1-(2-Fluorobenzyl)tetrahydrothiophenium bromide (6b)

2-Fluorobenzyl bromide (8 g, 42.3 mmol) was added to tetrahydrothiophene (25 mL, 284 mmol) and the mixture was stirred for 17 h. The resulting precipitate was collected by vacuum filtration and then slurried in Et$_2$O for 1 h before collecting by vacuum filtration, to give the title compound as a white solid (7.7 g, 66%).

1-(4-Fluorobenzyl)tetrahydrothiophenium bromide (6c)

To a stirred solution of 4-fluorobenzyl bromide (4.0 g, 21.1 mmol) in acetone (30 mL) was added tetrahydrothiophene (1.8 mL, 21.1 mmol) and the mixture was stirred for 17 h. The resulting precipitate was filtered to give the title compound as a white solid (160 mg, 3%).

Example 4

Reaction Scheme 4

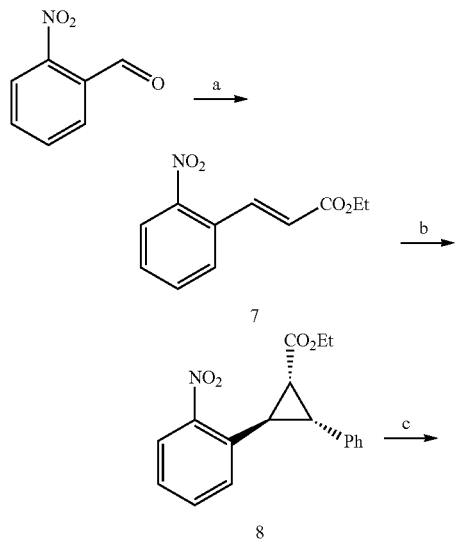

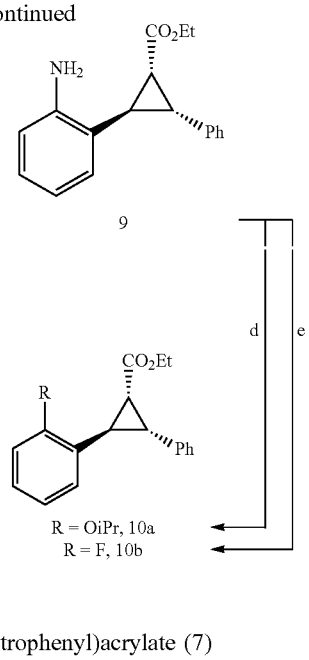

(E)-Ethyl-3-(2-nitrophenyl)acrylate (7)

Following method C from 2-nitrobenzaldehyde (5.0 g, 34.2 mmol). Purification by flash silica column chromatography (gradient elution i-hex to 50% DCM in i-hex) gave the title compound as a white solid (2.9 g, 38%).

(1R*,2R*,3R)-Ethyl-2-(2-nitrophenyl)-3-phenylcyclopropanecarboxylate (8)

To a stirred solution of 7 (2.90 g, 13.1 mmol) in anhydrous DCM/THF (75 mL/30 mL) was added sulfonium salt 6a (5.10 g, 19.7 mmol) and the mixture was cooled to −78° C. LiHMDS (26.2 mL, 1 M solution in THF) was slowly added via syringe pump (1 mL/min). After complete addition, the mixture was warmed to r.t., stirred for 16 h, quenched with water (50 mL) and extracted into DCM (2×100 mL). The combined organic layers were washed with water (2×250 mL) and brine (100 mL). The biphasic mixture was separated and the organic layer was dried (MgSO$_4$), filtered and concentrated. Purification by flash silica column chromatography (gradient elution i-hex to 10% EtOAc in i-hex) gave the title compound as a yellow oil (2.10 g, 51%).

(1R*,2R*,3R)-Ethyl-2-(2-aminophenyl)-3-phenylcyclopropanecarboxylate (9)

A solution of 8 (2.10 g, 6.75 mmol) and 10% Pd/C (200 mg) in MeOH (75 mL) was stirred at r.t. under H$_2$ (1 atmosphere), for 17 h. The mixture was filtered through Celite and purified by flash silica column chromatography (gradient elution i-hex to 20% EtOAc in i-hex) to give the title compound as a red oil (1.55 g, 82%). LCMS (ES+) 282 (M+H)$^+$.

(1R*,2R*,3R)-Ethyl-2-(2-isopropoxyphenyl)-3-phenylcyclopropanecarboxylate (10a)

To a stirred solution of compound 9 (500 mg, 1.78 mmol) in water (10 mL) was added concentrated H$_2$SO$_4$ (0.85 mL) and NaNO$_2$ (184 mg, 2.67 mmol). The reaction mixture was stirred at 00° C. for 1 h, then poured into boiling water (20 mL) and stirred for 30 min. The solution was allowed to cool to r.t. and extracted into DCM (3×20 mL). The combined organic layers were washed with brine (20 mL), dried (MgSO$_4$) and concentrated. The resulting red oil was dissolved in DMF (5 mL) and 2-bromopropane (0.17 mL, 1.77 mmol) and cesium carbonate (434 mg, 1.34 mmol) were added. The mixture was stirred at 80° C. for 16 h, then diluted with water (20 mL) and extracted into DCM (2×30 mL). The combined organic layers were washed with water (20 mL) and brine (20 mL), dried (MgSO$_4$), filtered and concentrated. Purification by flash silica column chromatography (gradient elution i-hex to 5% EtOAc in i-hex) gave the title compound as a colourless oil (125 mg, 44%). LCMS (ES+) 325 (M+H)$^+$.

(1R*,2R*,3R*)-Ethyl-2-(2-fluorophenyl)-3-phenyl-cyclopropanecarboxylate (10b)

A solution of nitrosonium tetrafluoroborate (125 mg, 1.07 mmol) and [bmim][PF$_6$](1.8 mL) was cooled to 0° C. Compound 9 (300 mg, 1.07 mmol) was added and the mixture was stirred for 30 min at 00° C., and 17 h at r.t. The mixture was then heated to 100° C. for 2 h (gas evolution observed) and cooled to r.t. DIPEA (0.18 mL, 1.07 mmol) and Et$_2$O (10 mL) were added. The organic layer was decanted from the ionic liquid and this process repeated twice more. The combined organic layers were concentrated and purified by flash silica column chromatography (gradient elution i-hex to 5% EtOAc in i-hex) to give the title compound as a colourless oil (135 mg, 45%). LCMS (ES+) 285 (M+H)$^+$.

(1R,2R,3R*)—N-Hydroxy-2-(2-isopropoxyphenyl)-3-phenylcyclopropanecarboxamide (11a)

Following method A from compound 100a (125 mg, 0.39 mmol). Purification by flash silica column chromatography (gradient elution DCM to 5% MeOH in DCM) gave the title compound as a white solid (28 mg, 23%). LCMS (ES+) 312 (M+H)+, (ES−) 310 (M−H)−, RT 3.41 min (Analytical method 1). $^1$H NMR δ (ppm)(CHCl$_3$-d): 7.99 (1H, s), 7.41 (2H, d, J=7.6 Hz), 7.31 (2H, t, J=7.1 Hz), 7.27-7.18 (2H, m), 7.11-7.07 (1H, m), 6.92-6.87 (2H, m), 4.66-4.59 (1H, septet, J=6.0), 3.29 (1H, t, J=6.4 Hz), 2.81 (1H, dd, J=9.2, 7.3 Hz), 2.02 (1H, br m), 1.36 (6H, dd, J=10.1, 6.0 Hz), OH not observed.

(1R*,2R*,3R*)-2-(2-Fluorophenyl)-N-hydroxy-3-phenylcyclopropanecarboxamide (11b)

Following method A from compound 100b (130 mg, 0.46 mmol). Purification by flash silica column chromatography (gradient elution DCM to 1% MeOH in DCM) gave the title compound as a white solid (18 mg, 14%). LCMS (ES+) 272 (M+H)+, (ES−) 270 (M−H)−, RT 3.02 min (Analytical method 1). $^1$H NMR δ (ppm) (DMSO-d$_6$): 10.60 (1H, s), 8.74 (1H, s), 7.34-7.14 (9H, m), 3.17 (1H, dd, J=7.0, 5.6 Hz), 2.86 (1H, dd, J=9.5, 7.0 Hz), 2.25 (1H, dd, J=9.5, 5.4 Hz).

Example 5

Reaction Scheme 5

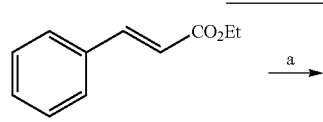

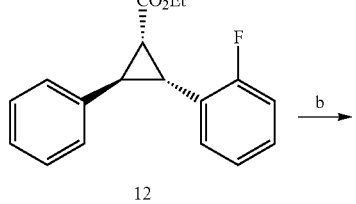

12

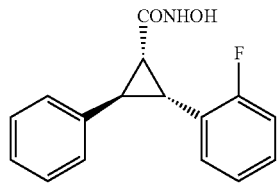

13

(1S*,2R*,3R*)-Ethyl-2-(2-fluorophenyl)-3-phenyl-cyclopropanecarboxylate (12)

A mixture of sulfonium salt 6b (500 mg, 1.80 mmol), ethyl cinnamate (0.20 mL, 1.20 mmol) and 12-crown-4 (0.19 mL, 1.20 mmol) in DCM (10 mL) was cooled to −78° C. LiHMDS (2.41 mL, 1 M solution in THF) was slowly added via syringe pump (2 mL/h). After complete addition, the mixture was warmed to r.t. and stirred for 16 h. The reaction mixture was quenched with H$_2$O (30 mL). The biphasic mixture was separated and the organic layers were washed with brine (2×30 mL), dried (MgSO$_4$), filtered and concentrated. Purification by flash silica column chromatography (gradient elution i-hex to 50% EtOAc in i-hex) gave the title compound as a colourless oil (190 mg, 56%). LCMS (ES+) 285 (M+H)$^+$.

(1S*,2R*,3R)-2-(2-Fluorophenyl)-N-hydroxy-3-phenylcyclopropanecarboxamide (13)

Following method A from compound 12 (190 mg, 0.67 mmol). Purification by flash silica column chromatography (gradient elution DCM to 5% MeOH in DCM) gave the title compound as a white solid (50 mg, 28%). LCMS (ES+) 272 (M+H)+, (ES−) 270 (M−H)−, RT 3.06 min (Analytical method 1). $^1$H NMR δ (ppm) (DMSO-d$_6$): 10.60 (1H, s), 8.73 (1H, s), 7.42-7.20 (7H, m), 7.13-7.06 (2H, m), 3.03 (1H, dd, J=6.8, 5.3 Hz), 2.77 (1H, dd, J=9.3, 6.9 Hz), 2.23 (1H, dd, J=9.3, 5.3 Hz).

Example 6

Reaction Scheme 6

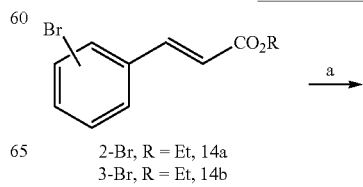

2-Br, R = Et, 14a
3-Br, R = Et, 14b

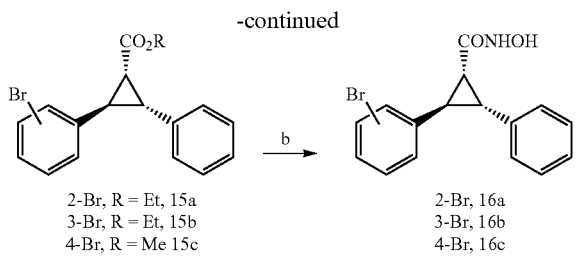

2-Br, R = Et, 15a
3-Br, R = Et, 15b
4-Br, R = Me 15c

2-Br, 16a
3-Br, 16b
4-Br, 16c

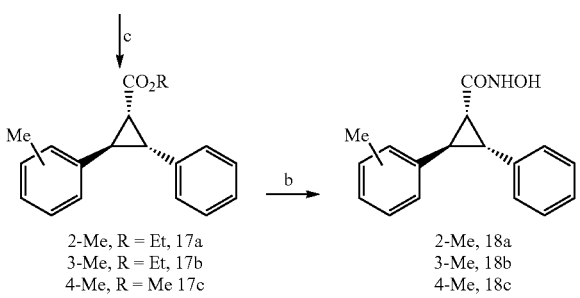

2-Me, R = Et, 17a
3-Me, R = Et, 17b
4-Me, R = Me 17c

2-Me, 18a
3-Me, 18b
4-Me, 18c (E)-Ethyl-3-(2-bromophenyl)acrylate (14a)

Following method C from 2-bromobenzaldehyde (4.66 g, 25.2 mmol). Purification by flash silica column chromatography (gradient elution i-hex to i-hex:DCM, 5:2) gave the title compound as a colourless oil (2.52 g, 39%). LCMS (ES+) 255, 257 (M+H)+.

(E)-Ethyl-3-(3-bromophenyl)acrylate (14b)

Following method C from 3-bromobenzaldehyde (10 g, 54.1 mmol). Purification by flash silica column chromatography (gradient elution i-hex to i-hex:DCM, 1:1) gave the title compound as a colourless oil (7.8 g, 56%). LCMS (ES+) 255, 257 (M+H)+.

(1R*,2R*,3R)-Ethyl-2-(2-bromophenyl)-3-phenylcyclopropanecarboxylate (15a)

A mixture of sulfonium salt 6a (1.52 g, 5.88 mmol) and cinnamate 14a (1.00 g, 3.92 mmol) in DCM/THF (5:2, 35 mL) was cooled to −78° C. LiHMDS (7.84 mL, 1 M solution in THF) was slowly added via syringe pump (1 mL/h). After complete addition, the mixture was warmed to r.t., stirred for 16 h and quenched with H$_2$O (30 mL). The biphasic mixture was separated and the aqueous portion re-extracted with DCM (30 mL). The combined organic layers were washed with water (50 mL) and brine (50 mL), separated, dried (MgSO$_4$), filtered and concentrated. Purification by flash silica column chromatography (gradient elution i-hex to 2.5% EtOAc in i-hex) gave the title compound as a colourless oil (1.05 g, 78%). LCMS (ES+) 345, 347 (M+H).

(1R*,2R*,3R*)-Ethyl-2-(3-bromophenyl)-3-phenylcyclopropanecarboxylate (15b)

A mixture of sulfonium salt 6a (2.10 g, 8.10 mmol) and cinnamate 14b (1.03 g, 4.04 mmol) in DCM (20 mL) was cooled to −78° C. LiHMDS (6.00 mL, 1 M solution in THF) was slowly added via syringe pump (6 mL/h). After complete addition, the mixture was warmed to r.t., stirred for 16 h and quenched with H$_2$O (30 mL). The biphasic mixture was separated and the aqueous layer was re-extracted with DCM (30 mL). The combined organic layers were washed with water (50 mL) and brine (50 mL), dried (MgSO$_4$), filtered and concentrated. Purification by flash silica column chromatography (gradient elution i-hex to 5% EtOAc in i-hex) gave the title compound as a colourless oil (350 mg, 25%). LCMS (ES+) 345, 347 (M+H)+.

(1R*,2R*,3R*)-Methyl 2-(4-bromophenyl)-3-phenylcyclopropanecarboxylate (15c)

A mixture of sulfonium salt 6a (3.39 g, 13.1 mmol) and (E)-methyl 3-(4-bromophenyl)acrylate (2.10 g, 8.71 mmol) in DCM (50 mL) was cooled to −78° C. and slowly treated with LiHMDS (13.1 mL, 1 M solution in THF) (via syringe pump, 1 mL/h). After complete addition, the mixture was warmed to r.t., stirred for 16 h and was quenched with H$_2$O (50 mL). The biphasic mixture was separated and the organic layer washed with brine (2×50 mL), dried (MgSO$_4$) and concentrated. Purification by flash silica column chromatography (gradient elution i-hex to 5% EtOAc in i-hex) gave the title compound as a colourless oil (600 mg, 20%). LCMS (ES+) 345, 347 (M+H)+.

(1R*,2R*,3R*)-2-(2-Bromophenyl)-N-hydroxy-3-phenylcyclopropanecarboxamide (16a)

Following method A from compound 15a (100 mg, 0.30 mmol). Purification by flash silica column chromatography (gradient elution DCM to 5% MeOH in DCM), then passage through a PEAX cartridge (DCM:MeOH, 1:1) gave the title compound as a white solid (32 mg, 33%). LCMS (ES+) 332, 334 (M+H)+, 330, 332 (M−H)−, RT 10.44 min (Analytical method 3). $^1$H NMR δ (ppm) (DMSO-d$_6$): 10.57 (1H, s), 8.73 (1H, s), 7.66 (1H, dd, J=7.9, 1.2 Hz), 7.41-7.33 (3H, m), 7.30-7.15 (5H, m), 3.28 (1H, dd, J=5.9, 6.9 Hz), 2.83 (1H, dd, J=9.5, 7.1 Hz), 2.20 (1H, dd, J=9.5, 5.6 Hz).

(1R*,2R*,3R*)-2-(3-Bromophenyl)-N-hydroxy-3-phenylcyclopropanecarboxamide (16b)

Following method A from compound 15b (100 mg, 0.29 mmol). Purification by flash silica column chromatography (gradient elution DCM to 5% MeOH in DCM) gave the title compound as a white solid (28 mg, 28%). LCMS (ES+) 332, 334 (M+H)+, 330, 332 (M−H)−, RT 3.81 min (Analytical method 1). $^1$H NMR δ (ppm) (DMSO-d$_6$): 10.54 (1H, s), 8.71 (1H, s), 7.50 (1H, s), 7.44-7.40 (1H, m), 7.35-7.22 (6H, m), 7.18 (1H, t, J=7.2 Hz), 3.12 (1H, dd, J=6.8, 5.4 Hz), 2.88 (1H, dd, J=9.6, 6.8 Hz), 2.23 (1H, dd, J=9.6, 5.4 Hz).

(1R*,2R*,3R*)-2-(4-Bromophenyl)-N-hydroxy-3-phenylcyclopropanecarboxamide (16c)

Following method A from compound 15c (100 mg, 0.30 mmol). The residue after work-up was passed through a PEAX cartridge (elution DCM-MeOH, 1:1) to give the title compound as a white solid (34 mg, 34%). LCMS (ES+) 332, 334 (M+H)+, 330, 332 (M−H)−. RT 3.30 min (Analytical method 1). $^1$H NMR δ (ppm) (DMSO-d$_6$): 10.54 (1H, s), 8.67 (1H, s), 7.51-7.45 (2H, m), 7.31-7.18 (6H, m), 7.15 (1H, t, J=7.2 Hz), 3.07 (1H, dd, J=6.9, 5.4 Hz), 2.81 (1H, dd, J=9.6, 6.9 Hz), 2.17 (1H, dd, J=9.6, 5.4 Hz).

(1R*,2R*,3R*)-Ethyl-2-phenyl-3-o-tolylcyclopropanecarboxylate (17a)

To a stirred solution of 15a (200 mg, 0.58 mmol) in dioxane/water (9:1, 3 mL) was added trimethylboroxine (80

μl, 0.58 mmol), Pd(PPh$_3$)$_4$ (67 mg, 0.058 mmol) and cesium carbonate (566 mg, 1.74 mmol). The mixture was degassed with nitrogen for 10 min and heated in the microwave at 115° C. for 10 min. The mixture was allowed to cool to r.t. and partitioned between DCM and H$_2$O (15 mL each). The organic layers were passed through a phase separator and concentrated. Purification by flash silica column chromatography (gradient elution i-hex to 5% EtOAc in i-hex) gave the title compound as a colourless oil (140 mg, 86%).

(1R*,2R*,3R)-Ethyl-2-phenyl-3-m-tolylcyclopropanecarboxylate (17b)

To a stirred solution of 15b (200 mg, 0.58 mmol) in dioxane/water (9:1, 3 mL) was added trimethylboroxine (80 μl, 0.58 mmol), Pd(PPh$_3$)$_4$ (67 mg, 0.058 mmol) and cesium carbonate (566 mg, 1.74 mmol). The mixture was degassed with nitrogen for 10 min and heated in the microwave at 115° C. for 10 min. The mixture was allowed to cool to r.t. and partitioned between DCM and H$_2$O (15 mL each). The organic layers were passed through a phase separator and concentrated. Purification by flash silica column chromatography (gradient elution i-hex to 5% EtOAc in i-hex) gave the title compound as a colourless oil (120 mg, 73%).

(1R*,2R*,3R*)-Methyl-2-phenyl-3-p-tolylcyclopropanecarboxylate (17c)

To a stirred solution of 15c (200 mg, 0.60 mmol) in dioxane/water (9:1, 3 mL) was added trimethylboroxine (80 μl, 0.60 mmol), Pd(PPh$_3$)$_4$ (69 mg, 0.06 mmol) and cesium carbonate (585 mg, 1.80 mmol). The mixture was degassed with nitrogen for 10 min and heated in the microwave at 115° C. for 10 min. The mixture was allowed to cool to r.t. and partitioned between DCM and H$_2$O (15 mL each). The organic layers were passed through a phase separator and concentrated. Purification by flash silica column chromatography (gradient elution i-hex to 10% EtOAc in i-hex) gave the title compound as a colourless oil (120 mg, 75%).

(1R*,2R*,3R*)—N-Hydroxy-2-phenyl-3-o-tolylcyclopropanecarboxamide (18a)

Following method A from compound 17a. Purification by flash silica column chromatography (gradient elution DCM to 5% MeOH in DCM), then passage through a PEAX cartridge (DCM/MeOH, 1:1) gave the title compound as a white solid (10 mg, 7%). LCMS (ES+) 266 (M−H)−, RT 9.54 min (Analytical method 2). $^1$H NMR δ (ppm) (DMSO-d$_6$): 10.54 (1H, s), 8.71 (1H, s), 7.36 (2H, d, J=7.5 Hz), 7.27 (2H, t, J=7.5 Hz), 7.21-7.10 (5H, m), 3.12 (1H, dd, J=7.2, 5.7 Hz), 2.76 (1H, dd, J=9.4, 7.3 Hz), 2.34 (3H, s), 2.07 (1H, dd, J=9.4, 5.6 Hz).

(1R*,2R*,3R*)—N-Hydroxy-2-phenyl-3-m-tolylcyclopropanecarboxamide (18b)

Following method A from compound 17b. Purification by flash silica column chromatography (gradient elution DCM to 5% MeOH in DCM) gave the title compound as a white solid (67 mg, 56%). LCMS (ES+) 268 (M+H)+, RT 3.71 min (Analytical method 1). $^1$H NMR δ (ppm) (DMSO-d$_6$): 10.54 (1H, s), 8.68 (1H, s), 7.32 (2H, d, J=7.5 Hz), 7.25 (2H, t, J=7.4 Hz), 7.20-7.09 (5H, m), 3.05 (1H, dd, J=6.9, 5.4 Hz), 2.77 (1H, dd, J=9.6, 6.9 Hz), 2.28 (3H, s), 2.15 (1H, dd, J=9.6, 5.4 Hz).

(1R*,2R*,3R*)—N-Hydroxy-2-phenyl-3-p-tolylcyclopropanecarboxamide (18c)

Following method A from compound 17c. Purification by flash silica column chromatography (gradient elution DCM to 5% MeOH in DCM) followed by elution through PEAX cartridge (1:1, DCM:MeOH) gave the title compound as a white solid (21 mg, 17%). LCMS (ES+) 268 (M+H)+, RT 3.71 min (Analytical method 1). $^1$H NMR δ (ppm) (DMSO-d$_6$): 10.54 (1H, s), 8.68 (1H, s), 7.32 (2H, d, J=7.5 Hz), 7.25 (2H, t, J=7.4 Hz), 7.20-7.10 (5H, m), 3.04 (1H, dd, J=6.9, 5.4 Hz), 2.77 (1H, dd, J=9.6, 6.9 Hz), 2.28 (3H, s), 2.15 (1H, dd, J=9.6, 5.4 Hz).

Example 7

Reaction Scheme 7

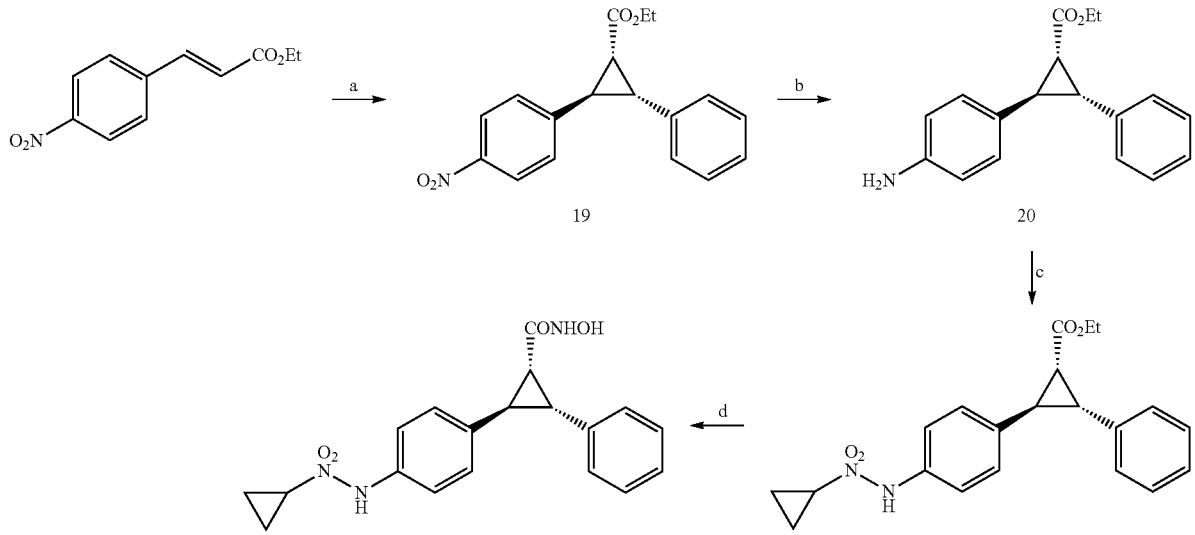

(1R*,2R,3R)-Ethyl-2-(4-nitrophenyl)-3-phenylcyclopropanecarboxylate (19)

A mixture of sulfonium salt 6a (1.00 g, 3.76 mmol) and ethyl-4-nitrocinnamate (553 mg, 2.51 mmol) in DCM (10 mL) was cooled to −78° C. LiHMDS (3.76 mL, 1 M solution in THF) was slowly added via syringe pump (1 mL/h). After complete addition, the mixture was warmed to r.t., stirred for 1 h and quenched with $H_2O$ (30 mL). The biphasic mixture was separated and the aqueous layer was re-extracted with DCM (30 mL). The combined organic layers were washed with water (50 mL) and brine (50 mL), dried ($MgSO_4$), filtered and concentrated. Purification by flash silica column chromatography (gradient elution i-hex to 5% EtOAc in i-hex) gave the title compound as a yellow oil (180 mg, 23%). LCMS (ES+) 312 (M+H)+.

(1R*,2R*,3R)-Ethyl-2-(4-aminophenyl)-3-phenylcyclopropanecarboxylate (20)

A solution of compound 19 (180 mg, 0.58 mmol) in MeOH (6 mL) was hydrogenated using a H-cube apparatus (Full $H_2$ mode, 10% Pd/C cartridge, 1 mL/min, r.t.). The reaction mixture was concentrated to give a yellow oil (165 mg, 100%) which was used directly in the next step of the synthesis.

(1R*,2R*,3R*)-Ethyl-2-(4-(cyclopropanesulfonamido)phenyl)-3-phenylcyclopropanecarboxylate (21)

To a stirred solution of compound 20 (165 mg, 0.59 mmol) in DCM (5 mL) was added cyclopropylsulfonyl chloride (248 mg, 1.76 mmol) and triethylamine (0.24 mL, 1.76 mmol). The mixture was stirred at r.t. for 16 h and washed with water (10 mL). The organic layers were collected by phase separator and concentrated. Purification by flash silica column chromatography (gradient elution i-hex to 50% EtOAc in i-hex) gave the title compound as a pale yellow solid (175 mg, 77%). LCMS (ES+) 386 (M+H)+.

(1R*,2R*,3R*)-2-(4-(cyclopropanesulfonamido)phenyl)-N-hydroxy-3-phenylcyclopropanecarboxamide (22)

Following method A from compound 21 (175 mg, 0.45 mmol). The carboxylic acid was obtained as the major product. The mixture was acidified with aqueous 1M HCl and extracted into EtOAc (3×10 mL). The organic layers were combined, dried ($MgSO_4$) and concentrated. The sample was then subjected to method B. Purification by preparative HPLC and passage through a PEAX cartridge (DCM/MeOH, 1:1) gave the title compound as a white solid (15 mg, 8%). LCMS (ES+) 373 (M+H)+, RT 8.20 min (Analytical method 3). $^1$H NMR δ (ppm) (DMSO-$d_6$): 10.55 (1H, s), 9.62 (1H, s), 8.68 (1H, s), 7.33-7.13 (9H, m), 3.05 (1H, dd, J=6.9, 5.4 Hz), 2.79 (1H, dd, J=9.5, 6.9 Hz), 2.60-2.53 (1H, qt, J=6.0 Hz), 2.15 (1H, dd, J=9.5, 5.3 Hz), 0.91 (4H, d, J=6.3 Hz).

Example 8

Reaction Scheme 8

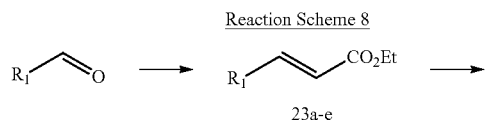

23a-e

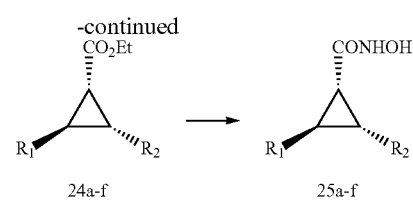

24a-f → 25a-f

TABLE 1

| R1 | R2 | Compound |
|---|---|---|
| cyclopentyl | Ph | 25a |
| 1-methyl-1H-pyrazol-4-yl | Ph | 25b |
| pyrimidin-5-yl | Ph | 25c |
| 2,3-dihydrobenzo[b][1,4]dioxin-6-yl | Ph | 25d |
| 8-chloro-2,3-dihydrobenzo[b][1,4]dioxin-6-yl | Ph | 25e |
| 8-chloro-2,3-dihydrobenzo[b][1,4]dioxin-6-yl | 2-fluorophenyl | 25f |

(E)-Ethyl-3-cyclopentylacrylate (23a)

Following method C from cyclopentanecarbaldehyde (2.00 g, 20.4 mmol). Purification by flash silica column chromatography (gradient elution i-hex to 5:2 i-hex:DCM) gave the title compound as a colourless oil (2.00 g, 58%). LCMS (ES+) 259 (M+H)+.

(E)-Ethyl-3-(1-methyl-1H-pyrazol-4-yl)acrylate (23b)

Following method C from 1-methyl-1H-pyrazole-4-carbaldehyde (500 mg, 4.50 mmol). Purification by flash silica column chromatography (gradient elution i-hex to EtOAc) gave the title compound as a yellow oil (900 mg, 99%). LCMS (ES+) 181 (M+H)+.

(E)-Ethyl-3-(pyrimidin-5-yl)acrylate (23c)

Following method C from pyrimidine-5-carbaldehyde (2 g, 19.2 mmol). Purification by flash silica column chromatography (gradient elution i-hex to 50% EtOAc in i-hex) gave the title compound as a colourless oil (2.34 g, 68%, 3:1 trans:cis). LCMS (ES+) 179 (M+H)+.

(E)-Ethyl-3-(2,3-dihydrobenzo[b][1,4]dioxin-6-yl) acrylate (23d)

Following method C from 2,3-dihydrobenzo[b][1,4]dioxine-6-carbaldehyde (2.00 g, 12.2 mmol). Purification by flash silica column chromatography (gradient elution i-hex to 5% EtOAc in i-hex) gave the title compound as a white solid (2.64 g, 93%). LCMS (ES+) 235 (M+H)+.

(E)-Ethyl-3-(8-chloro-2,3-dihydrobenzo[b][1,4]dioxin-6-yl)acrylate (23e)

Following method C from 8-chloro-2,3-dihydrobenzo[b][1,4]dioxine-6-carbaldehyde (700 mg, 3.53 mmol). The resulting yellow oil was used without further purification. LCMS (ES+) 269, 271 (M+H)+.

(1S*,2R*,3R)-Ethyl-2-cyclopentyl-3-phenylcyclopropanecarboxylate (24a)

A mixture of 6a (2.30 g, 8.92 mmol), compound 23a (1.00 g, 5.96 mmol) and 12-crown-4 (1.44 mL, 8.92 mmol) in DCM (20 mL) was cooled to −78° C. LiHMDS (8.92 mL, 1 M solution in THF) was slowly added via syringe pump (4 mL/h). After complete addition, the reaction mixture was warmed to r.t. and stirred for 16 h. The reaction mixture was quenched with H$_2$O (30 mL). The biphasic mixture was separated and the organic layers washed with brine (2×30 mL), separated, dried (MgSO$_4$), filtered and concentrated. Purification by flash silica column chromatography (gradient elution i-hex to 5% EtOAc in i-hex) gave the title compound as a colourless oil (263 mg, 7%).

(1R*,2R*,3R*)-Ethyl-2-(1-methyl-1H-pyrazol-4-yl)-3-phenylcyclopropanecarboxylate (24b)

Following method F from compound 23b (810 mg, 4.50 mmol) and 6a (1.94 mg, 7.50 mmol). Purification by flash silica column chromatography (gradient elution i-hex to 75% EtOAc in i-hex) gave the title compound as a colourless oil (493 mg, 41%, 3:1 trans:cis). LCMS (ES+) 271 (M+H)+.

(1R*,2R*,3R*)-Ethyl-2-phenyl-3-(pyrimidin-5-yl) cyclopropanecarboxylate (24c)

Following method F from 23c (1.00 g, 5.62 mmol) and 6a (2.18 g, 8.43 mmol). The addition was performed at −78° C. and allowed to stir at RT for 17 h. Purification by flash silica column chromatography (gradient elution i-hex to 50% EtOAc in i-hex) gave the title compound as a colourless oil (270 mg, 19%). LCMS (ES+) 269 (M+H)+.

(1R*,2R*,3R*)-Ethyl-2-(2,3-dihydrobenzo[b][1,4] dioxin-6-yl)-3-phenylcyclopropanecarboxylate (24d)

Following method F from compound 23d (2.64 g, 11.3 mmol) and 6a (4.4 g, 16.9 mmol). Purification by flash silica column chromatography (gradient elution i-hex to 7.5% EtOAc in i-hex) gave the title compound as a colourless oil (652 mg, 18%). LCMS (ES+) 325 (M+H)+.

(1R*,2R*,3R*)-Ethyl-2-(8-chloro-2,3-dihydrobenzo [b][1,4]dioxin-6-yl)-3-phenylcyclopropanecarboxylate (24e)

Following method F from 23e (946 mg, 3.52 mmol) and 6a (1.37 mg, 5.28 mmol). Purification by flash silica column chromatography (gradient elution i-hex to 10% EtOAc in i-hex) gave the title compound as a colourless oil (484 mg, 38%, 4:1 trans:cis). LCMS (ES+) 359, 361 (M+H)+.

(1S*,2R*,3R*)-Ethyl-2-(8-chloro-2,3-dihydrobenzo [b][1,4]dioxin-6-yl)-3-(2-fluorophenyl)-cyclopropanecarboxylate (24f)

Following method F from 23e (860 mg, 3.20 mmol) and 6b (1.33 mg, 4.80 mmol). Purification by flash silica column chromatography (gradient elution i-hex to 10% EtOAc in i-hex) gave the title compound as a colourless oil (472 mg, 39%, 3:1 trans:cis). LCMS (ES+) 377 (M+H)+ RT 3.48 min (Analytical method 1).

(1S*,2R*,3R)-2-Cyclopentyl-N-hydroxy-3-phenylcyclopropanecarboxamide (25a)

Using method A from compound 24a (1.05 g, 4.06 mmol). Purification by flash silica column chromatography (gradient elution DCM to 4% MeOH in DCM) and preparative HPLC gave the title compound as a white solid (23 mg, 9%). LCMS (ES+) 246 (M+H)+, RT 3.18 min (Analytical method 1). $^1$H NMR δ (ppm) (DMSO-d$_6$): 10.57 (1H, s), 8.76 (1H, s), 7.35-7.27 (2H, m), 7.24-7.18 (3H, m), 1.88 (1H, t, J=5.0 Hz), 1.71-1.60 (1H, m), 1.58-1.47 (2H, m), 1.50-1.16 (8H, m).

(1R,2R,3R)—N-Hydroxy-2-(1-methyl-1H-pyrazol-4-yl)-3-phenylcyclopropanecarboxamide (25b)

Following method A from 24b (493 mg, 1.83 mmol). Purification by flash silica column chromatography (gradient elution DCM to 5% MeOH in DCM) and then preparative HPLC gave the racemic mixture as a white solid (235 mg, 50%). Preparative chiral HPLC gave the title compound (Chiralpak IC 30/70 IPA/MeOH (50/50/0.1% formic acid)/Heptane, 1.0 mL/min, RT 10.3 min). LCMS (ES+) 258 (M+H)+, (ES−) 256 (M+H)−, RT 2.65 min (Analytical method 1). $^1$H NMR δ (ppm) (DMSO-d$_6$): 10.50 (1H, s), 8.63 (1H, s), 7.61 (1H, s), 7.34 (1H, s), 7.28-7.13 (5H, m), 3.78 (3H, s), 2.86 (1H, dd, J=6.9, 5.3 Hz), 2.63 (1H, dd, J=9.4, 6.9 Hz), 1.97 (1H, dd, J=9.4, 5.3 Hz).

(1R*,2R*,3R*)—N-Hydroxy-2-phenyl-3-(pyrimidin-5-yl)cyclopropanecarboxamide (25c)

Using method A, from compound 24c (270 mg, 1.08 mmol). Purification by flash silica chromatography gradient elution DCM to 7% MeOH in DCM) and reversed phase HPLC gave the title compound as a yellow solid (9 mg, 5%). LCMS (ES+) 256 (M+H)+, RT 2.52 min (Analytical method 1). $^1$H NMR δ (ppm) (DMSO-d$_6$): 10.61 (1H, s), 9.06 (1H, s), 8.79 (2H, s), 8.72 (1H, s), 7.34 (2H, d, J=7.6 Hz), 7.27 (2H, t, J=7.5 Hz), 7.22-7.17 (1H, m), 3.15 (1H, dd, J=6.8, 5.5 Hz), 3.04 (1H, dd, J=9.6, 6.9 Hz), 2.37 (1H, dd, J=9.7, 5.5 Hz).

(1R,2R,3R)-2-(2,3-Dihydrobenzo[b][1,4]dioxin-6-yl)-N-hydroxy-3-phenylcyclopropanecarboxamide (25d)

Following method A from compound 24d (652 mg, 2.01 mmol). Purification by flash silica column chromatography (gradient elution DCM to 5% MeOH in DCM) gave the racemic mixture as a white solid (420 mg, 67%). Preparative chiral HPLC gave the title compound (Chiralpak IC 30/70 IPA/MeOH (50/50/0.1% formic acid)/heptane, 1.0 mL/min, RT 8.1 min). LCMS (ES+) 312 (M+H)+, RT 8.59 min (Analytical method 5). $^1$H NMR δ (ppm) (DMSO-$d_6$): 10.57 (1H, s), 8.73 (1H, s), 7.35 (2H, d, J=7.59 Hz), 7.29 (2H, t, J=7.5 Hz), 7.24-7.17 (1H, m), 6.85 (1H, d, J=8.5 Hz), 6.80-6.74 (2H, m), 4.26 (4H, s), 3.02 (1H, dd, J=6.8, 5.4 Hz), 2.78 (1H, dd, J=9.6, 6.8 Hz), 2.14 (1H, dd, J=9.6, 5.4 Hz).

(1R,2R,3R)-2-(8-Chloro-2,3-dihydrobenzo[b][1,4]dioxin-6-yl)-N-hydroxy-3-phenylcyclopropanecarboxamide (25e)

Following method A from 24e (484 mg, 1.35 mmol). Purification by flash silica column chromatography (gradient elution DCM to 5% MeOH in DCM) and then preparative HPLC gave the racemic product as a white solid (174 mg, 37%). Preparative chiral HPLC gave the title compound (Chiralpak IC 20/80 IPA/MeOH (50/50/0.1% formic acid)/Heptane, 1.0 mL/min, RT 10.4 min). LCMS (ES+) 346, 348 (M+H)+, RT 3.57 min (Analytical method 1). $^1$H NMR δ (ppm) (DMSO-$d_6$): 10.50 (1H, s), 8.68 (1H, s), 7.31 (2H, d, J=7.6 Hz), 7.25 (2H, t, J=7.4 Hz), 7.21-7.13 (1H, m), 6.93 (1H, d, J=2.1 Hz), 6.77 (1H, d, J=2.1 Hz), 4.34-4.26 (4H, m), 3.00 (1H, dd, J=6.8, 5.4 Hz), 2.79 (1H, dd, J=9.6, 6.8 Hz), 2.14 (1H, dd, J=9.8, 5.4 Hz).

(1S,2R,3R)-2-(8-Chloro-2,3-dihydrobenzo[b][1,4]dioxin-6-yl)-3-(2-fluorophenyl)-N-hydroxycyclopropanecarboxamide (25f)

Following method A from 24f (472 mg, 1.25 mmol) to yield a white glass (480 mg). Purification by preparative HPLC gave the racemic product as a white glass (180 mg, 39%). Preparative chiral HPLC gave the title compound (Chiralpak IA 50/50 EtOH (0.1% formic acid)/Heptane, 1.0 mL/min). LCMS (ES+) 364 (M+H)+, RT 3.60 min (Analytical method 1). $^1$H NMR δ (ppm) (DMSO-$d_6$): 10.55 (1H, s), 8.72 (1H, s), 7.38 (1H, t, J=7.6 Hz), 7.28-7.20 (1H, m), 7.13-7.05 (2H, m), 6.95 (1H, d, J=2.1 Hz), 6.80 (1H, d, J=2.1 Hz), 4.36-4.24 (4H, m), 2.93 (1H, dd, J=6.9, 5.3 Hz), 2.72 (1H, dd, J=9.3, 6.9 Hz), 2.17 (1H, dd, J=9.4, 5.3 Hz).

Example 9

Reaction Scheme 9

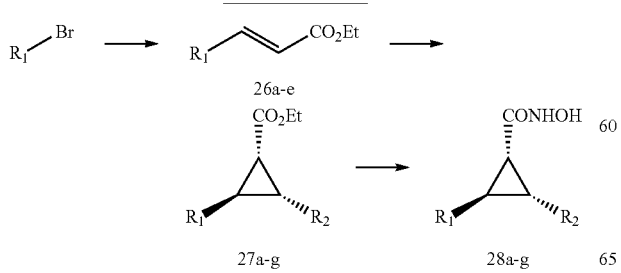

TABLE 2

| R1 | R2 | Compound |
|---|---|---|
| pyridazin-4-yl | Ph | 28a |
| 2-cyclopropylpyridin-4-yl | Ph | 28b |
| 2-cyclopropylpyridin-4-yl | 2-fluorophenyl | 28c |
| 2-cyclopropylpyridin-4-yl | 4-fluorophenyl | 28d |
| 2,2-difluorobenzo[d][1,3]dioxol-5-yl | Ph | 28e |
| 6-(trifluoromethyl)pyridin-3-yl | Ph | 28f |
| 2-(trifluoromethyl)pyridin-4-yl | Ph | 28g |

(E)-Ethyl 3-(pyridazin-4-yl)acrylate (26a)

Following method E from 4-bromopyridazine (500 mg, 3.14 mmol). Purification by flash silica column chromatography (gradient elution i-hex to EtOAc) gave the title compound as a colourless oil (94 mg, 17%). LCMS (ES+) 179 (M+H)+.

(E)-Ethyl-3-(2-cyclopropylpyridin-4-yl)acrylate (26b)

Following method D from 4-bromo-2-(cyclopropyl)pyridine (1.00 g, 5.05 mmol). Purification by flash silica column chromatography (gradient elution i-hex to 10% EtOAc in i-hex) gave the title compound as a white solid (530 mg, 48%). LCMS (ES+) 218 (M+H)+.

(E)-Ethyl-3-(2,2-difluorobenzo[d][1,3]dioxol-5-yl)acrylate (26c)

Following method E from 5-bromo-2,2-difluorobenzo[d][1,3]dioxole (2.00 g, 8.44 mmol). Purification by flash silica column chromatography (gradient elution i-hex to 7.5% EtOAc in i-hex) gave the title compound as a white solid (1.62 g, 75%). LCMS (ES+) 257 (M+H)+.

(E)-Ethyl-3-(6-(trifluoromethyl)pyridin-3-yl)acrylate (26d)

Following method D from 5-bromo-2-(trifluoromethyl)pyridine (1.0 g, 4.42 mmol). Purification by flash silica column chromatography (gradient elution i-hex to 10% EtOAc in i-hex) gave the title compound as a white solid (700 mg, 65%). LCMS (ES+) 246 (M+H)+.

(E)-Ethyl-3-(2-(trifluoromethyl)pyridin-4-yl)acrylate (26e)

Following method D from 4-bromo-2-(trifluoromethyl)pyridine (1.0 g, 4.42 mmol). Purification by flash silica column chromatography (gradient elution i-hex to 15% EtOAc in i-hex) gave the title compound as a white solid (100 mg, 9%). LCMS (ES+) 246 (M+H)+.

(1R*,2R*,3R*)-Ethyl-2-phenyl-3-(pyridazin-4-yl)cyclopropanecarboxylate (27a)

Following method F from 26a (94 mg, 0.53 mmol) and 6a. As the reaction was incomplete after 1 h, the reaction was cooled to −20° C. and additional amounts of sulfonium salt, 12-crown-4 and LiHMDS (0.5 eq each) were added. Purification by flash silica column chromatography (gradient elution i-hex to EtOAc) gave the title compound as a colourless oil (45 mg, 32%). LCMS (ES+) 269 (M+H).

(1R*,2R*,3R*)-Ethyl-2-(2-cyclopropylpyridin-4-yl)-3-phenylcyclopropanecarboxylate (27b)

Following method F from compound 26b (530 mg, 2.44 mmol) and 6a. Purification by flash silica column chromatography (gradient elution i-hex to 25% EtOAc in i-hex) gave the title compound as a colourless oil (330 mg, 44%, 5:4 trans:cis). LCMS (ES+) 308 (M+H).

(1S*,2R*,3R*)-Ethyl-2-(2-cyclopropylpyridin-4-yl)-3-(2-fluorophenyl)cyclopropanecarboxylate (27c)

Following method F from 26b (130 mg, 0.60 mmol) and 6b (249 mg, 0.90 mmol). Purification by flash silica column chromatography (gradient elution i-hex to 25% EtOAc in i-hex) gave the title compound as a colourless oil (150 mg, 77%, 3:1 trans:cis). LCMS (ES+) 326 (M+H).

(1R*,2R*,3R*)-Ethyl-2-(2-cyclopropylpyridin-4-yl)-3-(4-fluorophenyl)cyclopropanecarboxylate (27d)

Following method F from 26b (481 mg, 2.22 mmol) and 6c (921 mg, 3.32 mmol). Purification by flash silica column chromatography (gradient elution i-hex to 25% EtOAc in i-hex) gave the title compound as a colourless oil (510 mg, 71%, 4:1 trans:cis). LCMS (ES+) 326 (M+H)+.

(1R*,2R*,3R*)-Ethyl-2-(2,2-difluorobenzo[d][1,3]dioxol-5-yl)-3-phenylcyclopropanecarboxylate (27e)

Following method F from compound 26c (1.62 g, 6.33 mmol) and 6a (2.46 g, 9.49 mmol). Purification by flash silica column chromatography (gradient elution i-hex to 5% EtOAc in i-hex) gave the title compound as a colourless oil (400 mg, 18%). LCMS (ES+) 347 (M+H)+.

(1R*,2R*,3R)-Ethyl-2-phenyl-3-(6-(trifluoromethyl)pyridin-3-yl)cyclopropanecarboxylate (27f)

Following method F from compound 26d (700 mg, 2.86 mmol) and 6a (1.11 g, 4.29 mmol). The reaction was incomplete after 2 h. The reaction was cooled to 00° C. and additional 1 equivalent of sulfonium salt, 12-crown-4 and LiHMDS were added and the mixture was stirred at r.t. for 10 min. Purification by flash silica column chromatography (gradient elution i-hex to 5% EtOAc in i-hex) gave the title compound as a colourless oil (720 mg, 2:1 trans:cis, 65%). LCMS (ES+) 322 (M+H)+.

(1R*,2R*,3R*)-Ethyl-2-phenyl-3-(2-(trifluoromethyl)pyridin-4-yl)cyclopropanecarboxylate (27g)

Following method F from compound 26e (100 mg, 0.41 mmol) and 6a (159 mg, 0.61 mmol). Purification by flash silica column chromatography (gradient elution i-hex to 10% EtOAc in i-hex) gave the title compound as a colourless oil (130 mg, 2:1 trans:cis, 100%). LCMS (ES+) 322 (M+H).

(1R*,2R*,3R*)—N-Hydroxy-2-phenyl-3-(pyridazin-4-yl)cyclopropanecarboxamide (28a)

Following method A, from 27a (45 mg, 0.17 mmol). Purification by flash silica column chromatography (gradient elution DCM to 4% MeOH in DCM) and reversed phase HPLC gave the title compound as a white solid (3 mg, 21%). LCMS (ES+) 256 (M+H)+, RT 7.02 min (Analytical method 3). $^1$H NMR δ (ppm) (DMSO-$d_6$): 10.69 (1H, s), 9.34 (1H, s), 9.15 (1H, d, J=5.4 Hz), 8.81 (1H, s), 7.63-7.61 (1H, m), 7.40-7.30 (4H, m), 7.27-7.24 (1H, m), 3.22 (1H, dd, J=5.2, 6.4 Hz), 3.13 (1H, dd, J=6.4, 9.5 Hz), 2.45 (1H, dd, J=9.5, 5.3 Hz).

(1R,2R,3R)-2-(2-Cyclopropylpyridin-4-yl)-N-hydroxy-3-phenylcyclopropanecarboxamide (28b)

Following method A from compound 27b (330 mg, 1.07 mmol). Purification by flash silica column chromatography (gradient elution DCM to 5% MeOH in DCM) gave the racemic mixture as a white solid (60 mg, 19%). Preparative chiral HPLC gave the title compound (Chiralpak IC 30/70 IPA/MeOH (50/50/0.1 formic acid)/heptane, 1.0 mL/min, RT 9.6 min). LCMS (ES+) 295 (M+H)+, (ES−) 293 (M−H)−, RT 2.12 min (Analytical method 1). $^1$H NMR δ (ppm) (DMSO-$d_6$): 10.65 (1H, s), 8.78 (1H, s), 8.32 (1H, d, J=5.1 Hz), 7.37 (2H, d, J=7.6 Hz), 7.34-7.28 (2H, m), 7.25 (2H, d, J=8.2 Hz), 7.07 (1H, dd, J=5.2, 1.7 Hz), 3.10 (1H, dd, J=6.7, 5.6 Hz), 2.99 (1H, dd, J=9.7, 6.7 Hz), 2.34 (1H, dd, J=9.7, 5.6 Hz), 2.12-2.07 (1H, m), 0.98-0.93 (4H, m).

(1S,2R,3R)-2-(2-Cyclopropylpyridin-4-yl)-3-(2-fluorophenyl)-N-hydroxycyclopropanecarboxamide (28c)

Following method A from 27c (150 mg, 0.46 mmol). Purification by flash silica column chromatography (gradient elution DCM to 5% MeOH in DCM) gave the racemic mixture as an off-white solid (50 mg, 35%). Preparative chiral HPLC gave the title compound (Chiralpak IC 40/60 EtOH (0.1 formic acid)/heptanes, 1.0 mL/min, RT 9.3 min). LCMS (ES+) 313 (M+H)+, RT 2.18 min (Analytical method 1). $^1$H NMR δ (ppm) (DMSO-$d_6$): 10.68 (1H, s), 8.81 (1H, s), 8.34 (1H, d, J=5.1 Hz), 7.44 (1H, t, J=7.7 Hz), 7.34-7.27 (2H, m), 7.18-7.08 (3H, m), 3.04 (1H, dd, J=6.6, 5.0 Hz), 2.95 (1H, dd, J=9.2, 6.9 Hz), 2.36 (1H, dd, J=9.4, 5.3 Hz), 2.14-2.09 (1H, m), 0.99-0.92 (4H, m).

(1R,2R,3R)-2-(2-Cyclopropylpyridin-4-yl)-3-(4-fluorophenyl)-N-hydroxycyclopropanecarboxamide (28d)

Following method A from 27d (510 mg, 1.57 mmol). Purification by flash silica column chromatography (gradient elution DCM to 5% MeOH in DCM) gave the racemic mixture as a white solid (145 mg, 30%). Preparative chiral HPLC gave the title compound (Chiralpak IC 20/80 IPA/MeOH (50/50/0.1% formic acid)/Heptane, 1.0 mL/min, RT 13.7 min). LCMS (ES+) 313 (M+H)+, RT 2.87 min (Analytical method 4). $^1$H NMR δ (ppm) (DMSO-$d_6$): 10.65 (1H, br s), 8.82 (1H, br s), 8.33 (1H, d, J=5.1 Hz), 7.40 (2H, dd, J=8.4, 5.6 Hz), 7.25 (1H, s), 7.14 (2H, t, J=8.8 Hz), 7.07 (1H, dd, J=5.2, 1.7 Hz), 3.07 (1H, dd, J=6.8, 5.4 Hz), 2.99 (1H, dd, J=9.6, 6.8 Hz), 2.32 (1H, dd, J=9.6, 5.4 Hz), 2.14-2.06 (1H, m), 0.99-0.92 (4H, m).

(1R,2R,3R)-2-(2,2-Difluorobenzo[d][1,3]dioxol-5-yl)-N-hydroxy-3-phenylcyclopropanecarboxamide (28e)

Following method A from compound 27e (400 mg, 1.17 mmol). Purification by flash silica column chromatography (gradient elution DCM to 2% MeOH in DCM) gave the racemic mixture as a white solid (300 mg, 78%). Preparative chiral HPLC gave the title compound (Chiralpak IC 20/80 IPA/MeOH (50/50/0.1% formic acid)/Heptane, 1.5 mL/min, RT 6.3 min). LCMS (ES+) 334 (M+H)+, RT 3.89 min (Analytical method 1). $^1$H NMR δ (ppm) (DMSO-$d_6$): 10.63 (1H, s), 8.76 (1H, s), 7.44-7.33 (4H, m), 7.31 (2H, t, J=7.44 Hz), 7.25-7.18 (2H, m), 3.21 (1H, dd, J=6.8, 5.4 Hz), 2.92 (1H, dd, J=9.6, 6.8 Hz), 2.25 (1H, dd, J=9.6, 5.4 Hz).

(1R,2R,3R)—N-Hydroxy-2-phenyl-3-(6-(trifluoromethyl)pyridin-3-yl)cyclopropanecarboxamide (28f)

Following method A from compound 27f (720 mg, 2.24 mmol). Purification by flash silica column chromatography (gradient elution DCM to 5% MeOH in DCM) followed by preparative HPLC, gave the racemic mixture as a white solid (83 mg, 11%). Preparative chiral HPLC gave the title compound (Chiralpak IC 20/80 IPA/MeOH (50/50/0.1 formic acid)/heptane, 1.0 mL/min, RT 14.5 min). LCMS (ES+) 323 (M+H)+, RT 8.60 min (Analytical method 3). $^1$H NMR δ (ppm) (DMSO-$d_6$): 10.70 (1H, s), 8.84 (1H, s), 8.82 (1H, s), 8.02-7.97 (1H, m), 7.91 (1H, d, J=8.2 Hz), 7.40 (2H, d, J=7.6 Hz), 7.33 (2H, t, J=7.5 Hz), 7.28-7.22 (1H, m), 3.32 (1H, dd, J=6.7 and 5.6 Hz), 3.09 (1H, dd, J=9.7, 6.8 Hz), 2.43 (1H, dd, J=9.7 and 5.6 Hz).

(1R,2R,3R)—N-Hydroxy-2-phenyl-3-(2-(trifluoromethyl)pyridin-4-yl)cyclopropanecarboxamide (28g)

Following method A from compound 27g (130 mg, 0.41 mmol). Purification by flash silica column chromatography (gradient elution DCM to 5% MeOH in DCM) followed by preparative HPLC, gave the racemic mixture as a white solid (90 mg, 68%). Preparative chiral HPLC gave the title compound (Chiralpak IC 20/80 IPA/MeOH (50/50/0.1 formic acid)/heptane, 1.0 mL/min, RT 10.3 min). LCMS (ES+) 323 (M+H)+, RT 3.50 min (Analytical method 1). $^1$H NMR δ (ppm) (DMSO-$d_6$): 10.66 (1H, s), 8.81 (1H, s), 8.71 (1H, d, J=5.0 Hz), 7.92 (1H, s), 7.70 (1H, d, J=5.1 Hz), 7.40 (2H, d, J=7.5 Hz), 7.32 (2H, t, J=7.5 Hz), 7.27-7.22 (1H, m), 3.35 (1H, dd, J=6.6, 5.4 Hz), 3.16 (1H, dd, J=9.5, 6.6 Hz), 2.48 (1H, dd, J=9.5, 5.4 Hz).

Example 10

Reaction Scheme 10

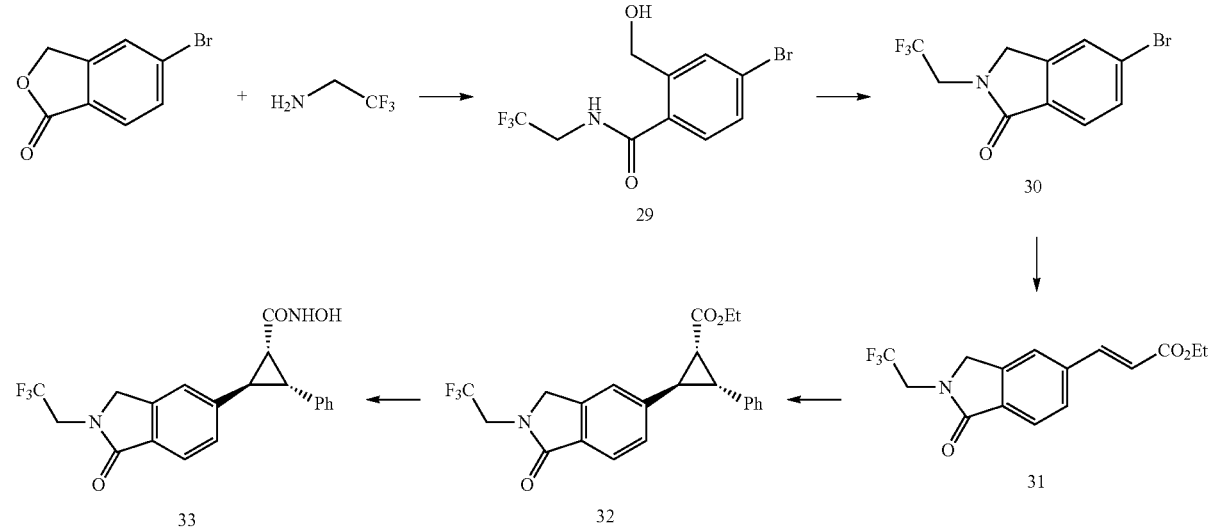

4-Bromo-2-(hydroxymethyl)-N-(2,2,2-trifluoroethyl)benzamide (29)

To a stirred suspension of aluminium trichloride (5.30 g, 39.8 mmol) in DCE (50 mL) at 000° C. was added 2,2,2-trifluoroethylamine (5 g, 50.5 mmol). This was stirred for 4 h before addition of 5-bromophthalide (5.30 g, 39.8 mmol) in one portion, and then heated to 80° C. for 17 h. The mixture was quenched with iced water (100 mL) and stirred for 30 min. DCM (50 mL) was added and the mixture was filtered through silica. The organic layers were washed with $H_2O$ (3×100 mL) and the aqueous layers were back-extracted into DCM (50 mL). The combined organic layers were dried ($MgSO_4$), filtered and concentrated to give an off-white solid. The crude mixture (2.2 g) containing ~50% residual 5-bromophthalide was progressed to the next step. LCMS (ES+) 312, 314 (M+H)+.

5-Bromo-2-(2,2,2-trifluoroethyl)isoindolin-1-one (30)

To a stirred solution of 29 (2.2 g, 7.05 mmol) and NMP (13 mL) in anhydrous THF (40 mL) at 5° C. was added i-PrMgCl.LiCl (10.8 mL, 14.1 mmol) keeping the temperature below 10° C. After addition (30 min), the reaction was stirred at 5° C. for 1 h and at r.t. for 1 h. The reaction was then cooled to 5° C. and N,N,N',N'-tetramethyphosphorodiamidic chloride (1.57 mL, 10.6 mmol) was added dropwise. The reaction mixture was heated at reflux for 2 days. The mixture was cooled, quenched with $H_2O$ (50 mL), acidified with aqueous 1 M HCl and extracted into EtOAc (3×50 mL). The organic layers were dried ($MgSO_4$), filtered and concentrated. Purification by flash silica column chromatography (gradient elution i-hex to 20% EtOAc in i-hex) gave the title compound as a white solid (3 g). The crude material was used in the next step. LCMS (ES+) 294, 296 (M+H)+.

(E)-Ethyl 3-(1-oxo-2-(2,2,2-trifluoroethyl)isoindolin-5-yl)acrylate (31)

A stirred mixture of 30 (2.96 g, 10.0 mmol), ethyl acrylate (1.62 mL, 15.0 mmol), palladium acetate (224 mg, 1.00 mmol), P(o-tol)$_3$ (608 mg, 2.00 mmol) and triethylamine (2.78 mL, 20.0 mmol) in MeCN (50 mL) was degassed under nitrogen for 15 min and heated to 80° C. for 3 h. An additional amount of palladium acetate (224 mg, 1.00 mmol), P(o-tol)$_3$ (608 mg, 2.00 mmol) and ethyl acrylate (1.00 mL, 9.26 mmol) were added and stirred at 80° C. for a further 2 h. The reaction mixture was cooled and the MeCN was removed in vacuo. The residue was partitioned between DCM and $H_2O$ and the organic layers were passed through a phase separator and concentrated. Purification by flash silica column chromatography (gradient elution i-hex to 75% EtOAc in i-hex) gave the title compound as a white solid (1.7 g). The crude material was used in the next step. LCMS (ES+) 314 (M+H)+.

(1R*,2R*,3R*)-Ethyl-2-(1-oxo-2-(2,2,2-trifluoroethyl)isoindolin-5-yl)-3-phenylcyclopropanecarboxylate (32)

Following method F from 31 (1.70 g, 5.40 mmol) and 6a (2.10 g, 8.10 mmol). Purification by flash silica column chromatography (gradient elution i-hex to 15% EtOAc in i-hex) gave the title compound as a white solid (340 mg). LCMS (ES+) 404 (M+H)+.

(1R,2R,3R)—N-Hydroxy-2-(1-oxo-2-(2,2,2-trifluoroethyl)isoindolin-5-yl)-3-phenylcyclopropanecarboxamide (33)

Following method A from 32 (340 mg, 0.84 mmol). Purification by flash silica column chromatography (gradient elution DCM to 6% MeOH in DCM) and then preparative HPLC gave the racemic mixture as a white solid. Preparative chiral HPLC gave the title compound (Chiralpak IC 30/70 EtOH (0.1 formic acid)/heptanes, 1.0 mL/min, RT 12.1 min). LCMS (ES+) 391 (M+H)+, RT 3.47 min (Analytical method 1). $^1$H NMR δ (ppm) (DMSO-d$_6$): 10.61 (1H, s), 8.72 (1H, s), 7.70 (1H, d, J=7.9 Hz), 7.56 (1H, s), 7.45 (1H, d, J=8.0 Hz), 7.35 (2H, d, J=7.6 Hz), 7.27 (2H, t, J=7.5 Hz), 7.19 (1H, t, J=7.2 Hz), 4.60 (2H, s), 4.39 (2H, q, J=9.7 Hz), 3.24 (1H, dd, J=6.8, 5.4 Hz), 2.93 (1H, dd, J=9.7, 6.8 Hz), 2.30 (1H, dd, J=9.7, 5.4 Hz).

Example 11

Reaction Scheme 11

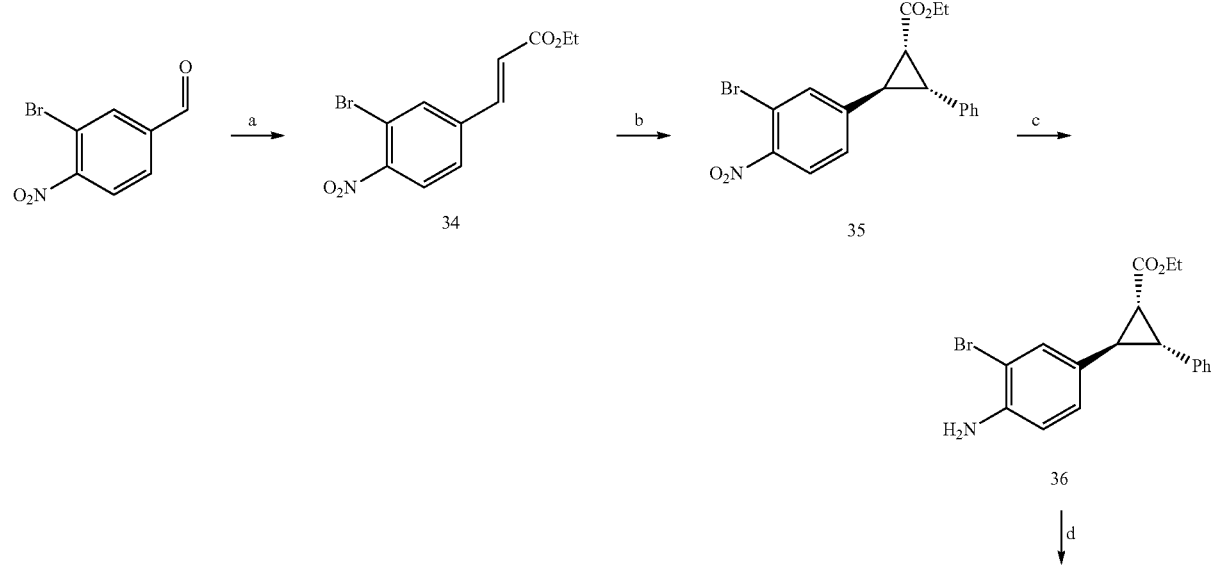

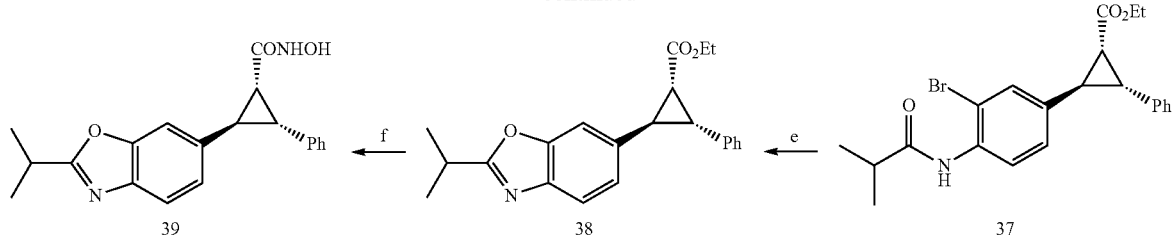

(E)-Ethyl-3-(3-bromo-4-nitrophenyl)acrylate (34)

Following method C from 3-bromo-4-nitrobenzaldehyde (5 g, 21.7 mmol). Purification by flash silica column chromatography (gradient elution i-hex to 10% EtOAc in i-hex) gave the title compound (2.4 g, 37%). LCMS (ES+) 300, 302 (M+H)$^+$.

(1R*,2R*,3R*)-Ethyl-2-(3-bromo-4-nitrophenyl)-3-phenylcyclopropanecarboxylate (35)

Following method F from compound 34 (2.35 g, 7.8 mmol) and 6a (4.04 g, 15.6 mmol). The reaction was incomplete after stirring at r.t. for 72 h. The reaction was cooled to −20° C. and an additional 1 equivalent of sulfonium salt, 12-crown-4 and LiHMDS were added and the mixture was stirred at r.t. for 3 h. Purification by flash silica column chromatography (gradient elution i-hex to 5% EtOAc in i-hex) gave the title compound as a yellow oil (630 mg, 21%). LCMS (ES+) 390, 391 (M+H)$^+$.

(1R*,2R*,3R*)-Ethyl-2-(4-amino-3-bromophenyl)-3-phenylcyclopropanecarboxylate (36)

To a solution of compound 35 (580 mg, 1.51 mmol) in ethanol (12 mL) and acetic acid (12 mL) was added iron powder (824 mg, 15.1 mmol) and the reaction mixture was stirred at r.t. for 3 h. The reaction mixture was filtered through Celite and concentrated. The residue was partitioned between 1N HCl and DCM-MeOH. The aqueous layer was extracted several times with DCM. The combined organic layers were concentrated to afford the title compound (470 mg, 88%). LCMS (ES+) 360, 362 (M+H)$^+$

(1R*,2R*,3R*)-Ethyl-2-(3-bromo-4-isobutyramidophenyl)-3-phenylcyclopropanecarboxylate (37)

To a solution of compound 36 (470 mg, 1.31 mmol) in DCM (10 mL) was added DIPEA (0.23 mL, 1.31 mmol) and isobutyryl chloride (140 mg, 1.31 mmol). The reaction mixture was stirred for 2 h, water was added, the organic phase isolated by phase separator and concentrated to afford the title compound (488 mg, 87%). LCMS (ES+) 430, 432 (M+H)$^+$.

(1R*,2R*,3R*)-Ethyl-2-(2-isopropylbenzo[d]oxazol-6-yl)-3-phenylcyclopropanecarboxylate (38)

A mixture of compound 37 (488 mg, 1.14 mmol), $K_2CO_3$ (314 mg, 2.28 mmol), pyridine (5 mL) in DMF (15 mL) was degassed for 30 min. Then copper(I)bromide (326 mg, 2.28 mmol) was added and the reaction mixture was heated under microwave irradiation at 140° C. for 4 h. The reaction mixture was diluted with DCM and washed several times with water and brine. The organic layers were combined, dried (MgSO$_4$), filtered and concentrated. Purification by flash silica column chromatography (gradient elution i-hex to 10% EtOAc in i-hex) gave the title compound (350 mg, 88%) as a yellow oil. LCMS (ES+) 350, 352 (M+H)$^+$.

(1R,2R,3R)—N-hydroxy-2-(2-isopropylbenzo[d]oxazol-6-yl)-3-phenylcyclopropanecarboxamide (39)

Following method A from compound 38 (350 mg, 1.00 mmol). Purification by flash silica column chromatography (gradient elution DCM to 5% MeOH in DCM) gave the racemic mixture as a tan solid (126 mg, 36%). Preparative chiral HPLC gave the title compound (Chiralpak IC, 20/80 EtOH (0.1% formic)/heptane, 1.0 mL/min, RT 15.7 min). LCMS (ES+) 337 (M+H)+, RT 3.59 min (Analytical method 1). $^1$H NMR δ (ppm) (DMSO-d$_6$): 10.63 (1H, s), 8.76 (1H, s), 7.66-7.64 (2H, m), 7.39 (2H, d, J=7.60 Hz), 7.35-7.29 (3H, m), 7.26-7.20 (1H, m), 3.36-3.23 (2H, m), 2.96 (1H, dd, J=9.6, 6.9 Hz), 2.30 (1H, dd, J=9.6, 5.4 Hz), 1.42 (6H, d, J=6.9 Hz).

Example 12

Reaction Scheme 12

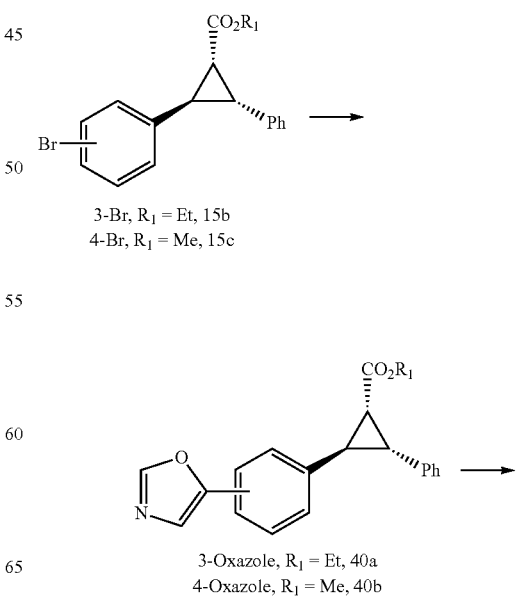

3-Br, R$_1$ = Et, 15b
4-Br, R$_1$ = Me, 15c

3-Oxazole, R$_1$ = Et, 40a
4-Oxazole, R$_1$ = Me, 40b

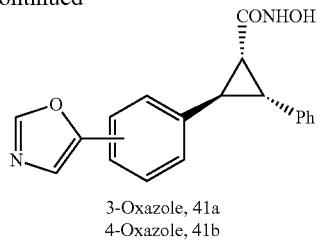

3-Oxazole, 41a
4-Oxazole, 41b

(1R*,2R*,3R*)-Ethyl-2-(3-(oxazol-5-yl)phenyl)-3-phenylcyclopropanecarboxylate (40a)

A stirred solution of 15b (500 mg, 1.45 mmol), oxazole (0.19 mL, 2.90 mmol), Pd(OAc)$_2$ (16 mg, 0.07 mmol), di-tert-butyl(2',4',6'-triisopropyl-3,4,5,6-tetramethylbiphenyl-2-yl)phosphine (67 mg, 0.14 mmol), K$_2$CO$_3$ (600 mg, 4.35 mmol), pivalic acid (59 mg, 0.58 mmol) in DMA (8 mL) was degassed with nitrogen for 15 min before heating at 110° C. for 16 h. The mixture was cooled and diluted with DCM (20 mL) and washed with H$_2$O (3×30 mL). The organic layers were passed through a phase separator and concentrated. Purification by flash silica column chromatography (gradient elution i-hex to 25% EtOAc in i-hex) gave the title compound as a colourless oil (494 mg, 100%). LCMS (ES+) 334 (M+H)$^+$.

(1R*,2R*,3R*)-Methyl 2-(4-(oxazol-5-yl)phenyl)-3-phenylcyclopropanecarboxylate (40b)

A stirred solution of 15c (482 mg, 1.46 mmol), oxazole (0.19 mL, 2.42 mmol), Pd(OAc)$_2$ (16 mg, 0.07 mmol), di-tert-butyl(2',4',6'-triisopropyl-3,4,5,6-tetramethylbiphenyl-2-yl)phosphine (70 mg, 0.146 mmol), K$_2$CO$_3$ (604 mg, 4.38 mmol), pivalic acid (59 mg, 0.58 mmol) in DMA (7.5 mL) was degassed with nitrogen for 15 min before heating at 110° C. for 16 h. The mixture was cooled and diluted with DCM (20 mL) and washed with H$_2$O (3×30 mL). The organic layers were passed through a phase separator and concentrated. Purification by flash silica column chromatography (gradient elution i-hex to 25% EtOAc in i-hex) gave the title compound as a colourless oil (300 mg, 65%). LCMS (ES+) 320 (M+H)$^+$.

(1R,2R,3R)—N-Hydroxy-2-(3-(oxazol-5-yl)phenyl)-3-phenylcyclopropanecarboxamide (41a)

Following method A from compound 40a (482 mg, 1.45 mmol). Purification by flash silica column chromatography (gradient elution DCM to 5% MeOH in DCM) gave the racemic mixture as a white solid (233 mg, 50%). Preparative chiral HPLC gave the title compound (Chiralpak IC 40/60 EtOH (0.1 formic acid)/heptane, 1.0 mL/min, RT 7.7 min). LCMS (ES+) 321 (M+H)+, RT 2.82 min (Analytical method 1). $^1$H NMR δ (ppm) (DMSO-d$_6$): 10.62 (1H, s), 8.76 (1H, s), 8.52 (1H, s), 7.80 (1H, s), 7.70 (1H, s), 7.64 (1H, d, J=7.8 Hz), 7.49 (1H, t, J=7.7 Hz), 7.42-7.28 (5H, m), 7.24 (1H, t, J=7.2 Hz), 3.22 (1H, dd, J=6.9, 5.4 Hz), 2.98 (1H, dd, J=9.6, 6.9 Hz), 2.32 (1H, dd, J=9.6, 5.4 Hz).

(1R,2R,3R)—N-Hydroxy-2-(4-(oxazol-5-yl)phenyl)-3-phenylcyclopropanecarboxamide (41b)

Following method A from compound 40b. Purification by flash silica column chromatography (gradient elution DCM to 5% MeOH in DCM) gave the racemic mixture as a white solid (88 mg, 29%). Preparative chiral HPLC gave the title compound (Chiralpak IC 20/80 EtOH (0.1 formic acid)/heptane, 1.0 mL/min, RT 18.7 min). LCMS (ES+) 321 (M+H)+, RT 2.77 min (Analytical method 1). $^1$H NMR δ (ppm) (DMSO-d$_6$): 10.63 (1H, s), 8.76 (1H, s), 8.49 (1H, s), 7.76-7.72 (3H, m), 7.47-7.36 (4H, m), 7.35-7.29 (2H, m), 7.25-7.20 (1H, m), 3.18 (1H, dd, J=6.8, 5.4 Hz), 2.94 (1H, dd, J=9.6, 6.8 Hz), 2.30 (1H, dd, J=9.6, 5.4 Hz).

Example 13

Reaction Scheme 13

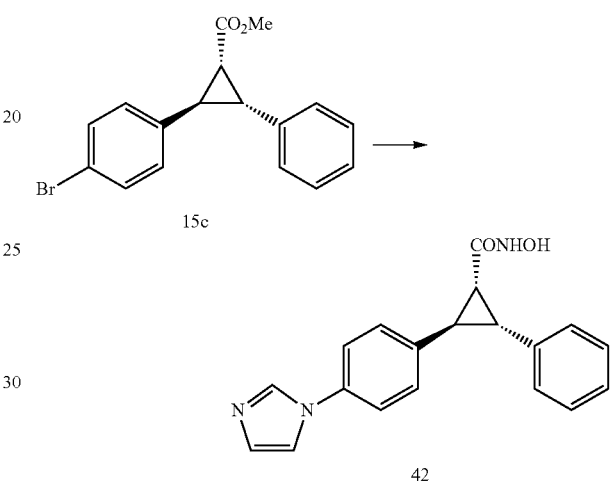

(1R*,2R*,3R*)-2-(4-(1H-imidazol-1-yl)phenyl)-N-hydroxy-3-phenylcyclopropanecarboxamide (42)

A stirred solution of 15c (100 mg, 0.30 mmol), CuCl (3 mg, 0.03 mmol) and K$_2$CO$_3$ (41 mg, 0.30 mmol) in NMP (0.1 mL) was degassed with nitrogen before addition of acetylacetone (7 μl, 0.075 mmol) and imidazole (26 mg, 0.39 mmol). The mixture was stirred at 130° C. for 17 h, cooled to r.t., diluted with DCM and washed with 1 M NaHCO$_3$ (2×20 mL). The organic layers were passed through a phase separator and concentrated (150 mg). The crude material was dissolved in THF:MeOH (1:1, 3 mL) and hydroxylamine (0.1 mL, 50% aqueous solution, 1.51 mmol) and potassium hydroxide (67 mg, 1.20 mmol) were added. The mixture was stirred at r.t. for 2 h., neutralized with 1 M HCl and extracted into EtOAc. The organic layers were concentrated and the residue re-dissolved in pyridine (1 mL). To this solution was added hydroxylamine hydrochloride (20 mg, 0.29 mmol), BOP (87 mg, 0.20 mmol) and triethylamine (82 μl, 0.59 mmol). The mixture was stirred at r.t. for 2 h, concentrated and partitioned between DCM and H$_2$O. The organic layers were isolated by phase separator and concentrated. Purification by preparative HPLC gave the racemic mixture as a white solid (10 mg, 11% over 3 steps). LCMS (ES+) 320 (M+H)+, RT 2.24 min (Analytical method 1). $^1$H NMR δ (ppm) (DMSO-d$_6$): 10.58 (1H, s), 8.71 (1H, s), 8.30 (1H, s), 7.77 (1H, s), 7.62 (2H, d, J=8.1 Hz), 7.43 (2H, d, J=8.1 Hz), 7.35 (2H, d, J=7.6 Hz), 7.31-7.24 (2H, m), 7.22-7.16 (2H, m), 3.17 (1H, dd, J=6.8, 5.4 Hz), 2.89 (1H, dd, J=9.6, 6.9 Hz), 2.24 (1H, dd, J=9.5, 5.3 Hz).

Example 14

Reaction Scheme 14

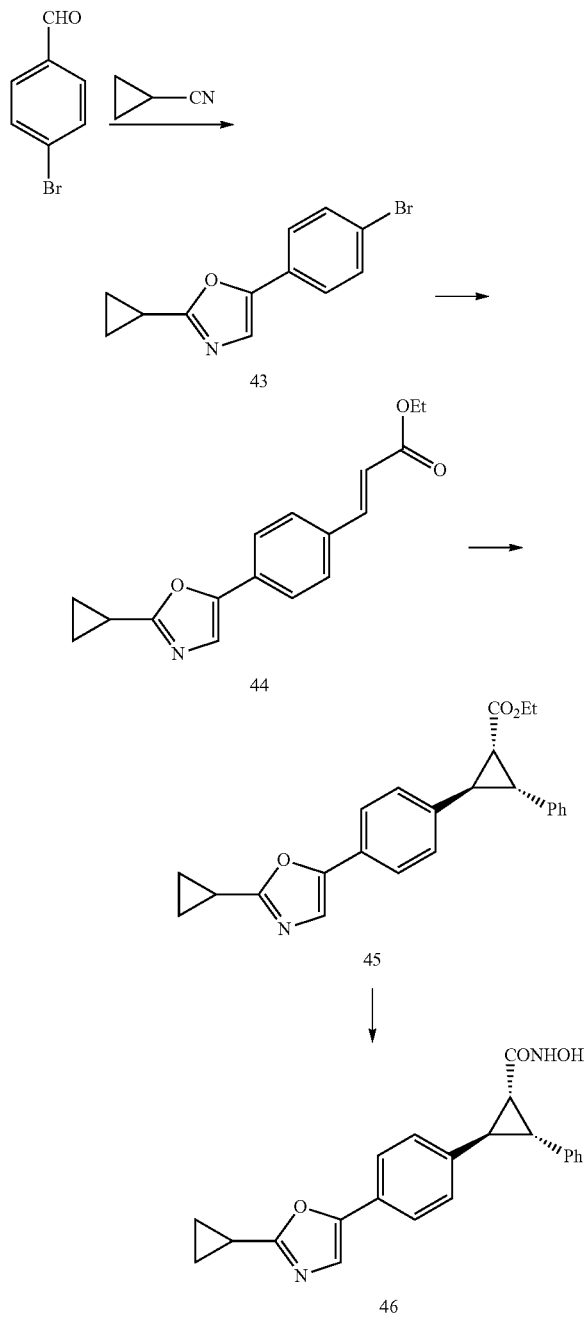

water. The organic layers were separated, dried ($Mg_2SO_4$), filtered and concentrated to give a dark red gum. Purification by flash silica column chromatography (gradient elution i-hex to 40% EtOAc in i-hex) gave the title compound as a pale yellow solid (3.97 g, 60%). LCMS (ES+) 264, 266 $(M+H)^+$.

(E)-Ethyl-3-(4-(2-cyclopropyloxazol-5-yl)phenyl) acrylate (44)

Compound 43 (3.97 g, 15 mmol), ethyl acrylate (2.1 mL, 19.5 mmol), $Pd(OAc)_2$ (337 mg, 1.5 mmol), tri-ortho-tolyl-phoshine (915 mg, 3 mmol), triethylamine (4.2 mL, 30 mmol) in MeCN (55 mL) were degassed with nitrogen for 15 min before heating the mixture to 80° C. for 18 h. The reaction mixture was concentrated and the brown residue was taken up in DCM (150 mL), washed with water, separated, dried ($Mg_2SO_4$), filtered and concentrated to give a brown gum. Purification by flash silica column chromatography (gradient elution i-hex to EtOAc) gave the title compound as a pale yellow solid (3.44 g, 80%). LCMS (ES+) 284 $(M+H)^+$.

(1R*,2R*,3R*)-Ethyl-2-(4-(2-cyclopropyloxazol-5-yl)phenyl)-3-phenylcyclopropanecarboxylate (45)

Following method F from compound 44 (360 mg, 1.27 mmol) and 6a (494 mg, 1.91 mmol). Purification by flash silica column chromatography (gradient elution i-hex to 25% EtOAc in i-hex) gave the title compound as a colourless oil (300 mg, 7:2, trans:cis, 63%). LCMS (ES+) 374 $(M+H)^+$.

(1R,2R,3R)-2-(4-(2-Cyclopropyloxazol-5-yl)phenyl)-N-hydroxy-3-phenylcyclopropanecarboxamide (46)

Following method A from compound 45 (300 mg, 0.80 mmol). Purification by flash silica column chromatography (gradient elution DCM to 3% MeOH in DCM) gave the racemic mixture as a white solid (300 mg, 78%). Preparative chiral HPLC gave the title compound (Chiralpak IC 30/70 EtOH (0.1 formic acid)/heptane, 1.0 mL/min, RT 19.8 min). LCMS (ES+) 361 (M+H)+, (ES−) 359 (M−H)−, RT 3.67 min (Analytical method 1). $^1$H NMR δ (ppm) (DMSO-$d_6$): 10.62 (1H, s), 8.76 (1H, s), 7.65 (2H, d, J=8.2 Hz), 7.52 (1H, s), 7.42-7.35 (4H, m), 7.31 (2H, t, J=7.5 Hz), 7.23 (1H, t, J=7.2 Hz), 3.17 (1H, dd, J=6.9, 5.4 Hz), 2.92 (1H, dd, J=9.7, 6.9 Hz), 2.28 (1H, dd, J=9.6, 5.4 Hz), 2.23-2.17 (1H, m), 1.15-1.08 (2H, m), 1.09-1.03 (2H, m).

Example 15

Reaction Scheme 15

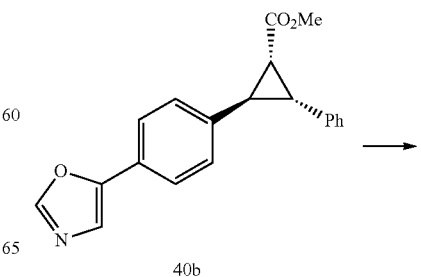

5-(4-Bromophenyl)-2-cyclopropyloxazole (43)

Triflic acid (18.6 mL, 0.113 mol) was added dropwise to a solution of thallium acetate (14.37 g, 0.037 mol) in cyclopropylnitrile (200 mL) at r.t. under nitrogen. The solution was stirred for 15 min before a solution of 4-bromoacetophenone in cyclopropylnitrile (120 mL) was added and the solution was heated to 90° C. for 2 h. The reaction mixture was concentrated and the red residue was taken up in DCM (500 mL), washed with saturated $NaHCO_3$ and

(1R*,2R*,3R*)-Methyl-2-phenyl-3-(4-(2-phenyloxazol-5-yl)phenyl)cyclopropanecarboxylate (47)

Compound 40b (75 mg, 0.23 mmol), pivalic acid (14 mg, 0.14 mmol), potassium tert-butoxide (78 mg, 0.69 mmol) and RuPhos (16 mg, 0.034 mmol) were dissolved in dry toluene (5 mL) and the reaction flask was evacuated and back-filled with nitrogen three times. Pd(OAc)$_2$ (4 mg, 0.017 mmol) and bromobenzene (54 mg, 0.34 mmol) were then added and the mixture was heated to 110° C. overnight. The reaction mixture was cooled and treated with 0.1 M HCl (5 mL) and extracted with Et$_2$O (3×10 mL). The combined organic layers were dried (MgSO$_4$), filtered and concentrated. Purification by flash silica column chromatography (gradient elution i-hex to 50% EtOAc in i-hex) gave the title compound as a colourless oil (22 mg, 26%). LCMS (ES+) 396 (M+H)$^+$.

(1R*,2R*,3R*)—N-Hydroxy-2-phenyl-3-(4-(2-phenyloxazol-5-yl)phenyl)cyclopropanecarboxamide (48)

Following method A from compound 47 (22 mg, 0.06 mmol). Purification by preparative HPLC gave the title compound as a white solid (16 mg, 70%). LCMS (ES+) 397 (M+H)+, RT 4.09 min (Analytical method 1). $^1$H NMR δ (ppm) (DMSO-d$_6$): 10.58 (1H, s), 8.71 (1H, s), 8.12-8.08 (2H, m), 7.81 (3H, d, J=8.2 Hz), 7.62-7.54 (3H, m), 7.42 (2H, d, J=8.0 Hz), 7.36 (2H, d, J=7.6 Hz), 7.31-7.23 (2H, m), 7.22-7.15 (1H, m), 3.17 (1H, dd, J=6.8, 5.3 Hz), 2.91 (1H, dd, J=9.6, 6.8 Hz), 2.27 (1H, dd, J=9.6, 5.3 Hz).

Example 16

Reaction Scheme 16

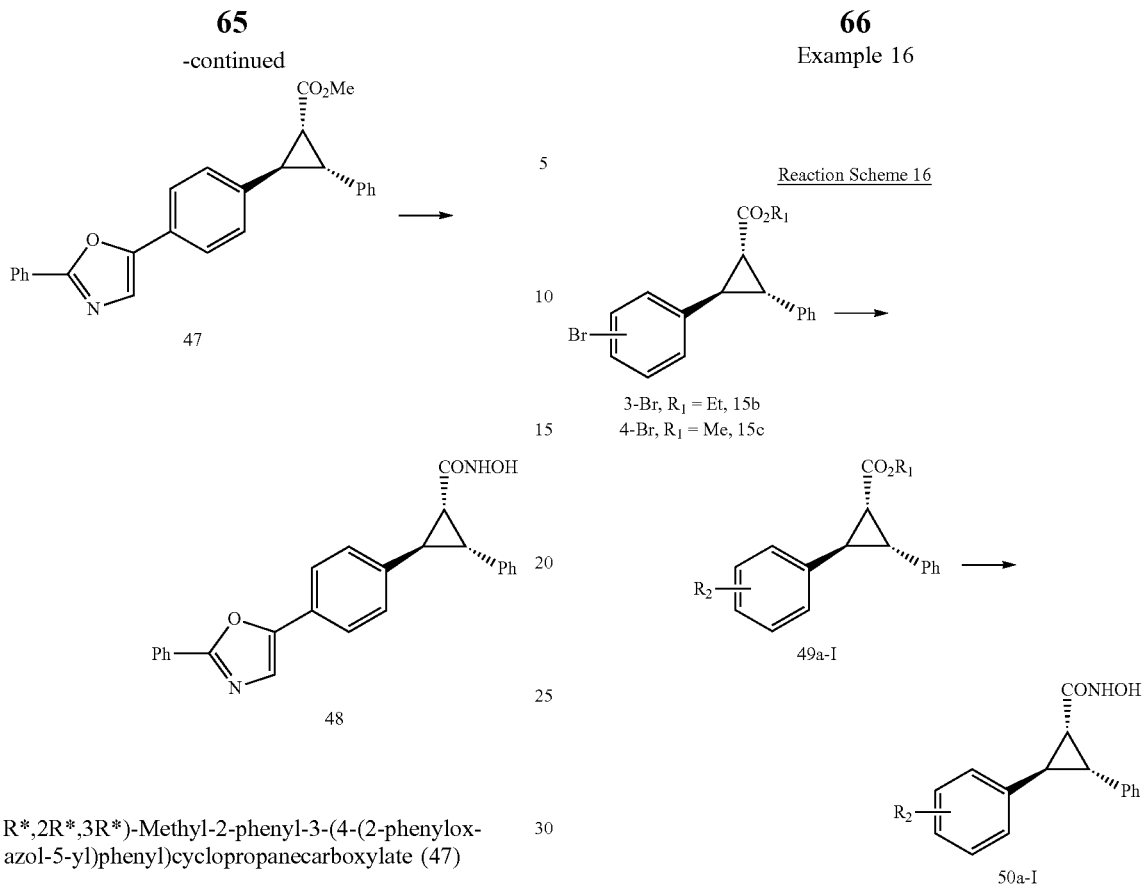

TABLE 3

| R2 | 3 or 4 Substitution | Compound |
|---|---|---|
| 5-F-pyrimidin-2-yl | 4 | 50a |
| 5-F-pyrimidin-2-yl | 3 | 50b |
| 5-cyclopropyl-pyrimidin-2-yl | 4 | 50c |
| 4-CF₃-pyrimidin-2-yl | 4 | 50d |

TABLE 3-continued

| R2 | 3 or 4 Substitution | Compound |
|---|---|---|
| 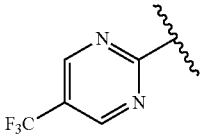 | 4 | 50e |
| 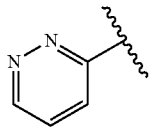 [SMILES: *c1cccnn1] | 4 | 50f |
| 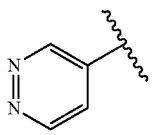 | 4 | 50g |
| 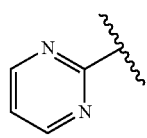 [SMILES: *c1ncccn1] | 4 | 50h |
| 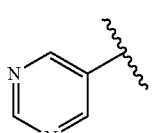 | 4 | 50i |
| 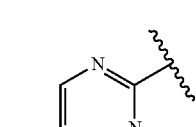 | 4 | 50j |
| 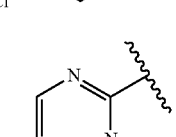 | 4 | 50k |
| 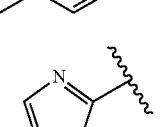 | 4 | 50l |

(1R*,2R*,3R*)-Methyl 2-(4-(5-fluoropyrimidin-2-yl)phenyl)-3-phenylcyclopropanecarboxylate (49a)

Following method G from the crude boronate derived from 15c (250 mg) and 2-chloro-5-fluoropyrimidine (91 mg, 0.69 mmol). Purification by flash silica column chromatography (gradient elution i-hex to 10% EtOAc in i-hex) gave the title compound as a colourless oil (240 mg, 100%). LCMS (ES+) 349 (M+H)$^+$.

(1R*,2R*,3R*)-Ethyl-2-(3-(5-fluoropyrimidin-2-yl)phenyl)-3-phenylcyclopropanecarboxylate (49b)

Following method G from the crude boronate derived from 15b (300 mg) and 2-chloro-5-fluoropyrimidine (107 mg, 0.81 mmol). Purification by flash silica column chromatography (gradient elution i-hex to 10% EtOAc in i-hex) gave the title compound as a colourless oil (140 mg, 50%). LCMS (ES+) 363 (M+H)$^+$.

(1R*,2R*,3R*)-Methyl-2-(4-(5-cyclopropylpyrimidin-2-yl)phenyl)-3-phenylcyclopropanecarboxylate (49c)

Following method G from the crude boronate derived from 15c (250 mg) and 2-bromo-5-cyclopropylpyrimidine (137 mg, 0.69 mmol). Purification by flash silica column chromatography (gradient elution i-hex to 10% EtOAc in i-hex) gave the title compound as a colourless oil (240 mg, 98%). LCMS (ES+) 371 (M+H)$^+$.

(1R*,2R*,3R*)-Methyl-2-phenyl-3-(4-(4-(trifluoromethyl)pyrimidin-2-yl)phenyl)cyclopropanecarboxylate (49d)

Following method G from the crude boronate derived from 15c (250 mg) and 2-chloro-4-trifluoromethylpyrimidine (126 mg, 0.69 mmol). Purification by flash silica column chromatography (gradient elution i-hex to 10% EtOAc in i-hex) gave the title compound as a colourless oil (220 mg, 84%). LCMS (ES+) 399 (M+H)$^+$.

(1R*,2R*,3R*)-Methyl-2-phenyl-3-(4-(5-(trifluoromethyl)pyrimidin-2-yl)phenyl)cyclopropanecarboxylate (49e)

Following method G from the crude boronate derived from 15c (480 mg) and 2-chloro-5-trifluoromethylpyrimidine (243 mg, 1.33 mmol). Purification by flash silica column chromatography (gradient elution i-hex to 20% EtOAc in i-hex) gave the title compound as a white solid (180 mg, 36%). LCMS (ES+) 399 (M+H)$^+$.

(1R*,2R*,3R*)-Methyl-2-phenyl-3-(4-(pyridazin-3-yl)phenyl)cyclopropanecarboxamide (49f)

Following method G from the crude boronate derived from 15c (400 mg), and 3-bromopyridazine (160 mg, 1.00 mmol). Purification by flash silica column chromatography (gradient elution i-hex to 10% EtOAc in i-hex) gave the title compound as a colourless oil (220 mg, 84%). LCMS (ES+) 331 (M+H)$^+$.

(1R*,2R*,3R*)-Methyl-2-phenyl-3-(4-(pyridazin-4-yl)phenyl)cyclopropanecarboxamide (49g)

Following method G from the crude boronate derived from 15c (400 mg), and 4-bromopyridazine (160 mg, 1.00 mmol). Purification by flash silica column chromatography (gradient elution i-hex to 10% EtOAc in i-hex) gave the title compound as a pale yellow solid (210 mg, 61%). LCMS (ES+) 331 (M+H)$^+$.

(1R*,2R*,3R*)-Methyl-2-phenyl-3-(4-(pyrimidin-2-yl)phenyl)cyclopropanecarboxylate (49h)

Following method G from the crude boronate derived from 15c (274 mg), and 2-chloropyrimidine (87 mg, 0.76 mmol). Purification by flash silica column chromatography (gradient elution i-hex to 25% EtOAc in i-hex) gave the title compound as a pale yellow oil (110 mg, 46%). LCMS (ES+) 331 (M+H)$^+$.

(1R*,2R*,3R*)-Methyl-2-phenyl-3-(4-(pyrimidin-5-yl)phenyl)cyclopropanecarboxylate (49i)

To a stirred solution of 15c (130 mg, 0.39 mmol) in MeOH:DME (1:5, 5 mL), was added Pd(PPh$_3$)$_4$ (45 mg, 0.039 mmol), cesium fluoride (119 mg, 0.78 mmol) and 5-pyrimidine boronic acid (58 mg, 0.47 mmol). The mixture was degassed with nitrogen for 15 min before heating in the microwave at 120° C. for 1 h. The reaction mixture was diluted with H$_2$O (10 mL) and extracted into DCM (50 mL). The organic layers were dried over MgSO$_4$, filtered and concentrated. Purification by column chromatography (gradient elution i-hex to 5% EtOAc in i-hex) gave the title compound as a colourless oil (120 mg, 93%). LCMS (ES+) 331 (M+H)$^+$.

(1R*,2R*,3R*)-Methyl-2-(4-(5-chloropyrimidin-2-yl)phenyl)-3-phenylcyclopropanecarboxylate (49j)

Following method G from the crude boronate derived from 15c (1.5 mmol), and 2,5-dichloropyrimidine (298 mg, 2.00 mmol). Purification by flash silica column chromatography (gradient elution i-hex to 50% EtOAc in i-hex) gave the title compound as a pale yellow oil (305 mg, 56%). LCMS (ES+) 365 (M+H)$^+$.

(1R*,2R*,3R*)-Methyl-2-(4-(5-methylpyrimidin-2-yl)phenyl)-3-phenylcyclopropanecarboxylate (49k)

Following method G from the crude boronate derived from 15c (250 mg), and 2-chloro-5-methylpyrimidine (89 mg, 0.69 mmol). Purification by flash silica column chromatography (gradient elution i-hex to 25% EtOAc in i-hex) gave the title compound as a pale yellow oil (180 mg, 79%). LCMS (ES+) 345 (M+H)$^+$.

(1R*,2R*,3R*)-Methyl-2-(4-(5-methyl-1H-imidazol-2-yl)phenyl)-3-phenylcyclopropanecarboxylate (49l)

Following method G from crude boronate derived from 15c (1.5 mmol) and 2-bromo-4-methylimidazole (242 mg, 1.5 mmol). The mixture was stirred at 100° C. for 48 h, diluted with H$_2$O (20 mL) and extracted into DCM (50 mL). The layers were passed through a phase separator and concentrated. Purification Following flash silica column chromatography (gradient elution DCM/MeOH 0% to 10%) gave the ester intermediate as a yellow oil (285 mg). The crude material was used in the next step. LCMS (ES+) 335 (M+H)$^+$.

(1R*,2R*,3R*)-2-(4-(5-Fluoropyrimidin-2-yl)phenyl)-N-hydroxy-3-phenylcyclopropanecarboxamide (50a)

Following method A from compound 49a (220 mg, 0.63 mmol). Purification by flash silica column chromatography (gradient elution DCM to 5% MeOH in DCM) gave the title compound as a white solid (81 mg, 37%). LCMS (ES+) 350 (M+H)+, RT 3.13 min (Analytical method 1). $^1$H NMR δ (ppm) (DMSO-d$_6$): 10.58 (1H, s), 8.97 (2H, d, J=0.8 Hz), 8.70 (1H, s), 8.30 (2H, d, J=8.2 Hz), 7.44 (2H, d, J=8.2 Hz), 7.36 (2H, d, J=7.6 Hz), 7.27 (2H, t, J=7.5 Hz), 7.20 (1H, d, J=7.2 Hz), 3.18 (1H, dd, J=6.7, 5.6 Hz), 2.93 (1H, dd, J=9.6, 6.7 Hz), 2.30 (1H, dd, J=9.6, 5.4 Hz)

(1R*,2R*,3R*)-2-(3-(5-Fluoropyrimidin-2-yl)phenyl)-N-hydroxy-3-phenylcyclopropanecarboxamide (50b)

Following method A from compound 49b (140 mg, 0.39 mmol). Purification by flash silica column chromatography (gradient elution DCM to 7% MeOH in DCM) and preparative HPLC gave the title compound as a racemic mixture (12 mg, 9%). LCMS (ES+) 350 (M+H)+, RT 3.61 min (Analytical method 1). $^1$H NMR δ (ppm) (DMSO-d$_6$): 10.59 (1H, s), 9.01 (2H, s), 8.71 (1H, s), 8.20 (2H, t, J=4.0 Hz), 7.51-7.48 (2H, m), 7.37 (2H, d, J=7.6 Hz), 7.29-7.24 (2H, m), 7.20 (1H, d, J=7.3 Hz), 3.22 (1H, dd, J=6.8, 5.5 Hz), 2.85 (1H, dd, J=9.6, 6.8 Hz), 2.32 (1H, dd, J=9.6, 5.4 Hz).

(1R*,2R*,3R*)-2-(4-(5-Cyclopropylpyrimidin-2-yl)phenyl)-N-hydroxy-3-phenylcyclopropanecarboxamide (50c)

Following method A from compound 49c (240 mg, 0.65 mmol). Purification by flash silica column chromatography (gradient elution DCM to 5% MeOH in DCM) gave the title compound as a white solid (155 mg, 64%). LCMS (ES+) 372 (M+H)+, RT 3.89 min (Analytical method 1). $^1$H NMR δ (ppm) (DMSO-d$_6$): 10.58 (1H, s), 8.70 (1H, s), 8.64 (1H, d, J=5.2 Hz), 8.30 (2H, d, J=8.2 Hz), 7.40 (2H, d, J=8.2 Hz), 7.38-7.29 (3H, m), 7.27 (2H, t, J=7.5 Hz), 7.22-7.15 (1H, m), 3.17 (1H, dd, J=6.8, 5.4 Hz), 2.90 (1H, dd, J=9.6, 6.9 Hz), 2.28 (1H, dd, J=9.6, 5.4 Hz), 2.21-2.13 (1H, m), 1.19-1.09 (4H, m).

(1R*,2R*,3R*)-2-(4-(4-Trifluoromethylpyrimidin-2-yl)phenyl)-N-hydroxy-3-phenylcyclopropanecarboxamide (50d)

Following method A from compound 49d (220 mg, 0.55 mmol). The carboxylic acid was obtained as the major product. The reaction mixture was acidified with aqueous 1M HCl and extracted into EtOAc (3×10 mL). The organic layers were combined, dried (MgSO$_4$), filtered and concentrated. The compound was then subjected to method B. Purification by flash silica column chromatography (gradient elution DCM to 5% MeOH in DCM) gave the title compound as a white solid (77 mg, 37%). LCMS (ES+) 400 (M+H)+, 398 (M−H)−, RT 13.26 min (Analytical method 3). $^1$H NMR δ (ppm) (DMSO-d$_6$): 10.60 (1H, s), 9.26 (1H, d, J=5.0 Hz), 8.71 (1H, s), 8.38 (2H, d, J=8.2 Hz), 7.93 (1H, d, J=5.0 Hz), 7.50 (2H, d, J=8.2 Hz), 7.36 (2H, d, J=7.6 Hz), 7.28 (2H, t, J=7.5 Hz), 7.22-7.15 (1H, m), 3.21 (1H, dd, J=6.8, 5.4 Hz), 2.94 (1H, dd, J=9.7, 6.9 Hz), 2.32 (1H, dd, J=9.7, 5.3 Hz).

(1R,2R,3R)-2-(4-(5-Trifluoromethylpyrimidin-2-yl)phenyl)-N-hydroxy-3-phenylcyclopropanecarboxamide (50e)

Following method A from compound 49e (180 mg, 0.45 mmol). Purification by flash silica column chromatography (gradient elution DCM to 5% MeOH in DCM) gave the racemic mixture as a white solid (99 mg, 55%). Preparative chiral HPLC gave the title compound (Chiralpak IC 10/90 IPA/MeOH (50/50/0.1% formic acid)/Heptane, 1.0 mL/min, RT 16.2 min). LCMS (ES+) 400 (M+H)+, RT 3.96 min (Analytical method 1). $^1$H NMR δ (ppm) (DMSO-d$_6$): 10.66 (1H, s), 9.39 (2H, s), 8.79 (1H, s), 8.47 (2H, d, J=8.2 Hz), 7.55 (2H, d, J=8.2 Hz), 7.41 (2H, d, J=7.6 Hz), 7.33 (2H, t, J=7.5 Hz), 7.24 (1H, t, J=7.2 Hz), 3.26 (1H, dd, J=6.8, 5.3 Hz), 3.00 (1H, dd, J=9.6, 6.8 Hz), 2.38 (1H, dd, J=9.6, 5.3 Hz).

(1R*,2R*,3R*)—N-Hydroxy-2-phenyl-3-(4-(pyridazin-3-yl)phenyl)cyclopropanecarboxamide (50f)

Following method A from compound 49f (68 mg, 0.21 mmol). Purification using an Isolute anion exchange SPE (elution DCM-MeOH, 1:1) gave the racemic mixture as a white solid (49 mg, 70%). LCMS (ES+) 332 (M+H)+, RT 2.95 min (Analytical method 1). $^1$H NMR δ (ppm) (DMSO-$d_6$): 10.59 (1H, s), 9.20 (1H, dd, J=4.8, 1.5 Hz), 8.71 (1H, s), 8.23 (1H, dd, J=8.6, 1.5 Hz), 8.14 (2H, d, J=8.1 Hz), 7.78 (1H, dd, J=8.6, 4.9 Hz), 7.48 (2H, d, J=8.1 Hz), 7.37 (2H, d, J=7.5 Hz), 7.32-7.24 (2H, m), 7.22-7.16 (1H, m), 3.19 (1H, dd, J=6.8, 5.4 Hz), 2.93 (1H, dd, J=9.6, 6.8 Hz), 2.31 (1H, dd, J=9.6, 5.4 Hz).

(1R*,2R*,3R*)—N-Hydroxy-2-phenyl-3-(4-(pyridazin-4-yl)phenyl)cyclopropanecarboxamide (50g)

Following method A from compound 49g (190 mg, 0.58 mmol). Purification by flash silica column chromatography (gradient elution DCM to 10% MeOH in DCM) gave the racemic mixture as an off-white solid (75 mg, 39%). LCMS (ES+) 332 (M+H)+, RT 2.77 min (Analytical method 4). $^1$H NMR δ (ppm) (DMSO-$d_6$): 10.59 (1H, s), 9.66 (1H, dd, J=2.5, 1.2 Hz), 9.26 (1H, dd, J=5.4, 1.23 Hz), 8.71 (1H, d, J=1.7 Hz), 8.02 (1H, dd, J=5.5, 2.5 Hz), 7.92 (2H, d, J=8.1 Hz), 7.48 (2H, d, J=8.1 Hz), 7.36 (2H, d, J=7.6 Hz), 7.31-7.23 (2H, m), 7.22-7.16 (1H, m), 3.22-3.16 (1H, m), 2.93 (1H, dd, J=9.6, 6.8 Hz), 2.29 (1H, dd, J=9.6, 5.4 Hz).

(1R*,2R*,3R)—N-Hydroxy-2-phenyl-3-(4-(pyrimidin-2-yl)phenyl)cyclopropanecarboxamide (50h)

Following method A from compound 49h (110 mg, 0.33 mmol). Purification by column chromatography (gradient elution DCM to 5% MeOH in DCM) gave the title compound as a white solid (75 mg, 67%). LCMS (ES+) 332 (M+H)+, (ES-) 330 (M+H)-, RT 2.78 min (Analytical method 1). $^1$H NMR δ (ppm) (DMSO-$d_6$): 10.59 (1H, s), 8.90 (2H, d, J=4.8 Hz), 8.72 (1H, s), 8.36 (2H, d, J=8.2 Hz), 7.48-7.40 (3H, m), 7.36 (2H, d, J=7.6 Hz), 7.27 (2H, t, J=7.6 Hz), 7.19 (1H, t, J=7.3 Hz), 3.18 (1H, dd, J=6.8, 5.4 Hz), 2.93 (1H, dd, J=9.6, 6.8 Hz), 2.30 (1H, dd, J=9.6, 5.4 Hz).

(1R*,2R*,3R)—N-Hydroxy-2-phenyl-3-(4-(pyrimidin-5-yl)phenyl)cyclopropanecarboxamide (50i)

Following method A from compound 49i (120 mg, 0.36 mmol). Purification by flash silica column chromatography (gradient elution DCM to 5% MeOH in DCM) and passage through an Isolute anion exchange SPE (elution DCM-MeOH, 1:1) gave the title compound as a white solid (21 mg, 17%). LCMS (ES+) 332 (M+H)+, RT 3.07 min (Analytical method 1). $^1$H NMR δ (ppm) (DMSO-$d_6$): 10.60 (1H, s), 9.18 (1H, s), 9.15 (2H, s), 8.72 (1H, s), 7.79 (2H, d, J=8.1 Hz), 7.45 (2H, d, J=8.1 Hz), 7.35 (2H, d, J=7.6 Hz), 7.27 (2H, t, J=7.6 Hz), 7.19 (1H, t, J=7.2 Hz), 3.18 (1H, dd, J=6.8, 5.4 Hz), 2.92 (1H, dd, J=9.6, 6.8 Hz), 2.27 (1H, dd, J=9.6, 5.4 Hz).

(1R,2R,3R)-2-(4-(5-Chloropyrimidin-2-yl)phenyl)-N-hydroxy-3-phenylcyclopropanecarboxamide (50j)

Following method A from compound 49j (300 mg, 0.82 mmol). The racemic mixture (119 mg, 40%) was obtained after purification using flash silica column chromatography (gradient elution DCM/MeOH 0% to 10%). Preparative chiral HPLC gave the title compound (Chiralpak IC 30/70 IPA/MeOH (50/50/0.1 formic acid)/heptanes, 1.0 mL/min, RT 8.21 min). LCMS (ES+) 366 (M+H), RT 3.90 min (Analytical method 1). $^1$H NMR δ (ppm) (DMSO-$d_6$): 10.64 (1H, s), 9.06 (2H, s), 8.77 (1H, s), 8.37 (2H, d, J=8.2 Hz), 7.50 (2H, d, J=8.2 Hz), 7.40 (2H, d, J=7.6 Hz), 7.32 (2H, t, J=7.5 Hz), 7.26-7.21 (1H, m), 3.23 (1H, dd, J=6.8, 5.4 Hz), 2.98 (1H, dd, J=9.7, 6.8 Hz), 2.35 (1H, dd, J=9.7, 5.4 Hz).

(1R*,2R*,3R*)—N-Hydroxy-2-(4-(5-methylpyrimidin-2-yl)phenyl)-3-phenylcyclopropanecarboxamide (50k)

Following method A from compound 49k (180 mg, 0.52 mmol). The carboxylic acid was obtained as the major product. The reaction mixture was acidified with aqueous 1M HCl and extracted into EtOAc (3×10 mL). The organic layers were combined, dried (MgSO$_4$), concentrated and the residue subjected to method B. Purification by flash silica column chromatography (gradient elution DCM to 5% MeOH in DCM) and preparative HPLC gave the title compound as a white solid (16 mg, 7%). LCMS (ES+) 346 (M+H)+, RT 3.50 min (Analytical method 1). $^1$H NMR δ (ppm) (DMSO-$d_6$): 10.58 (1H, s), 8.74 (2H, d, J=0.8 Hz), 8.70 (1H, s), 8.35-8.28 (2H, m), 7.45-7.32 (4H, m), 7.30-7.23 (2H, m), 7.22-7.15 (1H, m), 3.17 (1H, dd, J=6.7, 5.4 Hz), 2.91 (1H, dd, J=9.6, 6.8 Hz), 2.31 (3H, s), 2.29 (1H, dd, J=9.6, 5.4 Hz).

(1R*,2R*,3R*)—N-Hydroxy-2-(4-(5-methyl-1H-imidazol-2-yl)phenyl)-3-phenylcyclopropanecarboxamide (50l)

Following method A from compound 49l (280 mg, 0.84 mmol). Purification by preparative HPLC gave the title compound as a white solid (4.8 mg, 1% yield over 3 steps). LCMS (ES+) 334 (M+H)$^+$, RT 7.93 min (Analytical method 3). $^1$H NMR δ (ppm) (DMSO-$d_6$): 10.62 (1H, s), 8.42 (1H, s), 7.88 (2H, d, J=8.0 Hz), 7.41-7.28 (6H, m), 7.25-7.20 (1H, m), 6.84 (1H, s), 3.16 (1H, dd, J=6.9, 5.5 Hz), 2.92 (1H, dd, J=9.4, 6.7 Hz), 2.31-2.20 (4H, m), OH not observed.

Example 17

Reaction Scheme 17

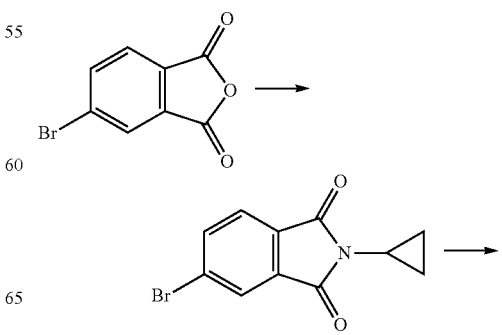

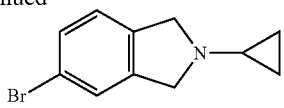

5-Bromo-2-cyclopropyl isoindoline

To a solution of phthalic anhydride (4.5 g, 20 mmol) in toluene (25 mL) was added cyclopropylamine (1.52 mL) at 0° C. and the reaction mixture was stirred at 90° C. for 17 h. The solvent was evaporated and THF (20 mL) was added. To this was added BH$_3$.Me$_2$S THF complex 1 M (80 mL, 80 mmol) and the mixture was stirred at 50° C. for 48 h. The reaction was cooled to 00° C. and poured onto a solution of 3 M HCl (27 mL) and stirred at 60° C. for 1 h. The mixture was washed with ethyl acetate, the aqueous phase was basified (pH 12) and extracted with DCM. The organic layer was dried, filtered and concentrated to afford the title compound as a yellow oil (1.6 g, 34%). LCMS (ES+) 238, 240 (M+H)$^+$.

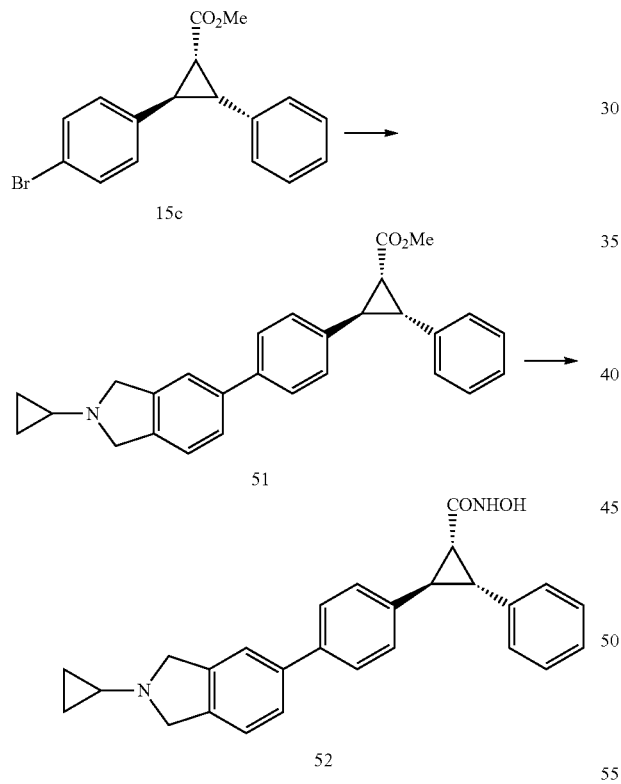

Example 18

(1R*,2R*,3R*)-methyl-2-(4-(2-cyclopropylisoindolin-5-yl)phenyl)-3-phenylcyclopropanecarboxylate (51)

Following method G from the boronate derived from 15c (1.5 mmol) and 5-bromo-2-cyclopropylisoindoline (240 mg, 1 mmol). The mixture was stirred at 90° C. for 2 h, diluted with H$_2$O (20 mL) and extracted into DCM (50 mL). The organic layers were passed through a phase separator and concentrated. Purification using flash silica column chromatography (gradient elution DCM/MeOH 1% to 7%) gave the ester intermediate as a yellow oil (360 mg, 59%). LCMS (ES+) 410 (M+H)$^+$.

(1R*,2R*,3R*)-2-(4-(2-cyclopropylisoindolin-5-yl)phenyl)-N-hydroxy-3-phenylcyclopropanecarboxamide (52)

Following method A from compound 51 (40 mg, 0.098 mmol). Purification by preparative HPLC gave the title compound as a white solid (6.9 mg, 17%). LCMS (ES+) 411 (M+H)+, RT 7.48 min (Analytical method 3). $^1$H NMR δ (ppm) (DMSO-d$_6$): 10.63 (1H, s), 8.75 (1H, s), 7.65 (2H, d, J=8.1 Hz), 7.56 (1H, s), 7.53 (1H, d, J=7.9 Hz), 7.44-7.27 (7H, m), 7.26-7.20 (1H, m), 4.05 (4H, d, J=9.3 Hz), 3.17 (1H, dd, J=6.7, 5.3 Hz), 2.90 (1H, dd, J=9.5, 6.8 Hz), 2.29 (1H, dd, J=9.5, 5.4 Hz), 2.14-2.08 (1H, m), 0.56-0.50 (2H, m), 0.51-0.45 (2H, m).

Example 19

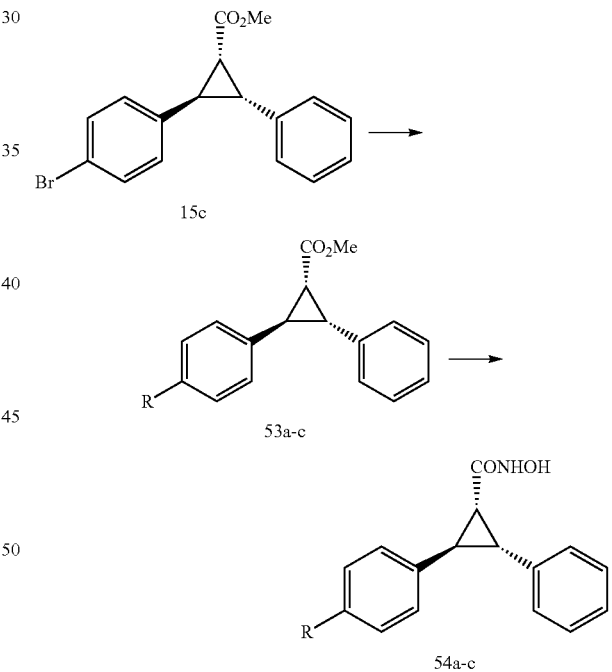

TABLE 4

| R | Compound |
|---|---|
|  | 54a |

TABLE 4-continued

| R | Compound |
|---|---|
| | 54b |
| | 54c |

(1R*,2R*,3R*)-Methyl-2-(3'-(benzyloxy)-[1,1'-biphenyl]-4-yl)-3-phenylcyclopropanecarboxylate (53a)

Following method H from compound 15c (660 mg, 2 mmol) and 3-(benzyloxy)phenyl boronic acid (547 mg, 2.40 mmol). Purification by flash silica column chromatography (gradient elution i-hex to 10% EtOAc in i-hex) gave the title compound as a yellow oil (710 mg, 82%). LCMS (ES+) 435 $(M+H)^+$.

(1R*,2R*,3R*)-Methyl-2-(4'-(9H-carbazol-9-yl)-[1,1'-biphenyl]-4-yl)-3-phenylcyclopropanecarboxylate (53b)

Following method H from compound 15c (660 mg, 2.0 mmol) and 4-(9H-carbazol-9-yl)phenyl boronic acid (886 mg, 2.40 mmol). Purification by flash silica column chromatography (gradient elution i-hex to 30% EtOAc in i-hex) gave the title compound as a yellow oil (310 mg, 31%). LCMS (ES+) 494 $(M+H)^+$.

(1R*,2R*,3R*)-Methyl-2-(4-(4-methyl-3,4-dihydro-2H-benzo[b][1,4]oxazin-7-yl)phenyl)-3-phenylcyclopropanecarboxylate (53c)

Following method H from compound 15c (330 mg, 1.0 mmol) and 4-methyl-7-(4,4,5,5-tetramethyl-1,3,2-dioxaborolan-2-yl)-3,4-dihydro-2H-benzo[b][1,4]oxazine (331 mg, 1.2 mmol). Purification by flash silica column chromatography (gradient elution i-hex-5% to 80% EtOAc in i-hex) gave the title compound as a yellow oil (280 mg, 70%). LCMS (ES+) 400 $(M+H)^+$.

(1R,2R,3R)-2-(3'-(Benzyloxy)-[1,1'-biphenyl]-4-yl)-N-hydroxy-3-phenylcyclopropanecarboxamide (54a)

Following method A from compound 53a (700 mg, 1.61 mmol). Purification by flash silica column chromatography (gradient elution EtOAc from 5% to 100% in i-hex) followed by PEAX cartridge (elution DCM-MeOH 1:1) gave the racemic mixture as a white solid (450 mg, 64%). Purification by chiral preparative HPLC gave the title compound (Chiralpak IC 20/80 EtOH (0.1% FA)/heptane, 1.0 mL/min, RT 13.0 min). LCMS (ES+) 436 (M+H)+, RT 4.47 min (Analytical method 1). $^1$H NMR δ (ppm) (DMSO-d$_6$): 10.63 (1H, s), 8.76 (1H, s), 7.68 (2H, d, J=8.1 Hz), 7.54 (2H, d, J=7.5 Hz), 7.50-7.21 (13H, m), 7.05 (1H, dd, J=8.1, 2.4 Hz), 5.25 (2H, s), 3.19 (1H, dd, J=6.8, 5.4 Hz), 2.93 (1H, dd, J=9.6, 6.8 Hz), 2.30 (1H, dd, J=9.6, 5.4 Hz).

(1R*,2R*,3R*)-2-(4'-(9H-carbazol-9-yl)-[1,1'-biphenyl]-4-yl)-N-hydroxy-3-phenylcyclopropanecarboxamide (54b)

Following method A from compound 53b (300 mg, 0.61 mmol). Purification by preparative HPLC gave the title compound as a white solid (8 mg, 3%). LCMS (ES+) 495 (M+H)+, RT 11.55 min (Analytical method 3). $^1$H NMR δ (ppm) (DMSO-d$_6$): 10.66 (1H, s), 8.79 (1H, s), 8.33 (2H, d, J=7.8 Hz), 8.03 (2H, d, J=8.2 Hz), 7.83 (2H, d, J=8.0 Hz), 7.78 (2H, d, J=8.2 Hz), 7.54-7.47 (6H, m), 7.44-7.30 (6H, m), 7.25 (1H, t, J=7.2 Hz), 3.23 (1H, dd, J=6.8, 5.4 Hz), 2.98 (1H, dd, J=9.6, 6.9 Hz), 2.34 (1H, dd, J=9.6, 5.4 Hz).

(1R,2R,3R)—N-hydroxy-2-(4-(4-methyl-3,4-dihydro-2H-benzo[b][1,4]oxazin-7-yl)phenyl)-3-phenylcyclopropanecarboxamide (54c)

Following method A from compound 53c (280 mg, 0.70 mmol). The carboxylic acid was obtained as the major product. The reaction mixture was acidified with aqueous 1 M HCl and extracted into EtOAc (3×10 mL). The organic layers were combined, dried (MgSO$_4$), filtered and concentrated. The sample was then subjected to method B. Purification by chiral preparative HPLC (Chiralpak IC 20/80 EtOH (0.1% FA)/heptane, 1.0 mL/min, RT 15.9 min) gave the title compound as a white solid. LCMS (ES+) 401 (M+H)+, RT 4.02 min (Analytical method 1). $^1$H NMR δ (ppm) (DMSO-d$_6$): 10.63 (1H, s), 8.75 (1H, s), 7.56 (2H, d, J=8.1 Hz), 7.38 (2H, d, J=7.6 Hz), 7.35-7.27 (3H, m), 7.26-7.20 (1H, m), 7.15 (1H, dd, J=8.3, 2.1 Hz), 7.02 (1H, d, J=2.1 Hz), 6.81 (1H, d, J=8.4 Hz), 4.33-4.29 (2H, m), 3.33-3.28 (3H, m), 3.14 (1H, dd, J=6.8, 5.3 Hz), 2.91 (3H, s), 2.91-2.85 (1H, m), 2.26 (1H, dd, J=9.6, 5.3 Hz).

Example 20

Reaction Scheme 20

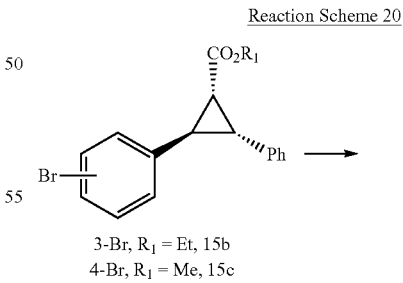

3-Br, $R_1$ = Et, 15b
4-Br, $R_1$ = Me, 15c

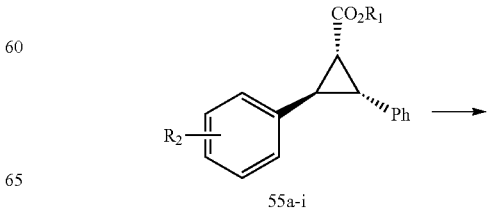

55a-i

-continued

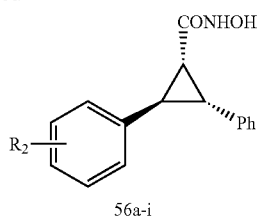

56a-i

TABLE 5

| R2 | 3 or 4 Substitution | Compound |
|---|---|---|
| 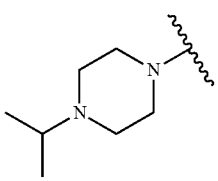 [SMILES: *N1CCN(C(C)C)CC1] | 4 | 56a |
| 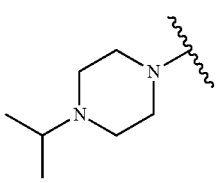 [SMILES: *N1CCN(C(C)C)CC1] | 3 | 56b |
| 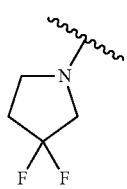 [SMILES: *N1CCC(F)(F)C1] | 4 | 56c |
| 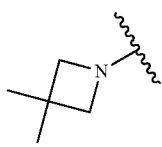 [SMILES: *N1CC(C)(C)C1] | 4 | 56d |
| 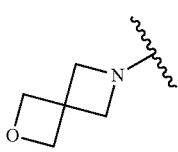 [SMILES: *N1CC2(COC2)C1] | 4 | 56e |
| 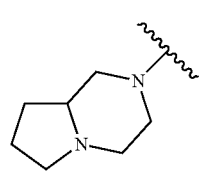 [SMILES: *N1CCN2CCCC2C1] | 3 | 56f |
| 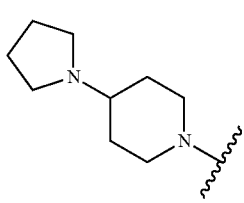 [SMILES: *N1CCC(N2CCCC2)CC1] | 3 | 56g |

TABLE 5-continued

| R2 | 3 or 4 Substitution | Compound |
|---|---|---|
| | 3 | 56h |
| | 4 | 56i |

(1R*,2R*,3R*)-Methyl-2-(4-(4-isopropylpiperazin-1-yl)phenyl)-3-phenylcyclopropanecarboxylate (55a)

Following method I from compound 15c (250 mg, 0.76 mmol) and iso-propylpiperazine (125 μl, 0.86 mmol). Purification using flash silica column chromatography (gradient elution i-hex/EtOAc 0% to 100%) gave the title compound as a yellow oil (187 mg, 65%). LCMS (ES+) 379 (M+H)+.

(1R*,2R*,3R*)-Ethyl-2-(3-(4-isopropylpiperazin-1-yl)phenyl)-3-phenylcyclopropanecarboxylate (55b)

Following method I from compound 15b (250 mg, 0.76 mmol) and iso-propylpiperazine (125 μl, 0.86 mmol). Purification using flash silica column chromatography (gradient elution DCM/MeOH 0% to 8%) gave the title compound as a yellow oil (180 mg, 58%). LCMS (ES+) 393 (M+H)+.

(1R*,2R*,3R*)-Methyl-2-(4-(3,3-difluoropyrrolidin-1-yl)phenyl)-3-phenylcyclopropanecarboxylate (55c)

Following method I from compound 15c (250 mg, 0.76 mmol) and 3,3-difluoropyrrolidine (124 mg, 0.86 mmol). Purification by flash silica column chromatography (gradient elution i-hex/EtOAc 0% to 100%) gave the title compound as a clear oil (210 mg, 59%). LCMS (ES+) 358 (M+H)+.

(1R*,2R*,3R*)-Methyl-2-(4-(3,3-dimethylazetidin-1-yl)phenyl)-3-phenylcyclopropanecarboxylate (55d)

Following method I from compound 15c (250 mg, 0.76 mmol) and 3,3-dimethylazatidine (105 mg, 0.86 mmol). Purification by flash silica column chromatography (gradient elution i-hex/EtOAc 0% to 100%) gave the title compound as a clear oil (210 mg, 59%). LCMS (ES+) 336 (M+H)+.

(1R*,2R*,3R*)-Methyl-2-(4-(2-oxa-6-azaspiro[3.3]heptan-6-yl)phenyl)-3-phenylcyclopropanecarboxylate (55e)

Following method I from compound 15c (250 mg, 0.76 mmol) and 2-oxa-6-azaspiro[3.3]heptane formate salt (160 mg, 0.86 mmol). Purification by flash silica column chromatography (gradient elution i-hex/EtOAc 0% to 100%) gave the title compound as a clear oil (210 mg, 59%). LCMS (ES+) 350 (M+H)+.

(1R*,2R*,3R*)-Ethyl-2-(3-(hexahydropyrrolo[1,2-a]pyrazin-2(1H)-yl)phenyl)-3-phenylcyclopropanecarboxylate (55f)

Following method I from compound 15b (500 mg, 1.56 mmol) and octahydropyrrolo[1,2-a]pyrazine (195 mg, 1.72 mmol). Purification by flash silica column chromatography (gradient elution DCM/MeOH 0% to 8%) gave the title compound as a yellow oil (265 mg, 44%). LCMS (ES+) 391 (M+H)+.

(1R*,2R,3R*)-Ethyl-2-phenyl-3-(3-(4-(pyrrolidin-1-yl)piperidin-1-yl)phenyl)cyclopropanecarboxylate (55g)

Following method I from compound 15b (500 mg, 1.56 mmol) and 4-(pyrrolidin-1-yl)piperidine (241 mg, 1.72 mmol). Purification by flash silica column chromatography (gradient elution DCM/MeOH 0% to 8%) gave the title compound as a yellow oil (230 mg, 35%). LCMS (ES+) 491 (M+H)+.

(1R*,2R*,3R*)-Ethyl-2-(3-(6,7-dihydropyrazolo[1,5-a]pyrimidin-4(5H)-yl)phenyl)-phenylcyclopropanecarboxylate (55h)

Following method I from compound 15b (250 mg, 0.78 mmol) and 4,5,6,7-tetrahydropyrazolo[1,5-a]pyrimidine (106 mg, 0.86 mmol). Purification by flash silica column chromatography (gradient elution DCM/MeOH 0% to 8%) gave the title compound as a yellow oil (165 mg, 42%). LCMS (ES+) 388 (M+H).

(1R*,2R*,3R*)-Methyl-2-(4-(4-methylpiperazin-1-yl)phenyl)-3-phenylcyclopropanecarboxylate (55i)

Following method I from compound 15c (250 mg, 0.76 mmol) and N-methylpiperazine (95 µl, 0.86 mmol). Purification using Isolute cation exchange SCX (elution DCM-MeOH 50% and 5-10% 7N NH$_3$ in MeOH) gave the title compound as a yellow oil (72 mg, 27%). LCMS (ES+) 351 (M+H)+.

(1R*,2R*,3R*)—N-Hydroxy-2-(4-(4-isopropylpiperazin-1-yl)phenyl)-3-phenylcyclopropanecarboxamide (56a)

Following method A from compound 55a (170 mg, 0.49 mmol). Purification by preparative HPLC gave the title compound as a white solid (36 mg, 21%). LCMS (ES+) 380 (M+H)+, RT 2.30 min (Analytical method 1). $^1$H NMR δ (ppm) (DMSO-d$_6$): 10.50 (1H, d, J=1.9 Hz), 8.64 (1H, d, J=1.7 Hz), 7.31 (2H, m), 7.25 (2H, m), 7.20-7.07 (3H, m), 6.88 (2H, d, J=8.4 Hz), 3.08 (4H, m), 2.99 (1H, m), 2.75-2.61 (2H, m), 2.56 (4H, dd, J=7.4, 4.1 Hz), 2.12-2.06 (1H, m), 1.00 (6H, d, J=6.5 Hz).

(1R*,2R*,3R*)—N-Hydroxy-2-(3-(4-isopropylpiperazin-1-yl)phenyl)-3-phenylcyclopropanecarboxamide (56b)

Following method A from compound 55b (180 mg, 0.46 mmol). Purification by preparative HPLC gave the title compound as a white solid (73 mg, 42%). LCMS (ES+) 380 (M+H)+, RT 7.23 min (Analytical method 3). $^1$H NMR δ (ppm) (DMSO-d$_6$): 10.56 (1H, s), 7.37 (2H, d, J=7.6 Hz), 7.30 (2H, t, J=7.5 Hz), 7.25-7.17 (2H, m), 6.88 (1H, s), 6.84-6.80 (1H, m), 6.69 (1H, d, J=7.5 Hz), 3.18 (5H, t, J=4.5 Hz), 3.08 (1H, dd, J=6.8, 5.4 Hz), 2.87 (1H, dd, J=9.5, 6.9 Hz), 2.73 (1H, t, J=6.5 Hz), 2.62 (4H, t, J=4.6 Hz), 2.22 (1H, dd, J=9.6, 5.4 Hz), 1.06 (6H, d, J=6.5 Hz).

(1R*,2R*,3R*)—N-Hydroxy-2-(4-(3,3-difluoropyrrolidin-1-yl)phenyl)-3-phenylcyclopropanecarboxamide (56c)

Following method A from compound 55c (205 mg, 0.57 mmol). Purification by preparative HPLC gave the title compound as a white solid (35 mg, 17%). LCMS (ES+) 359 (M+H)+, RT 9.27 min (Analytical method 6). $^1$H NMR δ (ppm) (DMSO-d$_6$): 10.50 (1H, s), 8.64 (1H, d, J=1.8 Hz), 7.31 (2H, d, J=7.6 Hz), 7.25 (2H, t, J=7.4 Hz), 7.19-7.08 (3H, m), 6.60 (2H, d, J=8.2 Hz), 3.66 (2H, t, J=13.4 Hz), 3.44 (2H, m), 2.99 (1H, m), 2.70-2.65 (2H, m), 2.33 (1H, m), 2.08 (1H, dd, J=9.5, 5.4 Hz).

(1R*,2R*,3R*)-2-(4-(3,3-Dimethylazetidin-1-yl)phenyl)-N-hydroxy-3-phenylcyclopropanecarboxamide (56d)

Following method A from compound 55d (200 mg, 0.59 mmol). Purification by preparative HPLC gave the title compound as a white solid (23 mg, 14%). LCMS (ES+) 337 (M+H)+, RT 3.42 min (Analytical method 1). $^1$H NMR δ (ppm) (DMSO-d$_6$): 10.49 (1H, s), 8.63 (1H, s), 7.33-7.20 (4H, m), 7.19-7.12 (1H, m), 7.05 (2H, d, J=8.2 Hz), 6.37 (2H, d, J=8.2 Hz), 3.48 (4H, s), 2.97 (1H, dd, J=6.9, 5.4 Hz), 2.68 (1H, dd, J=9.5, 6.9 Hz), 2.06 (1H, dd, J=9.5, 5.4 Hz), 1.27 (6H, s).

(1R*,2R*,3R*)-2-(4-(2-Oxa-6-azaspiro[3.3]heptan-6-yl)phenyl)-N-hydroxy-3-phenylcyclopropanecarboxamide (56e)

Following method A from compound 55e (214 mg, 0.61 mmol). Purification by preparative HPLC gave the title compound as a white solid (23 mg, 14%). LCMS (ES+) 351 (M+H)+, RT 8.07 min (Analytical method 3). $^1$H NMR δ (ppm) (DMSO-d$_6$): 10.50 (1H, s), 8.64 (1H, d, J=1.8 Hz), 7.31 (2H, d, J=7.6 Hz), 7.28-7.21 (2H, m), 7.19-7.08 (3H, m), 6.60 (2H, d, J=8.2 Hz), 3.70-3.61 (4H, m), 3.48-3.39 (4H, m), 2.99 (1H, dd, J=6.9, 5.4 Hz), 2.70 (1H, dd, J=9.5, 6.9 Hz), 2.08 (1H, dd, J=9.5, 5.4 Hz).

(1R*,2R*,3R*)-2-(3-(Hexahydropyrrolo[1,2-a]pyrazin-2(1H)-yl)phenyl)-N-hydroxy-3-phenylcyclopropanecarboxamide (56f)

Following method A from compound 55f (265 mg, 0.68 mmol). Purification by preparative HPLC gave the title compound as a white solid (9 mg, 4%). LCMS (ES+) 378 (M+H)+, RT 8.26 min (Analytical method 3). $^1$H NMR δ (ppm) (DMSO-d$_6$): 10.56 (1H, s), 7.38 (2H, d, J=7.6 Hz), 7.30 (2H, t, J=7.5 Hz), 7.24-7.15 (2H, m), 6.89 (1H, s), 6.84 (1H, dd, J=8.4, 2.4 Hz), 6.69 (1H, d, J=7.6 Hz), 3.87 (1H, d, J=11.2 Hz), 3.71 (2H, d, J=12.2 Hz), 3.13-3.03 (4H, m), 2.87 (1H, dd, J=9.6, 6.9 Hz), 2.81-2.71 (1H, m), 2.30-2.19 (2H, m), 2.16-2.04 (2H, m), 1.91-1.83 (1H, m), 1.81-1.70 (2H, m), 1.48-1.39 (1H, m).

(1R*,2R*,3R*)—N-Hydroxy-2-phenyl-3-(3-(4-(pyrrolidin-1-yl)piperidin-1-yl)phenyl)cyclopropanecarboxamide (56g)

Following method A from compound 55g (230 mg, 0.55 mmol). Purification by preparative HPLC gave the title compound as a white solid (40 mg, 10%). LCMS (ES+) 406 (M+H)+, RT 2.42 min (Analytical method 1). $^1$H NMR δ (ppm) (DMSO-d$_6$): 10.56 (1H, s), 8.72 (1H, s), 7.38 (2H, d, J=7.61 Hz), 7.33-7.24 (2H, m), 7.25-7.14 (2H, m), 6.90 (1H, s), 6.90-6.80 (1H, m), 6.67 (1H, d, J=7.59 Hz), 3.84-3.69 (2H, m), 3.08 (1H, dd, J=6.93 5.4 Hz), 2.90-2.82 (1H, m), 2.82-2.72 (7H, m), 2.22 (1H, dd, J=9.6, 5.4 Hz), 2.00 (2H, d, J=12.01 Hz), 1.79 (4H, s), 1.65-1.51 (2H, m).

(1R,2R,3R)-2-(3-(6,7-Dihydropyrazolo[1,5-a]pyrimidin-4(5H)-yl)phenyl)-N-hydroxy-3-phenylcyclopropanecarboxamide (56h)

Following method A from compound 55h (180 mg, 0.46 mmol). The racemic mixture was obtained after purification by preparative HPLC as a white solid (41.5 mg, 24%). Purification by chiral preparative HPLC (Chiralpak IA 40/60 IPA/MeOH (50/50/0.1% formic acid)/heptane, 1.0 mL/min, RT 10.1 min) gave the title compound. LCMS (ES+) 375 (M+H)+, RT 2.90 min (Analytical method 1). $^1$H NMR δ (ppm) (DMSO-d$_6$): 10.59 (1H, s), 8.74 (1H, s), 7.39-7.28 (5H, m), 7.26-7.20 (4H, m), 7.02 (1H, d, J=1.4 Hz), 5.66 (1H, d, J=1.9 Hz), 4.15 (2H, t, J=6.1 Hz), 3.74 (2H, t, J=5.2 Hz), 3.14 (1H, dd, J=6.8, 5.4 Hz), 2.88 (1H, dd, J=9.5, 6.8 Hz), 2.28-2.22 (3H, m).

(1R*,2R*,3R*)—N-Hydroxy-2-(4-(4-methyl piperazin-1-yl)phenyl)-3-phenylcyclopropanecarboxamide (56i)

Following method A from compound 55i (70 mg, 0.20 mmol). Purification by preparative HPLC gave the title compound as a white solid (49 mg, 70%). LCMS (ES+) 352 (M+H)+, RT 6.86 min (Analytical method 3). $^1$H NMR δ (ppm) (DMSO-d$_6$) 10.50 (1H, s), 8.64 (1H, s), 7.31 (2H, d, J=7.6 Hz), 7.25 (2H, t, J=7.4 Hz), 7.20-7.08 (3H, m), 6.89 (2H, d, J=8.5 Hz), 3.09 (4H, t, J=4.8 Hz), 2.99 (1H, dd, J=6.8, 5.4 Hz), 2.71 (1H, dd, J=9.5, 6.9 Hz), 2.44 (4H, t, J=4.7 Hz), 2.22 (3H, s), 2.09 (1H, dd, J=9.5, 5.4 Hz).

Example 21

Reaction Scheme 21

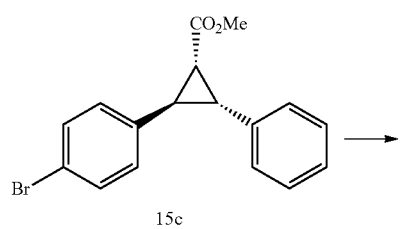

(1R*,2R*,3R*)-Methyl-2-(4-(oxazol-2-yl)phenyl)-3-phenylcyclopropanecarboxamide (57)

A mixture of compound 15c (250 mg, 0.75 mmol), 2-(tri-n-butylstannyl)oxazole (0.230 mL, 1.1 mmol), Pd(PPh$_3$)$_4$ (43 mg, 0.038 mmol) in 1,4-dioxane (4 mL) was heated in the microwave at 150° C. for 1 h. The mixture was concentrated and purified by flash silica column chromatography (gradient elution DCM to 10% MeOH in DCM) to afford the title compound as a white solid (175 mg, 73%). LCMS (ES+) 320 (M+H)+.

(1R*2R*,3R*)—N-Hydroxy-2-(4-(oxazol-2-yl)phenyl)-3-phenylcyclopropanecarboxamide (58)

Following method A from compound 57 (160 mg, 0.50 mmol). Crystallization from MeOH gave the title compound as a white solid (71 mg, 45%). LCMS (ES+) 321 (M+H)+, RT 2.80 min (Analytical method 1). $^1$H NMR δ (ppm) (DMSO-d$_6$): 10.58 (1H, s), 8.70 (1H, s), 8.21 (1H, d, J=0.8 Hz), 7.94 (2H, d, J=8.1 Hz), 7.45 (2H, d, J=8.1 Hz), 7.39-7.33 (3H, m), 7.31-7.23 (2H, m), 7.22-7.15 (1H, m), 3.20-3.13 (1H, m), 2.91 (1H, dd, J=9.6, 6.8 Hz), 2.28 (1H, dd, J=9.6, 5.3 Hz).

Example 22

Reaction Scheme 22

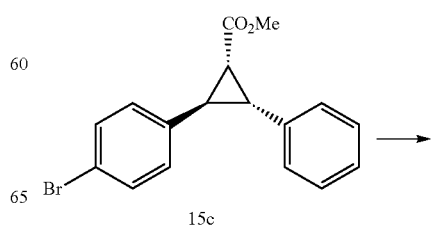

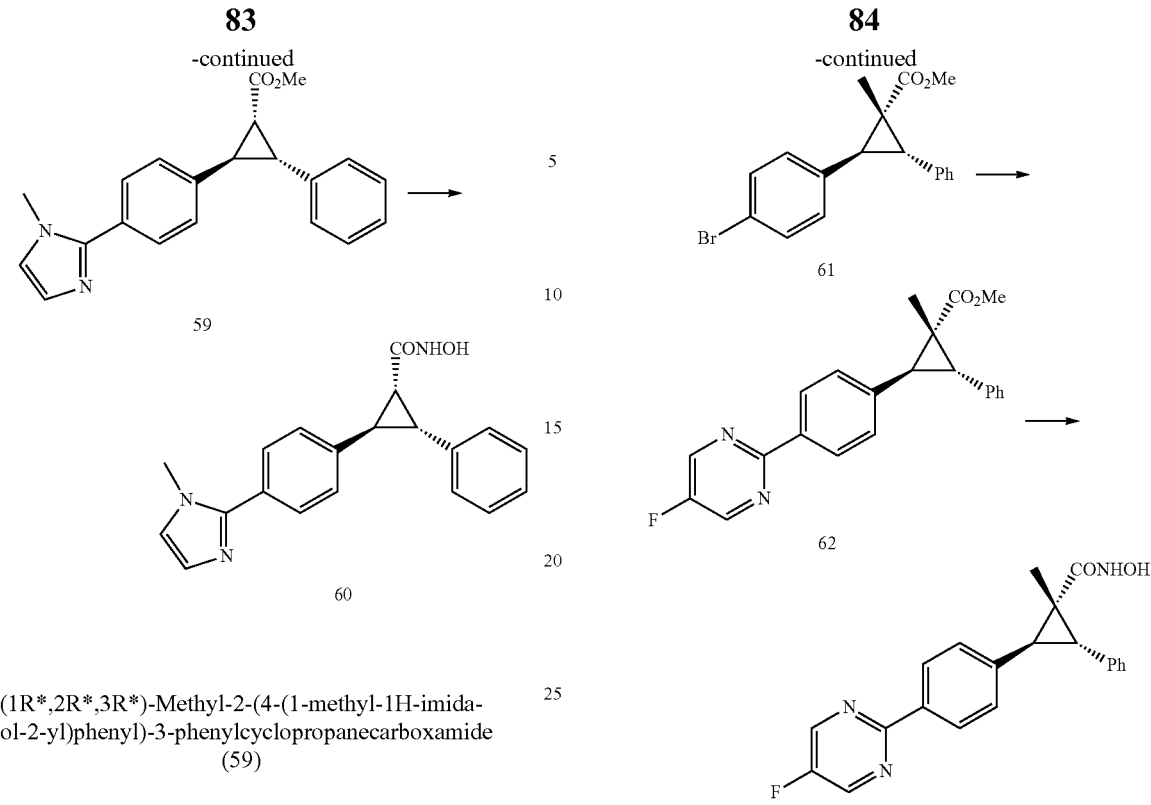

(1R*,2R*,3R*)-Methyl-2-(4-(1-methyl-1H-imidazol-2-yl)phenyl)-3-phenylcyclopropanecarboxamide (59)

Following the method described for compound 57, from 15c (222 mg, 0.67 mmol) and 1-methyl-2-(tributylstannyl)imidazole (300 mg, 0.81 mmol). Purification by flash silica column chromatography (gradient elution DCM to 10% MeOH in DCM) gave the title compound as a yellow solid (187 mg, 84%). LCMS (ES+) 333 (M+H)+.

(1R*,2R*,3R*)—N-Hydroxy-2-(4-(1-methyl-1H-imidazol-2-yl)phenyl)-3-phenylcyclopropanecarboxamide (60)

Following method A from compound 59 (187 mg, 0.56 mmol). Crystallization from DCM and washes with MeOH, gave the title compound as a white solid (98 mg, 53%). LCMS (ES+) 334 (M+H)+, RT 9.74 min (Analytical method 3). $^1$H NMR δ (ppm) (DMSO-$d_6$): 10.58 (1H, s), 8.70 (1H, s), 7.65 (2H, d, J=8.1 Hz), 7.44-7.31 (4H, m), 7.30-7.24 (3H, m), 7.23-7.15 (1H, m), 6.99 (1H, d, J=1.1 Hz), 3.75 (3H, s), 3.19-3.13 (1H, dd, J=6.8, 5.4 Hz), 2.90 (1H, dd, J=9.6, 6.8 Hz), 2.26 (1H, dd, J=9.6, 5.4 Hz).

Example 23

Reaction Scheme 23

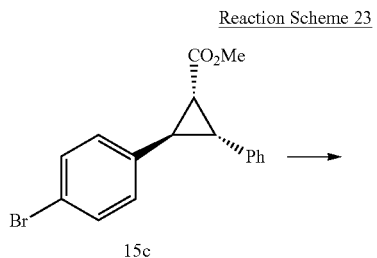

(1R*,2S*,3S*)-Methyl-2-(4-bromophenyl)-1-methyl-3-phenylcyclopropanecarboxylate (61)

To a solution of 15c (331 mg, 1 mmol) in dry THF at −78° C., was added LDA (2 M in THF, 0.5 mL) dropwise and the reaction mixture was stirred at −78° C. for 30 min. Methyl iodide (0.065 mL, 1 mmol) was added and the reaction mixture was allowed to warm up to r.t. and stirred for 1 h. The reaction mixture was quenched with water and the compound was extracted into DCM. The organic phase was dried (MgSO$_4$), filtered and concentrated. Purification by flash silica column chromatography (gradient elution i-hex to 50% EtOAc in i-hex) gave the title compound as a colourless oil (346 mg, 100%). LCMS (ES+) 346 (M+H)+.

(1R*,2S*,3S*)-Methyl-2-(4-(5-fluoropyrimidin-2-yl)phenyl)-1-methyl-3-phenylcyclopropanecarboxylate (62)

Following method G from 61 (346 mg, 1.0 mmol) and 2-chloro-5-fluoropyrimidine (170 μl, 1.1 mmol). Purification by flash silica column chromatography (gradient elution i-hex to 10% EtOAc in i-hex) gave the title compound as a colourless oil (160 mg, 44%). LCMS (ES+) 363 (M+H)+.

(1R*,2S*,3S*)-2-(4-(5-Fluoropyrimidin-2-yl)phenyl)-N-hydroxy-1-methyl-3-phenylcyclopropanecarboxamide (63)

Following method A from 62 (350 mg, 0.97 mmol). Purification by flash silica column chromatography (gradient elution DCM to 10% MeOH in DCM) followed by preparative HPLC gave the title compound as a white solid (2 mg, 2%). LCMS (ES+) 364 (M+H)+, RT 10.83 min (Analytical method 3). $^1$H NMR δ (ppm) (DMSO-$d_6$): 10.62

(1H, s), 8.98 (2H, d, J=0.7 Hz), 8.64 (1H, s), 8.31 (2H, d, J=8.1 Hz), 7.51 (2H, d, J=8.1 Hz), 7.31-7.23 (4H, m), 7.22-7.15 (1H, m), 3.46 (1H, d, J=7.2 Hz), 2.78 (1H, d, J=7.2 Hz), 1.12 (3H, s).

Example 24

Reaction Scheme 24

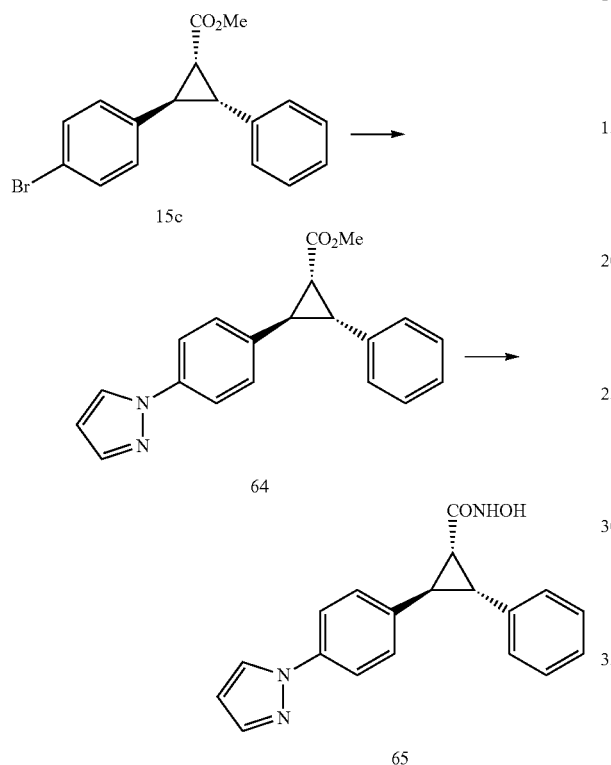

(1R*,2R*,3R*)-Methyl-2(4-(1H-pyrazol-1-yl)phenyl)-3-phenylcyclopropanecarboxylate (64)

To a stirred solution of compound 15c (1.0 g, 3.02 mmol) in dioxane (5 mL) was added bis-pinacolato diboron (844 mg, 3.32 mmol), Pd(dppf)Cl₂ (246 mg, 0.30 mmol) and potassium acetate (1.48 g, 15.1 mmol). The mixture was degassed with nitrogen, heated to 100° C. for 2 h, diluted with H₂O (20 mL) and extracted into DCM (2×20 mL). The organic layers were passed through a phase separator and concentrated. Part of this crude residue (400 mg, 1.00 mmol) was dissolved in a mixture of MeOH (4 mL) and THF (2 mL) and to this was added pyrazole (82 mg, 1.2 mmol) and Cu₂O (8 mg, 0.056 mmol). The mixture was stirred at 100° C. for 16 h, diluted with H₂O (10 mL) and extracted into DCM (20 mL). The organic layers were passed through a phase separator and concentrated. Purification by flash silica column chromatography (gradient elution DCM to 5% MeOH in DCM) afforded the title compound as a cream solid (161 mg, 51%). LCMS (ES+) 319 (M+H)⁺.

(1R*,2R*,3R*)-2-(4-(1H-pyrazol-1-yl)phenyl)-N-hydroxy-3-phenylcyclopropanecarboxamide (65)

Following method A from compound 64 (121 mg, 0.38 mmol) The carboxylic acid was obtained as the major product. The acid (43 mg, 0.14 mmol) was subjected to method B. Purification by preparative HPLC gave the title compound as a cream solid (9 mg, 21%). LCMS (ES+) 320 (M+H)+, RT 8.49 min (Analytical method 3). ¹H NMR δ (ppm) (DMSO-d₆) 10.56 (1H, s), 8.69 (1H, s), 8.48 (1H, d, J=2.5 Hz), 7.80 (2H, d, J=8.4 Hz), 7.73 (1H, d, J=1.7 Hz), 7.40 (2H, d, J=8.3 Hz), 7.35 (2H, d, J=7.6 Hz), 7.27 (2H, m), 7.19 (1H, m), 6.54 (1H, dd, J=2.4, 1.7 Hz), 3.19-3.13 (1H, dd, J=6.8, 5.3 Hz), 2.89 (1H, dd, J=9.6, 6.8 Hz), 2.24 (1H, dd, J=9.6, 5.3 Hz).

Example 25

Reaction Scheme 25

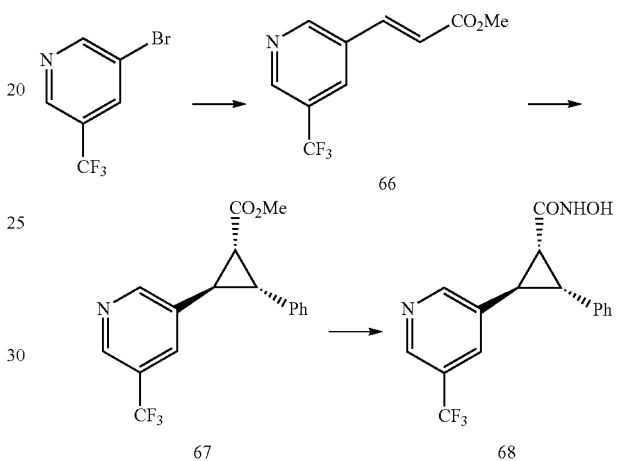

(E)-Methyl-3-(5-(trifluoromethyl)pyridin-3-yl)acrylate (66)

A stirred solution of 5-bromo-3-(trifluoromethyl)pyridine (1.0 g, 4.42 mmol), (E)-ethyl-3-(4,4,5,5-tetramethyl-1,3,2-dioxaborolan-2-yl)acrylate (1.0 g, 4.43 mmol), Pd(PPh₃)₄ (511 mg, 0.44 mmol) and Na₂CO₃ (13.3 mL, 1 M solution, 13.3 mmol) was degassed with nitrogen for 10 min and then heated to 100° C. for 17 h. The mixture was allowed to cool, diluted with water (20 mL), and extracted into DCM (3×20 mL). The product was extracted from the organic layers with sat. NaHCO₃ (20 mL). The pH was adjusted to 5.5 and the resulting white precipitate collected by vacuum filtration (431 mg, 45%). LCMS indicated that the corresponding carboxylic acid had formed. In a separate flask, thionyl chloride (0.19 mL, 1.99 mmol) was added slowly to MeOH (5 mL) at −78° C., and the acid (431 mg, 1.99 mmol) was added. The mixture was refluxed for 1.5 h, cooled to r.t. and concentrated. The residue was dissolved in sat. NaHCO₃ (20 mL) and extracted into DCM (3×20 mL), and the combined organic layers passed through a phase separator and concentrated to give the title compound as a colourless oil (403 mg, 88%). LCMS (ES+) 232 (M+H)⁺.

(1R*,2R*,3R)-Ethyl-2-phenyl-3-(5-(trifluoromethyl)pyridin-3-yl)cyclopropanecarboxylate (67)

Following method F from compound 66 (403 mg, 1.74 mmol) and 6a (678 mg, 2.62 mmol). After stirring at 00° C. for 2 h an additional 1.5 equivalents of LiHMDS were added. Purification by flash silica column chromatography (gradient elution i-hex to 10% EtOAc in i-hex) gave the title compound as a colourless oil (250 mg, 2:1 trans:cis, 45%). LCMS (ES+) 322 (M+H)+.

(1R,2R,3R)—N-Hydroxy-2-phenyl-3-(5-(trifluoromethyl)pyridin-3-yl)cyclopropanecarboxamide (68)

Following method A from compound 67 (250 mg, 0.78 mmol). Purification by flash silica column chromatography (gradient elution DCM to 5% MeOH in DCM) followed by preparative HPLC gave the racemic mixture as a white solid (83 mg, 11%). Preparative chiral HPLC gave the title compound (Chiralpak IC 20/80 EtOH (0.1% formic acid)/heptane, 1.0 mL/min, RT 11.3 min). LCMS (ES+) 323 (M+H)+, RT 3.30 min (Analytical method 1). $^1$H NMR δ (ppm) (DMSO-$d_6$): 10.64 (1H, s), 8.96 (1H, s), 8.88 (1H, s), 8.79 (1H, s), 8.15 (1H, s), 7.41 (2H, d, J=7.6 Hz), 7.32 (2H, t, J=7.4 Hz), 7.24 (1H, t, J=7.2 Hz), 3.41 (1H, obscured by water), 3.15 (1H, dd, J=9.8, 6.9 Hz), 2.44 (1H, dd, J=9.8, 5.4 Hz).

Example 26

Reaction Scheme 26

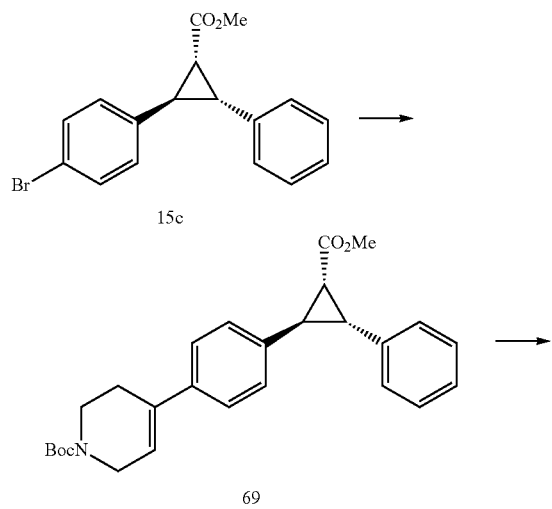

tert-Butyl-4-(4-((1R*,2R*,3R*)-2-(methoxycarbonyl)-3-phenylcyclopropyl)phenyl)-5,6-dihydropyridine-1(2H)-carboxylate (69)

Following method H from compound 15c (660 mg, 2 mmol) and (1-(tert-butoxycarbonyl)-1,2,3,6-tetrahydropyridin-4-yl)boronic acid (750 mg, 2.4 mmol). The crude compound was used in the next step without further purification.

(1R*,2R*,3R*)-Methyl-2-phenyl-3-(4-(1,2,3,6-tetrahydropyridin-4-yl)phenyl)cyclopropanecarboxylate (70)

A solution of 69 (2 mmol) in a mixture of TFA (6 mL) and DCM (14 mL) was stirred at r.t. for 3 h. The reaction mixture was concentrated and the residue dissolved in DCM-MeOH 1:1 (2 mL) and passed through a SCX cartridge (elution 7 M $NH_3$ in MeOH). The free amine was isolated as a yellow oil (655 mg, 96%). This was dissolved in $CH_3CN$ (20 mL) and $Cs_2CO_3$ (1.2 g, 3.9 mmol) and benzyl bromide (255 µL, 2.15 mmol) were added. The reaction mixture was stirred for 17 h and concentrated. The residue was dissolved in DCM and washed with water and brine. The organic layer was passed through a phase separator and concentrated. Purification by flash silica column chromatography (gradient elution i-hex to 15% EtOAc in i-hex) gave the title compound as a yellow oil (305 mg, 36%). LCMS (ES+) 424 (M+H)+.

(1R,2R,3R)-2-(4-(1-Benzyl-1,2,3,6-tetrahydropyridin-4-yl)phenyl)-N-hydroxy-3-phenylcyclopropanecarboxamide (71)

Following method A from compound 70 (300 mg, 0.71 mmol). Purification by PEAX cartridge (elution DCM-MeOH 1:1) gave the racemic mixture as a yellow solid (230 mg, 94%). Purification by chiral preparative HPLC (Chiralpak IC 40/60 EtOH (0.1% FA)/heptane, 1.0 mL/min, RT 14.2 min) gave the title compound as a yellow solid. LCMS (ES+) 425 (M+H)+, RT 7.59 min (Analytical method 3). $^1$H NMR δ (ppm) (DMSO-$d_6$): 10.61 (1H, s), 8.75 (1H, s), 7.45-7.20 (14H, m), 6.18 (1H, s), 3.63 (2H, s), 3.15-3.08 (3H, m), 2.86 (1H, dd, J=9.4, 6.7 Hz), 2.69 (2H, t, J=5.6 Hz), 2.55-2.46 (2H, m), 2.23 (1H, dd, J=9.6, 5.3 Hz).

Example 27

Reaction Scheme 27

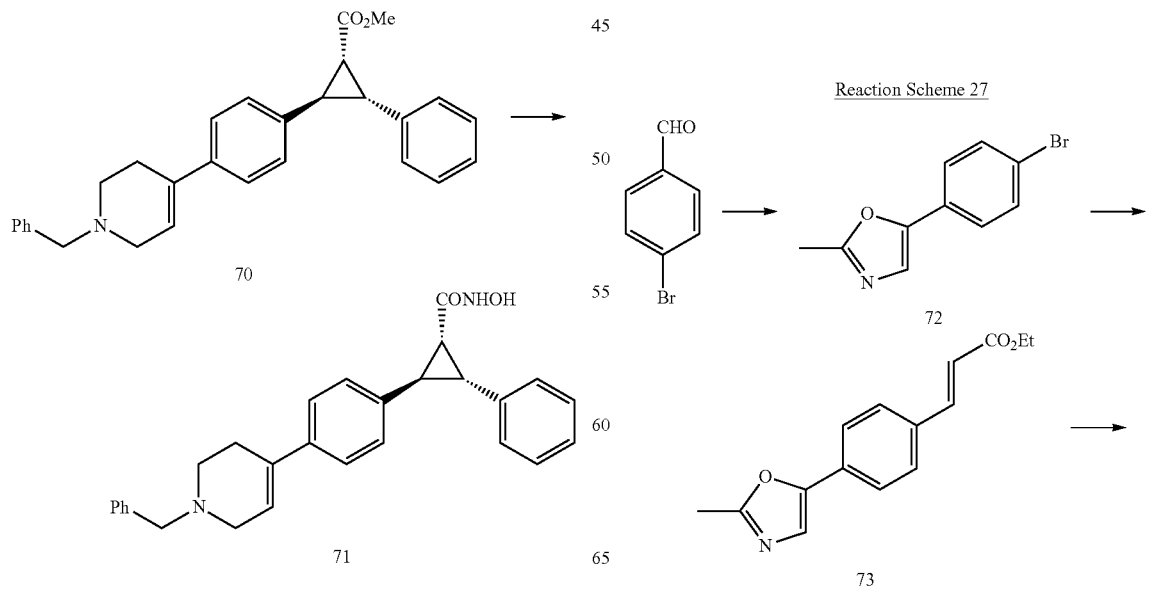

-continued

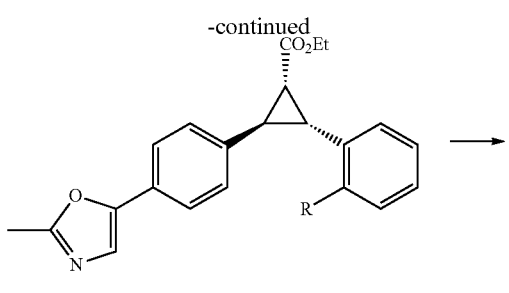

R = H, 74a
R-F, 74b

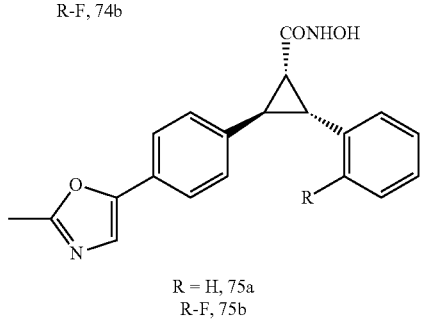

R = H, 75a
R-F, 75b 5-(4-Bromophenyl)-2-methyloxazole (72)

Triflic acid (37 mL, 0.22 mol) was added dropwise to a solution of thallium acetate (28.7 g, 0.07 mol) in acetonitrile (400 mL) at r.t under nitrogen. The solution was stirred for 15 min before a solution of 4-bromobenzaldehyde in acetonitrile (200 mL) was added and the solution heated to 90° C. for 2.5 h. The reaction mixture was concentrated and the red residue was taken up in DCM (600 mL), washed with saturated NaHCO$_3$, water, dried (MgSO$_4$) and concentrated to give a brown gum (12.7 g). Purification by flash silica column chromatography (gradient elution i-hex to 70% EtOAc in i-hex) gave the title compound as an orange solid (8.68 g, 72%). LCMS (ES+) 238,240 (M+H)$^+$.

Ethyl-3-(4-(2-methyloxazol-5-yl)phenyl)acrylate (73)

Following method E from compound 72 (8.68 g, 36 mmol).mLmLmL The reaction solution was decanted from the palladium residues and salts and then concentrated to give an orange solid. This was taken up in DCM (150 mL), washed with water, dried (MgSO$_4$) and concentrated to give an orange solid. This was triturated with diethyl ether to give the title compound as a beige solid (6.18 mg, 66%). LCMS (ES+) 258 (M+H)$^+$.

(1R*,2R*,3R*)-Ethyl-2-(4-(2-methyloxazol-5-yl)phenyl)-3-phenylcyclopropanecarboxylate (74a)

Following method F from compound 73 (500 mg, 1.95 mmol) and 6a (756 mg, 2.92 mmol). The reaction was incomplete after 2 h. The reaction was cooled to −20° C. and an additional 1.5 equivalents of sulfonium salt, 12-crown-4 and LiHMDS were added and the mixture stirred at r.t. overnight. Purification by flash silica column chromatography (gradient elution i-hex to 30% EtOAc in i-hex) gave the title compound as an orange oil (460 mg, 12:2:1 cinnammate:trans:cis). LCMS (ES+) 348 (M+H)$^+$.

(1S*,2R*,3R*)-Ethyl-2-(2-fluorophenyl)-3-(4-(2-methyloxazol-5-yl)phenyl)cyclopropanecarboxylate (74b)

Following method F from compound 73 (500 mg, 1.95 mmol) and 1-(2-fluorobenzyl)tetrahydrothiophenium bromide (811 mg, 2.93 mmol). Purification by flash silica column chromatography (gradient elution i-hex to 25% EtOAc in i-hex) gave the title compound as an orange oil (888 mg, >100%, 3:1, trans:cis). LCMS (ES+) 366 (M+H)$^+$.

(1R,2R,3R)—N-Hydroxy-2-(4-(2-methyloxazol-5-yl)phenyl)-3-phenylcyclopropanecarboxamide (75a)

Following method A from compound 74a (460 mg, 13% pure). Purification by flash silica column chromatography (gradient elution DCM to 5% MeOH in DCM) and then preparative HPLC gave the racemic mixture as a white solid (35 mg, 59%). Preparative chiral HPLC gave the title compound (Chiralpak IC 40/60 EtOH (0.1% formic acid)/Heptane, 1.0 mL/min, RT 12.0 min). LCMS (ES+) 335 (M+H)$^+$. RT 3.28 min (Analytical method 1). $^1$H NMR δ (ppm) (DMSO-d$_6$): 10.50 (1H, s), 8.63 (1H, s), 7.55 (2H, d, J=8.1 Hz), 7.43 (1H, s), 7.34-7.23 (4H, m), 7.23-7.15 (2H, m), 7.14-7.07 (1H, m), 3.05 (1H, dd, J=6.8, 5.4 Hz), 2.81 (1H, dd, J=9.6, 6.8 Hz), 2.40 (3H, s), 2.16 (1H, dd, J=9.6, 5.4 Hz).

(1S,2R,3R)-2-(2-Fluorophenyl)-N-hydroxy-3-(4-(2-methyloxazol-5-yl)phenyl)cyclopropanecarboxamide (75b)

Following method A from compound 74b (200 mg, 0.55 mmol). Purification by flash silica column chromatography (gradient elution DCM to 5% MeOH in DCM) and then preparative HPLC gave the racemic mixture as a white solid (99 mg, 54%). Preparative chiral HPLC gave the title compound (Chiralpak IC 20/80 IPA/MeOH (50/50/0.1% formic acid)/Heptane, 1.0 mL/min, RT 17.4 min). LCMS (ES+) 353 (M+H)$^+$. RT 3.41 min (Analytical method 1). $^1$H NMR δ (ppm) (DMSO-d$_6$): 10.67 (1H, s), 8.80 (1H, s), 7.68 (2H, d, J=8.1 Hz), 7.56 (1H, s), 7.45 (3H, dd, J=12.1, 7.7 Hz), 7.33-7.26 (1H, m), 7.21-7.11 (2H, m), 3.12 (1H, dd, J=6.9, 5.3 Hz), 2.88 (1H, dd, J=9.3, 6.9 Hz), 2.53 (3H, s), 2.32 (1H, dd, J=9.3, 5.3 Hz).

Example 28

Reaction Scheme 28

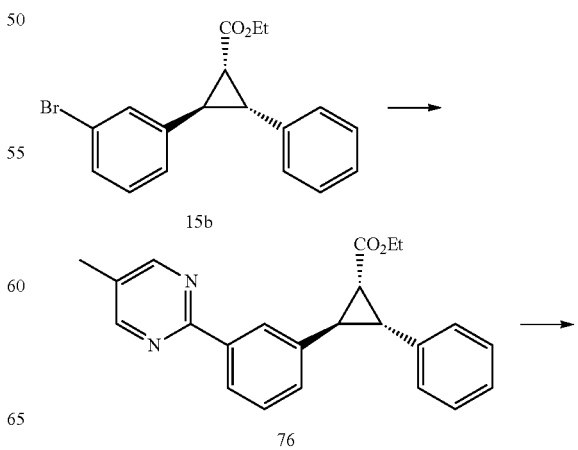

-continued

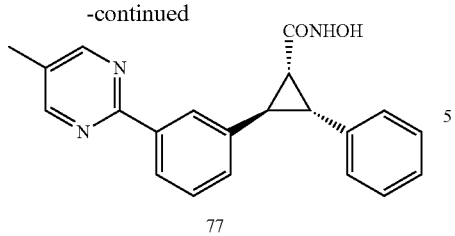

77

(1R*,2R*,3R*)-Ethyl-2-(3-(5-methylpyrimidin-2-yl)phenyl)-3-phenylcyclopropanecarboxylate (76)

Following method G from the crude boronate derived from 15b (565 mg) and 2-chloro-5-methylpyrimidine (194 mg, 1.51 mmol). Purification by flash silica column chromatography (gradient elution i-hex to 25% EtOAc in i-hex) gave the title compound as a colourless oil (260 mg, 50%). LCMS (ES+) 359 (M+H)+.

(1R,2R,3R)—N-Hydroxy-2-(3-(5-methylpyrimidin-2-yl)phenyl)-3-phenylcyclopropanecarboxamide (77)

Following method A from compound 76 (260 mg, 0.73 mmol). Purification by flash silica column chromatography (gradient elution DCM to 5% MeOH in DCM) gave the racemic mixture as a white solid (220 mg, 88%). Preparative chiral HPLC gave the title compound (Chiralpak IC 40/60 EtOH (0.1% formic acid)/Heptane, 1.0 mL/min, RT 18.0 min). LCMS (ES+) 346 (M+H)+. RT 3.47 min (Analytical method 1). $^1$H NMR δ (ppm) (DMSO-$d_6$): 10.52 (1H, s), 8.70 (2H, s), 8.65 (1H, s), 8.19-8.13 (2H, m), 7.40 (2H, d, J=5.2 Hz), 7.30 (2H, d, J=7.6 Hz), 7.20 (2H, t, J=7.5 Hz), 7.12 (1H, t, J=7.2 Hz), 3.15 (1H, dd, J=6.8, 5.4 Hz), 2.78 (1H, dd, J=9.6, 6.8 Hz), 2.30-2.20 (4H, m).

Example 29

Reaction Scheme 29

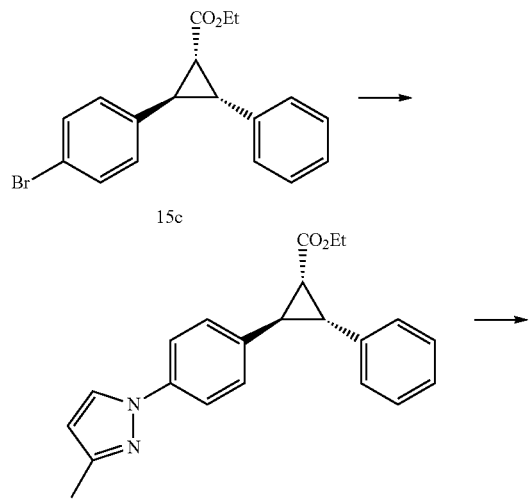

-continued

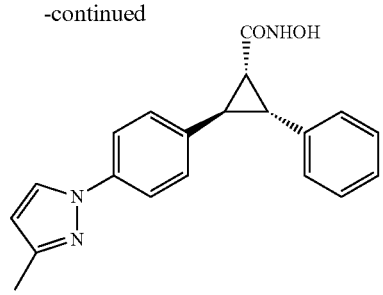

79

(1R*,2R*,3R*)-Methyl 2-(4-(3-methyl-1H-pyrazol-1-yl)phenyl)-3-phenylcyclopropanecarboxylate (78)

To a stirred solution of 15c (1.0 g, 3.02 mmol) in dioxane (5 mL) was added bis-pinacolato diboron (844 mg, 3.32 mmol), Pd(dppf)Cl$_2$ (246 mg, 0.30 mmol) and potassium acetate (1.48 g, 15.1 mmol). The mixture was degassed with nitrogen, heated to 100° C. for 2 h, diluted with H$_2$O (20 mL) and extracted into DCM (2×20 mL). The organic layers were passed through a phase separator and concentrated. Part of this crude residue (600 mg, 1.5 mmol) was dissolved in a mixture of MeOH (6 mL) and THF (4 mL) and to this was added 3-methylpyrazole (145 µL, 1.8 mmol) and Cu$_2$O (15 mg, 0.11 mmol). The mixture was stirred at 100° C. for 48 h, diluted with H$_2$O (20 mL) and extracted into DCM (50 mL). The organic layers were passed through a phase separator and concentrated. Purification by flash silica column chromatography (gradient elution i-hex to 60% EtOAc in i-hex) afforded the title compound as a cream solid (150 mg, 30%). LCMS (ES+) 333 (M+H)+.

(1R,2R,3R)—N-Hydroxy-2-(4-(3-methyl-1H-pyrazol-1-yl)phenyl)-3-phenylcyclopropanecarboxamide (79)

Following method A from compound 78 (148 mg, 0.45 mmol). Purification by preparative HPLC gave the racemic mixture as a cream solid (69.8 mg, 47%). Preparative chiral HPLC gave the title compound (Chiralpak IC 40/60 IPA/MeOH (50/50/0.1 formic acid)/heptane, 1.0 mL/min, RT 9.0 min). RT 3.56 min (Analytical method 1). LCMS (ES+) 334 (M+H)+, RT 8.67 min. $^1$H NMR δ (ppm) (DMSO-$d_6$) 10.62 (1H, s), 8.75 (1H, s), 8.40 (1H, d, J=2.4 Hz), 7.79 (2H, d, J=8.4 Hz), 7.47-7.37 (4H, m), 7.32 (2H, t, J=7.5 Hz), 7.27-7.19 (1H, m), 6.37 (1H, d, J=2.4 Hz), 3.18 (1H, dd, J=6.8, 5.4 Hz), 2.91 (1H, dd, J=9.6, 6.8 Hz), 2.32 (3H, s), 2.27 (1H, dd, J=9.6, 5.4 Hz).

Example 30

Reaction Scheme 30

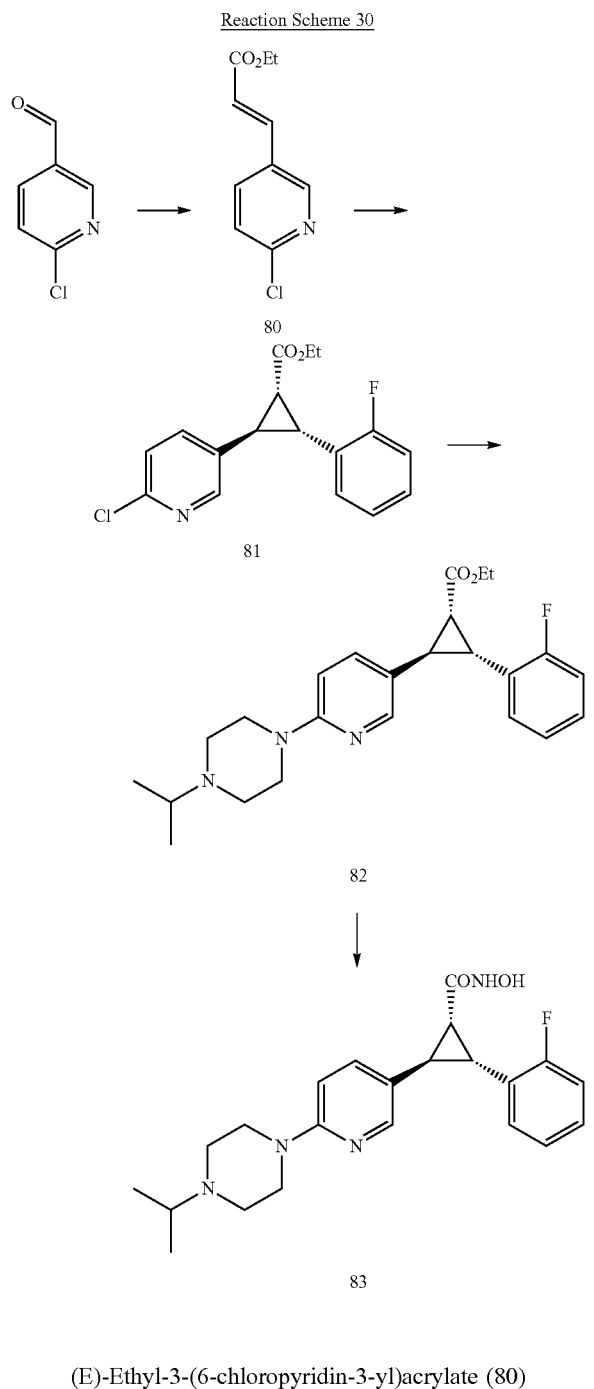

(E)-Ethyl-3-(6-chloropyridin-3-yl)acrylate (80)

NaH (792 mg, 20.0 mmol) was added portion wise to stirred anhydrous DMSO (18 mL). The mixture was heated to 80° C. until evolution of gas ceased and then cooled to 0° C. A solution of (carbethoxymethyl)-triphenylphosphonium bromide (4.3 g, 10.0 mmol) in DMSO (36 mL) was then added and the mixture stirred at r.t for 30 min. The mixture was cooled to 000° C. and a solution of 6-chloroisonicotinaldehyde (1.4 g, 10.0 mmol) in DMSO (36 mL) was added and the mixture was stirred at r.t for 1 h. The mixture was then poured into aqueous 1 M HCl and extracted into DCM (3×70 mL). The organics were combined and washed with $H_2O$ (3×100 mL) and brine (3×100 mL), separated, dried ($MgSO_4$) and concentrated. Purification by flash silica column chromatography (gradient elution i-hex to 80% EtOAc in i-hex) gave the title compound as a yellow solid (0.95 g, 45%). LCMS (ES+) 212 (M+H)+.

(1S*,2R*,3R*)-Ethyl-2-(6-chloropyridin-3-yl)-3-(2-fluorophenyl)cyclopropanecarboxylate (81)

Following method F from compound 80 (730 mg, 3.45 mmol) and 6b (1.43 g, 5.18 mmol). Purification by flash silica column chromatography (gradient elution i-hex to 40% EtOAc in i-hex) gave the title compound (810 mg, 73%). LCMS (ES+) 320 (M+H)+.

(1S*,2R,3R)-Ethyl-2-(2-fluorophenyl)-3-(6-(4-isopropyl piperazin-1-yl)pyridin-3-yl)cyclopropanecarboxylate (82)

A mixture of compound 81 (200 mg, 0.63 mmol) and isopropylpiperazine (0.75 mL) was heated in the microwave at 180° C. for 1 h. The reaction mixture was dissolved in DCM (30 mL) and washed with water (2×20 mL). The organic layer was passed through a phase separator and concentrated to afford a crude compound used in the next step (205 mg). LCMS (ES+) 412 (M+H)+.

(1S,2R,3R)-2-(2-Fluorophenyl)-N-hydroxy-3-(6-(4-isopropylpiperazin-1-yl)pyridin-3-yl)cyclopropanecarboxamide (83)

Following method A from compound 82 (200 mg, 0.45 mmol). Purification by preparative HPLC gave the racemic mixture as a white solid (49.8 mg, 26%). Preparative chiral HPLC gave the title compound (Chiralpak IC 50/50 IPA/MeOH (50/50/0.1 formic acid)/heptane, 1.0 mL/min, RT 13.2 min). RT 2.18 min (Analytical method 1). LCMS (ES+) 399. $^1$H NMR δ (ppm) (DMSO-$d_6$) 10.63 (1H, s), 8.77 (1H, s), 8.17 (1H, s), 7.46-7.41 (2H, m), 7.30-7.27 (1H, m), 7.17-7.14 (2H, m), 6.86 (1H, d, J=8.8 Hz), 3.55-3.42 (5H, m), 2.99-2.95 (1H, m), 2.78-2.74 (2H, m), 2.67-2.57 (3H, m), 2.19 (1H, dd, J=9.0, 5.2 Hz), 1.06 (6H, d, J=6.4 Hz).

Example 31

Reaction Schme 31

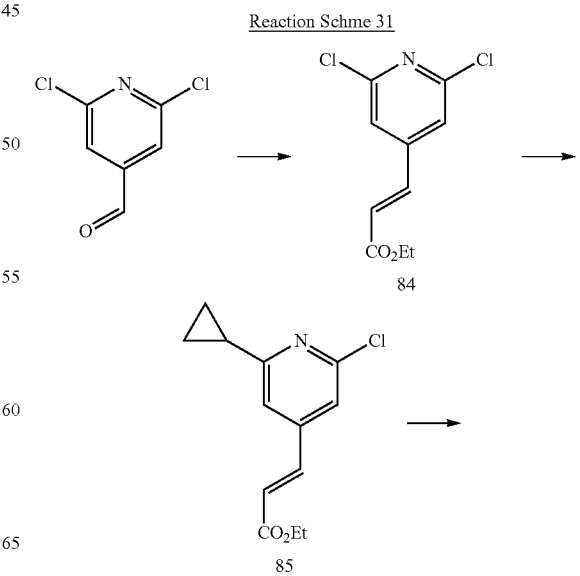

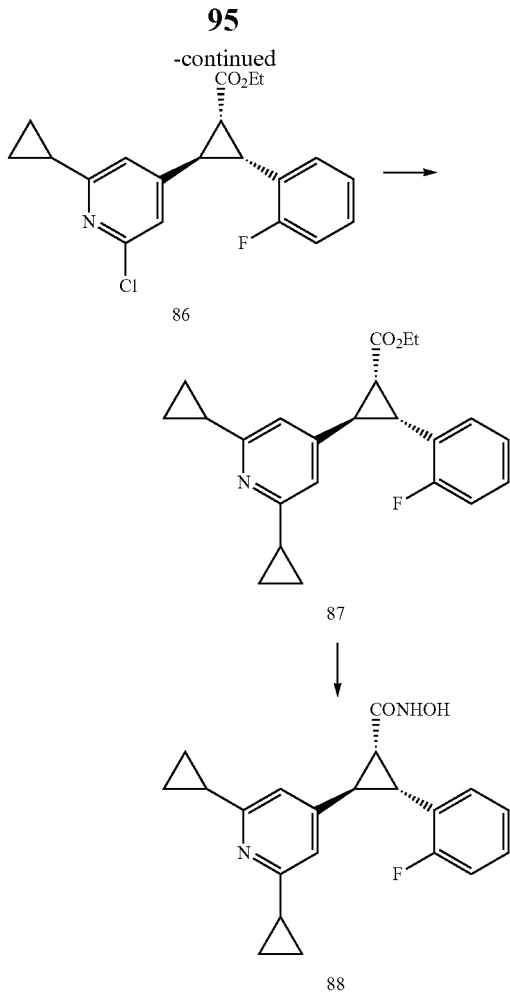

(E)-Ethyl-3-(2,6-dichloropyridin-4-yl)acrylate (84)

NaH (613 mg, 15.4 mmol) was added portion wise to stirred anhydrous DMSO (10 mL). The mixture was heated to 80° C. until evolution of gas ceased and then cooled to 000° C. A solution of (carbethoxymethyl)-triphenylphosphonium bromide (3.29 g, 7.74 mmol) in DMSO (5 mL) was then added and the mixture stirred at r.t for 30 min. The mixture was cooled to 0° C. and a solution of 2,6-dichloroisonicotinaldehyde (1.35 g, 7.74 mmol) in DMSO (5 mL) was added and the mixture was stirred at r.t for 1 h. The mixture was then poured into aqueous 1 M HCl and extracted into DCM (3×50 mL). The organics were combined and washed with H₂O (3×100 mL) and brine (2×100 mL), separated, dried (MgSO₄) and concentrated. Purification by flash silica column chromatography (gradient elution i-hex to 20% EtOAc in i-hex) gave the title compound as a yellow solid (1.25 g, 66%). LCMS (ES+) 247 (M+H)⁺.

(E)-Ethyl-3-(2-chloro-6-cyclopropyl pyridin-4-yl)acrylate (85)

A stirred solution of compound 84 (1.29 g, 5.24 mmol), cyclopropyl boronic acid (496 mg, 5.77 mmol), potassium phosphate (tribasic) (3.88 g, 18.3 mmol), Pd(OAc)₂ (117 mg, 0.52 mmol) and tricyclohexylphosphine (1.05 mL, 1 M in toluene, 1.05 mmol) in toluene/H₂O (30 mL/1.5 mL) was degassed using nitrogen for 15 min and then heated at 100° C. for 17 h. The reaction mixture was allowed to cool, diluted with H₂O (50 mL) and extracted into DCM (3×50 mL). The combined organics were washed with H₂O (2×50 mL) and brine (50 mL), separated, dried (MgSO₄) and concentrated. Purification by flash silica column chromatography (gradient elution i-hex to 5% EtOAc in i-hex) gave the title compound as a yellow solid (561 mg, 43%). LCMS (ES+) 252.5 (M+H)⁺.

(1S*,2R*,3R*)-Ethyl-2-(2-chloro-6-cyclopropylpyridin-4-yl)-3-(2-fluorophenyl)cyclopropanecarboxylate (86)

Following method F from compound 85 and 6b (894 mg, 3.23 mmol). Purification by flash silica column chromatography (gradient elution i-hex to 4% EtOAc in i-hex) gave the title compound (790 mg, 99%, 5:1 trans:cis). LCMS (ES+) 360.5 (M+H)⁺.

(1S*,2R*,3R*)-Ethyl-2-(2,6-dicyclopropylpyridin-4-yl)-3-(2-fluorophenyl)cyclopropanecarboxylate (87)

A stirred solution of compound 86 (162 mg, 0.45 mmol), cyclopropyl boronic acid (62 mg, 0.72 mmol), potassium phosphate (tribasic) (0.49 g, 2.30 mmol), Pd(OAc)₂ (14 mg, 0.065 mmol) and tricyclohexylphosphine (0.13 mL, 1 M in toluene, 0.13 mmol) in toluene/H₂O (5 mL/0.25 mL) was degassed using nitrogen for 15 min and then heated at 100° C. for 17 h. The mixture was allowed to cool, diluted with H₂O (10 mL) and extracted into DCM (3×10 mL). The combined organics were washed with H₂O (2×10 mL) and brine (10 mL), separated, dried (MgSO₄) and concentrated. Purification by flash silica column chromatography (gradient elution i-hex to 5% EtOAc in i-hex) gave the title compound (164 mg, 100%). LCMS (ES+) 366 (M+H)⁺.

(1S,2R,3R)-2-(2,6-Dicyclopropylpyridin-4-yl)-3-(2-fluorophenyl)-N-hydroxycyclopropanecarboxamide (88)

Following method A from compound 87 (164 mg, 0.45 mmol). Purification by flash silica column chromatography (gradient elution DCM to 3% MeOH in DCM) gave the racemic mixture as a white solid (85 mg, 53%). Preparative chiral HPLC gave the title compound (Chiralpak IC 15/85 IPA/MeOH (50/50)/heptane, 1.0 mL/min, RT 9.3 min). RT 2.48 min (Analytical method 1). LCMS (ES+) 353 (M+H)⁺. ¹H NMR δ (ppm) (DMSO-d₆): 10.86 (1H, s), 9.01 (1H, s), 7.64-7.59 (1H, m), 7.53-7.46 (1H, m), 7.38-7.31 (2H, m), 7.24 (0.2H, s), 7.20 (1.8H, s), 3.20-3.10 (2H, m), 2.54 (1H, dd, J=9.3, 5.3 Hz), 2.26-2.17 (2H, m), 1.12-1.07 (8H, m).

Example 32

Reaction Scheme 32

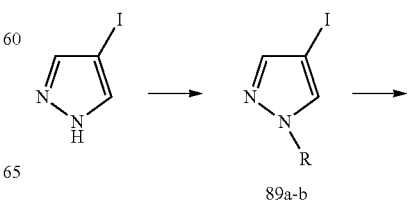

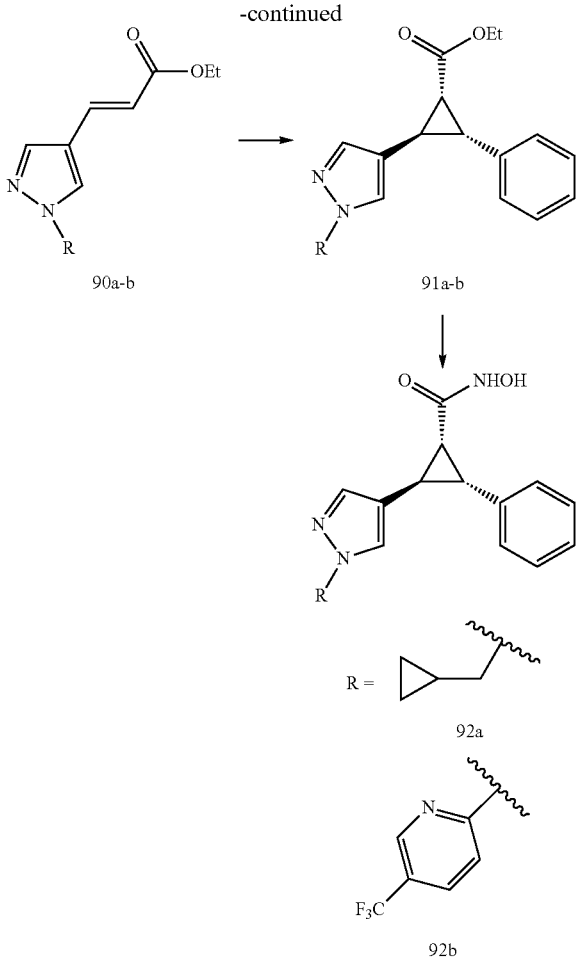

1-(Cyclopropylmethyl)-4-iodo-1H-pyrazole (89a)

To a solution of 4-iodopyrazole (960 mg, 5 mmol) in DMF (6 mL) at 0° C. was added NaH (227 mg, 5.9 mmol) and the mixture was stirred for 1 h. Then cyclopropyl bromide (755 mg, 5.9 mmol) was added and the reaction mixture was stirred at r.t. overnight. The reaction mixture was quenched with sat NaHCO$_3$ and extracted with EtOAc. The organic layer was dried (MgSO$_4$), filtered and concentrated to afford a crude used in the next step without further purification (905 mg, 73%). LCMS (ES+) 249 (M+H)$^+$.

2-(4-Iodo-1H-pyrazol-1-yl)-5-(trifluoromethyl)pyridine (89b)

To a solution of 4-iodopyrazole (960 mg, 5 mmol) in DMF (10 mL) at 0° C. was added Cs$_2$CO$_3$ (2.4 g, 7.4 mmol) and 5-trifluoromethyl-2-chloropyridine (1.5 g, 8.3 mmol). The reaction mixture was stirred at 60° C. overnight. The reaction mixture was quenched with H$_2$O and extracted with EtOAc. The organic layer was dried (MgSO$_4$), filtered and concentrated to afford a crude used in the next step without further purification (1.29 g, 76%). LCMS (ES+) 340 (M+H)$^+$.

(E)-Ethyl-3-(1-(cyclopropylmethyl)-1H-pyrazol-4-yl)acrylate (90a)

A mixture of compound 89a (900 mg, 3.6 mmol), palladium acetate (10 mg, 0.04 mmol), P(OEt)$_3$ (27 µL, 0.16 mmol), Et$_3$N (1 mL, 7.2 mmol) and ethyl acrylate in DMF (10 mL) was stirred at 80° C. for 17 h. The reaction mixture was partitioned between water and EtOAc, the organic layer was washed with water and 4% aq. LiCl, dried (MgSO$_4$), filtered and concentrated. Purification by flash silica column chromatography (gradient elution i-hex to 40% EtOAc in i-hex) gave the title compound as a yellow oil (489 mg, 62%). LCMS (ES+) 221 (M+H)$^+$.

(E)-Ethyl 3-(1-(5-(trifluoromethyl)pyridin-2-yl)-1H-pyrazol-4-yl)acrylate (90b)

To a solution of compound 89b (960 mg, 5 mmol) in DMF (10 mL) at 0° C. was added Cs$_2$CO$_3$ (2.4 g, 7.4 mmol) and 5-trifluoromethyl-2-chloropyridine (1.5 g, 8.3 mmol). The reaction mixture was stirred at 60° C. overnight. The reaction mixture was quenched with H$_2$O and extracted with EtOAc. The organic layer was dried (MgSO$_4$), filtered and concentrated to afford a crude used in the next step without further purification (1.29 g, 76%). LCMS (ES+) 340 (M+H)$^+$.

(1R*,2R*,3R*)-Ethyl-2-(1-(cyclopropylmethyl)-1H-pyrazol-4-yl)-3-phenylcyclopropanecarboxylate (91a)

Following method F from compound 90a (195 mg, 0.89 mmol) and 1-benzyltetrahydrothiophenium triflate (436 mg, 1.33 mmol). The reaction was incomplete after 1 h. The reaction was cooled to −20° C. and an additional 1.5 equivalents of sulfonium salt, 12-crown-4 and LiHMDS were added and the mixture stirred at r.t. overnight. Purification by flash silica column chromatography (gradient elution i-hex to 25% EtOAc in i-hex) gave the title compound as a yellow oil (250 mg, 93%, 1:1 trans:cis). LCMS (ES+) 311 (M+H)$^+$.

(1R*,2R*,3R*)-Ethyl-2-phenyl-3-(1-(5-(trifluoromethyl)pyridin-2-yl)-1H-pyrazol-4-yl)cyclopropanecarboxylate (91b)

Following method F from compound 90b (263 mg, 0.85 mmol) and 1-benzyltetrahydrothiophenium triflate (416 mg, 1.27 mmol). The reaction was incomplete after 1 h. The reaction was cooled to −20° C. and an additional 1.5 equivalents of sulfonium salt, 12-crown-4 and LiHMDS were added and the mixture stirred at r.t. overnight. Purification by flash silica column chromatography (gradient elution i-hex to 10% EtOAc in i-hex) gave the title compound as a yellow oil (207 mg, 61%, 5:4 trans:cis). LCMS (ES+) 402 (M+H)$^+$.

(1R,2R,3R)-2-(1-(Cyclopropylmethyl)-1H-pyrazol-4-yl)-N-hydroxy-3-phenylcyclopropanecarboxamide (92a)

Following method A from compound 91a (250 mg, 0.81 mmol). Purification by flash silica column chromatography (gradient elution DCM to 5% MeOH in DCM) gave the racemic mixture as a white solid (65 mg, 27%). Preparative chiral HPLC gave the title compound (Chiralpak IC 20/80 IPA/MeOH (50/50/0.1% formic acid)/Heptane, 1.0 mL/min, RT 12.0 min). RT 3.12 min (Analytical method 1). LCMS (ES+) 298 (M+H)$^+$. NMR δ (ppm) (DMSO-d$_6$): 10.42 (1H, s), 8.57 (1H, s), 7.65 (0.1H, s), 7.63 (0.9H, s), 7.31 (0.1H, s), 7.28 (0.9H, s), 7.24-7.13 (4H, m), 7.11-7.06 (1H, m), 3.82 (2H, d, J=7.1 Hz), 2.80 (1H, dd, J=6.8, 5.3 Hz), 2.59 (1H, dd, J=9.4, 6.8 Hz), 1.91 (1H, dd, J=9.4, 5.3 Hz), 1.17-1.07 (1H, m), 0.46-0.39 (2H, m), 0.29-0.24 (2H, m)

(1R,2R,3R)—N-Hydroxy-2-phenyl-3-(1-(5-(trifluoromethyl)pyridin-2-yl)-1H-pyrazol-4-yl)cyclopropanecarboxamide (92b)

Following method A from compound 91b (263 mg, 0.85 mmol). Purification by flash silica column chromatography (gradient elution DCM to 5% MeOH in DCM), then preparative chiral HPLC (Chiralpak IC 20/80 IPA/MeOH (50/50/0.1% formic acid)/Heptane, 1.0 mL/min, RT 10.2 min) and preparative achiral HPLC gave the title compound (15 mg, 20%). RT 3.12 min (Analytical method 4). LCMS (ES+) 389 (M+H)+. $^1$H NMR δ (ppm) (DMSO-$d_6$): 10.51 (1H, s), 8.84 (1H, s), 8.64 (1H, s), 8.61 (1H, s), 8.33 (1H, dd, J=8.7, 2.4 Hz), 8.03 (1H, d, J=8.7 Hz), 7.89 (1H, s), 7.27 (2H, d, J=7.5 Hz), 7.22 (2H, t, J=7.5 Hz), 7.14 (1H, d, J=7.2 Hz), 2.99 (1H, dd, J=6.9, 5.3 Hz), 2.84 (1H, dd, J=9.4, 6.9 Hz), 2.12 (1H, dd, J=9.4, 5.3 Hz)

Example 33 with nitrogen and then heated at 90° C. for 17 h. The reaction mixture was diluted with $H_2O$ and extracted into DCM. The organic layer was passed through a phase separator and concentrated. Purification by flash silica column chromatography (gradient elution i-hex to 25% EtOAc in i-hex) gave the title compound as a yellow oil (267 mg, 57%). LCMS (ES+) 320 (M+H)+.

(E)-tert-Butyl-7-(3-methoxy-3-oxoprop-1-en-1-yl)-2,3-dihydrobenzo[f][1,4]oxazepine-4(5H)-carboxylate (94)

To a stirred solution of compound 93 (267 mg, 0.84 mmol) in MeOH (30 mL) was added $H_2SO_4$ (3 drops) and the mixture heated to 80° C. for 17 h. The reaction mixture was concentrated and purified by flash silica column chromatography (gradient elution DCM to 25% MeOH in DCM) to give the deprotected amine (270 mg, 1.16 mmol). This was dissolved in DCM (10 mL) and di-tert-butyl dicarbonate (304 mg, 1.39 mmol) and DIPEA (0.4 mL, 2.32 mmol) added. The solution was stirred at r.t for 2 h and then diluted Reaction Scheme 33

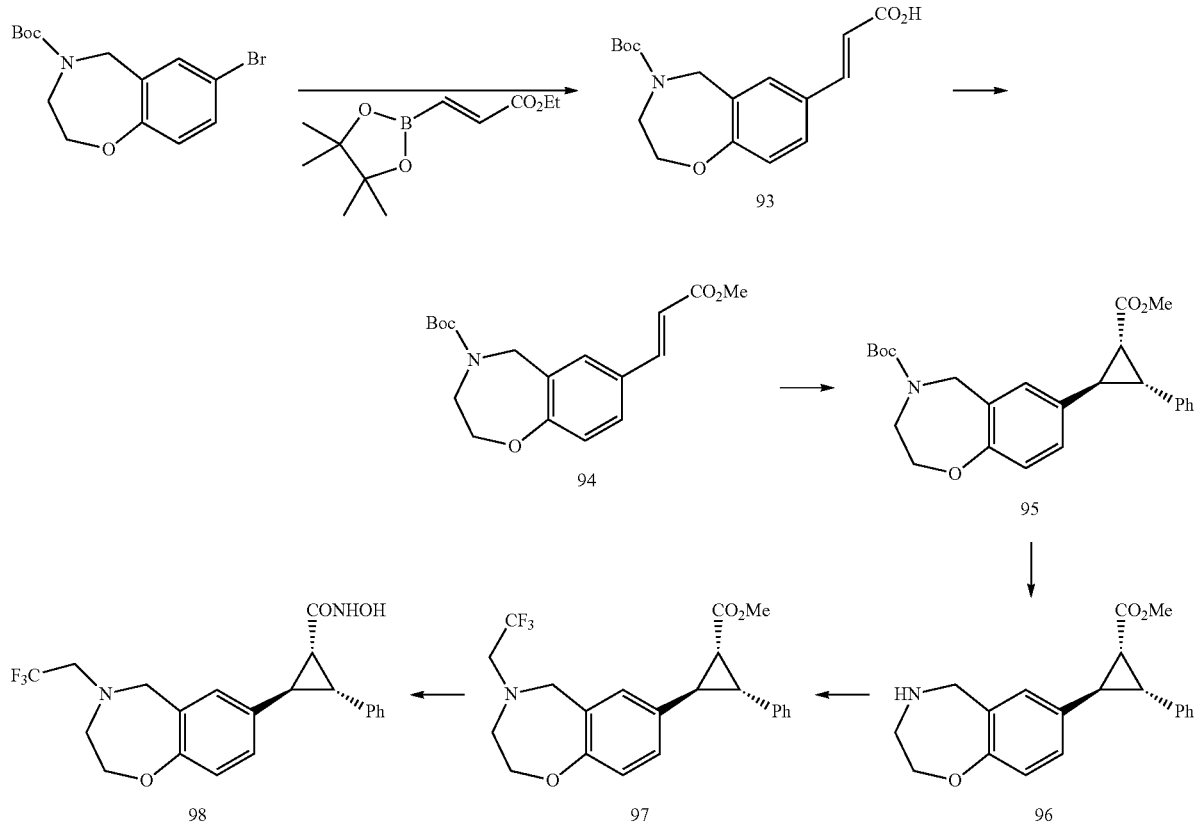

(E)-3-(4-(tert-Butoxycarbonyl)-2,3,4,5-tetrahydrobenzo[t][1,4]oxazepin-7-yl)acrylic acid (93)

To a stirred solution of tert-butyl-7-bromo-2,3-dihydrobenzo[t][1,4]oxazepine-4(5H)-carboxylate (480 mg, 1.46 mmol) in dioxane (20 mL) was added (E)-ethyl-3-(4,4,5,5-tetramethyl-1,3,2-dioxaborolan-2-yl)acrylate (360 mg, 1.61 mmol), aqueous $Na_2CO_3$ (1.44 mL, 2 M, 2.92 mmol) and Pd(dppf)$Cl_2$ (33 mg, 0.04 mmol). The mixture was degassed with $H_2O$ (50 mL) and DCM (40 mL). The biphasic mixture was shaken and the organics collected. The aqueous layer was re-extracted with DCM (50 mL) and the combined organics passed through a phase separator and concentrated. Purification by flash silica column chromatography (gradient elution i-hex to 25% EtOAc in i-hex) gave the title compound as a yellow oil (230 mg, 60%). LCMS (ES+) 333 (M+H)+.

tert-Butyl-7-((1R*,2R*,3R*)-2-(methoxycarbonyl)-3-phenylcyclopropyl)-2,3-dihydrobenzo[f][1,4]oxazepine-4(5H)-carboxylate (95)

Following method F from compound 94 (200 mg, 0.60 mmol) and 1-benzyltetrahydrothiophenium triflate (296 mg, 0.90 mmol). Purification by flash silica column chromatography (gradient elution i-hex to 20% EtOAc in i-hex) gave the title compound as a colourless oil (206 mg, 84%, 5:4 trans:cis). LCMS (ES+) 424 (M+H)+.

(1R*,2R*,3R*)-Methyl-2-phenyl-3-(2,3,4,5-tetrahydrobenzo[f][1,4]oxazepin-7-yl)cyclopropanecarboxylate (96)

To a stirred solution of compound 95 (206 mg, 0.50 mmol) in MeOH (10 mL) was added $H_2SO_4$ (3 drops) and the mixture heated to 80° C. for 1 h. The reaction mixture was concentrated, dissolved in a minimum quantity of DCM:MeOH (1:1) and loaded onto an SCX-cartridge (elution with 5% (7 M $NH_3$ in MeOH) in DCM:MeOH (1:1)). The sample was concentrated to give a colourless oil (137 mg, 88%).

(1R*,2R*,3R*)-Methyl-2-phenyl-3-(4-(2,2,2-trifluoroethyl)-2,3,4,5-tetrahydrobenzo[f][1,4]oxazepin-7-yl)cyclopropanecarboxylate (97)

To a stirred solution of compound 96 (137 mg, 0.45 mmol) in DMF (5 mL) was added DIPEA (0.23 mL, 1.35 mmol) and 2,2,2-trifluoroethyl-4-methylbenzenesulfonate (172 mg, 0.68 mmol) and the mixture heated to 80° C. for 2 h. The reaction was partitioned between DCM (50 mL) and $H_2O$ (50 mL), and the organics collected. The aqueous portion was extracted with DCM (50 mL), and the combined organics washed with $H_2O$ (5×50 mL) and 4% aqueous LiCl (100 ml). The organics were collected, dried ($MgSO_4$), filtered and concentrated. Purification by flash silica column chromatography (gradient elution i-hex to 10% EtOAc in i-hex) gave the title compound as a colourless oil (126 mg, 72%). LCMS (ES+) 390 (M+H)+.

(1R*,2R,3R*)—N-Hydroxy-2-phenyl-3-(4-(2,2,2-trifluoroethyl)-2,3,4,5-tetrahydrobenzo[f][1,4]oxazepin-7-yl)cyclopropanecarboxamide (98)

Following method A from compound 97 (126 mg, 0.32 mmol). Purification by preparative HPLC gave the racemic mixture as a white solid (33 mg, 25%). Preparative chiral HPLC gave the title compound (Chiralpak IC 10/90 EtOH (0.1% formic acid)/heptane, 1.0 mL/min, RT 12.9 min). RT 3.70 min (Analytical method 1). LCMS (ES+) 407 (M+H)+.
$^1$H NMR δ (ppm) (DMSO-$d_6$): 10.46 (1H, s), 8.60 (1H, s), 7.24 (2H, d, J=7.6 Hz), 7.21-7.15 (2H, m), 7.13-7.07 (1H, m), 7.05-7.01 (2H, m), 6.87 (1H, d, J=7.9 Hz), 3.92-3.88 (2H, m), 3.84 (2H, s), 3.19-3.03 (4H, m), 2.97 (1H, dd, J=6.8, 5.4 Hz), 2.72 (1H, dd, J=9.5, 6.8 Hz), 2.07 (1H, dd, J=9.5, 5.4 Hz).

Example 34

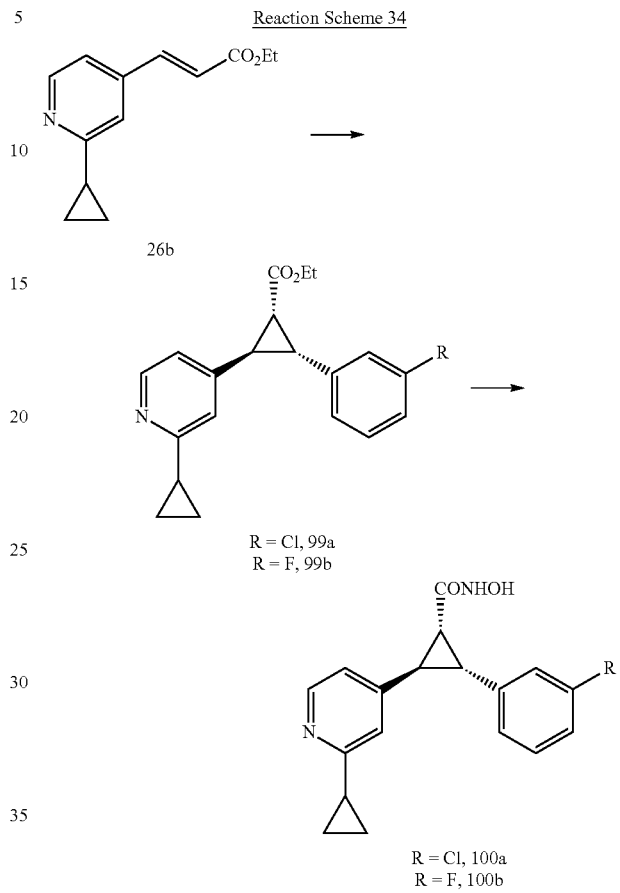

Reaction Scheme 34

(1S*,2R*,3R*)-Ethyl-2-(3-chlorophenyl)-3-(2-cyclopropylpyridin-4-yl)cyclopropanecarboxylate (99a)

1-(3-Chlorobenzyl)tetrahydro-1H-thiophen-1-ium bromide was synthesized using the same preparation as compound 6b, from 1-(bromomethyl)-3-chlorobenzene. Following method F from compound 26b (190 mg, 0.88 mmol) and 1-(3-chlorobenzyl)tetrahydro-1H-thiophen-1-ium bromide (385 mg, 1.31 mmol). Purification by flash silica column chromatography (gradient elution i-hex to 25% EtOAc in i-hex) gave the title compound as a colourless oil (299 mg, >99%, 3:2 trans:cis). LCMS (ES+) 342.5 (M+H)+.

(1S*,2R*,3R*)-Ethyl-2-(3-fluorophenyl)-3-(2-cyclopropylpyridin-4-yl)cyclopropanecarboxylate (99b)

1-(3-Fluorobenzyl)tetrahydro-1H-thiophen-1-ium bromide was synthesized using the same preparation as compound 6b, from 1-(bromomethyl)-3-fluorobenzene. Following method F from compound 26b (190 mg, 0.88 mmol) and 1-(3-chlorobenzyl)tetrahydro-1H-thiophen-1-ium bromide (363 mg, 1.31 mmol). Purification by flash silica column chromatography (gradient elution i-hex to 25% EtOAc in i-hex) gave the title compound as a colourless oil (243 mg, 85%, 3:2 trans:cis). LCMS (ES+) 326 (M+H)+.

(1S,2R,3R)-2-(3-Chlorophenyl)-3-(2-cyclopropylpyridin-4-yl)-N-hydroxycyclopropanecarboxamide (100a)

Following method A from compound 99a (299 mg, 0.88 mmol). Purification by flash silica column chromatography (gradient elution DCM to 5% MeOH in DCM) and preparative HPLC gave the racemic mixture as a white solid (100 mg, 35%). Preparative chiral HPLC gave the title compound (Chiralpak IC 30/70 EtOH (0.1% formic acid)/heptane, 1.0 mL/min, RT 8.6 min). RT 2.36 min (Analytical method 1). LCMS (ES+) 329 (M+H)+. $^1$H NMR δ (ppm) (DMSO-$d_6$): 10.56 (1H, s), 8.72 (1H, s), 8.21 (1H, d, J=5.1 Hz), 7.32 (1H, s), 7.27-7.13 (4H, m), 6.96 (1H, dd, J=5.2, 1.7 Hz), 3.03 (1H, dd, J=6.7, 5.3 Hz), 2.92 (1H, dd, J=9.6, 6.8 Hz), 2.23 (1H, dd, J=9.6, 5.4 Hz), 2.02-1.94 (1H, m), 0.88-0.80 (4H, m).

(1S,2R,3R)-2-(2-Cyclopropylpyridin-4-yl)-3-(3-fluorophenyl)-N-hydroxycyclopropanecarboxamide (100b)

Following method A from compound 99b (243 mg, 0.75 mmol). Purification by flash silica column chromatography (gradient elution DCM to 5% MeOH in DCM) and preparative HPLC gave the racemic mixture as a white solid (95 mg, 41%). Preparative chiral HPLC gave the title compound (Chiralpak IC 20/80 IPA/MeOH (50/50/0.1% formic acid)/heptane, 1.0 mL/min, RT 12.1 min). RT 2.21 min (Analytical method 1). LCMS (ES+) 313 (M+H)+. $^1$H NMR δ (ppm) (DMSO-$d_6$): 10.55 (1H, s), 8.70 (1H, s), 8.21 (1H, d, J=5.1 Hz), 7.27-7.18 (1H, m), 7.16-7.04 (3H, m), 6.97-6.90 (2H, m), 3.02 (1H, dd, J=6.6, 5.2 Hz), 2.91 (1H, dd, J=9.6, 6.7 Hz), 2.24 (1H, dd, J=9.7, 5.4 Hz), 2.01-1.94 (1H, m), 0.88-0.80 (4H, m).

Example 35

Reaction Scheme 35

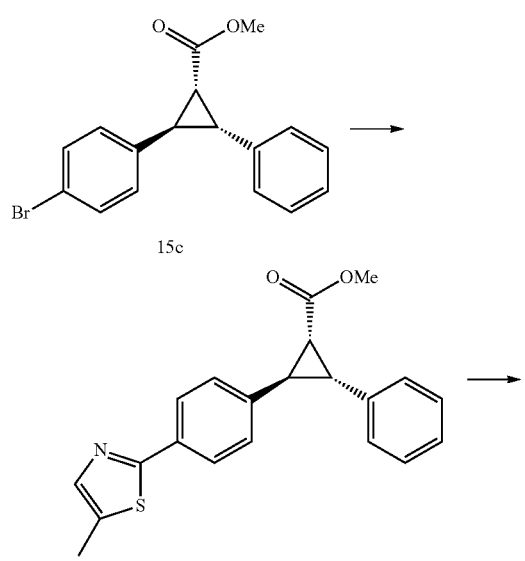

(1S*,2R*,3R)-2-(2,6-Dicyclopropylpyridin-4-yl)-3-(2-fluorophenyl)-N-hydroxycyclopropanecarboxamide (101)

A mixture of 15c (250 mg, 0.75 mmol), 5-methyl-2-(tributylstannyl)thiazole (350 mg, 0.90 mmol) and Pd(PPh$_3$)$_4$ (43 mg, 0.037 mmol) in dioxane (4 mL) was heated under microwave irradiation at 150° C. for 1 h. The reaction mixture was concentrated and purified by flash silica column chromatography (gradient elution i-hex to 20% EtOAc in i-hex) to give the title compound (180 mg, 69%). LCMS (ES+) 350 (M+H)+.

(1R,2R,3R)—N-hydroxy-2-(4-(5-methylthiazol-2-yl)phenyl)-3-phenylcyclopropanecarboxamide (102)

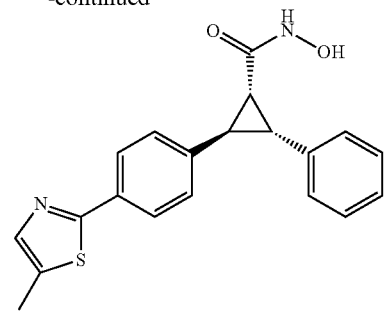

Following method A from compound 101 (160 mg, 0.46 mmol). Purification by flash silica column chromatography (gradient elution DCM to 5% MeOH in DCM) gave the racemic mixture as a white solid (150 mg, 93%). Preparative chiral HPLC gave the title compound (Chiralpak IC 40/60 IPA/MeOH (50/50/0.1% formic acid)/heptane, 1.0 mL/min, RT 11.8 min). RT 3.72 min (Analytical method 1). LCMS (ES+) 351 (M+H)+. $^1$H NMR δ (ppm) (DMSO-$d_6$): 10.53 (1H, s), 8.65 (1H, s), 7.75 (2H, d, J=8.1 Hz), 7.51 (1H, d, J=1.4 Hz), 7.34-7.23 (4H, m), 7.19 (2H, t, J=7.5 Hz), 7.11 (1H, t, J=7.2 Hz), 3.07 (1H, dd, J=6.8, 5.4 Hz), 2.82 (1H, dd, J=9.6, 6.8 Hz), 2.42 (3H, under DMSO), 2.19 (1H, dd, J=9.6, 5.4 Hz).

Example 36

Reaction Scheme 36

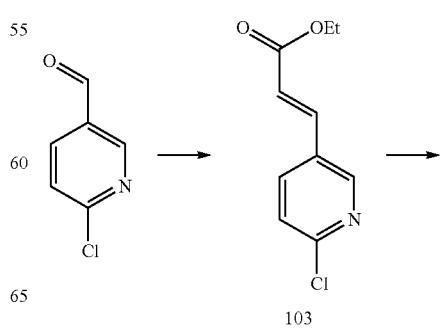

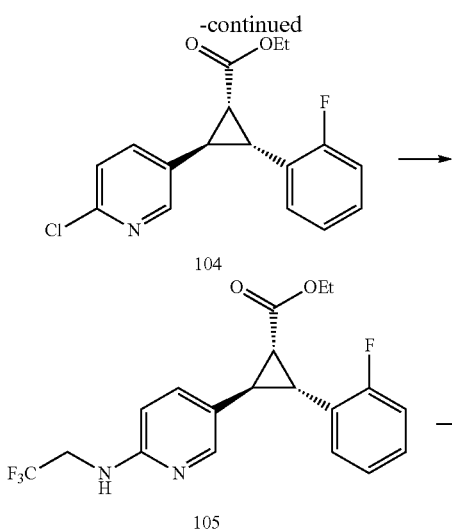

(E)-Ethyl-3-(6-chloropyridin-3-yl)acrylate (103)

NaH (792 mg, 20.0 mmol) was added portion wise to stirred anhydrous DMSO (18 mL). The mixture was heated to 80° C. until evolution of gas ceased and then cooled to 0° C. A solution of (carbethoxymethyl)-triphenylphosphonium bromide (4.3 g, 10.0 mmol) in DMSO (36 mL) was then added and the mixture stirred at r.t for 30 min. The mixture was cooled to 00° C. and a solution of 6-chloroisonicotinaldehyde (1.4 g, 10 mmol) in DMSO (36 mL) was added and the mixture was stirred at r.t for 1 h. The mixture was then poured into aqueous 1 M HCl and extracted into DCM (3×70 mL). The organics were combined and washed with $H_2O$ (3×100 mL) and brine (3×100 mL), separated, dried ($MgSO_4$) and concentrated. Purification by flash silica column chromatography (gradient elution i-hex to 80% EtOAc in i-hex) gave the title compound as a yellow solid (0.95 g, 45%). LCMS (ES+) 212 (M+H)+.

(1S*,2R*,3R*)-Ethyl-2-(6-chloropyridin-3-yl)-3-(2-fluorophenyl)cyclopropanecarboxylate (104)

Following method F from compound 103 (730 mg, 3.45 mmol) and 6b (1.43 g, 5.18 mmol). Purification by flash silica column chromatography (gradient elution i-hex to 40% EtOAc in i-hex) gave the title compound (810 mg, 73%). LCMS (ES+) 320 (M+H)+.

(1S*,2R*,3R*)-Ethyl-2-(2-fluorophenyl)-3-(6-((2,2,2-trifluoroethyl)amin)pyridin-3-yl)cyclopropanecarboxylate (105)

A mixture of compound 104 (65 mg, 0.203 mmol), trifluoroethylamine (1.0 mL) and NMP (1.0 mL) was heated in the microwave at 225° C. for 1.30 h. The reaction mixture was concentrated and the crude compound purified by flash silica column chromatography (gradient elution DCM to 10% MeOH in DCM) gave the title compound as a yellow solid (42 mg, 54%). LCMS (ES+) 383 (M+H)+.

(1S,2R,3R)-2-(2-Fluorophenyl)-N-hydroxy-3-(6-((2,2,2-trifluoroethyl)amino)pyridin-3-yl)cyclopropanecarboxamide (106)

Following method A from compound 105 (40 mg, 0.105 mmol). Post work-up the racemic compound was obtained as a white solid (38 mg, 98%). Preparative chiral HPLC gave the title compound (Chiralpak IC 15/85 EtOH/heptane, 1.0 mL/min, RT 9.2 min). RT 2.60 min (Analytical method 1) LCMS (ES+) 370. $^1$H NMR δ (ppm) (DMSO-$d_6$): 10.52 (1H, s), 8.65 (1H, s), 7.96 (1H, t, J=2.4 Hz), 7.33-7.25 (2H, m), 7.20-7.13 (1H, m), 7.07-6.93 (3H, m), 6.53 (1H, d, J=8.6 Hz), 4.14-4.01 (2H, m), 2.83 (1H, dd, J=6.9, 5.3 Hz), 2.63 (1H, dd, J=9.2, 7.0 Hz), 2.05 (1H, dd, J=9.2, 5.3 Hz).

Example 37

Reaction Scheme 37

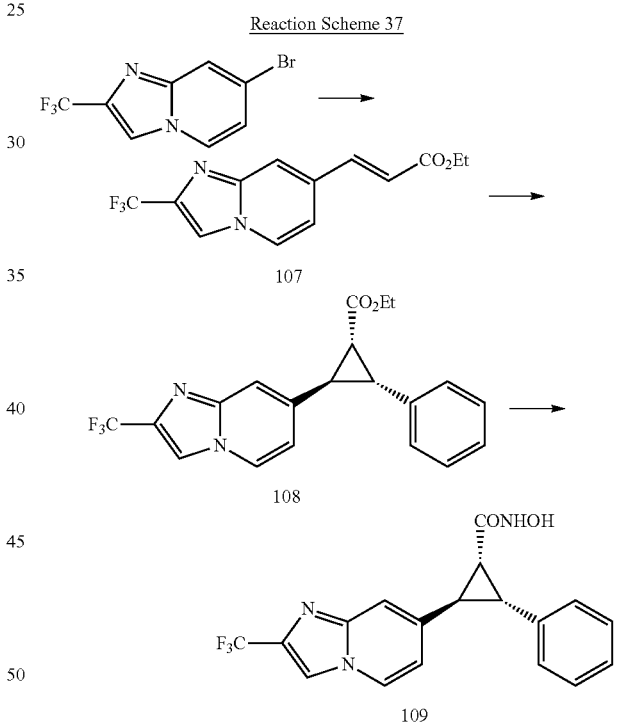

(E)-Ethyl-3-(2-(trifluoromethyl)imidazo[1,2-a]pyridin-7-yl)acrylate (107)

A stirred mixture of 7-bromo-2-(trifluoromethyl)imidazo[1,2-a]pyridine (1.00 g, 3.77 mmol), ethyl acrylate (0.53 mL, 4.91 mmol), palladium acetate (84.6 mg, 0.38 mmol), P(o-tol)$_3$ (33 mg, 0.76 mmol) and triethylamine (1.05 mL, 7.55 mmol) in MeCN (10 mL) was degassed under nitrogen for 15 min and heated to 80° C. for 18 h. The reaction mixture was cooled and the MeCN was removed in vacuo. The residue was partitioned between DCM and $H_2O$ and the organic layers were passed through a phase separator and concentrated. Purification by flash silica column chromatography (gradient elution i-hex to 100% EtOAc) gave the title compound as a pale yellow solid (1.09 g, 100%). LCMS (ES+) 285 (M+H)+.

(1R*,2R*,3R*)-Ethyl-2-phenyl-3-(2-(trifluoromethyl)imidazo[1,2-a]pyridin-7-yl)cyclopropanecarboxylate (108)

Following method F from compound 107 (0.83 mg, 2.92 mmol) and 1-(2-fluorobenzyl)tetrahydro-1H-thiophenium triflate (1.44 mg, 4.38 mmol). Purification by flash silica column chromatography (gradient elution i-hex to 30% EtOAc in i-hex) gave the title compound as a pale yellow oil (540 mg, 49%, 2:1 trans:cis). LCMS (ES+) 375 (M+H)+.

(1R,2R,3R)—N-Hydroxy-2-phenyl-3-(2-(trifluoromethyl)imidazo[1,2-a]pyridin-7-yl)cyclopropanecarboxamide (109)

Following method A from compound 108 (540 mg, 1.44 mmol). Purification by preparative-HPLC gave the racemic product as a pale yellow solid (215 mg, 41%). Preparative chiral purification afforded the title compound (Chiralpak IC 40/60 IPA/MeOH (50/50)/Heptane 5.0 ml/min, RT 7.46 min.) LCMS (ES+) 362 (M+H)+, RT 3.35 min. (Analytical method 1); $^1$H NMR δ (ppm) (DMSO-$d_6$): 10.62 (1H, s), 8.72 (1H, s), 8.64 (1H, s), 8.43 (1H, s), 7.66 (1H, d, J=9.4 Hz), 7.39-7.33 (3H, m), 7.32-7.24 (2H, m), 7.23-7.16 (1H, m), 3.19 (1H, dd, J=6.8, 5.4 Hz), 2.91 (1H, dd, J=9.6, 6.9 Hz), 2.26 (1H, dd, J=9.6, 5.4 Hz).

Example 38

Reaction Scheme 38

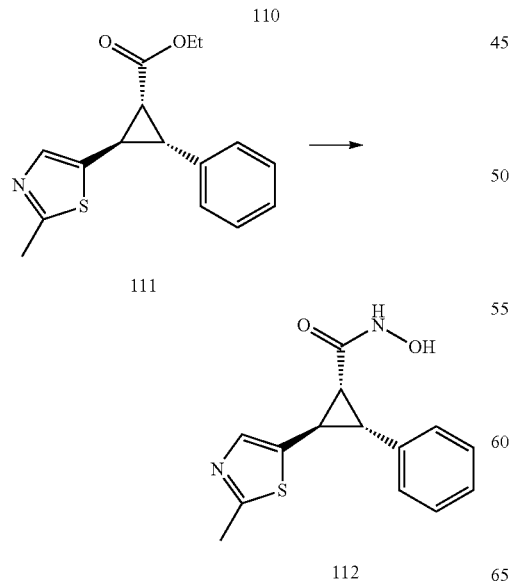

(E)-Ethyl-3-(2-methylthiazol-5-yl)acrylate (110)

Following method C to a stirred solution of 2-methyl-1,3 thiazole-50 carboxaldehyde (1.00 g, 7.86 mmol) in anhydrous THF (10 mL) at −10° C. was added sodium hydride (0.63 g, 16.0 mmol) portionwise over 10 min. This was stirred for a further 30 min at −10° C. then triethylphoshonoacetate (3.12 mL, 16.0 mmol) in THF (10 mL) was added dropwise at −10° C. The solution was warmed to RT and stirred for 18 h. The reaction mixture was poured into iced water and extracted with ethyl acetate. The organic layer was washed with brine, dried (MgSO$_4$), filtered and concentrated to give a dark brown gum (1.97 g). Purification by flash silica column chromatography (gradient elution i-hex to 100% EtOAc in i-hex) gave the title compound as a pale yellow solid (1.39 g, 89%). LCMS (ES+) 198 (M+H)+.

(1R*,2R*,3S*)-Ethyl-2-(2-methylthiazol-5-yl)-3-phenylcyclopropanecarboxy (111)

Following method F from compound 110 (0.72 g, 3.65 mmol) and 1-(2-fluorobenzyl)tetrahydro-1H-thiophenium triflate (1.80 g, 5.48 mmol). Purification by flash silica column chromatography (gradient elution i-hex to 30% EtOAc in i-hex) gave the title compound as a pale yellow oil (392 mg, 37%, 4:1 trans:cis). LCMS (ES+) 287 (M+H)+.

(1R,2R,3S)—N-Hydroxy-2-(2-methylthiazol-5-yl)-3-phenylcyclopropanecarboxamide (112)

Following method A from 111 (390 mg, 1.36 mmol). Purification by preparative-HPLC gave the racemic product as a pale yellow solid (240 mg, 64%). Preparative chiral purification gave the title compound (Chiralpak IC 40/60 IPA/MeOH (50/50)/Heptane 5.0 ml/min, RT 6.05 min). LCMS (ES+) 275 (M+H)+, RT 2.86 min. (Analytical method 1); $^1$H NMR δ (ppm) (DMSO-$d_6$): 10.59 (1H, s), 8.72 (1H, s), 7.53 (1H, s), 7.33-7.21 (4H, m), 7.22-7.15 (1H, m), 3.26-3.20 (1H, m), 2.81 (1H, dd, J=9.6, 6.8 Hz), 2.60 (3H, s), 2.16 (1H, dd, J=9.6, 5.3 Hz).

Example 39

Reaction Scheme 39

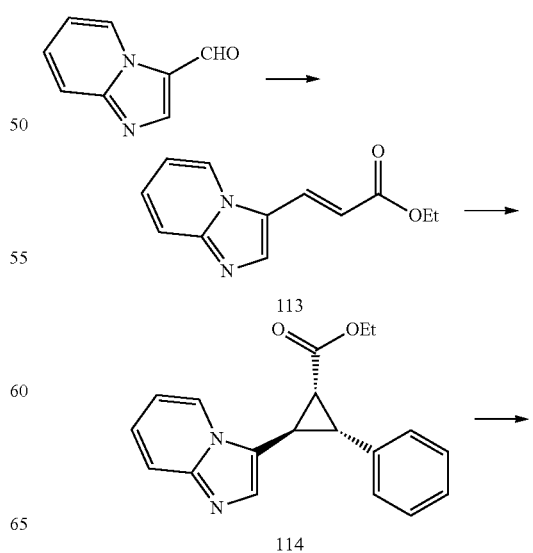

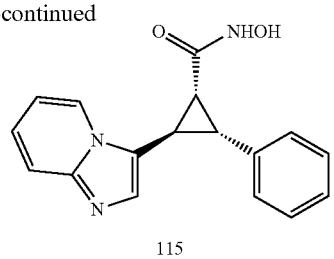

115

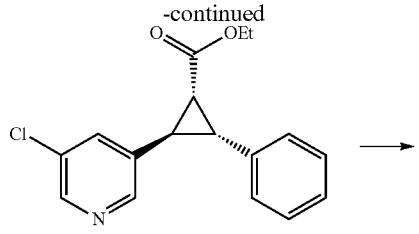

117

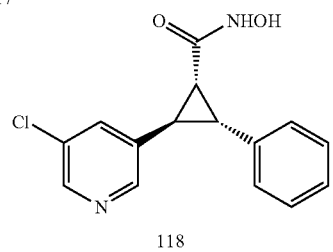

118

(E)-Ethyl-3-(imidazo[1,2-a]pyridin-3-yl)acrylate (113)

Following method C from imidazo[1,2-a]pyridine-3-carbaldehyde (1 g, 6.85 mmol). Purification by flash silica column chromatography (gradient elution i-hex to 75% EtOAc in i-hex) gave the title compound (800 mg, 54%). LCMS (ES+) 217 (M+H)+.

(1R*,2R*,3R*)-Ethyl-2-(imidazo[1,2-a]pyridin-3-yl)-3-phenylcyclopropanecarboxylate (114)

Following method F from 113 (800 mg, 3.70 mmol) and 1-(2-fluorobenzyl)tetrahydro-1H-thiophenium triflate (1.82 mg, 5.56 mmol). Purification by flash silica column chromatography (gradient elution i-hex to 100% EtOAc in i-hex) gave the title compound (813 mg, 72%). LCMS (ES+) 307 (M+H)+.

(1R,2R,3R)—N-hydroxy-2-(imidazo[1,2-a]pyridin-3-yl)-3-phenylcyclopropanecarboxamide (115)

Following method A from 114 (813 mg, 2.66 mmol). Precipitation from DCM gave the title compound as a white solid (400 mg, 51%). Preparative chiral purification gave 8 (Chiralpak IC 40/60 IPA/MeOH (50/50)/Heptane 5.0 ml/min, RT 10.4 min). LCMS (ES+) 294 (M+H)+, RT 2.05 min. (Analytical method 1); $^1$H NMR δ (ppm) (DMSO-d$_6$): 10.56 (1H, s), 8.72 (1H, s), 8.14 (1H, d, J=6.7 Hz), 7.52 (1H, d, J=9.0 Hz), 7.43 (0.1H, s), 7.41 (1H, s), 7.35 (2H, d, J=7.5 Hz), 7.26-7.13 (4H, m), 6.97-6.93 (1H, m), 3.20 (1H, dd, J=6.8, 5.4 Hz), 2.84 (1H, dd, J=9.5, 6.8 Hz), 2.09 (1H, dd, J=9.5, 5.4 Hz).

Example 40

Reaction Scheme 40

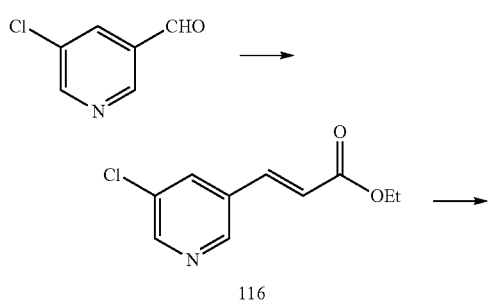

116

(E)-Ethyl-3-(5-chloropyridin-3-yl)acrylate (116)

NaH (570 mg, 14.24 mmol) was added portion wise to stirred anhydrous DMSO (10 mL). The mixture was heated to 80° C. until evolution of gas ceased and then cooled to 0° C. A solution of (carbethoxymethyl)-triphenylphosphonium bromide (3.05 g, 7.12 mmol) in DMSO (10 mL) was then added and the mixture stirred at r.t for 30 min. The mixture was cooled to 00° C. and a solution of 5-chloronicotinaldehyde (1.0 g, 7.12 mmol) in DMSO (10 mL) was added and the mixture was stirred at r.t for 1 h. The mixture was then poured into aqueous 1 M HCl and extracted into DCM (3×50 mL). The organics were combined and washed with H$_2$O (3×100 mL) and brine (3×100 mL), separated, dried (MgSO$_4$) and concentrated. Purification by flash silica column chromatography (gradient elution i-hex to 25% EtOAc in i-hex) gave the title compound as a yellow solid (1.1 g, 57%). LCMS (ES+) 271 (M+H)+.

(1R*,2R*,3R*)-Ethyl-2-(5-chloropyridin-3-yl)-3-phenylcyclopropanecarboxylate (117)

Following method F from 116 (1.1 g, 4.07 mmol) and 1-(2-fluorobenzyl)tetrahydro-1H-thiophenium triflate (2.0 g, 6.10 mmol). Purification by flash silica column chromatography (gradient elution i-hex to 15% EtOAc in i-hex) gave the title compound (396 mg, 54%). LCMS (ES+) 361 (M+H)+.

(1R,2R,3R)-2-(5-Chloropyridin-3-yl)-N-hydroxy-3-phenylcyclopropanecarboxamide (118)

Following method A from 117 (396 mg, 1.10 mmol). Purification by flash silica column chromatography (gradient elution DCM to 5% MeOH in DCM) and preparative HPLC purification gave the racemic compound (161 mg, 51%). Preparative chiral purification gave the title compound (Chiralpak IC 40/60 IPA/MeOH (50/50/0.1% formic acid)/heptane 5.0 ml/min, RT 7.74 min). LCMS (ES+) 289 (M+H)+, RT 3.10 min. (Analytical method 1); $^1$H NMR δ (ppm) (DMSO-d$_6$): 10.47 (1H, s), 8.61 (1H, s), 8.49 (1H, d, J=1.9 Hz), 8.40 (1H, d, J=2.3 Hz), 7.78-7.73 (1H, m), 7.26 (2H, d, J=7.6 Hz), 7.19 (2H, t, J=7.5 Hz), 7.11 (1H, t, J=7.2 Hz), 3.10 (1H, dd, J=6.8, 5.4 Hz), 2.93 (1H, dd, J=9.6, 6.9 Hz), 2.26 (1H, dd, J=9.6, 5.4 Hz).

Example 41

The following examples may be prepared according to methods substantially as described above.

TABLE 6

| Structure | IUPAC Name |
|---|---|
| 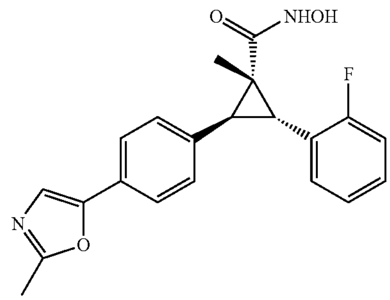 | (1S,2R,3S)-2-(2-fluorophenyl)-N-hydroxy-1-methyl-3-(4-(2-methyloxazol-5-yl)phenyl)cyclopropanecarboxamide |
| 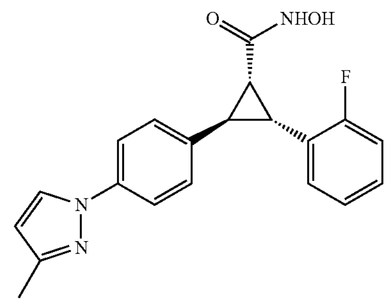 | (1S,2R,3R)-2-(2-fluorophenyl)-N-hydroxy-3-(4-(3-methyl-1H-pyrazol-1-yl)phenyl)cyclopropanecarboxamide |
| 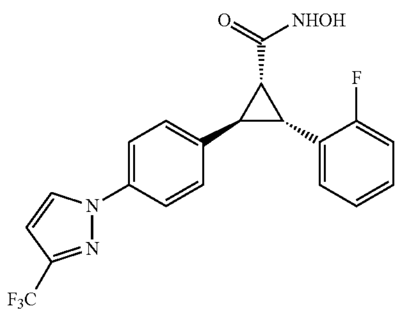 | (1S,2R,3R)-2-(2-fluorophenyl)-N-hydroxy-3-(4-(3-(trifluoromethyl)-1H-pyrazol-1-yl)phenyl)cyclopropanecarboxamide |
| 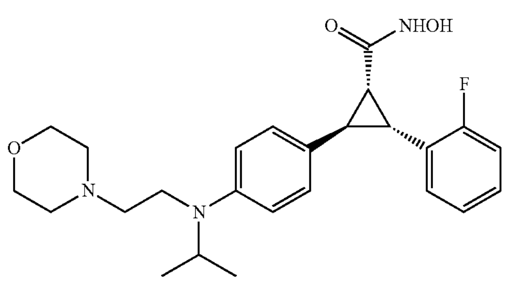 | (1S,2R,3R)-2-(2-fluorophenyl)-N-hydroxy-3-(4-(isopropyl(2-morpholinoethyl)amino)phenyl)cyclopropanecarboxamide |
| 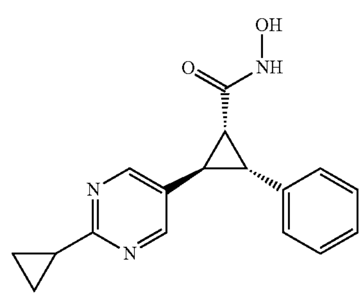 [SMILES: O=C(NO)[C@@H]1[C@H](c2ccccc2)[C@H]1c1cnc(C2CC2)nc1] | (1R,2R,3R)-2-(2-cyclopropylpyrimidin-5-yl)-N-hydroxy-3-phenylcyclopropanecarboxamide |

TABLE 6-continued

| Structure | IUPAC Name |
|---|---|
| 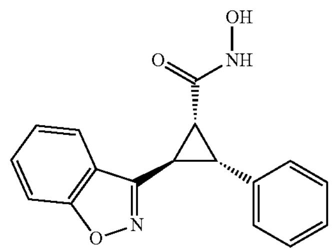 [SMILES: O=C(NO)[C@@H]1[C@H](c2ccccc2)[C@H]1c1noc2ccccc12] | (1R,2R,3R)-2-(benzo[d]isoxazol-3-yl)-N-hydroxy-3-phenylcyclopropanecarboxamide |
| 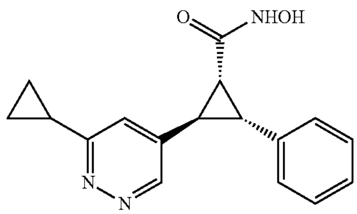 | (1R,2R,3R)-2-(6-cyclopropylpyridazin-4-yl)-N-hydroxy-3-phenylcyclopropanecarboxamide |
| 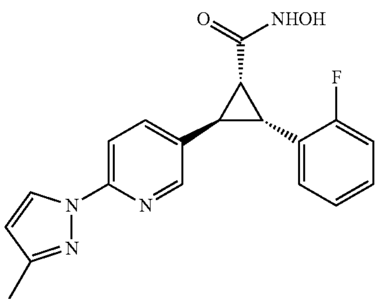 | (1S,2R,3R)-2-(2-fluorophenyl)-N-hydroxy-3-(6-(3-methyl-1H-pyrazol-1-yl)pyridin-3-yl)cyclopropanecarboxamide |
| 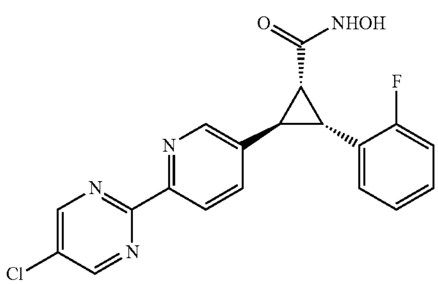 | (1S,2R,3R)-2-(6-(5-chloropyrimidin-2-yl)pyridin-3-yl)-3-(2-fluorophenyl)-N-hydroxycyclopropanecarboxamide |
| 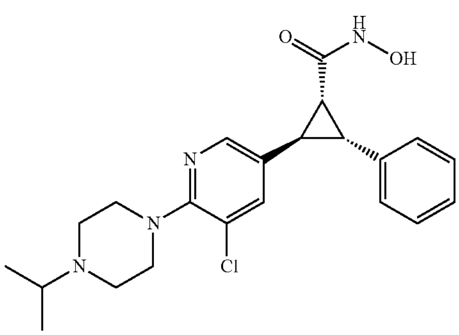 [SMILES: CC(C)N1CCN(c2ncc([C@H]3[C@H](C(=O)NO)[C@@H]3c3ccccc3)cc2Cl)CC1] | (1R,2R,3R)-2-(5-chloro-6-(4-isopropylpiperazin-1-yl)pyridin-3-yl)-N-hydroxy-3-phenylcyclopropanecarboxamide |

TABLE 6-continued

| Structure | IUPAC Name |
|---|---|
| 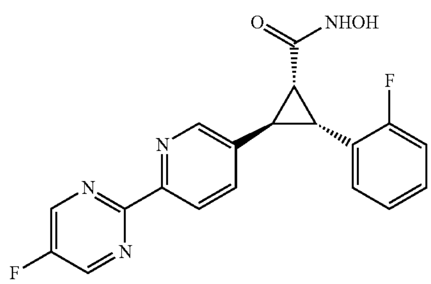 | (1S,2R,3R)-2-(2-fluorophenyl)-3-(6-(5-fluoropyrimidin-2-yl)pyridin-3-yl)-N-hydroxycyclopropanecarboxamide |
| 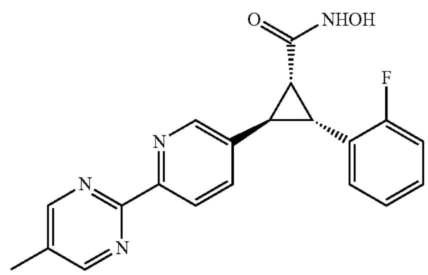 | (1S,2R,3R)-2-(2-fluorophenyl)-N-hydroxy-3-(6-(5-methylpyrimidin-2-yl)pyridin-3-yl)cyclopropanecarboxamide |
| 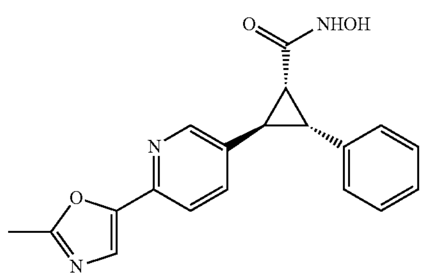 | (1R,2R,3R)-N-hydroxy-2-(6-(2-methyloxazol-5-yl)pyridin-3-yl)-3-phenylcyclopropanecarboxamide |
| 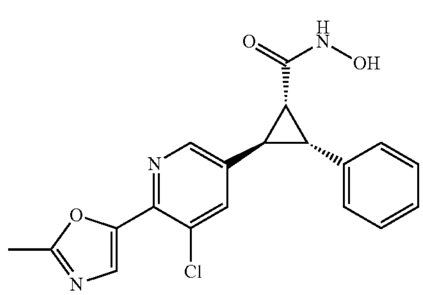 [SMILES: Cc1ncc(-c2ncc([C@H]3[C@H](C(=O)NO)[C@@H]3c3ccccc3)cc2Cl)o1] | (1R,2R,3R)-2-(5-chloro-6-(2-methyloxazol-5-yl)pyridin-3-yl)-N-hydroxy-3-phenylcyclopropanecarboxamide |
| 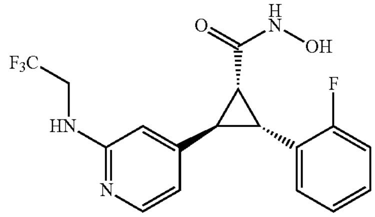 [SMILES: O=C(NO)[C@H]1[C@H](c2ccnc(NCC(F)(F)F)c2)[C@H]1c1ccccc1F] | (1S,2R,3R)-2-(2-fluorophenyl)-N-hydroxy-3-(2-(2,2,2-trifluoroethylamino)pyridin-4-yl)cyclopropanecarboxamide |

TABLE 6-continued

| Structure | IUPAC Name |
| --- | --- |
| 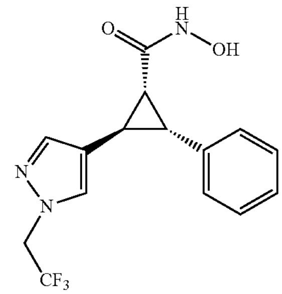 [SMILES: O=C(NO)[C@@H]1[C@H](c2ccccc2)[C@H]1c1cnn(CC(F)(F)F)c1] | (1R,2R,3R)-N-hydroxy-2-phenyl-3-(1-(2,2,2-trifluoroethyl)-1H-pyrazol-4-yl)cyclopropanecarboxamide |
| 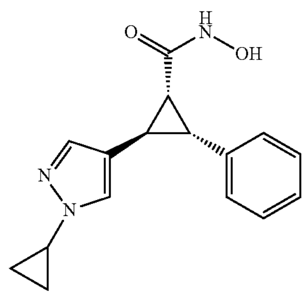 [SMILES: O=C(NO)[C@@H]1[C@H](c2ccccc2)[C@H]1c1cnn(C2CC2)c1] | (1R,2R,3R)-2-(1-cyclopropyl-1H-pyrazol-4-yl)-N-hydroxy-3-phenylcyclopropanecarboxamide |
| 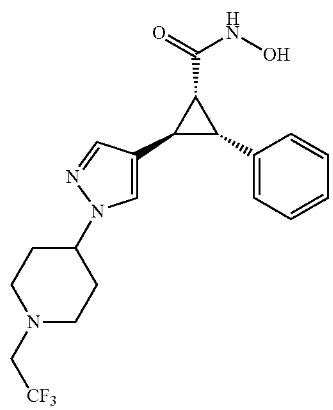 [SMILES: O=C(NO)[C@@H]1[C@H](c2ccccc2)[C@H]1c1cnn(C2CCN(CC(F)(F)F)CC2)c1] | (1R,2R,3R)-N-hydroxy-2-phenyl-3-(1-(1-(2,2,2-trifluoroethyl)piperidin-4-yl)-1H-pyrazol-4-yl)cyclopropanecarboxamide |
| 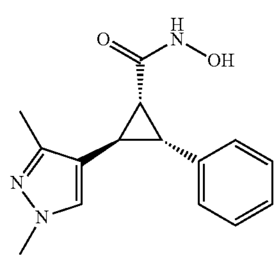 [SMILES: Cc1nn(C)cc1[C@H]1[C@H](C(=O)NO)[C@@H]1c1ccccc1] | (1R,2R,3R)-2-(1,3-dimethyl-1H-pyrazol-4-yl)-N-hydroxy-3-phenylcyclopropanecarboxamide |
| 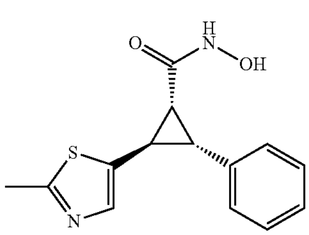 [SMILES: Cc1ncc([C@H]2[C@H](C(=O)NO)[C@@H]2c2ccccc2)s1] | (1R,2R,3S)-N-hydroxy-2-(2-methylthiazol-5-yl)-3-phenylcyclopropanecarboxamide |

TABLE 6-continued

| Structure | IUPAC Name |
|---|---|
| 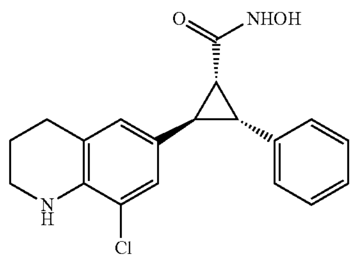 | (1R,2R,3R)-2-(8-chloro-1,2,3,4-tetrahydroquinolin-6-yl)-N-hydroxy-3-phenylcyclopropanecarboxamide |
| 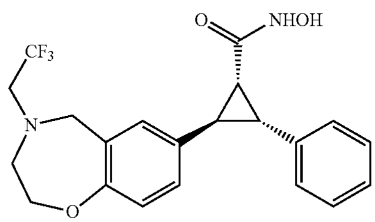 | (1R,2R,3R)-N-hydroxy-2-phenyl-3-(4-(2,2,2-trifluoroethyl)-2,3,4,5-tetrahydrobenzo[f][1,4]oxazepin-7-yl)cyclopropanecarboxamide |
| 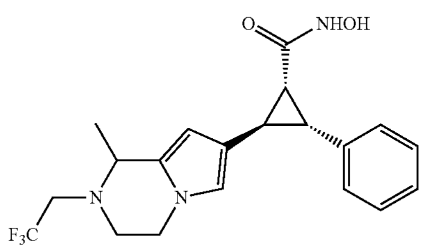 | (1R,2R,3R)-N-hydroxy-2-(1-methyl-2-(2,2,2-trifluoroethyl)-1,2,3,4-tetrahydropyrrolo[1,2-a]pyrazin-7-yl)-3-phenylcyclopropanecarboxamide |
| 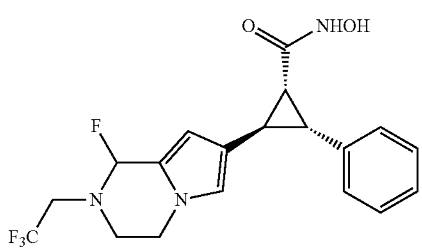 | (1R,2R,3R)-2-(1-fluoro-2-(2,2,2-trifluoroethyl)-1,2,3,4-tetrahydropyrrolo[1,2-a]pyrazin-7-yl)-N-hydroxy-3-phenylcyclopropanecarboxamide |
| 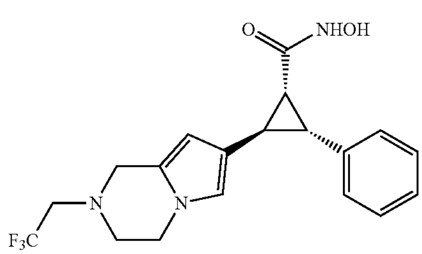 | (1R,2R,3R)-N-hydroxy-2-phenyl-3-(2-(2,2,2-trifluoroethyl)-1,2,3,4-tetrahydropyrrolo[1,2-a]pyrazin-7-yl)cyclopropanecarboxamide |
| 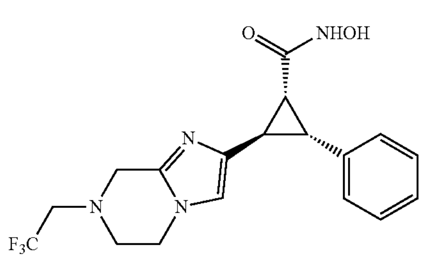 | (1R,2R,3R)-N-hydroxy-2-phenyl-3-(7-(2,2,2-trifluoroethyl)-5,6,7,8-tetrahydroimidazo[1,2-a]pyrazin-2-yl)cyclopropanecarboxamide |

TABLE 6-continued

| Structure | IUPAC Name |
|---|---|
| 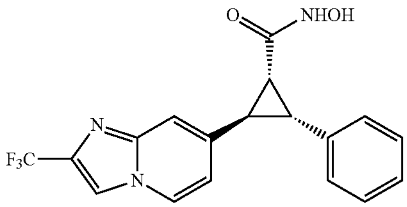 | (1R,2R,3R)-N-hydroxy-2-phenyl-3-(2-(trifluoromethyl)imidazo[1,2-a]pyridin-7-yl)cyclopropanecarboxamide |
| 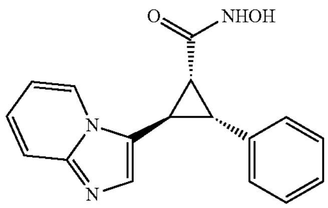 | (1R,2R,3R)-N-hydroxy-2-(imidazo[1,2-a]pyridin-3-yl)-3-phenylcyclopropanecarboxamide |
| 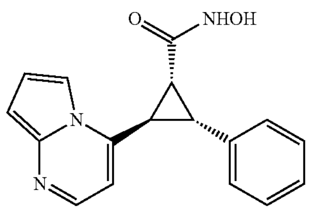 | (1R,2R,3R)-N-hydroxy-2-phenyl-3-(pyrrolo[1,2-a]pyrimidin-4-yl)cyclopropanecarboxamide |
| 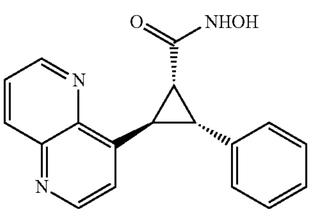 | (1R,2R,3R)-N-hydroxy-2-(1,5-naphthyridin-4-yl)-3-phenylcyclopropanecarboxamide |
| 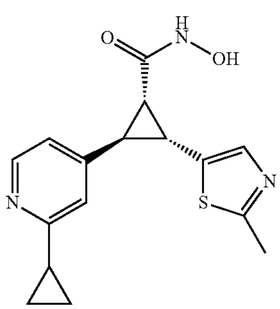 [SMILES: Cc1ncc([C@H]2[C@@H](C(=O)NO)[C@@H]2c2ccnc(C3CC3)c2)s1] | (1S,2S,3R)-2-(2-cyclopropylpyridin-4-yl)-N-hydroxy-3-(2-methylthiazol-5-yl)cyclopropanecarboxamide |
| 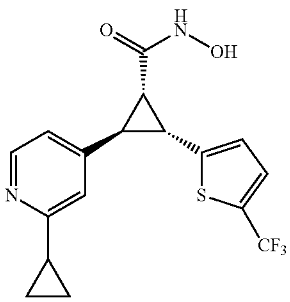 [SMILES: O=C(NO)[C@H]1[C@H](c2ccnc(C3CC3)c2)[C@H]1c1ccc(C(F)(F)F)s1] | (1S,2S,3R)-2-(2-cyclopropylpyridin-4-yl)-N-hydroxy-3-(5-(trifluoromethyl)thiophen-2-yl)cyclopropanecarboxamide |

TABLE 6-continued

| Structure | IUPAC Name |
|---|---|
| 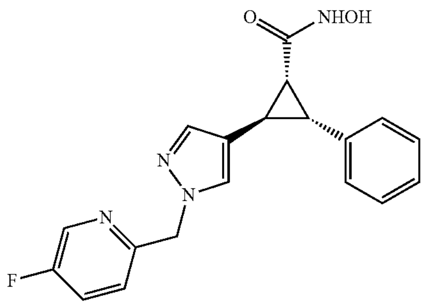 | (1R,2R,3R)-2-(1-((5-fluoropyridin-2-yl)methyl)-1H-pyrazol-4-yl)-N-hydroxy-3-phenylcyclopropanecarboxamide |
| 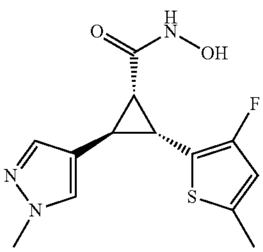 [SMILES: Cc1cc(F)c([C@H]2[C@@H](C(=O)NO)[C@@H]2c2cnn(C)c2)s1] | (1S,2R,3S)-2-(3-fluoro-5-methylthiophen-2-yl)-N-hydroxy-3-(1-methyl-1H-pyrazol-4-yl)cyclopropanecarboxamide |
| 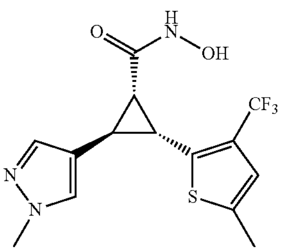 [SMILES: Cc1cc(C(F)(F)F)c([C@H]2[C@@H](C(=O)NO)[C@@H]2c2cnn(C)c2)s1] | (1S,2S,3R)-N-hydroxy-2-(1-methyl-1H-pyrazol-4-yl)-3-(5-methyl-3-(trifluoromethyl)thiophen-2-yl)cyclopropanecarboxamide |
| 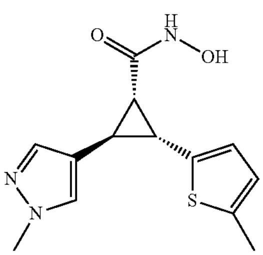 [SMILES: Cc1ccc([C@H]2[C@@H](C(=O)NO)[C@@H]2c2cnn(C)c2)s1] | (1S,2S,3R)-N-hydroxy-2-(1-methyl-1H-pyrazol-4-yl)-3-(5-methylthiophen-2-yl)cyclopropanecarboxamide |
| 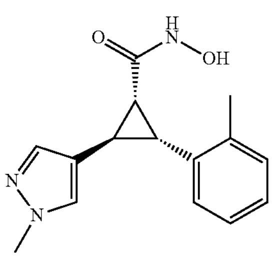 [SMILES: Cc1ccccc1[C@H]1[C@@H](C(=O)NO)[C@@H]1c1cnn(C)c1] | (1R,2R,3R)-N-hydroxy-2-(1-methyl-1H-pyrazol-4-yl)-3-o-tolylcyclopropanecarboxamide |
| 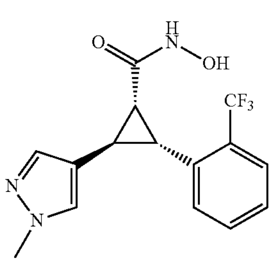 [SMILES: Cn1cc([C@H]2[C@H](C(=O)NO)[C@@H]2c2ccccc2C(F)(F)F)cn1] | (1R,2R,3R)-N-hydroxy-2-(1-methyl-1H-pyrazol-4-yl)-3-(2-(trifluoromethyl)phenyl)cyclopropanecarboxamide |

TABLE 6-continued

| Structure | IUPAC Name |
|---|---|
| 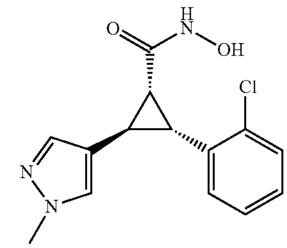 [SMILES: Cn1cc([C@H]2[C@H](C(=O)NO)[C@@H]2c2ccccc2Cl)cn1] | (1S,2R,3R)-2-(2-chlorophenyl)-N-hydroxy-3-(1-methyl-1H-pyrazol-4-yl)cyclopropanecarboxamide |
| 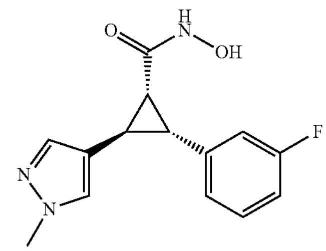 [SMILES: Cn1cc([C@H]2[C@H](C(=O)NO)[C@@H]2c2cccc(F)c2)cn1] | (1R,2R,3R)-2-(3-fluorophenyl)-N-hydroxy-3-(1-methyl-1H-pyrazol-4-yl)cyclopropanecarboxamide |
| 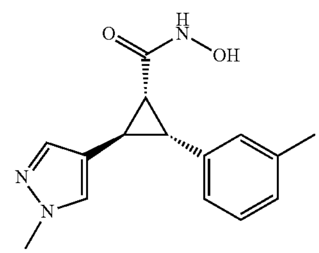 [SMILES: Cc1cccc([C@H]2[C@@H](C(=O)NO)[C@@H]2c2cnn(C)c2)c1] | (1R,2R,3R)-N-hydroxy-2-(1-methyl-1H-pyrazol-4-yl)-3-m-tolylcyclopropanecarboxamide |
| 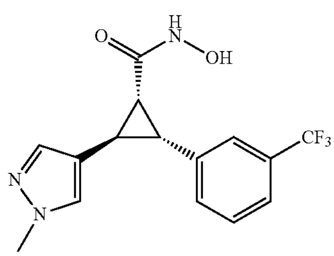 [SMILES: Cn1cc([C@H]2[C@H](C(=O)NO)[C@@H]2c2cccc(C(F)(F)F)c2)cn1] | (1R,2R,3R)-N-hydroxy-2-(1-methyl-1H-pyrazol-4-yl)-3-(3-(trifluoromethyl)phenyl)cyclopropanecarboxamide |
| 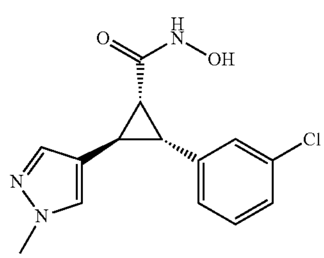 [SMILES: Cn1cc([C@H]2[C@H](C(=O)NO)[C@@H]2c2cccc(Cl)c2)cn1] | (1R,2R,3R)-2-(3-chlorophenyl)-N-hydroxy-3-(1-methyl-1H-pyrazol-4-yl)cyclopropanecarboxamide |
| 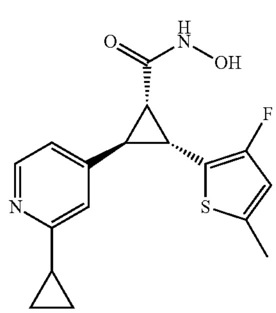 [SMILES: Cc1cc(F)c([C@H]2[C@@H](C(=O)NO)[C@@H]2c2ccnc(C3CC3)c2)s1] | (1S,2S,3R)-2-(2-cyclopropylpyridin-4-yl)-3-(3-fluoro-5-methylthiophen-2-yl)-N-hydroxycyclopropanecarboxamide |

TABLE 6-continued

| Structure | IUPAC Name |
|---|---|
| 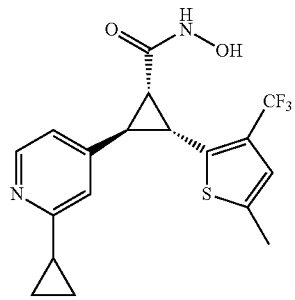 [SMILES: Cc1cc(C(F)(F)F)c([C@H]2[C@@H](C(=O)NO)[C@@H]2c2ccnc(C3CC3)c2)s1] | (1S,2S,3R)-2-(2-cyclopropylpyridin-4-yl)-N-hydroxy-3-(5-methyl-3-(trifluoromethyl)thiophen-2-yl)cyclopropanecarboxamide |
| 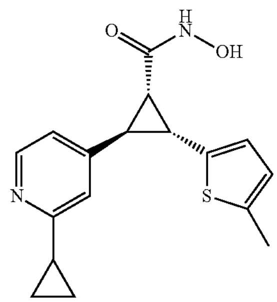 [SMILES: Cc1ccc([C@H]2[C@@H](C(=O)NO)[C@@H]2c2ccnc(C3CC3)c2)s1] | (1S,2S,3R)-2-(2-cyclopropylpyridin-4-yl)-N-hydroxy-3-(5-methylthiophen-2-yl)cyclopropanecarboxamide |
| 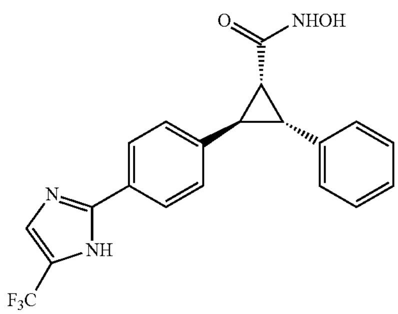 | (1R,2R,3R)-N-hydroxy-2-phenyl-3-(4-(5-(trifluoromethyl)-1H-imidazol-2-yl)phenyl)cyclopropanecarboxamide |
| 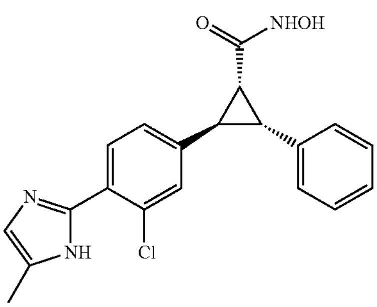 | (1R,2R,3R)-2-(3-chloro-4-(5-methyl-1H-imidazol-2-yl)phenyl)-N-hydroxy-3-phenylcyclopropanecarboxamide |
| 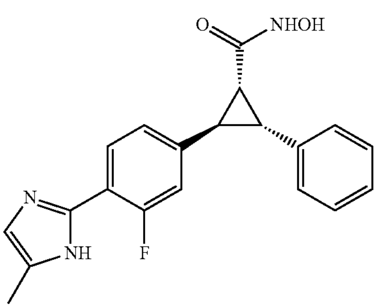 | (1R,2R,3R)-2-(3-fluoro-4-(5-methyl-1H-imidazol-2-yl)phenyl)-N-hydroxy-3-phenylcyclopropanecarboxamide |

Example 42: Analysis of inhibition of HDAC4 with Class IIa Histone Deacetylase (HDAC) Inhibitors The potency of Class IIa Histone Deacetylase (HDAC) inhibitors is quantified by measuring the Histone Deacetylase 4 (HDAC4) catalytic domain enzymatic activity using the Class IIa selective substrate, Boc-Lys(Tfa)-AMC. The substrate is deacetylated to Boc-Lys-AMC by HDAC4. Cleavage by trypsin results in the release of the fluorophore AMC from the deacetylated substrate. The fluorescence of the sample is directly related to the histone deacetylase activity in the sample.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% dimethyl sulfoxide (DMSO). Stocks of 60 µl aliquots of the 10 mM compound in DMSO are prepared and stored at −20° C. From one stock aliquot of each compound to be tested and the reference compound, a 16-point serial dilution is prepared according to Table 7 using a 125 µl 16-channel Matrix multi-channel pipette (Matrix Technologies Ltd).

TABLE 7

Serial Dilution of Compounds

| Diluted Solutions | Well | Concentration (µM) | Dilution ratio | Volumes |
|---|---|---|---|---|
| Concentration 1 | A | 10000 | — | 60 µl 10 mM Test compound/reference control |
| Concentration 2 | B | 5000 | 1:2 | 30 µl A + 30 µl DMSO |
| Concentration 3 | C | 2500 | 1:2 | 30 µl B + 30 µl DMSO |
| Concentration 4 | D | 1000 | 1:2.5 | 30 µl C + 45 µl DMSO |
| Concentration 5 | E | 500 | 1:2 | 30 µl D + 30 µl DMSO |
| Concentration 6 | F | 250 | 1:2 | 30 µl E + 30 µl DMSO |
| Concentration 7 | G | 125 | 1:2 | 30 µl F + 30 µl DMSO |
| Concentration 8 | H | 62.5 | 1:2 | 30 µl G + 30 µl DMSO |
| Concentration 9 | I | 31.25 | 1:2 | 30 µl H + 30 µl DMSO |
| Concentration 10 | J | 15.63 | 1:2 | 30 µl I + 30 µl DMSO |
| Concentration 11 | K | 7.81 | 1:2 | 30 µl J + 30 µl DMSO |
| Concentration 12 | L | 3.91 | 1:2 | 30 µl K + 30 µl DMSO |
| Concentration 13 | M | 1.95 | 1:2 | 30 µl L + 30 µl DMSO |
| Concentration 14 | N | 0.98 | 1:2 | 30 µl M + 30 µl DMSO |
| Concentration 15 | O | 0.49 | 1:2 | 30 µl N + 30 µl DMSO |
| Concentration 16 | P | 0.24 | 1:2 | 30 µl O + 30 µl DMSO |

2 µl (200×) of each diluted solution and each control (full activity: 100% DMSO alone or full inhibition 1 mM) is stamped into V-bottomed polypropylene 384-well compound plates using either the Bravo (384-well head from Agilent) or 12.5 µl 16-channel Matrix multi-channel pipette (Matrix Technologies Ltd). Each well with the 200× compound solution is diluted 1:20 by the addition of 38 µl assay buffer+DMSO (10.5% DMSO, 45 mM Tris-HCl, 123 mM NaCl, 2.4 mM KCl, and 0.9 mM MgCl$_2$ at pH 8.0 and equilibrated to room temperature).

Prepare HDAC4 Catalytic Domain Enzyme (0.86 µg/ml).

The HDAC4 catalytic domain enzyme is human catalytic domain HDAC4 protein (amino acids 648-1057, but with a replacement of amino acids 730-744 with 4 amino acid GSGS linker) made from VCID 3428 and provided by Emerald Biostructures at 1.2 mg/ml. A working solution of enzyme is prepared from a 1.2 mg/ml stock aliquot of HDAC4 catalytic domain (thawed on ice) diluted to 0.86 µg/ml with assay buffer (50 mM Tris-HCl, 137 mM NaCl, 2.7 mM KCl, and 1 mM MgCl$_2$ at pH 8 and equilibrated to room temperature) just prior to the addition of the enzyme to the assay.

Prepare 5× (50 µM) Boc-Lys(Tfa)-AMC Substrate.

5× (50 µM) substrate is prepared just prior to the addition to the assay. A 1 mM substrate stock is made by diluting a 100 mM Boc-Lys(Tfa)-AMC in DMSO solution 1:100 by adding it drop-wise to assay buffer (equilibrated to room temperature) while vortexing at slow speed to prevent precipitation. The 5× substrate is prepared by diluting the 1 mM substrate solution 1:20 by adding it drop-wise to assay buffer (equilibrated to room temperature) while vortexing at slow speed to prevent precipitation.

Prepare 3× (30 µM) Developer/Stop Solution.

3× (30 µM) Developer/Stop Solution is prepared just prior to addition to the plate by diluting a stock solution of 10 mM reference compound 1:333 in 25 mg/ml trypsin (PAA Laboratories Ltd.) equilibrated to room temperature.

Assay.

5 µl of each solution of 1:20 diluted compound from above is transferred to a clear bottomed, black, 384-well assay plate using the Bravo or the Janus (384-well MDT head from Perkin Elmer). Using a 16-channel Matrix multi-channel pipette, 35 pII of the working solution of HDAC4 catalytic domain enzyme (0.86 µg/ml in assay buffer) is transferred to the assay plate. The assay is then started by adding 10 µl of 5× (50 µM) substrate to the assay plates using either the Bravo, Janus or 16-channel Matrix multi-channel pipette. The assay plate is then shaken for two minutes on an orbital shaker at 900 rpm (rotations per minute). Next the plate is incubated for 15 minutes at 37° C. The reaction is stopped by adding 25 µl of 3× (30 µM) developer/stop solution to the assay plates using either the Bravo, Janus or a 16-channel Matrix multi-channel pipette. Assay plates are then shaken for 5 minutes on an orbital shaker at 1200 rpm. Next, the assay plates are incubated at 37° C. for 1 hour in a tissue culture incubator. Finally, the fluorescence is measured (Excitation: 355 nm, Emission: 460 nm) using PerkinElmer EnVision in top read mode.

Example 43: Analysis of Inhibition of HDAC5 with Class IIa Histone Deacetylase (HDAC) Inhibitors The potency of Class IIa Histone Deacetylase (HDAC) inhibitors is quantified by measuring the Histone Deacetylase 5 (HDAC5) enzymatic activity using the Class IIa selective substrate, Boc-Lys(Tfa)-AMC. The substrate is deacetylated to Boc-Lys-AMC by HDAC5. Cleavage by trypsin results in the release of the fluorophore AMC from the deacetylated substrate. The fluorescence of the sample is directly related to the histone deacetylase activity in the sample.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 60 µl aliquots of the 10 mM compound in DMSO are prepared and stored at −20° C. From one stock aliquot of each compound to be tested and the reference compound, a 16-point serial dilution is prepared according to Table 7 using a 125 µl 16-channel Matrix multi-channel pipette.

2 µl (200×) of each diluted solution and each control (full activity: 100% DMSO alone or full inhibition 1 mM) is stamped into V-bottom polypropylene 384-well compound plates using either Bravo, Janus, or a 12.5 µl 16-channel Matrix multi-channel pipette. Each well with the 2 µl of the 200× stamped compound solution is diluted 1:20 by the addition of 38 µl assay buffer+DMSO (10.5% DMSO, 45 mM Tris-HCl, 123 mM NaCl, 2.4 mM KCl, and 0.9 mM MgCl$_2$ at pH 8.0 and equilibrated to 37° C.).

Prepare HDAC5 Catalytic Domain Enzyme (0.57 µg/ml).

The HDAC5 catalytic domain enzyme is human HDAC5 catalytic domain (GenBank Accession No. NM_001015053), amino acids 657-1123 with a C-terminal His tag and can be obtained from BPS BioScience. The protein is 51 kDa and is expressed in a baculovirus expression system. A working solution of enzyme is prepared from a 1.65 mg/ml stock aliquot of HDAC5 catalytic domain (thawed on ice) diluted to 0.57 µg/ml with assay buffer (50 mM Tris-HCl, 137 mM NaCl, 2.7 mM KCl, and 1 mM MgCl$_2$ at pH 8 and equilibrated to 37° C.) just prior to the addition of the enzyme to the assay.

Prepare 5× (40 µM) Boc-Lys(Tfa)-AMC Substrate.

5× (40 µM) substrate is prepared just prior to the addition to the assay. The 5× substrate is prepared by diluting the 100 mM Boc-Lys(Tfa)-AMC in DMSO solution 1:2500 by adding it drop-wise to assay buffer (equilibrated to 37° C.) while vortexing at slow speed to prevent precipitation.

Prepare 3× (30 µM) Developer/Stop Solution.

3× (30 µM) Developer/Stop Solution is prepared just prior to addition to the plate by diluting a stock solution of 10 mM reference compound 1:333 in 25 mg/ml trypsin equilibrated to 37° C.

Assay.

5 µl of each solution of the 1:20 diluted inhibitor compounds and controls from above is transferred to a clear bottomed, black, 384-well assay plate using the Bravo or Janus. Using a 16-channel Matrix multi-channel pipette, 35 µl of the working solution of the HDAC5 catalytic domain enzyme (0.57 µg/ml in assay buffer) is transferred to the assay plate. The assay is then started by adding 10 µl of 5× (40 µM) substrate to the assay plates using either the Bravo, Janus or 16-channel Matrix multi-channel pipette. The assay plate is then shaken for one minute on an orbital shaker at 900 rpm. Next, the plates are incubated for 15 minutes at 37° C. The reaction is stopped by adding 25 µl of 3× (30 µM) developer/stop solution to the assay plates using either the Bravo, Janus or a 16-channel Matrix multi-channel pipette. Assay plates are then shaken for 2 minutes on an orbital shaker at 900 rpm. Next, the assay plates are incubated at 37° C. for 1 hour in a tissue culture incubator followed by shaking for 1 minute at the maximum rpm on an orbital shaker before reading on the EnVision. Finally, the fluorescence is measured (Excitation: 355 nm, Emission: 460 nm) using PerkinElmer EnVision in top read mode.

Example 44: Analysis of Inhibition of HDAC7 with Class IIa Histone Deacetylase (HDAC) Inhibitors The potency of Class IIa Histone Deacetylase (HDAC) inhibitors is quantified by measuring the Histone Deacetylase 7 (HDAC7) enzymatic activity using the Class IIa selective substrate, Boc-Lys(Tfa)-AMC. The substrate is deacetylated to Boc-Lys-AMC by HDAC7. Cleavage by trypsin results in the release of the fluorophore AMC from the deacetylated substrate. The fluorescence of the sample is directly related to the histone deacetylase activity in the sample.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 60 µl aliquots of the 10 mM compound in DMSO are prepared and stored at −20° C. From one stock aliquot of each compound to be tested and the reference compound, a 16-point serial dilution is prepared according to Table 7 using a 125 µl 16-channel Matrix multi-channel pipette.

2 µl (200×) of each diluted solution and each control (full activity: 100% DMSO alone or full inhibition 1 mM) is stamped into V-bottom polypropylene 384-well compound plates using either the Bravo, Janus, or a 12.5 µl 16-channel Matrix multi-channel pipette. Each well with the 200× compound solution is diluted 1:20 by the addition of 38 µl assay buffer+DMSO (10.5% DMSO, 45 mM Tris-HCl, 123 mM NaCl, 2.4 mM KCl, and 0.9 mM MgCl$_2$ at pH 8.0 and equilibrated to 37° C.).

Prepare HDAC7 Enzyme (71 ng/ml).

The HDAC7 enzyme is human HDAC7 (GenBank Accession No. AY302468) amino acids 518-end with a N-terminal Glutathione S-transferase (GST) tag and can be obtained from BPS BioScience. The protein is 78 kDa and is expressed in a baculovirus expression system. A working solution of enzyme is prepared from a 0.5 mg/ml stock aliquot of HDAC7 (thawed on ice) diluted to 71 ng/ml with assay buffer (50 mM Tris-HCl, 137 mM NaCl, 2.7 mM KCl, and 1 mM MgCl$_2$ at pH 8 and equilibrated to 37° C.) just prior to the addition of enzyme to the assay.

Prepare 5× (50 µM) Boc-Lys(Tfa)-AMC Substrate.

5× (50 µM) substrate is prepared just prior to the addition to the assay. The 5× substrate is prepared by diluting a 100 mM Boc-Lys(Tfa)-AMC in DMSO solution 1:2000 by adding it drop-wise to assay buffer (equilibrated to 37° C.) while vortexing at slow speed to prevent precipitation.

Prepare 3× (30 µM) Developer/Stop Solution.

3× (30 µM) Developer/Stop Solution is prepared just prior to addition to the plate by diluting a stock solution of 10 mM reference compound 1:333 in 25 mg/ml trypsin equilibrated to 37° C.

Assay.

5 µl of each solution of 1:20 diluted compound from above is transferred to a clear bottomed, black, 384-well assay plate using the Bravo or Janus. Using a 16-channel Matrix multi-channel pipette, 35 µl of the working solution of the HDAC7 enzyme (71 ng/ml in assay buffer) is transferred to the assay plate. The assay is then started by adding 10 µl of 5× (50 µM) substrate to the assay plate using either the Bravo, Janus or 16-channel Matrix multi-channel pipette. The assay plate is then shaken for one minute on an orbital shaker at 900 rpm. Next, the plate is incubated for 15 minutes at 37° C. The reaction is then stopped by adding 25 µl of 3× (30 µM) developer/stop solution to the assay plates using either the Bravo, Janus or a 16-channel Matrix multi-channel pipette. The assay plate is then shaken for 2 minutes on an orbital shaker at 900 rpm. Next, the assay plate is incubated at 37° C. for 1 hour in a tissue culture incubator followed by shaking for 1 minute at maximum rpm on an orbital shaker. Finally, the fluorescence is measured (Excitation: 355 nm, Emission: 460 nm) using PerkinElmer EnVision in top read mode.

Example 45: Analysis of Inhibition of HDAC9 with Class IIa Histone Deacetylase (HDAC) Inhibitors The potency of Class IIa Histone Deacetylase (HDAC) inhibitors is quantified by measuring the Histone Deacetylase 9 (HDAC9) enzymatic activity using the Class IIa selective substrate, Boc-Lys(Tfa)-AMC. The substrate is deacetylated to Boc-Lys-AMC by HDAC9. Cleavage by trypsin results in the release of the fluorophore AMC from the deacetylated substrate. The fluorescence of the sample is directly related to the histone deacetylase activity in the sample.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 60 µl aliquots of the 10 mM compound in DMSO are prepared and stored at −20° C. From one stock aliquot of each compound to be tested and the reference compound, a 16-point serial dilution is prepared according to Table 7 using a 125 µl 16-channel Matrix multi-channel pipette.

2 µl (200×) of each diluted solution and each control (full activity: 100% DMSO alone or full inhibition 1 mM) is stamped into V-bottom polypropylene 384-well compound plates using either the Bravo, Janus, or 12.5 µl 16-channel Matrix multi-channel pipette. Each well with the stamped 200× compound solution is diluted 1:20 by the addition of 38 µl assay buffer+DMSO (10.5% DMSO, 45 mM Tris-HCl, 123 mM NaCl, 2.4 mM KCl, and 0.9 mM $MgCl_2$ at pH 8.0 and equilibrated to 37° C.).

Prepare HDAC9 Enzyme (0.57 µg/ml).

The HDAC9 enzyme is human HDAC9 (GenBank Accession No. NM_178423) amino acids 604-1066 with a C-terminal His tag and can be obtained from BPS BioScience. The protein is 50.7 kDa and is expressed in a baculovirus expression system. A working solution of enzyme is prepared from a 0.5 mg/ml stock aliquot of HDAC9 (thawed on ice) diluted to 0.57 µg/ml with assay buffer (50 mM Tris-HCl, 137 mM NaCl, 2.7 mM KCl, and 1 mM $MgCl_2$ at pH 8 and equilibrated to 37° C.) just prior to the addition of enzyme to the assay.

Prepare 5× (125 µM) Boc-Lys(Tfa)-AMC Substrate.

5× (125 µM) substrate is prepared just prior to the addition to the assay. The 5× substrate is prepared by diluting a 100 mM Boc-Lys(Tfa)-AMC in DMSO solution 1:800 by adding it drop-wise to assay buffer (equilibrated to 37° C.) while vortexing at slow speed to prevent precipitation.

Prepare 3× (30 µM) Developer/Stop Solution.

3× (30 µM) Developer/Stop Solution is prepared just prior to addition to the plate by diluting a stock solution of 10 mM reference compound 1:333 in 25 mg/ml trypsin equilibrated to 37° C.

Assay.

5 µl of each solution of 1:20 diluted compound from above is transferred to a clear bottomed, black, 384-well assay plate using the Bravo or Janus. Using a 16-channel Matrix multi-channel pipette, 35 µl of the working solution of the HDAC9 enzyme (0.57 µg/ml in assay buffer) is transferred to the assay plate. The assay is then started by adding 10 µl of 5× (125 µM) substrate to the assay plate using either the Bravo, Janus or 16-channel Matrix multi-channel pipette. The assay plate is then shaken for one minute on an orbital shaker at 900 rpm. Next, the plate is incubated for 15 minutes at 37° C. The reaction is stopped by adding 25 µl of 3× developer/stop solution to the assay plates using either the Bravo, Janus or a 16-channel Matrix multi-channel pipette. The assay plate is then shaken for 2 minutes on an orbital shaker at 900 rpm. Next, the assay plate is incubated at 37° C. for 1 hour in a tissue culture incubator followed by shaking for 1 minute at maximum rpm on an orbital shaker before reading on the enVision. Finally, the fluorescence is measured (Excitation: 355 nm, Emission: 460 nm) using PerkinElmer EnVision in top read mode.

Example 46: Analysis of Inhibition of Cellular HDAC Activity with Class IIa Histone Deacetylase (HDAC) Inhibitors The potency of Class IIa Histone Deacetylase (HDAC) inhibitors is quantified by measuring the cellular histone deacetylase enzymatic activity using the Class IIa selective substrate, Boc-Lys(Tfa)-AMC. After penetration in Jurkat E6-1 cells, the substrate is deacetylated to Boc-Lys-AMC. After cell lysis and cleavage by trypsin, the fluorophore AMC is released from the deacetylated substrate only. The fluoresence of the sample is directly related to the histone deacetylase activity in the sample.

Jurkat E6.1 Cell Culture and Plating.

Jurkat E6.1 cells are cultured according to standard cell culture protocols in Jurkat E6.1 Growth Media (RPMI without phenol red, 10% FBS, 10 mM HEPES, and 1 mM Sodium Pyruvate). Jurkat E6.1 cells are counted using a Coulter Counter and resuspended in Jurkat E6.1 growth media at a concentration of 75,000 cells/35 µl. 35 µl or 75,000 cells is seeded into Greiner microtitre assay plates. The plates are then incubated at 37° C. and 5% $CO_2$ while other assay components are being prepared.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 70 µl aliquots of the 10 mM compound in DMSO are prepared and stored at −20° C. From one stock aliquot of each compound to be tested and the reference compound, a 16-point serial dilution is prepared according to Table 7 using a 125 µl 16-channel Matrix multi-channel pipette.

2 µl (200×) of each diluted solution and each control (full activity: 100% DMSO alone or full inhibition 1 mM) is stamped into V-bottom polypropylene 384-well compound plates using either the Bravo, Janus, or 12.5 pII 16-channel Matrix multi-channel pipette. Each well with the 200× compound solution is diluted 1:20 by the addition of 38 µl Jurkat assay buffer+DMSO (9.5% DMSO, RPMI without phenol red, 0.09% FBS, 9 mM Hepes, and 0.9 mM Sodium Pyruvate equilibrated to room temperature)

Prepare 5× (500 µM) Boc-Lys(Tfa)-AMC Substrate.

5× (500 µM) substrate is prepared just prior to the addition to the assay. The 5× substrate is prepared by diluting a 100 mM Boc-Lys(Tfa)-AMC in DMSO solution 1:200 by adding it drop-wise to Jurkat assay medium (RPMI without phenol red, 0.1% FBS, 10 mM Hepes, and 1 mM Sodium Pyruvate equilibrated to 37° C.) while vortexing at slow speed to prevent precipitation.

Prepare 3× Lysis Buffer.

10 ml of 3× lysis buffer is prepared with 8.8 ml of 3× stock lysis buffer (50 mM Tris-HCl, pH 8.0, 137 mM NaCl, 2.7 mM KCl, 1 mM $MgCl_2$, 1% Nonidet P40 Substitute equilibrated to room temperature) and 1.2 ml of 3 mg/ml Trypsin equilibrated to room temperature.

Assay.

5 µl of each solution of 1:20 diluted compound from above is transferred to the Greiner microtitre assay plates with 75,000 cells/well using the Bravo. Cells are then incubated for 2 hours at 37° C. and 5% $CO_2$. The assay is then started by adding 10 μl of 5× (500 μM) substrate to the assay plate using either the Bravo or 16-channel Matrix multi-channel pipette. The cells are then incubated for 3 hours at 37° C. and 5% $CO_2$. Next, 25 μl of 3× lysis buffer is added to each well using either the 125 μl 16 channel pipette or the Bravo. The assay plate is then incubated overnight (15-16 hours) at 37° C. and 5% $CO_2$. The following day, the plates are shaken on an orbital shaker for 1 minute at 900 rpm. Finally the top read fluorescence (Excitation: 355 nm, Emission: 460 nm) is measured using PerkinElmer EnVision.

Example 47

Using the synthetic methods similar to those described above and the assay protocols described above, the following compounds were synthesized and tested.

TABLE 8

| Chemical Name | Compound Number | Biochemical HDAC-4 $IC_{50}$ (μM) | Cellular $IC_{50}$ (μM) |
|---|---|---|---|
| (1R*,2R*,3R*)-N-Hydroxy-2-phenyl-3-(4-(pyrimidin-5-yl)phenyl)cyclopropanecarboxamide | 50i | 0.10 | 1.25 |
| (1R*,2R*,3R*)-2-(2-Bromophenyl)-N-hydroxy-3-phenylcyclopropanecarboxamide | 16a | 0.62 | 6.53 |
| (1R*,2R*,3R*)-N-Hydroxy-2-phenyl-3-o-tolylcyclopropanecarboxamide | 18a | 1.72 | 13.16 |
| (1R*,2R*,3R*)-N-Hydroxy-2-phenyl-3-(4-(pyrimidin-2-yl)phenyl)cyclopropanecarboxamide | 50h | 0.06 | 0.62 |
| (1S*,2R*,3R*)-2-(2-Fluorophenyl)-N-hydroxy-3-phenylcyclopropanecarboxamide | 13 | 0.94 | 7.67 |
| (1R*,2R*,3R*)-N-Hydroxy-2-(2-isopropoxyphenyl)-3-phenylcyclopropanecarboxamide | 11a | 20.57 | 50 |
| (1R*,2R*,3R*)-2-(2-Fluorophenyl)-N-hydroxy-3-phenylcyclopropanecarboxamide | 11b | 0.32 | 1.83 |
| (1R*,2R*,3R*)-N-Hydroxy-2-phenyl-3-(pyrimidin-5-yl)cyclopropanecarboxamide | 25c | 1.81 | 19.68 |
| (1S*,2R*,3R*)-2-Cyclopentyl-N-hydroxy-3-phenylcyclopropanecarboxamide | 25a | 8.96 | 48.08 |
| (1R*,2R*,3R*)-N-Hydroxy-2-(4-(5-methylpyrimidin-2-yl)phenyl)-3-phenylcyclopropanecarboxamide | 50k | 0.09 | 0.48 |
| (1R*,2R*,3R*)-2-(4-(4-Trifluoromethylpyrimidin-2-yl)phenyl)-N-hydroxy-3-phenylcyclopropanecarboxamide | 50d | 0.21 | 0.88 |
| (1R*,2R*,3R*)-2-(4-(5-Cyclopropylpyrimidin-2-yl)phenyl)-N-hydroxy-3-phenylcyclopropanecarboxamide | 50c | 0.22 | 0.81 |
| (1R*,2R*,3R*)-2-(4-(5-Fluoropyrimidin-2-yl)phenyl)-N-hydroxy-3-phenylcyclopropanecarboxamide | 50a | 0.06 | 0.39 |
| (1R*,2R*,3R*)-2-(3-(5-Fluoropyrimidin-2-yl)phenyl)-N-hydroxy-3-phenylcyclopropanecarboxamide | 50b | 0.10 | 1.02 |
| (1R*,2R*,3R*)-N-Hydroxy-2-phenyl-3-(pyridazin-4-yl)cyclopropanecarboxamide | 28a | 1.09 | 23.52 |
| (1R,2R,3R)-N-Hydroxy-2-(4-(oxazol-5-yl)phenyl)-3-phenylcyclopropanecarboxamide | 41b | 0.02 | 0.22 |
| (1R,2R,3R)-N-Hydroxy-2-(3-(oxazol-5-yl)phenyl)-3-phenylcyclopropanecarboxamide | 41a | 0.04 | 0.39 |
| (1R,2R,3R)-N-hydroxy-2-(2-isopropylbenzo[d]oxazol-6-yl)-3-phenylcyclopropanecarboxamide | 39 | 0.02 | 0.22 |
| (1R,2R,3R)-N-Hydroxy-2-phenyl-3-(5-(trifluoromethyl)pyridin-3-yl)cyclopropanecarboxamide | 68 | 0.23 | 2.31 |
| (1R,2R,3R)-N-Hydroxy-2-phenyl-3-(6-(trifluoromethyl)pyridin-3-yl)cyclopropanecarboxamide | 28f | 0.34 | 5.67 |
| (1R,2R,3R)-2-(2-Cyclopropylpyridin-4-yl)-N-hydroxy-3-phenylcyclopropanecarboxamide | 28b | 0.02 | 0.67 |

TABLE 8-continued

| Chemical Name | Compound Number | Biochemical HDAC-4 IC$_{50}$ (μM) | Cellular IC$_{50}$ (μM) |
|---|---|---|---|
| (1R,2R,3R)-2-(2-Cyclopropylpyridin-4-yl)-3-(4-fluorophenyl)-N-hydroxycyclopropanecarboxamide | 25d | 0.03 | 0.62 |
| (1R,2R,3R)-2-(2,2-Difluorobenzo[d][1,3]dioxol-5-yl)-N-hydroxy-3-phenylcyclopropanecarboxamide | 28e | 0.12 | 2.03 |
| (1R,2R,3R)-2-(4-(2-Cyclopropyloxazol-5-yl)phenyl)-N-hydroxy-3-phenylcyclopropanecarboxamide | 46 | 0.04 | 0.28 |
| (1R,2R,3R)-N-Hydroxy-2-phenyl-3-(2-(trifluoromethyl)pyridin-4-yl)cyclopropanecarboxamide | 28g | 0.30 | 2.58 |
| (1R,2R,3R)-N-Hydroxy-2-(1-oxo-2-(2,2,2-trifluoroethyl)isoindolin-5-yl)-3-phenylcyclopropanecarboxamide | 33 | 0.03 | 0.34 |
| (1S,2R,3R)-2-(2-Cyclopropylpyridin-4-yl)-3-(2-fluorophenyl)-N-hydroxycyclopropanecarboxamide | 28c | 0.04 | 0.53 |
| (1R,2R,3R)-2-(2-Cyclopropylpyridin-4-yl)-3-(4-fluorophenyl)-N-hydroxycyclopropanecarboxamide | 28d | 0.12 | 0.79 |
| (1R,2R,3R)-N-Hydroxy-2-(1-methyl-1H-pyrazol-4-yl)-3-phenylcyclopropanecarboxamide | 25b | 0.54 | 2.62 |
| (1R,2R,3R)-2-(4-(5-Trifluoromethylpyrimidin-2-yl)phenyl)-N-hydroxy-3-phenylcyclopropanecarboxamide | 50e | 0.18 | 0.69 |
| (1R,2R,3R)-2-(8-Chloro-2,3-dihydrobenzo[b][1,4]dioxin-6-yl)-N-hydroxy-3-phenylcyclopropanecarboxamide | 25e | 0.02 | 0.13 |
| (1R*,2R*,3R*)-N-Hydroxy-2-phenyl-3-(4-(pyridazin-3-yl)phenyl)cyclopropanecarboxamide | 50f | 0.08 | 0.62 |
| (1R*,2R*,3R*)-N-Hydroxy-2-phenyl-3-(4-(pyridazin-4-yl)phenyl)cyclopropanecarboxamide | 50g | 0.11 | 0.66 |
| (1R*,2R*,3R*)-N-Hydroxy-2-(4-(4-methylpiperazin-1-yl)phenyl)-3-phenylcyclopropanecarboxamide | 56i | 0.14 | 1.31 |
| (1R*,2R*,3R*)-N-Hydroxy-2-(4-(oxazol-2-yl)phenyl)-3-phenylcyclopropanecarboxamide | 58 | 0.05 | 0.35 |
| (1R*,2R*,3R*)-N-Hydroxy-2-(4-(1-methyl-1H-imidazol-2-yl)phenyl)-3-phenylcyclopropanecarboxamide | 60 | 0.29 | 2.05 |
| (1R*,2R*,3R*)-2-(4-(1H-pyrazol-1-yl)phenyl)-N-hydroxy-3-phenylcyclopropanecarboxamide | 65 | 0.09 | 0.97 |
| (1R*,2R*,3R*)-2-(4-(3,3-Dimethylazetidin-1-yl)phenyl)-N-hydroxy-3-phenylcyclopropanecarboxamide | 56d | 0.33 | 3.17 |
| (1R*,2R*,3R*)-N-Hydroxy-2-(4-(4-isopropylpiperazin-1-yl)phenyl)-3-phenylcyclopropanecarboxamide | 56a | 0.09 | 0.76 |
| (1R*,2R*,3R*)-N-Hydroxy-2-(4-(3,3-difluoropyrrolidin-1-yl)phenyl)-3-phenylcyclopropanecarboxamide | 56c | 0.15 | 1.77 |
| (1R*,2R*,3R*)-2-(4-(2-Oxa-6-azaspiro[3.3]heptan-6-yl)phenyl)-N-hydroxy-3-phenylcyclopropanecarboxamide | 56e | 0.15 | 1.33 |
| (1R,2R,3R)-2-(3'-(Benzyloxy)-[1,1'-biphenyl]-4-yl)-N-hydroxy-3-phenylcyclopropanecarboxamide | 54a | 0.99 | 8.85 |
| (1R,2R,3R)-2-(4-(1-Benzyl-1,2,3,6-tetrahydropyridin-4-yl)phenyl)-N-hydroxy-3-phenylcyclopropanecarboxamide | 71 | 0.35 | 0.75 |
| (1R,2R,3R)-N-hydroxy-2-(4-(4-methyl-3,4-dihydro-2H-benzo[b][1,4]oxazin-7-yl)phenyl)-3-phenylcyclopropanecarboxamide | 54c | 0.26 | 1.43 |

TABLE 8-continued

| Chemical Name | Compound Number | Biochemical HDAC-4 IC$_{50}$ (μM) | Cellular IC$_{50}$ (μM) |
|---|---|---|---|
| (1R*,2R*,3R*)-2-(4-(2-cyclopropylisoindolin-5-yl)phenyl)-N-hydroxy-3-phenylcyclopropanecarboxamide | 52 | 0.48 | 1.79 |
| (1R*,2R*,3R*)-2-(4'-(9H-carbazol-9-yl)-[1,1'-biphenyl]-4-yl)-N-hydroxy-3-phenylcyclopropanecarboxamide | 54b | 5.66 | 50 |
| (1R*,2S*,3S*)-2-(4-(5-Fluoropyrimidin-2-yl)phenyl)-N-hydroxy-1-methyl-3-phenylcyclopropanecarboxamide | 63 | 0.27 | 1.55 |
| (1R*,2R*,3R*)-N-Hydroxy-2-(3-(4-isopropylpiperazin-1-yl)phenyl)-3-phenylcyclopropanecarboxamide | 56b | 1.43 | 5.08 |
| (1R,2R,3R)-2-(3-(6,7-Dihydropyrazolo[1,5-a]pyrimidin-4(5H)-yl)phenyl)-N-hydroxy-3-phenylcyclopropanecarboxamide | 56h | 0.17 | 0.77 |
| (1R*,2R*,3R*)-2-(3-(Hexahydropyrrolo[1,2-a]pyrazin-2(1H)-yl)phenyl)-N-hydroxy-3-phenylcyclopropanecarboxamide | 56f | 0.63 | 1.85 |
| (1R*,2R*,3R*)-N-Hydroxy-2-phenyl-3-(3-(4-(pyrrolidin-1-yl)piperidin-1-yl)phenyl)cyclopropanecarboxamide | 56g | 0.39 | 2.18 |
| (1R,2R,3R)-2-(4-(5-Chloropyrimidin-2-yl)phenyl)-N-hydroxy-3-phenylcyclopropanecarboxamide | 50j | 0.14 | 0.42 |
| (1R*,2R*,3R*)-N-Hydroxy-2-(4-(5-methyl-1H-imidazol-2-yl)phenyl)-3-phenylcyclopropanecarboxamide | 50l | 0.10 | 0.46 |
| (1S,2R,3R)-2-(8-Chloro-2,3-dihydrobenzo[b][1,4]dioxin-6-yl)-3-(2-fluorophenyl)-N-hydroxycyclopropanecarboxamide | 25f | 0.03 | 0.24 |
| (1R*,2R*,3R*)-N-Hydroxy-2-phenyl-3-(4-(2-phenyloxazol-5-yl)phenyl)cyclopropanecarboxamide | 48 | 0.28 | 1.26 |
| trans-N-Hydroxy-2,3-diphenylcyclopropanecarboxamide | 2 | 0.34 | 2.52 |
| (1R*,2R*,3R*)-2-Cyclohexyl-N-hydroxy-3-phenylcyclopropanecarboxamide | 5 | 6.22 | 36.91 |
| (1R*,2R*,3R*)-2-(4-Bromophenyl)-N-hydroxy-3-phenylcyclopropanecarboxamide | 16c | 0.37 | 2.87 |
| (1R*,2R*,3R*)-2-(4-(1H-imidazol-1-yl)phenyl)-N-hydroxy-3-phenylcyclopropanecarboxamide | 42 | 0.20 | 1.63 |
| (1R*,2R*,3R*)-2-(4-(cyclopropanesulfonamido)phenyl)-N-hydroxy-3-phenylcyclopropanecarboxamide | 22 | 0.05 | 1.32 |
| (1R*,2R*,3R*)-N-Hydroxy-2-phenyl-3-p-tolylcyclopropanecarboxamide | 18c | 0.15 | 2.25 |
| (1R*,2R*,3R*)-2-(3-Bromophenyl)-N-hydroxy-3-phenylcyclopropanecarboxamide | 16b | 0.07 | 1.41 |
| (1R*,2R*,3R*)-N-Hydroxy-2-phenyl-3-m-tolylcyclopropanecarboxamide | 18b | 0.15 | 2.74 |
| (1R,2R,3R)-N-Hydroxy-2-(4-(2-methyloxazol-5-yl)phenyl)-3-phenylcyclopropanecarboxamide | 75a | 0.03 | 0.33 |
| (1S,2R,3R)-2-(2-Fluorophenyl)-N-hydroxy-3-(4-(2-methyloxazol-5-yl)phenyl)cyclopropanecarboxamide | 75b | 0.05 | 0.47 |
| (1R,2R,3R)-N-Hydroxy-2-(3-(5-methylpyrimidin-2-yl)phenyl)-3-phenylcyclopropanecarboxamide | 77 | 0.16 | 0.78 |
| (1S,2R,3R)-2-(2,6-Dicyclopropylpyridin-4-yl)-3-(2-fluorophenyl)-N-hydroxycyclopropanecarboxamide | 88 | 0.20 | 1.48 |
| (1R,2R,3R)-N-Hydroxy-2-(4-(3-methyl-1H-pyrazol-1-yl)phenyl)-3-phenylcyclopropanecarboxamide | 79 | 0.09 | 0.65 |
| (1S,2R,3R)-2-(2-Fluorophenyl)-N-hydroxy-3-(6-(4-isopropylpiperazin-1-yl)pyridin-3-yl)cyclopropanecarboxamide | 83 | 0.12 | 0.75 |

TABLE 8-continued

| Chemical Name | Compound Number | Biochemical HDAC-4 $IC_{50}$ (μM) | Cellular $IC_{50}$ (μM) |
|---|---|---|---|
| (1R,2R,3R)-N-Hydroxy-2-phenyl-3-(1-(5-(trifluoromethyl)pyridin-2-yl)-1H-pyrazol-4-yl)cyclopropanecarboxamide | 92b | 0.18 | 1.17 |
| (1R,2R,3R)-N-hydroxy-2-(imidazo[1,2-a]pyridin-3-yl)-3-phenylcyclopropanecarboxamide | 115 | 0.55 | 6.66 |
| (1R,2R,3R)-N-Hydroxy-2-phenyl-3-(2-(trifluoromethyl)imidazo[1,2-a]pyridin-7-yl)cyclopropanecarboxamide | 109 | 0.23 | 2.5 |
| (1S,2R,3R)-2-(2-Cyclopropylpyridin-4-yl)-3-(3-fluorophenyl)-N-hydroxycyclopropanecarboxamide | 100b | 0.02 | 0.42 |
| (1R,2R,3R)-N-hydroxy-2-(4-(5-methylthiazol-2-yl)phenyl)-3-phenylcyclopropanecarboxamide | 102 | 0.04 | 0.44 |
| (1S,2R,3R)-2-(2-Fluorophenyl)-N-hydroxy-3-(6-((2,2,2-trifluoroethyl)amino)pyridin-3-yl)cyclopropanecarboxamide | 106 | 0.17 | 1.41 |

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed:

1. A compound of Formula I:

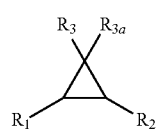

Formula I or a pharmaceutically acceptable salt thereof, wherein
$R_1$ and $R_2$ are independently chosen from optionally substituted cycloalkyl, optionally substituted heterocycloalkyl, optionally substituted aryl, and optionally substituted heteroaryl;
$R_3$ is —C(O)NH(OH); and
$R_3$ is hydrogen or lower alkyl optionally substituted with halo.

2. The compound of claim 1, or a pharmaceutically acceptable salt thereof, wherein the compound of Formula I is a compound of Formula II:

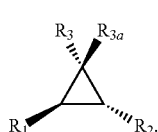

Formula II

3. The compound of claim 1, or a pharmaceutically acceptable salt thereof, wherein the compound of Formula I is a compound of Formula III:

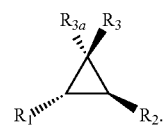

Formula III

4. The compound of claim 1, or a pharmaceutically acceptable salt thereof, wherein $R_{3a}$ is hydrogen or methyl.

5. The compound of claim 1, or a pharmaceutically acceptable salt thereof, wherein $R_{3a}$ is —$CF_3$.

6. The compound of claim 1, or a pharmaceutically acceptable salt thereof, wherein the compound of Formula I is a compound of Formula IV:

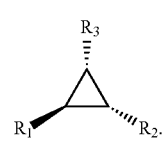

Formula IV

7. The compound of claim 1, or a pharmaceutically acceptable salt thereof, wherein the compound of Formula I a compound of Formula V:

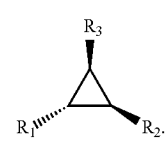

Formula V

8. The compound of claim 1, or a pharmaceutically acceptable salt thereof, wherein $R_2$ is cycloalkyl, heterocycloalkyl, aryl or heteroaryl, each of which is optionally substituted with one, two, or three groups independently chosen from —$R_{21}$, —$OR_{22}$, halo, and —$NR_{23}SO_2R_{21}$, wherein
$R_{21}$ is chosen from optionally substituted $C_1$-$C_6$ alkyl, optionally substituted cycloalkyl, optionally substituted aryl, optionally substituted heterocycloalkyl, and optionally substituted heteroaryl;

$R_{22}$ is chosen from H, optionally substituted $C_1$-$C_6$ alkyl, optionally substituted cycloalkyl, optionally substituted aryl, optionally substituted arylalkyl, optionally substituted heterocycloalkyl, optionally substituted heteroaryl, and optionally substituted heteroarylalkyl; and $R_{23}$ is chosen from hydrogen and optionally substituted $C_1$-$C_4$ alkyl.

9. The compound of claim 8, or a pharmaceutically acceptable salt thereof, wherein $R_2$ is cyclohexyl, thiophen-2-yl, thiazol-5-yl, or phenyl, each of which is optionally substituted with one, two, or three groups independently chosen from —$R_{21}$, —$OR_{22}$, and halo.

10. The compound of claim 9, or a pharmaceutically acceptable salt thereof, wherein $R_2$ is thiophen-2-yl or phenyl, each of which is optionally substituted with one, two, or three groups independently chosen from $C_1$-$C_6$ alkyl, $C_1$-$C_6$ alkoxy, trifluoromethyl, and halo.

11. The compound of claim 10, or a pharmaceutically acceptable salt thereof, wherein $R_2$ is phenyl, 2-chlorophenyl, 2-fluorophenyl, 2-methylphenyl, 2-trifluoromethylphenyl, 3-fluorophenyl, 3-methylphenyl, 3-trifluoromethylphenyl, 4-fluorophenyl, 5-methylthiophen-2-yl, 3-fluoro-5-methylthiophen-2-yl, 5-methyl-3-(trifluoromethyl)thiophen-2-yl, or 5-(trifluoromethyl)thiophen-2-yl.

12. The compound of claim 11, or a pharmaceutically acceptable salt thereof, wherein $R_2$ is phenyl, 2-fluorophenyl, 3-fluorophenyl, or 4-fluorophenyl.

13. The compound of claim 12, or a pharmaceutically acceptable salt thereof, wherein $R_2$ is phenyl.

14. The compound of claim 1, or a pharmaceutically acceptable salt thereof, wherein $R_1$ is cycloalkyl, aryl, heterocycloalkyl, or heteroaryl, each of which is optionally substituted with one, two, or three groups independently chosen from —$R_{11}$, —$OR_{12}$, halo, —$NR_{12}R_{13}$, —$C(O)R_{12}$, —$C(O)OR_{12}$, —$C(O)NR_{12}R_{13}$, —$OC(O)R_{12}$, —$OC(O)OR_{11}$, —$OC(O)NR_{12}R_{13}$, —$NR_{13}C(O)R_{12}$, —$NR_{13}C(O)OR_{11}$, —$NR_{13}C(O)NR_{12}R_{13}$, —$S(O)R_{11}$, —$SO_2$—$R_{11}$, —$SO_2NR_{12}R_{13}$, and —$NR_{13}SO_2R_{11}$, wherein $R_{11}$ is chosen from optionally substituted $C_1$-$C_6$ alkyl, optionally substituted cycloalkyl, optionally substituted cycloalkenyl, optionally substituted aryl, optionally substituted heterocycloalkyl, optionally substituted heterocycloalkenyl, and optionally substituted heteroaryl;

$R_{12}$ is chosen from H, optionally substituted $C_1$-$C_6$ alkyl, optionally substituted cycloalkyl, optionally substituted aryl, optionally substituted arylalkyl, optionally substituted heterocycloalkyl, optionally substituted heteroaryl, and optionally substituted heteroarylalkyl; and $R_{13}$ is chosen from hydrogen and optionally substituted $C_1$-$C_4$ alkyl.

15. The compound of claim 14, or a pharmaceutically acceptable salt thereof, wherein $R_1$ is phenyl optionally substituted with one, two, or three groups independently chosen from —$R_{11}$, —$OR_{12}$, halo, —$C(O)R_{12}$, —$NR_{12}R_{13}$, and —$NR_{13}SO_2R_{11}$.

16. The compound of claim 15, or a pharmaceutically acceptable salt thereof, wherein $R_1$ is phenyl optionally substituted with one, two or three groups independently selected from
halo,
$C_1$-$C_6$ alkyl,
aryl optionally substituted with one or two groups independently chosen from lower alkyl, trifluoromethyl, cycloalkyl, phenyl, and benzyloxy, heteroaryl optionally substituted with one or two groups independently chosen from lower alkyl, trifluoromethyl, cycloalkyl, and phenyl,
(cycloalkyl)sulfonamido, and
heterocycloalkyl optionally substituted with one or two groups independently chosen from halo, lower alkyl, trifluoromethyl, cycloalkyl, heterocycloalkyl, and phenyl.

17. The compound of claim 1, or a pharmaceutically acceptable salt thereof, wherein $R_1$ is phenyl optionally substituted with one, two or three groups independently selected from halo, lower alkyl, oxazol-2-yl, oxazol-5-yl, pyrimidin-2-yl, pyrimidin-5-yl, pyridazin-3-yl, pyridazin-4-yl, 1H-pyrazol-1-yl, (cycloalkyl)sulfonamido, 1H-imidazol-1-yl, imidazol-2-yl, 1,2,3,6-tetrahydropyridin-4-yl, azetidin-1-yl, pyrrolidin-1-yl, 2-oxa-6-azaspiro[3.3]heptan-6-yl, phenyl, hexahydropyrrolo[1,2-a]pyrazin-2(1H)-yl, piperidin-1-yl, piperazin-1-yl, and 6,7-dihydropyrazolo[1,5-a]pyrimidin-4(5H)-yl, each of which is optionally substituted with one or two groups independently chosen from halo, lower alkyl, trifluoromethyl, phenyl, cycloalkyl, benzyl, benzyloxy, and pyrrolidin-1-yl.

18. The compound of claim 17, or a pharmaceutically acceptable salt thereof, wherein $R_1$ is chosen from phenyl, 2-methylphenyl, 3-methylphenyl, 4-methylphenyl, 2-fluorophenyl, 3-fluorophenyl, 4-fluorophenyl, 2-bromophenyl, 3-bromophenyl, 4-bromophenyl, 4-(1-benzyl-1,2,3,6-tetrahydropyridin-4-yl)phenyl, 4-(pyrimidin-2-yl)phenyl, 4-(pyrimidin-5-yl)phenyl, 4-(5-methylpyrimidin-2-yl)phenyl, 3-(5-fluoropyrimidin-2-yl)phenyl, 4-(5-chloropyrimidin-2-yl)phenyl, 4-(5-fluoropyrimidin-2-yl)phenyl, 4-(4-(trifluoromethyl)pyrimidin-2-yl)phenyl, 4-(5-trifluoromethylpyrimidin-2-yl)phenyl, 4-(5-cyclopropylpyrimidin-2-yl)phenyl, 4-(pyridazin-3-yl)phenyl, 4-(pyridazin-4-yl)phenyl, 4-(1H-imidazol-1-yl)phenyl, 4-(1-methyl-1H-imidazol-2-yl)phenyl, 4-(5-methyl-1H-imidazol-2-yl)phenyl), 4-(1H-pyrazol-1-yl)phenyl, 4-(3-methyl-1H-pyrazol-1-yl)phenyl, 4-(3-(trifluoromethyl)-1H-pyrazol-1-yl)phenyl, 3-(oxazol-5-yl)phenyl, 4-(oxazol-2-yl)phenyl, 4-(oxazol-5-yl)phenyl, 4-(2-methyloxazol-5-yl)phenyl, 4-(2-cyclopropyloxazol-5-yl)phenyl, 4-(2-phenyloxazol-5-yl)phenyl, 4-(cyclopropanesulfonamido)phenyl, 4-(3,3-dimethylazetidin-1-yl)phenyl, 4-(3,3-difluoropyrrolidin-1-yl)phenyl, 4-(2-oxa-6-azaspiro[3.3]heptan-6-yl)phenyl, 3'-(benzyloxy)biphenyl-4-yl, 3-(hexahydropyrrolo[1,2-a]pyrazin-2(1H)-yl)phenyl, 3-(4-(pyrrolidin-1-yl)piperidin-1-yl)phenyl, 4-(4-methylpiperazin-1-yl)phenyl, 4-(4-isopropylpiperazin-1-yl)phenyl, or 3-(6,7-dihydropyrazolo[1,5-a]pyrimidin-4(5H)-yl)phenyl.

19. The compound of claim 1, or a pharmaceutically acceptable salt thereof, wherein $R_1$ is 4-(1-benzyl-1,2,3,6-tetrahydropyridin-4-yl)phenyl, 4-(pyrimidin-2-yl)phenyl, 4-(5-methylpyrimidin-2-yl)phenyl, 4-(5-chloropyrimidin-2-yl)phenyl, 4-(5-fluoropyrimidin-2-yl)phenyl, 4-(4-(trifluoromethyl)pyrimidin-2-yl)phenyl, 4-(5-cyclopropylpyrimidin-2-yl)phenyl, 4-(pyridazin-3-yl)phenyl, 4-(pyridazin-4-yl)phenyl, 4-(5-methyl-1H-imidazol-2-yl)phenyl), 4-(5-(trifluoromethyl)-1H-imidazol-2-yl)phenyl, 3-chloro-4-(5-methyl-1H-imidazol-2-yl)phenyl, 3-fluoro-4-(5-methyl-1H-imidazol-2-yl)phenyl, 4-(1H-pyrazol-1-yl)phenyl, 3-(oxazol-5-yl)phenyl, 4-(oxazol-2-yl)phenyl, 4-(oxazol-5-yl)phenyl, 4-(2-cyclopropyloxazol-5-yl)phenyl, 4-(4-isopropylpiperazin-1-yl)phenyl, or 3-(6,7-dihydropyrazolo[1,5-a]pyrimidin-4(5H)-yl)phenyl.

20. The compound of claim 14, or a pharmaceutically acceptable salt thereof, wherein $R_1$ is 1,2,3,4-tetrahydroquinolin-6-yl, 2,3,4,5-tetrahydrobenzo[f][1,4]oxazepin-7-yl, 1,2,3,4-tetrahydropyrrolo[1,2-a]pyrazin-7-yl, imidazo[1,2- a]pyridin-7-yl, imidazo[1,2-a]pyridin-3-yl, pyrrolo[1,2-a]pyrimidin-4-yl, 1,5-naphthyridin-4-yl, 2,3-dihydrobenzo[b][1,4]dioxin-6-yl, benzo[d][1,3]dioxol-5-yl, or 1-oxo-isoindolin-5-yl, each of which is optionally substituted with one or two groups independently chosen from halo and $C_1$-$C_6$ alkyl optionally substituted with one, two, or three halo groups.

21. The compound of claim 14, or a pharmaceutically acceptable salt thereof, wherein $R_1$ is heteroaryl optionally substituted with one, two, or three groups independently chosen from —$R_{11}$, —$OR_{12}$, halo, and —$NR_{13}SO_2R_{11}$.

22. The compound of claim 21, or a pharmaceutically acceptable salt thereof, wherein $R_1$ is chosen from pyridin-3-yl, pyridin-4-yl, 1H-pyrazol-4-yl, pyrimidin-5-yl, pyridazin-4-yl, benzo[d]isoxazol-3-yl, benzo[d]oxazol-6-yl, or thiazol-5-yl, each of which is optionally substituted with one, two, or three groups independently chosen from —$R_{11}$, —$OR_{12}$, halo, and —$NR_{13}SO_2R_{11}$.

23. The compound of claim 1, or a pharmaceutically acceptable salt thereof, wherein $R_1$ is pyridin-3-yl, pyridin-4-yl, 1H-pyrazol-4-yl, pyrimidin-5-yl, pyridazin-4-yl, benzo[d]isoxazol-3-yl, benzo[d]oxazol-6-yl, or thiazol-5-yl, each of which is optionally substituted with one or two groups independently chosen from halo, lower alkyl, 2,2,2-trifluoroethylamino, trifluoromethyl, 2,2,2-trifluoroethyl, cycloalkyl, cyclopropylmethyl, 1H-pyrazol-1-yl optionally substituted with lower alkyl, pyrimidin-2-yl optionally substituted with lower alkyl or halo, oxazol-5-yl optionally substituted with lower alkyl, piperazin-1-yl optionally substituted with lower alkyl, piperidin-4-yl optionally substituted with 2,2,2-trifluoroethyl, and pyridin-2-yl optionally substituted with lower alkyl or trifluoromethyl.

24. The compound of claim 23, or a pharmaceutically acceptable salt thereof, wherein $R_1$ is 2 cyclopropylpyridin-4-yl, 6-(trifluoromethyl)pyridin-3-yl, 2-(trifluoromethyl)pyridin-4-yl, 5-(trifluoromethyl)pyridin-3-yl, 2-(2,2,2-trifluoroethylamino)pyridin-4-yl, 6-(2,2,2-trifluoroethylamino)pyridin-3-yl, 6-(3-methyl-1H-pyrazol-1-yl)pyridin-3-yl, 6-(5-methylpyrimidin-2-yl)pyridin-3-yl, 6-(2-methyloxazol-5-yl)pyridin-3-yl, 6-(5-chloropyrimidin-2-yl)pyridin-3-yl, 6-(4-isopropylpiperazin-1-yl)pyridin-3-yl, 2,6-dicyclopropylpyridin-4-yl, 6-(5-fluoropyrimidin-2-yl)pyridin-3-yl, 2-(5-chloropyrimidin-2-yl)-6-cyclopropylpyridin-4-yl, 1-methyl-1H-pyrazol-4-yl, 1-(2,2,2-trifluoroethyl)-1H-pyrazol-4-yl, 1-(cyclopropylmethyl)-1H-pyrazol-4-yl, 1-cyclopropyl-1H-pyrazol-4-yl, 1,3-dimethyl-1H-pyrazol-4-yl, 1-(1-(2,2,2-trifluoroethyl)piperidin-4-yl)-1H-pyrazol-4-yl, 1-(5-(trifluoromethyl)pyridin-2-yl)-1H-pyrazol-4-yl, pyrimidin-5-yl, 2-cyclopropylpyrimidin-5-yl, 3-cyclopropylpyrimidin-5-yl, pyridazin-4-yl, 6-cyclopropylpyridazin-4-yl, benzo[d]isoxazol-3-yl, 2-isopropylbenzo[d]oxazol-6-yl, or 2-methylthiazol-5-yl.

25. A compound chosen from
trans-N-Hydroxy-2,3-diphenylcyclopropanecarboxamide;
(1R*,2R*,3R*)-2-Cyclohexyl-N-hydroxy-3-phenylcyclopropanecarboxamide;
(1R*,2R*,3R*)—N-Hydroxy-2-(2-isopropoxyphenyl)-3-phenylcyclopropanecarboxamide;
(1R*,2R*,3R*)-2-(2-Fluorophenyl)-N-hydroxy-3-phenylcyclopropanecarboxamide;
(1S*,2R*,3R*)-2-(2-Fluorophenyl)-N-hydroxy-3-phenylcyclopropanecarboxamide;
(1R*,2R*,3R*)-2-(2-Bromophenyl)-N-hydroxy-3-phenylcyclopropanecarboxamide;
(1R*,2R*,3R*)-2-(3-Bromophenyl)-N-hydroxy-3-phenylcyclopropanecarboxamide;
(1R*,2R*,3R*)-2-(4-Bromophenyl)-N-hydroxy-3-phenylcyclopropanecarboxamide;
(1R*,2R*,3R*)—N-Hydroxy-2-phenyl-3-o-tolylcyclopropanecarboxamide;
(1R*,2R*,3R*)—N-Hydroxy-2-phenyl-3-m-tolylcyclopropanecarboxamide;
(1R*,2R*,3R*)—N-Hydroxy-2-phenyl-3-p-tolylcyclopropanecarboxamide;
(1R*,2R*,3R*)-2-(4-(cyclopropanesulfonamido)phenyl)-N-hydroxy-3-phenylcyclopropanecarboxamide;
(1S*,2R*,3R*)-2-Cyclopentyl-N-hydroxy-3-phenylcyclopropanecarboxamide;
(1R,2R,3R)—N-Hydroxy-2-(1-methyl-1H-pyrazol-4-yl)-3-phenylcyclopropanecarboxamide;
(1R*,2R*,3R*)—N-Hydroxy-2-phenyl-3-(pyrimidin-5-yl)cyclopropanecarboxamide;
(1R,2R,3R)-2-(2,3-Dihydrobenzo[b][1,4]dioxin-6-yl)-N-hydroxy-3-phenylcyclopropanecarboxamide;
(1R,2R,3R)-2-(8-Chloro-2,3-dihydrobenzo[b][1,4]dioxin-6-yl)-N-hydroxy-3-phenylcyclopropanecarboxamide;
(1S,2R,3R)-2-(8-Chloro-2,3-dihydrobenzo[b][1,4]dioxin-6-yl)-3-(2-fluorophenyl)-N-hydroxycyclopropanecarboxamide;
(1R*,2R*,3R*)—N-Hydroxy-2-phenyl-3-(pyridazin-4-yl)cyclopropanecarboxamide;
(1R,2R,3R)-2-(2-Cyclopropylpyridin-4-yl)-N-hydroxy-3-phenylcyclopropanecarboxamide;
(1S,2R,3R)-2-(2-Cyclopropylpyridin-4-yl)-3-(2-fluorophenyl)-N-hydroxycyclopropanecarboxamide;
(1R,2R,3R)-2-(2-Cyclopropylpyridin-4-yl)-3-(4-fluorophenyl)-N-hydroxycyclopropanecarboxamide;
(1R,2R,3R)-2-(2,2-Difluorobenzo[d][1,3]dioxol-5-yl)-N-hydroxy-3-phenylcyclopropanecarboxamide;
(1R,2R,3R)—N-Hydroxy-2-phenyl-3-(6-(trifluoromethyl)pyridin-3-yl)cyclopropanecarboxamide;
(1R,2R,3R)—N-Hydroxy-2-phenyl-3-(2-(trifluoromethyl)pyridin-4-yl)cyclopropanecarboxamide;
(1R,2R,3R)—N-Hydroxy-2-(1-oxo-2-(2,2,2-trifluoroethyl)isoindolin-5-yl)-3-phenylcyclopropanecarboxamide;
(1R,2R,3R)—N-hydroxy-2-(2-isopropylbenzo[d]oxazol-6-yl)-3-phenylcyclopropanecarboxamide;
(1R,2R,3R)—N-Hydroxy-2-(3-(oxazol-5-yl)phenyl)-3-phenylcyclopropanecarboxamide;
(1R,2R,3R)—N-Hydroxy-2-(4-(oxazol-5-yl)phenyl)-3-phenylcyclopropanecarboxamide;
(1R*,2R*,3R*)-2-(4-(1H-imidazol-1-yl)phenyl)-N-hydroxy-3-phenylcyclopropanecarboxamide;
(1R,2R,3R)-2-(4-(2-Cyclopropyloxazol-5-yl)phenyl)-N-hydroxy-3-phenylcyclopropanecarboxamide;
(1R*,2R*,3R*)—N-Hydroxy-2-phenyl-3-(4-(2-phenyloxazol-5-yl)phenyl)cyclopropanecarboxamide;
(1R*,2R*,3R*)-2-(4-(5-Fluoropyrimidin-2-yl)phenyl)-N-hydroxy-3-phenylcyclopropanecarboxamide;
(1R*,2R*,3R*)-2-(3-(5-Fluoropyrimidin-2-yl)phenyl)-N-hydroxy-3-phenylcyclopropanecarboxamide;
(1R*,2R*,3R*)-2-(4-(5-Cyclopropylpyrimidin-2-yl)phenyl)-N-hydroxy-3-phenylcyclopropanecarboxamide;
(1R*,2R*,3R*)-2-(4-(4-Trifluoromethylpyrimidin-2-yl)phenyl)-N-hydroxy-3-phenylcyclopropanecarboxamide;
(1R,2R,3R)-2-(4-(5-Trifluoromethylpyrimidin-2-yl)phenyl)-N-hydroxy-3-phenylcyclopropanecarboxamide;
(1R*,2R*,3R*)—N-Hydroxy-2-phenyl-3-(4-(pyridazin-3-yl)phenyl)cyclopropanecarboxamide;

(1R*,2R*,3R*)—N-Hydroxy-2-phenyl-3-(4-(pyridazin-4-yl)phenyl)cyclopropanecarboxamide;
(1R*,2R*,3R*)—N-Hydroxy-2-phenyl-3-(4-(pyrimidin-2-yl)phenyl)cyclopropanecarboxamide;
(1R*,2R*,3R*)—N-Hydroxy-2-phenyl-3-(4-(pyrimidin-5-yl)phenyl)cyclopropanecarboxamide;
(1R,2R,3R)-2-(4-(5-Chloropyrimidin-2-yl)phenyl)-N-hydroxy-3-phenylcyclopropanecarboxamide;
(1R*,2R*,3R*)—N-Hydroxy-2-(4-(5-methylpyrimidin-2-yl)phenyl)-3-phenylcyclopropanecarboxamide;
(1R*,2R*,3R*)—N-Hydroxy-2-(4-(5-methyl-1H-imidazol-2-yl)phenyl)-3-phenylcyclopropanecarboxamide;
(1R*,2R*,3R*)-2-(4-(2-cyclopropylisoindolin-5-yl)phenyl)-N-hydroxy-3-phenylcyclopropanecarboxamide;
(1R,2R,3R)-2-(3'-(Benzyloxy)-[1,1'-biphenyl]-4-yl)-N-hydroxy-3-phenylcyclopropanecarboxamide;
(1R*,2R*,3R*)-2-(4'-(9H-carbazol-9-yl)-[1,1'-biphenyl]-4-yl)-N-hydroxy-3-phenylcyclopropanecarboxamide;
(1R,2R,3R)—N-hydroxy-2-(4-(4-methyl-3,4-dihydro-2H-benzo[b][1,4]oxazin-7-yl)phenyl)-3-phenylcyclopropanecarboxamide;
(1R*,2R*,3R*)—N-Hydroxy-2-(4-(4-isopropylpiperazin-1-yl)phenyl)-3-phenylcyclopropanecarboxamide;
(1R*,2R*,3R*)—N-Hydroxy-2-(3-(4-isopropylpiperazin-1-yl)phenyl)-3-phenylcyclopropanecarboxamide;
(1R*,2R*,3R*)—N-Hydroxy-2-(4-(3,3-difluoropyrrolidin-1-yl)phenyl)-3-phenylcyclopropanecarboxamide;
(1R*,2R*,3R*)-2-(4-(3,3-Dimethylazetidin-1-yl)phenyl)-N-hydroxy-3-phenylcyclopropanecarboxamide;
(1R*,2R*,3R*)-2-(4-(2-Oxa-6-azaspiro[3.3]heptan-6-yl)phenyl)-N-hydroxy-3-phenylcyclopropanecarboxamide;
(1R*,2R*,3R*)-2-(3-(Hexahydropyrrolo[1,2-a]pyrazin-2(1H)-yl)phenyl)-N-hydroxy-3-phenylcyclopropanecarboxamide;
(1R*,2R*,3R*)—N-Hydroxy-2-phenyl-3-(3-(4-(pyrrolidin-1-yl)piperidin-1-yl)phenyl)cyclopropanecarboxamide;
(1R,2R,3R)-2-(3-(6,7-Dihydropyrazolo[1,5-a]pyrimidin-4(5H)-yl)phenyl)-N-hydroxy-3-phenylcyclopropanecarboxamide;
(1R*,2R*,3R*)—N-Hydroxy-2-(4-(4-methylpiperazin-1-yl)phenyl)-3-phenylcyclopropanecarboxamide;
(1R*,2R*,3R*)—N-Hydroxy-2-(4-(oxazol-2-yl)phenyl)-3-phenylcyclopropanecarboxamide;
(1R*,2R*,3R*)—N-Hydroxy-2-(4-(1-methyl-1H-imidazol-2-yl)phenyl)-3-phenylcyclopropanecarboxamide;
(1R*,2S*,3S*)-2-(4-(5-Fluoropyrimidin-2-yl)phenyl)-N-hydroxy-1-methyl-3-phenylcyclopropanecarboxamide;
(1R*,2R*,3R*)-2-(4-(1H-pyrazol-1-yl)phenyl)-N-hydroxy-3-phenylcyclopropanecarboxamide;
(1R,2R,3R)—N-Hydroxy-2-phenyl-3-(5-(trifluoromethyl)pyridin-3-yl)cyclopropanecarboxamide;
(1R,2R,3R)-2-(4-(1-Benzyl-1,2,3,6-tetrahydropyridin-4-yl)phenyl)-N-hydroxy-3-phenylcyclopropanecarboxamide;
(1S,2R,3R)-2-(2-fluorophenyl)-N-hydroxy-3-(4-(2-methyloxazol-5-yl)phenyl)cyclopropanecarboxamide;
(1S,2R,3S)-2-(2-fluorophenyl)-N-hydroxy-1-methyl-3-(4-(2-methyloxazol-5-yl)phenyl)cyclopropanecarboxamide;
(1S,2R,3R)-2-(2-fluorophenyl)-N-hydroxy-3-(4-(3-methyl-1H-pyrazol-1-yl)phenyl)cyclopropanecarboxamide;
(1S,2R,3R)-2-(2-fluorophenyl)-N-hydroxy-3-(4-(3-(trifluoromethyl)-1H-pyrazol-1-yl)phenyl)cyclopropanecarboxamide;
(1S,2R,3R)-2-(2-fluorophenyl)-N-hydroxy-3-(4-(isopropyl(2-morpholinoethyl)amino)phenyl)cyclopropanecarboxamide;
(1R,2R,3R)-2-(2-cyclopropylpyrimidin-5-yl)-N-hydroxy-3-phenylcyclopropanecarboxamide;
(1R,2R,3R)-2-(benzo[d]isoxazol-3-yl)-N-hydroxy-3-phenylcyclopropanecarboxamide;
(1R,2R,3R)-2-(6-cyclopropylpyridazin-4-yl)-N-hydroxy-3-phenylcyclopropanecarboxamide;
(1S,2R,3R)-2-(2-fluorophenyl)-N-hydroxy-3-(6-(3-methyl-1H-pyrazol-1-yl)pyridin-3-yl)cyclopropanecarboxamide;
(1S,2R,3R)-2-(6-(5-chloropyrimidin-2-yl)pyridin-3-yl)-3-(2-fluorophenyl)-N-hydroxycyclopropanecarboxamide;
(1R,2R,3R)-2-(5-chloro-6-(4-isopropylpiperazin-1-yl)pyridin-3-yl)-N-hydroxy-3-phenylcyclopropanecarboxamide;
(1S,2R,3R)-2-(2-fluorophenyl)-3-(6-(5-fluoropyrimidin-2-yl)pyridin-3-yl)-N-hydroxycyclopropanecarboxamide;
(1S,2R,3R)-2-(2-fluorophenyl)-N-hydroxy-3-(6-(5-methylpyrimidin-2-yl)pyridin-3-yl)cyclopropanecarboxamide;
(1R,2R,3R)—N-hydroxy-2-(6-(2-methyloxazol-5-yl)pyridin-3-yl)-3-phenylcyclopropanecarboxamide;
(1R,2R,3R)-2-(5-chloro-6-(2-methyloxazol-5-yl)pyridin-3-yl)-N-hydroxy-3-phenylcyclopropanecarboxamide;
(1S,2R,3R)-2-(2-fluorophenyl)-N-hydroxy-3-(2-(2,2,2-trifluoroethylamino)pyridin-4-yl)cyclopropanecarboxamide;
(1R,2R,3R)—N-hydroxy-2-phenyl-3-(1-(2,2,2-trifluoroethyl)-1H-pyrazol-4-yl)cyclopropanecarboxamide;
(1R,2R,3R)-2-(1-cyclopropyl-1H-pyrazol-4-yl)-N-hydroxy-3-phenylcyclopropanecarboxamide;
(1R,2R,3R)—N-hydroxy-2-phenyl-3-(1-(1-(2,2,2-trifluoroethyl)piperidin-4-yl)-1H-pyrazol-4-yl)cyclopropanecarboxamide;
(1R,2R,3R)-2-(1,3-dimethyl-1H-pyrazol-4-yl)-N-hydroxy-3-phenylcyclopropanecarboxamide;
(1R,2R,3S)—N-hydroxy-2-(2-methylthiazol-5-yl)-3-phenylcyclopropanecarboxamide;
(1R,2R,3R)-2-(8-chloro-1,2,3,4-tetrahydroquinolin-6-yl)-N-hydroxy-3-phenylcyclopropanecarboxamide;
(1R,2R,3R)—N-hydroxy-2-phenyl-3-(4-(2,2,2-trifluoroethyl)-2,3,4,5-tetrahydrobenzo[f][1,4]oxazepin-7-yl)cyclopropanecarboxamide;
(1R,2R,3R)—N-hydroxy-2-(1-methyl-2-(2,2,2-trifluoroethyl)-1,2,3,4-tetrahydropyrrolo[1,2-a]pyrazin-7-yl)-3-phenylcyclopropanecarboxamide;
(1R,2R,3R)-2-(1-fluoro-2-(2,2,2-trifluoroethyl)-1,2,3,4-tetrahydropyrrolo[1,2-a]pyrazin-7-yl)-N-hydroxy-3-phenylcyclopropanecarboxamide;
(1R,2R,3R)—N-hydroxy-2-phenyl-3-(2-(2,2,2-trifluoroethyl)-1,2,3,4-tetrahydropyrrolo[1,2-a]pyrazin-7-yl)cyclopropanecarboxamide;
(1R,2R,3R)—N-hydroxy-2-phenyl-3-(7-(2,2,2-trifluoroethyl)-5,6,7,8-tetrahydroimidazo[1,2-a]pyrazin-2-yl)cyclopropanecarboxamide;
(1R,2R,3R)—N-hydroxy-2-phenyl-3-(2-(trifluoromethyl)imidazo[1,2-a]pyridin-7-yl)cyclopropanecarboxamide
(1R,2R,3R)—N-hydroxy-2-(imidazo[1,2-a]pyridin-3-yl)-3-phenylcyclopropanecarboxamide;
(1R,2R,3R)—N-hydroxy-2-phenyl-3-(pyrrolo[1,2-a]pyrimidin-4-yl)cyclopropanecarboxamide;

(1R,2R,3R)—N-hydroxy-2-(1,5-naphthyridin-4-yl)-3-phenylcyclopropanecarboxamide;

(1S,2S,3R)-2-(2-cyclopropylpyridin-4-yl)-N-hydroxy-3-(2-methylthiazol-5-yl)cyclopropanecarboxamide;

(1S,2S,3R)-2-(2-cyclopropylpyridin-4-yl)-N-hydroxy-3-(5-(trifluoromethyl)thiophen-2-yl)cyclopropanecarboxamide;

(1R,2R,3R)-2-(1-((5-fluoropyridin-2-yl)methyl)-1H-pyrazol-4-yl)-N-hydroxy-3-phenylcyclopropanecarboxamide;

(1S,2R,3S)-2-(3-fluoro-5-methylthiophen-2-yl)-N-hydroxy-3-(1-methyl-1H-pyrazol-4-yl)cyclopropanecarboxamide;

(1S,2S,3R)—N-hydroxy-2-(1-methyl-1H-pyrazol-4-yl)-3-(5-methyl-3-(trifluoromethyl)thiophen-2-yl)cyclopropanecarboxamide;

(1S,2S,3R)—N-hydroxy-2-(1-methyl-1H-pyrazol-4-yl)-3-(5-methylthiophen-2-yl)cyclopropanecarboxamide;

(1R,2R,3R)—N-hydroxy-2-(1-methyl-1H-pyrazol-4-yl)-3-o-tolylcyclopropanecarboxamide;

(1R,2R,3R)—N-hydroxy-2-(1-methyl-1H-pyrazol-4-yl)-3-(2-(trifluoromethyl)phenyl)cyclopropanecarboxamide;

(1S,2R,3R)-2-(2-chlorophenyl)-N-hydroxy-3-(1-methyl-1H-pyrazol-4-yl)cyclopropanecarboxamide;

(1R,2R,3R)-2-(3-fluorophenyl)-N-hydroxy-3-(1-methyl-1H-pyrazol-4-yl)cyclopropanecarboxamide;

(1R,2R,3R)—N-hydroxy-2-(1-methyl-1H-pyrazol-4-yl)-3-m-tolylcyclopropanecarboxamide;

(1R,2R,3R)—N-hydroxy-2-(1-methyl-1H-pyrazol-4-yl)-3-(3-(trifluoromethyl)phenyl)cyclopropanecarboxamide;

(1R,2R,3R)-2-(3-chlorophenyl)-N-hydroxy-3-(1-methyl-1H-pyrazol-4-yl)cyclopropanecarboxamide;

(1S,2S,3R)-2-(2-cyclopropylpyridin-4-yl)-3-(3-fluoro-5-methylthiophen-2-yl)-N-hydroxycyclopropanecarboxamide;

(1S,2S,3R)-2-(2-cyclopropylpyridin-4-yl)-N-hydroxy-3-(5-methyl-3-(trifluoromethyl)thiophen-2-yl)cyclopropanecarboxamide;

(1S,2S,3R)-2-(2-cyclopropylpyridin-4-yl)-N-hydroxy-3-(5-methylthiophen-2-yl)cyclopropanecarboxamide;

(1R,2R,3R)—N-hydroxy-2-phenyl-3-(4-(5-(trifluoromethyl)-1H-imidazol-2-yl)phenyl)cyclopropanecarboxamide;

(1R,2R,3R)-2-(3-chloro-4-(5-methyl-1H-imidazol-2-yl)phenyl)-N-hydroxy-3-phenylcyclopropanecarboxamide; and (1R,2R,3R)-2-(3-fluoro-4-(5-methyl-1H-imidazol-2-yl)phenyl)-N-hydroxy-3-phenylcyclopropanecarboxamide, or a pharmaceutically acceptable salt thereof.

26. A pharmaceutical composition comprising a compound of claim 1, or a pharmaceutically acceptable salt thereof, and at least one pharmaceutically acceptable excipient.

27. A pharmaceutical composition comprising a compound of claim 25, or a pharmaceutically acceptable salt thereof, and at least one pharmaceutically acceptable excipient.

\* \* \* \* \*

UNITED STATES PATENT AND TRADEMARK OFFICE
CERTIFICATE OF CORRECTION

PATENT NO. : 9,765,054 B2
APPLICATION NO. : 13/981107
DATED : September 19, 2017
INVENTOR(S) : Roland W. Bürli et al.

Page 1 of 2

It is certified that error appears in the above-identified patent and that said Letters Patent is hereby corrected as shown below:

In the Claims

In Claim 1, Column 141, Lines 51-52, please replace "$R_3$ is hydrogen or lower alkyl optionally substituted with halo." with --$R_{3a}$ is hydrogen or lower alkyl optionally substituted with halo.--.

In Claim 2, Column 141, Lines 56-64, please replace

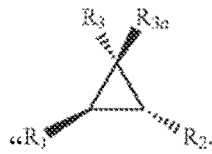

" with --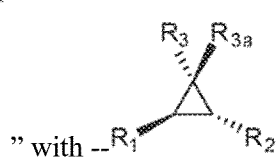    --.

In Claim 3, Column 142, Lines 25-31, please replace

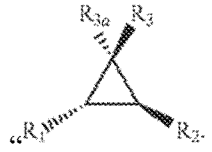

" with --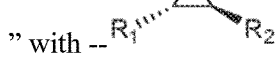    --.

In Claim 6, Column 142, Lines 40-47, please replace

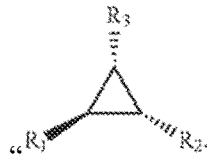

" with --    --.

In Claim 7, Column 142, Lines 49-50, please replace "acceptable salt thereof, wherein the compound of Formula I a compound of Formula V:" with --acceptable salt thereof, wherein the compound of Formula I is a compound of Formula V:--.

Signed and Sealed this
Seventeenth Day of October, 2023

*Katherine Kelly Vidal*
Katherine Kelly Vidal
*Director of the United States Patent and Trademark Office*

In Claim 7, Column 142, Lines 51-59, please replace

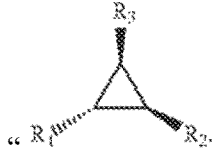 " with -- 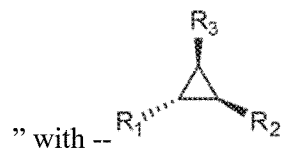 --.

In Claim 20, Column 144, Lines 64-65, please replace "The compound of claim 14, or a pharmaceutically acceptable salt thereof," with --The compound of claim 1, or a pharmaceutically acceptable salt thereof,--.

In Claim 24, Column 145, Lines 34-35, please replace "acceptable salt thereof, wherein $R_1$ is 2 cyclopropylpyridin-4-yl," with --acceptable salt thereof, wherein $R_1$ is 2-cyclopropylpyridin-4-yl,--.

In Claim 25, Column 148, Lines 61-63, please replace "(1R,2R,3R)-N-hydroxy-2-phenyl-3-(2-(trifluoromethyl)imidazo[1,2-a]pyridin-7-yl)cyclopropanecarboxamide" with --(1R,2R,3R)-N-hydroxy-2-phenyl-3-(2-(trifluoromethyl)imidazo[1,2-a]pyridin-7-yl)cyclopropanecarboxamide;--.